(12) United States Patent
Khvorova et al.

(10) Patent No.: US 10,240,149 B2
(45) Date of Patent: Mar. 26, 2019

(54) REDUCED SIZE SELF-DELIVERING RNAI COMPOUNDS

(71) Applicant: Phio Pharmaceuticals Corp., Marlborough, MA (US)

(72) Inventors: Anastasia Khvorova, Westborough, MA (US); William Salomon, Worcester, MA (US); Joanne Kamens, Newton, MA (US); Dmitry Samarsky, Westborough, MA (US); Tod M. Woolf, Sudbury, MA (US); James Cardia, Franklin, MA (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 0 days.

(21) Appl. No.: 14/729,006

(22) Filed: Jun. 2, 2015

(65) Prior Publication Data
US 2016/0130578 A1 May 12, 2016

Related U.S. Application Data

(63) Continuation of application No. 13/636,728, filed as application No. PCT/US2011/029824 on Mar. 24, 2011, now Pat. No. 9,080,171.

(60) Provisional application No. 61/317,597, filed on Mar. 25, 2010, provisional application No. 61/317,261, filed on Mar. 24, 2010.

(51) Int. Cl.
*C12N 15/11* (2006.01)
*C12N 15/113* (2010.01)
*C07H 21/02* (2006.01)

(52) U.S. Cl.
CPC .......... *C12N 15/113* (2013.01); *C07H 21/02* (2013.01); *C12N 15/111* (2013.01); *C12N 2310/14* (2013.01); *C12N 2310/315* (2013.01); *C12N 2310/32* (2013.01); *C12N 2310/321* (2013.01); *C12N 2310/322* (2013.01); *C12N 2310/334* (2013.01); *C12N 2310/335* (2013.01); *C12N 2310/344* (2013.01); *C12N 2310/351* (2013.01); *C12N 2310/3515* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,415,732 A | 11/1983 | Caruthers et al. |
| 4,426,330 A | 1/1984 | Sears |
| 4,897,355 A | 1/1990 | Eppstein et al. |
| 4,904,582 A | 2/1990 | Tullis |
| 4,958,013 A | 9/1990 | Letsinger |
| 5,013,556 A | 5/1991 | Woodle et al. |
| 5,023,243 A | 6/1991 | Tullis |
| 5,051,257 A | 9/1991 | Pietronigro |
| 5,053,228 A | 10/1991 | Mori et al. |
| 5,108,921 A | 4/1992 | Low et al. |
| 5,112,963 A | 5/1992 | Pieles et al. |
| 5,149,782 A | 9/1992 | Chang et al. |
| 5,151,510 A | 9/1992 | Stec et al. |
| 5,162,115 A | 11/1992 | Pietronigro |
| 5,188,897 A | 2/1993 | Suhadolnik et al. |
| 5,213,804 A | 5/1993 | Martin et al. |
| 5,227,170 A | 7/1993 | Sullivan |
| 5,264,423 A | 11/1993 | Cohen et al. |
| 5,264,562 A | 11/1993 | Matteucci |
| 5,284,656 A | 2/1994 | Platz et al. |
| 5,354,844 A | 10/1994 | Beug et al. |
| 5,356,633 A | 10/1994 | Woodle et al. |
| 5,391,723 A | 2/1995 | Priest |
| 5,405,939 A | 4/1995 | Suhadolnik et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,419,966 A | 5/1995 | Reed et al. |
| 5,432,272 A | 7/1995 | Benner |
| 5,451,569 A | 9/1995 | Wong et al. |
| 5,453,496 A | 9/1995 | Caruthers et al. |
| 5,459,127 A | 10/1995 | Felgner et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,512,667 A | 4/1996 | Reed et al. |
| 5,514,786 A | 5/1996 | Cook et al. |
| 5,525,465 A | 6/1996 | Haralambidis et al. |

(Continued)

FOREIGN PATENT DOCUMENTS

| | | | |
|---|---|---|---|
| AU | 2004/206255 B2 | | 8/2004 |
| CN | 1 568 373 A | | 1/2005 |

(Continued)

OTHER PUBLICATIONS

Vermeulen et al. RNA 2005, 11:674-682.*
Rozners et al. Chem. Commun., 2005 5778-5780.*
Holmes et al.Eur. J. Org. Chem 2005, 5171-5183.*
[No Author Listed], RedChip Small-Cap Investor Conference. RXi Pharmaceuticals (Nasdaq RXII). Jun. 16, 2009 Presentation. 22 pages.
[No Author Listed], RXi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

(Continued)

Primary Examiner — Brian Whiteman
(74) Attorney, Agent, or Firm — Wolf, Greenfield & Sacks, P.C.

(57) ABSTRACT

The present invention relates to methods for in vivo administration of sd-rxRNA molecules.

21 Claims, 95 Drawing Sheets

Specification includes a Sequence Listing.

(56) References Cited

U.S. PATENT DOCUMENTS

| | | | |
|---|---|---|---|
| 5,527,528 A | 6/1996 | Allen et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,574,142 A | 11/1996 | Meyer, Jr. et al. |
| 5,578,718 A | 11/1996 | Cook et al. |
| 5,580,731 A | 12/1996 | Chang et al. |
| 5,580,972 A | 12/1996 | Tu et al. |
| 5,583,020 A | 12/1996 | Sullivan |
| 5,587,469 A | 12/1996 | Cook et al. |
| 5,591,721 A | 1/1997 | Agrawal et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,674,683 A | 10/1997 | Kool |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| 5,466,786 B1 | 4/1998 | Buhr et al. |
| 5,750,666 A | 5/1998 | Caruthers et al. |
| 5,770,713 A | 6/1998 | Imbach et al. |
| 5,777,153 A | 7/1998 | Lin et al. |
| 5,789,416 A | 8/1998 | Lum et al. |
| 5,792,847 A | 8/1998 | Buhr et al. |
| 5,808,023 A | 9/1998 | Sanghvi et al. |
| 5,814,014 A | 9/1998 | Elsberry et al. |
| 5,817,781 A | 10/1998 | Swaminathan et al. |
| 5,830,430 A | 11/1998 | Unger et al. |
| 5,830,653 A | 11/1998 | Froehler et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,094 A | 12/1999 | Simon et al. |
| 6,005,096 A | 12/1999 | Matteucci et al. |
| 6,013,786 A | 1/2000 | Chen |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,093,180 A | 7/2000 | Elsberry |
| 6,096,875 A | 8/2000 | Khan et al. |
| 6,107,094 A | 8/2000 | Crooke |
| 6,111,085 A | 8/2000 | Cook et al. |
| 6,121,437 A | 9/2000 | Guzaev et al. |
| 6,153,737 A | 11/2000 | Manoharan et al. |
| 6,172,208 B1 | 1/2001 | Cook |
| 6,207,819 B1 | 3/2001 | Manoharan et al. |
| 6,242,594 B1 | 6/2001 | Kelly |
| 6,248,878 B1 | 6/2001 | Matulic-Adamic et al. |
| 6,271,358 B1 | 8/2001 | Manoharan et al. |
| 6,299,895 B1 | 10/2001 | Hammang et al. |
| 6,300,319 B1 | 10/2001 | Manoharan |
| 6,326,358 B1 | 12/2001 | Manoharan |
| 6,328,765 B1 | 12/2001 | Hardwick et al. |
| 6,331,617 B1 | 12/2001 | Weeks et al. |
| 6,333,152 B1 | 12/2001 | Vogelstein et al. |
| 6,335,434 B1 | 1/2002 | Guzaev et al. |
| 6,335,437 B1 | 1/2002 | Manoharan |
| 6,344,436 B1 | 2/2002 | Smith et al. |
| 6,355,787 B1 | 3/2002 | Beckvermit et al. |
| 6,358,931 B1 | 3/2002 | Cook et al. |
| 6,378,526 B1 | 4/2002 | Bowman et al. |
| 6,395,474 B1 | 5/2002 | Buchardt et al. |
| 6,395,492 B1 | 5/2002 | Manoharan et al. |
| 6,397,849 B1 | 6/2002 | Bowman et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,436,427 B1 | 8/2002 | Hammang et al. |
| 6,440,943 B1 | 8/2002 | Cook et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,476,205 B1 | 11/2002 | Buhr et al. |
| 6,506,559 B1 | 1/2003 | Fire et al. |
| 6,525,031 B2 | 2/2003 | Manoharan |
| 6,528,631 B1 | 3/2003 | Cook et al. |
| 6,531,584 B1 | 3/2003 | Cook et al. |
| 6,559,279 B1 | 5/2003 | Manoharan et al. |
| 6,656,730 B1 | 12/2003 | Manoharan |
| 6,673,611 B2 | 1/2004 | Thompson et al. |
| 6,683,167 B2 | 1/2004 | Metelev et al. |
| 6,815,432 B2 | 11/2004 | Wheeler et al. |
| 6,849,726 B2 | 2/2005 | Usman et al. |
| 6,858,225 B2 | 2/2005 | Semple et al. |
| 6,887,906 B1 | 5/2005 | Teng et al. |
| 6,923,833 B2 | 8/2005 | Wasielewski |
| 7,041,824 B2 | 5/2006 | Bordon-Pallier et al. |
| 7,056,704 B2 | 6/2006 | Tuschl et al. |
| 7,078,196 B2 | 7/2006 | Tuschl et al. |
| 7,132,530 B2 | 11/2006 | Bennett et al. |
| 7,148,342 B2 | 12/2006 | Tolentino et al. |
| 7,205,297 B2 | 4/2007 | Beauchamp et al. |
| 7,309,361 B2 | 12/2007 | Wasielewski |
| 7,432,250 B2 | 10/2008 | Crooke |
| 7,521,431 B2 | 4/2009 | Reich et al. |
| 7,534,774 B2 | 5/2009 | Sosnowski et al. |
| 7,538,095 B2 | 5/2009 | Fire et al. |
| 7,560,438 B2 | 7/2009 | Fire et al. |
| 7,595,387 B2 | 9/2009 | Leake et al. |
| 7,615,083 B2 | 11/2009 | Wasielewski et al. |
| 7,622,455 B2 | 11/2009 | Bennett et al. |
| 7,622,633 B2 | 11/2009 | Fire et al. |
| 7,629,321 B2 | 12/2009 | Crooke |
| 7,695,902 B2 | 4/2010 | Crooke |
| 7,745,608 B2 | 6/2010 | Manoharan et al. |
| 7,750,144 B2 | 7/2010 | Zamore et al. |
| 7,786,290 B2 | 8/2010 | Woppmann et al. |
| 7,789,841 B2 | 9/2010 | Huckle et al. |
| 7,829,693 B2 | 11/2010 | Kreutzer et al. |
| 7,902,163 B2 | 3/2011 | Bennett et al. |
| 8,110,674 B2 | 2/2012 | Manoharan et al. |
| 8,202,845 B2 | 6/2012 | Drumm et al. |
| 8,227,444 B2 | 7/2012 | Dejneka |
| 8,263,569 B2 | 9/2012 | Baulcombe et al. |
| 8,268,794 B2 | 9/2012 | Nakajima et al. |
| 8,293,719 B2 | 10/2012 | Fougerolles et al. |
| 8,383,600 B2 | 2/2013 | Czech et al. |
| 8,470,792 B2 | 6/2013 | Frost et al. |
| 8,664,189 B2 * | 3/2014 | Khvorova ............ C12N 15/111 |
| | | 514/44 A |
| 8,796,443 B2 * | 8/2014 | Khvorova ............ C12N 15/111 |
| | | 536/23.1 |
| 8,815,818 B2 | 8/2014 | Samarsky et al. |
| 9,074,211 B2 | 7/2015 | Woolf et al. |
| 9,080,171 B2 | 7/2015 | Khvorova et al. |

(56) References Cited

U.S. PATENT DOCUMENTS

| | | | |
|---|---|---|---|
| 9,095,504 B2 * | 8/2015 | Libertine | ............ A61K 9/0051 |
| 9,175,289 B2 * | 11/2015 | Khvorova | ............ C12N 15/111 |
| 9,222,092 B2 | 12/2015 | Giese et al. | |
| 9,303,259 B2 | 4/2016 | Khvorova et al. | |
| 9,340,786 B2 | 5/2016 | Khvorova et al. | |
| 9,493,774 B2 | 11/2016 | Kamens | |
| 9,745,574 B2 | 8/2017 | Woolf et al. | |
| 9,938,530 B2 | 4/2018 | Khvorova et al. | |
| 9,963,702 B2 | 5/2018 | Khvorova et al. | |
| 10,041,073 B2 | 8/2018 | Khvorova et al. | |
| 2002/0081736 A1 | 6/2002 | Conroy et al. | |
| 2002/0086013 A1 | 7/2002 | King | |
| 2002/0132788 A1 | 9/2002 | Lewis et al. | |
| 2002/0147332 A1 | 10/2002 | Kaneko et al. | |
| 2002/0160393 A1 | 10/2002 | Symonds et al. | |
| 2002/0162126 A1 | 10/2002 | Beach et al. | |
| 2003/0004325 A1 | 1/2003 | Cook et al. | |
| 2003/0027780 A1 | 2/2003 | Hardee et al. | |
| 2003/0077829 A1 | 4/2003 | MacLachlan | |
| 2003/0108923 A1 | 6/2003 | Tuschl et al. | |
| 2003/0139585 A1 | 7/2003 | Uhlmann et al. | |
| 2003/0148979 A1 | 8/2003 | Sosnowski et al. | |
| 2003/0157030 A1 | 8/2003 | Davis et al. | |
| 2003/0158403 A1 | 8/2003 | Manoharan et al. | |
| 2003/0166282 A1 | 9/2003 | Brown et al. | |
| 2003/0175276 A1 | 9/2003 | Thorpe et al. | |
| 2004/0009938 A1 | 1/2004 | Manoharan et al. | |
| 2004/0014956 A1 | 1/2004 | Woolf et al. | |
| 2004/0014957 A1 | 1/2004 | Eldrup et al. | |
| 2004/0018999 A1 | 1/2004 | Beach et al. | |
| 2004/0054155 A1 | 3/2004 | Woolf et al. | |
| 2004/0072785 A1 | 4/2004 | Wolff et al. | |
| 2004/0137471 A1 | 7/2004 | Vickers et al. | |
| 2004/0167090 A1 | 8/2004 | Monahan et al. | |
| 2004/0171033 A1 | 9/2004 | Baker et al. | |
| 2004/0180351 A1 | 9/2004 | Giese et al. | |
| 2004/0192629 A1 | 9/2004 | Xu et al. | |
| 2004/0204377 A1 | 10/2004 | Rana | |
| 2004/0219520 A1 | 11/2004 | Mirkin et al. | |
| 2004/0229266 A1 | 11/2004 | Tuschl et al. | |
| 2004/0241845 A1 | 12/2004 | Desgroseillers et al. | |
| 2004/0248839 A1 | 12/2004 | Kowalik | |
| 2004/0259247 A1 | 12/2004 | Tuschl et al. | |
| 2005/0020521 A1 | 1/2005 | Rana | |
| 2005/0032733 A1 | 2/2005 | McSwiggen et al. | |
| 2005/0042227 A1 | 2/2005 | Zankel et al. | |
| 2005/0080246 A1 | 4/2005 | Allerson et al. | |
| 2005/0107325 A1 | 5/2005 | Manoharan et al. | |
| 2005/0142535 A1 | 6/2005 | Damha et al. | |
| 2005/0181382 A1 | 8/2005 | Zamore et al. | |
| 2005/0222066 A1 | 10/2005 | Richards et al. | |
| 2005/0239731 A1 | 10/2005 | McSwiggen et al. | |
| 2005/0245474 A1 | 11/2005 | Baker et al. | |
| 2005/0246794 A1 | 11/2005 | Khvorova et al. | |
| 2005/0255487 A1 | 11/2005 | Khvorova et al. | |
| 2005/0281781 A1 | 12/2005 | Ostroff | |
| 2006/0009409 A1 | 1/2006 | Woolf | |
| 2006/0069050 A1 | 3/2006 | Rana | |
| 2006/0127891 A1 | 6/2006 | McSwiggen et al. | |
| 2006/0142228 A1 | 6/2006 | Ford et al. | |
| 2006/0160133 A1 | 7/2006 | Czech et al. | |
| 2006/0160766 A1 | 7/2006 | Cheung | |
| 2006/0178324 A1 | 8/2006 | Hadwiger et al. | |
| 2006/0178327 A1 | 8/2006 | Yeung | |
| 2006/0211642 A1 | 9/2006 | McSwiggen et al. | |
| 2006/0211766 A1 | 9/2006 | Kaplan et al. | |
| 2007/0032441 A1 | 2/2007 | McSwiggen et al. | |
| 2007/0166734 A1 | 7/2007 | Bhat et al. | |
| 2007/0173473 A1 | 7/2007 | McSwiggen et al. | |
| 2007/0173476 A1 | 7/2007 | Leake et al. | |
| 2007/0231392 A1 | 10/2007 | Wagner et al. | |
| 2007/0248659 A1 | 10/2007 | Shanahan et al. | |
| 2007/0254850 A1 | 11/2007 | Lieberman et al. | |
| 2007/0269889 A1 | 11/2007 | Leake et al. | |
| 2008/0008697 A1 | 1/2008 | Mintier et al. | |
| 2008/0071068 A1 | 3/2008 | Oba et al. | |
| 2008/0085869 A1 | 4/2008 | Yamada et al. | |
| 2008/0108583 A1 | 5/2008 | Feinstein et al. | |
| 2008/0152654 A1 | 6/2008 | Reich | |
| 2008/0286866 A1 | 11/2008 | Quay et al. | |
| 2008/0311040 A1 | 12/2008 | Berry et al. | |
| 2009/0023216 A1 | 1/2009 | Woolf | |
| 2009/0098549 A1 * | 4/2009 | Schneider | ............ C12N 15/111 435/6.11 |
| 2009/0131360 A1 | 5/2009 | Woolf et al. | |
| 2009/0156524 A1 | 6/2009 | Feinstein et al. | |
| 2009/0171075 A1 | 7/2009 | Li | |
| 2009/0186802 A1 | 7/2009 | Alluis et al. | |
| 2009/0208564 A1 | 8/2009 | Li et al. | |
| 2009/0220582 A1 | 9/2009 | Min | |
| 2009/0220583 A1 | 9/2009 | Pereswetoff-Morath et al. | |
| 2009/0239814 A1 * | 9/2009 | Manoharan | ...... A61K 47/48092 514/26 |
| 2009/0247608 A1 | 10/2009 | Manoharan et al. | |
| 2010/0040656 A1 | 2/2010 | Franklin et al. | |
| 2010/0069620 A1 | 3/2010 | Zon | |
| 2010/0081705 A1 | 4/2010 | Bennett et al. | |
| 2010/0136695 A1 | 6/2010 | Woolf | |
| 2010/0286236 A1 | 11/2010 | Schlingensiepen et al. | |
| 2011/0021605 A1 | 1/2011 | Schulte et al. | |
| 2011/0039914 A1 | 2/2011 | Pavco et al. | |
| 2011/0237522 A1 * | 9/2011 | Khvorova | ............ C12N 15/111 514/20.9 |
| 2011/0237648 A1 * | 9/2011 | Khvorova | ............ C12N 15/111 514/44 A |
| 2011/0251258 A1 | 10/2011 | Samarsky et al. | |
| 2011/0263680 A1 | 10/2011 | Khvorova et al. | |
| 2011/0268761 A1 | 11/2011 | Levis et al. | |
| 2011/0288147 A1 | 11/2011 | Brown et al. | |
| 2012/0016005 A1 | 1/2012 | Samarsky et al. | |
| 2012/0040459 A1 | 2/2012 | Khvorova et al. | |
| 2012/0046186 A1 | 2/2012 | Pelham et al. | |
| 2012/0059046 A1 | 3/2012 | Woolf et al. | |
| 2012/0065243 A1 | 3/2012 | Woolf et al. | |
| 2012/0094374 A1 | 4/2012 | Bentwich et al. | |
| 2013/0131142 A1 | 5/2013 | Libertine et al. | |
| 2013/0197055 A1 * | 8/2013 | Kamens | ............ C12N 15/1137 514/44 A |
| 2014/0030319 A1 | 1/2014 | Tocque et al. | |
| 2014/0072613 A1 | 3/2014 | Lander et al. | |
| 2014/0113950 A1 | 4/2014 | Khvorova et al. | |
| 2014/0315974 A1 | 10/2014 | Khvorova et al. | |
| 2014/0364482 A1 | 12/2014 | Khvorova et al. | |
| 2015/0057362 A1 | 2/2015 | Levis et al. | |
| 2016/0115482 A1 | 4/2016 | Libertine et al. | |
| 2016/0115484 A1 | 4/2016 | Woolf et al. | |
| 2016/0130578 A1 | 5/2016 | Khvorova et al. | |
| 2016/0244765 A1 | 8/2016 | Khvorova et al. | |
| 2016/0304873 A1 | 10/2016 | Wolfson et al. | |
| 2016/0304875 A1 | 10/2016 | Cauwenbergh et al. | |
| 2016/0319278 A1 | 11/2016 | Khvorova et al. | |
| 2016/0355808 A1 | 12/2016 | Khvorova et al. | |
| 2016/0355826 A1 | 12/2016 | Khvorova et al. | |
| 2017/0009239 A1 | 1/2017 | Khvorova et al. | |
| 2017/0051288 A1 | 2/2017 | Byrne et al. | |
| 2017/0051290 A1 | 2/2017 | Byrne et al. | |
| 2017/0067056 A1 | 3/2017 | Khvorova et al. | |
| 2017/0137823 A1 | 5/2017 | Kamens et al. | |
| 2018/0030451 A1 | 2/2018 | Cauwenbergh | |
| 2018/0155718 A1 | 6/2018 | Woolf et al. | |
| 2018/0195066 A1 | 7/2018 | Byrne et al. | |
| 2018/0195072 A1 | 7/2018 | Cardia et al. | |

FOREIGN PATENT DOCUMENTS

| | | |
|---|---|---|
| DE | 197 27 932 A1 | 1/1999 |
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |

(56) References Cited

FOREIGN PATENT DOCUMENTS

| JP | 2004-500846 | 1/2004 |
|---|---|---|
| JP | 4 095 895 B2 | 9/2004 |
| JP | 2009-519033 | 5/2009 |
| JP | 2009-540011 | 11/2009 |
| WO | WO 92/03464 A1 | 3/1992 |
| WO | WO 1992/007065 A1 | 4/1992 |
| WO | WO 94/23028 A2 | 10/1994 |
| WO | WO 95/11910 A1 | 5/1995 |
| WO | WO 95/23162 A1 | 8/1995 |
| WO | WO 96/40964 A2 | 12/1996 |
| WO | WO 98/14172 A1 | 4/1998 |
| WO | WO 99/13915 A1 | 3/1999 |
| WO | WO 99/60012 A1 | 11/1999 |
| WO | WO 01/85941 A2 | 11/2001 |
| WO | WO 03/012052 A2 | 2/2003 |
| WO | WO 2003/064626 A2 | 8/2003 |
| WO | WO 2003/087367 A2 | 10/2003 |
| WO | WO 2003/087368 A2 | 10/2003 |
| WO | WO 2004/042027 A2 | 5/2004 |
| WO | WO 2004/064760 A2 | 8/2004 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/019453 A2 | 3/2005 |
| WO | WO 2005/078096 A2 | 8/2005 |
| WO | WO 2005/079533 A2 | 9/2005 |
| WO | WO 2005/097992 A2 | 10/2005 |
| WO | WO 2006/019430 A2 | 2/2006 |
| WO | WO 2006/039656 A2 | 4/2006 |
| WO | WO 2006/065601 A2 | 6/2006 |
| WO | WO 2006/113679 A2 | 10/2006 |
| WO | WO 2006/128141 A2 | 11/2006 |
| WO | WO 2007/021142 A1 | 2/2007 |
| WO | WO 2007/030167 A1 | 3/2007 |
| WO | WO 2007/044362 A2 | 4/2007 |
| WO | WO 2007/069068 A2 | 6/2007 |
| WO | WO 2007/089607 A2 | 8/2007 |
| WO | WO 2007/146953 A2 | 12/2007 |
| WO | WO 2008/021157 A1 | 2/2008 |
| WO | WO 2008/028965 A2 | 3/2008 |
| WO | WO 2008/028968 A2 | 3/2008 |
| WO | WO 2008/036825 A2 | 3/2008 |
| WO | WO 2008/109353 A1 | 9/2008 |
| WO | WO 2008/125908 A2 | 10/2008 |
| WO | WO 2009/020344 A2 | 2/2009 |
| WO | WO 2009/029688 A2 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/126933 A2 | 10/2009 |
| WO | WO 2010/006237 A2 | 1/2010 |
| WO | WO 2010/011346 A1 | 1/2010 |
| WO | WO 2010/027830 A2 | 3/2010 |
| WO | WO 2010/033247 A2 | 3/2010 |
| WO | WO 2010/042281 A2 | 4/2010 |
| WO | WO 2011/109698 A1 | 9/2011 |
| WO | WO 2011/154542 A1 | 12/2011 |
| WO | WO 2012/112079 A1 | 8/2012 |
| WO | WO 2013/101436 A1 | 7/2013 |

OTHER PUBLICATIONS

Akinc et al., Development of lipidoid-siRNA formulations for systemic delivery to the liver. Mol Ther. May 2009;17(5):872-9. doi: 10.1038/mt.2009.36. Epub Mar. 3, 2009.
Alahari et al., Inhibition of expression of the multidrug resistance-associated P-glycoprotein of by phosphorothioate and 5' cholesterol-conjugated phosphorothioate antisense oligonucleotides. Mol Pharmacol. Oct. 1996;50(4):808-19.
Aleckovic et al., RNAi at Oxford. J RNAi Gene Silencing. May 27, 2008;4(1):266-8.
Aouadi et al., Orally delivered siRNA targeting macrophage Map4k4 suppresses systemic inflammation. Nature. Apr. 30, 2009;458(7242):1180-4. doi: 10.1038/nature07774.
Baigude et al., Design and creation of new nanomaterials for therapeutic RNAi. ACS Chem Biol. Apr. 24, 2007;2(4):237-41.
Behlke, Progress towards in vivo use of siRNAs. Mol Ther. Apr. 2006;13(4):644-70. Epub Feb. 14, 2006.
Bergan et al., Electroporation enhances c-myc antisense oligodeoxynucleotide efficacy. Nucleic Acids Res. Jul. 25, 1993;21(15):3567-73.
Bjerke et al., Histone H3.3. mutations drive pediatric glioblastoma through upregulation of MYCN. Cancer Discov. May 2003;3(5):512-9.
Bongartz et al., Improved biological activity of antisense oligonucleotides conjugated to a fusogenic peptide. Nucleic Acids Res. Nov. 11, 1994;22(22):4681-8.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA Interference in Mammalian Cells by Chemically-Modified RNA. Biochem. 2003;42(26):7967-75.
Brown et al., RNAi off-targeting: Light at the end of the tunnel. J RNAi Gene Silencing. Jul. 28, 2006;2(2):175-7.
Cardia et al., Novel self-delivering RNAi compounds with enhanced cellular updatake and distribution properties. Keystone RNAi Silencing: Mechanism, Biology and Application Conference. Jan. 14-19, 2010. Poster. 1 Page.
Chiu et al., siRNA function in RNAi: a Chemical modification analysis. RNA. Sep. 2003;9(9):1034-48.
Chiu et al., Visualizing a correlation between siRNA localization, cellular uptake, and RNAi in living cells. Chem Biol. Aug. 2004;11(8):1165-75.
Choung et al. Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Cload et al., Polyether tethered oligonucleotide probes. Journal of the American Chemical Society. 1991;113 (16): 6324-6326.
Collins et al., A small interfering RNA screen for modulators of tumor cell motility identifies MAP4K4 as a promigratory kinase. Proc Natl Acad Sci U S A. Mar. 7, 2006; 103(10): 3775-3780.
Crombez et al., A non-covalent peptide-based strategy for siRNA delivery. Biochem Soc Trans. Feb. 2007;35(Pt 1):44-6.
Czauderna et al., Structural variations and stabilising modifications of synthetic siRNAs in mammalian cells. Nucleic Acids Res. Jun. 1, 2003;31(11):2705-16.
De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Distler et al., Imatinib mesylate reduces production of extracellular matrix and prevents development of experimental dermal fibrosis. Arthritis Rheum. Jan. 2007;56(1):311-22.
Dykxhoorn et al., The silent treatment: siRNAs as small molecule drugs. Gene Ther. Mar. 2006;13(6):541-52.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Ferguson et al., Scar-free healing: from embryonic mechanisms to adult therapeutic intervention. Philos Trans R Soc Lond B Biol Sci. May 29, 2004;359(1445):839-50.
Florence, The oral absorption of micro- and nanoparticulates: neither exceptional not unusual. Pharm Res. Mar. 1997;14(3):259-66.
Frank-Kamenetsky et al., Therapeutic RNAi targeting PCSK9 acutely lowers plasma cholesterol in rodents and LDL cholesterol in non-

(56) References Cited

OTHER PUBLICATIONS human primates. Proc Natl Acad Sci U S A. Aug. 19, 2008;105(33):11915-20. Epub Aug. 11, 2008.
GenBank Submission; NCBI, Accession No. NM_004834; Han et al.; Feb. 9, 2011.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Glaser, Oligonucleotide therapies move toward efficacy trials to treat HIV, CMV, cancer. Genetic Engineering News. Feb. 1, 1996;16:1-21.
Grosse et al., In vivo gene delivery in the mouse lung with lactosylated polyethylenimine, questioning the relevance of in vitro experiments. J Control Release. Dec. 8, 2008;132(2):105-12. Epub Sep. 4, 2008.
Ito et al., Expression of connective tissue growth factor in human renal fibrosis. Kidney Int. Apr. 1998;53(4):853-61.
Jablonski et al., Preparation of oligodeoxynucleotide-alkaline phosphatase conjugates and their use as hybridization probes. Nucleic Acids Res. Aug. 11, 1986;14(15):6115-28.
Jackson et al., Position-specific chemical modification of siRNAs reduces "off-target" transcript silencing. RNA. Jul. 2006;12(7):1197-1205. Epub May 8, 2006.
Kamens et al., Novel, chemically modified RNAi compounds with improved potency, stability and specificity. Keystone RNAi Silencing: Mechanism, Biology and Application Conference. Jan. 14-19, 2010. Poster. 1 Page.
Kim et al., Systemic and specific delivery of small interfering RNAs t0 the liver mediated by apolipoprotein A-I. Mol Ther. Jun. 2007;15(6):1145-52. Epub Apr. 17, 2007.
Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.
Kubo et al., Modified 27-nt dsRNAs with dramatically enhanced stability in serum and long-term RNAi activity. Oligonucleotides. 2007 Winter;17(4):445-64.
Layzer et al., In vivo activity of nuclease-resistant siRNAs. RNA. May 2004;10(5):766-71.
Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.
Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.
Leuschner et al., Cleavage of the siRNA passenger strand during RISC assembly in human cells. EMBO Rep. Mar. 2006;7(3):314-20. Epub Jan. 20, 2006.
Li et al., Inhibition of connective tissue growth factor by siRNA prevents liver fibrosis in rats. J Gene Med. Jul. 2006;8(7):889-900.
Li et al., Surface-modified LPD nanoparticles for tumor targeting. Ann N Y Acad Sci. Oct. 2006;1082:1-8.
Lynch et al., Role of platelet-derived growth factor in wound healing: synergistic effects with other growth factors. Proc Natl Acad Sci U S A. Nov. 1987;84(21):7696-700.
Ma et al., Design and synthesis of RNA miniduplexes via a synthetic linker approach. Biochemistry. Feb. 23, 1993;32(7):1751-8.
Ma et al., Design and synthesis of RNA miniduplexes Via a synthetic linker approach. 2. Generation of covalently closed, double-stranded cyclic HIV-1 TAR RNA analogs with high Tat-binding affinity. Nucleic Acids Res. Jun. 11, 1993;21(11):2585-9.
Manoharan et al., Chemical modifications to improve uptake and bioavailability of antisense oligonucleotides. Ann N Y Acad Sci. Oct. 28, 1992;660:306-9.
Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.

Martins et al., Sterol side Chain length and structure affect the clearance of chylomicron-like lipid emulsions in rats and mice. J Lipid Res. Feb. 1998;39(2):302-12.
Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.
Medarova et al., In vivo imaging of siRNA delivery and silencing in tumors. Nat Med. Mar. 2007;13(3):372-7. Epub Feb. 25, 2007.
Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.
Niessen et al., Keratinocyte-derived growth factors play a role in the formation of hypertrophic scars. J Pathol. Jun. 2006;194(2):207-16.
Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.
Overhoff et al., Phosphorothioate-stimulated uptake of short interfering RNA by human cells. EMBO Rep. Dec. 2005;6(12):1176-81.
Parrish et al., Functional anatomy of a dsRNA trigger: differential requirement for the two trigger strands in RNA interference. Mol Cell. Nov. 2000;6(5):1077-87.
Pavco et al., Robust Intradermal efficacy with novel chemically modified self-delivering RNAi compounds. Keystone RNAi Silencing: Mechanism, Biology and Application Conference. Jan. 14-19, 2010. Poster. 1 Page.
Rajeev et al., 2'-modified-2-thiothymidine oligonucleotides. Org Lett. Aug. 21, 2003;5(17):3005-8.
Rozema et al., Dynamic PolyConjugates for targeted in vivo delivery of siRNA to hepatocytes. Proc Natl Acad Sci U S A. Aug. 7, 2007;104(32):12982-7. Epub Jul. 24, 2007.
Rump et al., Preparation of conjugates of oligodeoxynucleotides and lipid structures and their interaction with low-density lipoprotein. Bioconjug Chem. May-Jun. 1998;9(3):341-9.
Salomon et al., Modified dsRNAs that are not processed by Dicer maintain potency and are incorporated into the RISC. Nucleic Acids Res. Jun. 2010;38(11):3771-9. doi: 10.1093/nar/gkq9055. Epub Feb. 18, 2010.
Sato et al., Tumor targeting and imaging of intraperitoneal tumors by use of antisense oligo-DNA complexed with dendrimers and/or avidin in mice. Clin Cancer Res. Nov. 2001;7(11):3606-12.
Seela et al., Oligodeoxyribonucleotides containing 1,3-propanediol as nucleoside substitute. Nucleic Acids Res. Apr. 10, 1987;15(7):3113-29.
Shen, Advances in the development of siRNA-based therapeutics for cancer. IDrugs. Aug. 2008;11(8):572-8.
Shi, Mammalian RNAi for the masses. Trends Genet. Jan. 2003;19(1):9-12.
Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008.01.002.
Smith et al., Pulmonary deposition and clearance of aerosolized alpha-1-proteinase inhibitor administered to dogs and to sheep. J Clin Invest. Oct. 1989;84(4):1145-54.
Soto et al., Characterization of multilayered nanoparticles encapsulated in yeast cell wall particles for DNA delivery. Bioconjug Chem. Apr. 2008;19(4):840-8. doi: 10.1021/bc700329p. Epub Apr. 1, 2008.
Soto et al., Oral Macrophage Mediated Gene Delivery System. 2007 NSTI Nanotechnology Conference and Trade Show, May 20-24, 2007, Santa Clara, CA. NSTI Nanotech 2007 Proceedings; 2:378-81.
Soutschek et al., Therapeutic silencing of an endogenous gene by systemic administration of modified siRNAs. Nature. Nov. 11, 2004;432(7014):173-8.
Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008.

(56) References Cited

OTHER PUBLICATIONS

Takanashi et al., Therapeutic silencing of an endogenous gene by siRNA cream in an arthritis model mouse. Gene Ther. Aug. 2009;16(8):982-9. doi:10.1038/gt.2009.66. Epub May 28, 2009.

Tan et al., Quantum-dot based nanoparticles for targeted silencing of HER2/neu gene via RNA interference. Biomaterials. Mar. 2007;28(8):1565-71. Epub Dec. 11, 2006.

Tang et al., An RNA interference-based screen identifies MAP4K4/NIK as a negative regulator of PPARgamma, adipogenesis, and insulin-responsive hexose transport. Proc Natl Acad Sci U S A. Feb. 14, 2006;103(7):2087-92. Epub Feb. 3, 2006.

Taylor et al., Curbing activation: proprotein convertases in homeostasis and pathology. FASEB J. Jul. 2003;17(10):1215-27.

Ohlmann et al., Antisense oligonucleotides: a new therapeutic principle. Chem Rev. 1990;90(4):543-84.

Vaught et al., Expanding the chemistry of DNA for in vitro selection. J Am Chem Soc. Mar. 31, 2010;132(12):4141-51. doi: 10.1021/ja908035g.

Wolfrum et al., Mechanisms and optimization of in vivo delivery of lipophilic siRNAs. Nat Biotechnol. Oct. 2007;25(10):1149-57. Epub Sep. 16, 2007.

Wu et al., Durable protection from Herpes Simplex Virus-2 transmission following intravaginal application of siRNAs targeting both a viral and host gene. Cell Host Microbe. Jan. 22, 2009;5(1):84-94. doi:10.1016/j.chom.2008.12.003.

Xu et al., Retinoblastoma has properties of a cone precursor tumor and depends upon cone-specific MDM2 signaling. Cell. Jun. 12, 2009;137(6):1018-31. doi: 10.1016/j.cell.2009.03.051.

Xue et al., Mesodermal patterning defect in mice lacking the Ste20 NCK interacting kinase (NIK). Development. May 2001;128(9):1559-72.

Yamada et al., Lysophosphatidic acid stimulates the proliferation and motility of malignant pleural mesothelioma cells through lysophosphatidic acid receptors, LPA1 and LPA2. Cancer Sci. Aug. 2008;99(8):1603-10.

Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

Zhang et al., Inhibition of vascular endothelial growth factor expression in keloid fibroblasts by vector-mediated vascular endothelial growth factor shRNA: a therapeutic potential strategy for keloid. Arch Dermatol Res. Apr. 2008;300(4):177-84. doi: 10.1007/s00403-007-0825-y. Epub Feb. 1, 2008.

Zhou et al., Controlled release of PEI/DNA complexes from mannose-bearing chitosan microspheres as a potent delivery system to enhance immune response to HBV DNA vaccine. J Control Release. Aug. 28, 2007;121(3):200-7. Epub May 25, 2007.

Zimmermann et al., RNAi-mediated gene silencing in non-human primates. Nature. May 4, 2006;441(7089):111-4. Epub Mar. 26, 2006.

[No Author Listed] EMBL Accession No. FZ272901 . WO 2005/116204. Apr. 20, 2011.

[No Author Listed] RXi Pharmaceuticals Completes Apthera Acquisition. Press Release. BusinessWire. Apr. 14, 2011. 2 pages.

[No Author Listed] RXi Pharmaceutical Corporation. Ex 99.1. OTC: RXII. Mar. 2013. 38 pages.

Augustyns et al., Incorporation of hexose nucleoside analogues into oligonucleotides: synthesis, base-pairing properties and enzymatic stability. Nucleic Acids Res. Sep. 25, 1992;20(18):4711-6.

Chen et al., Functionalization of single-walled carbon nanotubes enables efficient intracellular delivery of siRNA targeting MDM2 to inhibit breast cancer cells growth. Biomed Pharmacother. Jul. 2012;66(5):334-8. doi: 10.1016/j.biopha.2011.12.005. Epub Feb. 17, 2012.

Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.

Chen et al., Mdm2 deficiency suppresses MYCN-Driven neuroblastoma tumorigenesis in vivo. Neoplasia. Aug. 2009;11(8):753-62.

Chiang et al., Antisense oligonucleotides inhibit intercellular adhesion molecule 1 expression by two distinct mechanisms. J Biol Chem. Sep. 25, 1991;266(27):18162-71.

Fabbri et al., MicroRNA-29 family reverts aberrant methylation in lung cancer by targeting DNA methyltransferases 3A and 3B. Proc Natl Acad Sci U S A. Oct. 2, 2007;104(40):15805-10. Epub Sep. 21, 2007.

Fisher et al., Intracellular disposition and metabolism of fluorescently-labeled unmodified and modified oligonucleotides microinjected into mammalian cells. Nucleic Acids Res. Aug. 11, 1993;21(16):3857-65.

Heemskerk et al., T-cell receptor gene transfer for the treatment of leukemia and other tumors. Haematologica. Jan. 2010;95(1):15-9. doi: 10.3324/haematol.2009.016022.

Hueng et al., Enhancing dendritic cell vaccine potency by combining a BAK/BAX siRNA-mesiated antiapoptotic strategy to prolong dendritic cell life with an intracellular strategy to target antigen to lysosomal compartments. Apr. 15, 2007. MEDLINE Database Accession No. NLM17230516.

Miska et al., Autoimmunity-mediated antitumor immunity: tumor as an immunoprivileged self. Eur J Immunol. Oct. 2012;42(10):2584-96. doi: 10.1002/eji.201242590. Epub Aug. 10, 2012.

Ortigão et al., Antisense effect of oligodeoxynucleotides with inverted terminal internucleotidic linkages: a minimal modification protecting against nucleolytic degradation. Antisense Res Dev. 1992 Summer;2(2):129-46.

Snead et al., RNA interference trigger variants: getting the most out of RNA for RNA interference-based therapeutics. Nucleic Acid Ther. Jun. 2012;22(3):139-46. doi: 10.1089/nat.2012.0361. Review.

Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.

Stein et al., A specificity comparison of four antisense types: morpholino, 2'-O-methyl RNA, DNA, and phosphorothioate DNA. Antisense Nucleic Acid Drug Dev. Jun. 1997;7(3):151-7.

Summerton et al., Morpholino and phosphorothioate antisense oligomers compared in cell-free and in-cell systems. Antisense Nucleic Acid Drug Dev. Apr. 1997;7(2):63-70.

\* cited by examiner

Comparison of subcutaneous and IV routes of administration for efficacy in liver

FIG. 9
Reverse Trends in sd-rxRNA Visualization in Liver over 24 Hours for SC vs IV
| | 6 hrs | 12 hrs | 24 hrs |
|---|---|---|---|
| s.c | 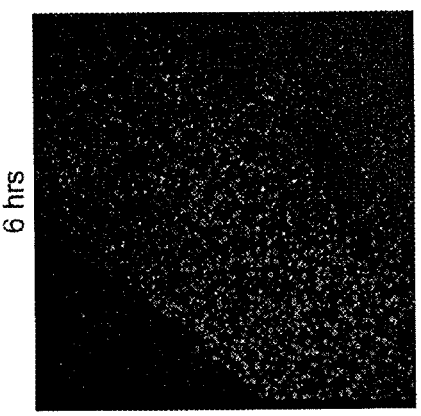 | 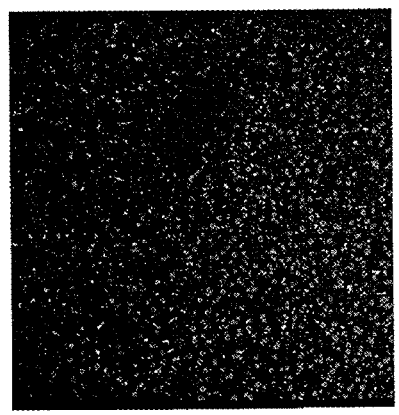 | 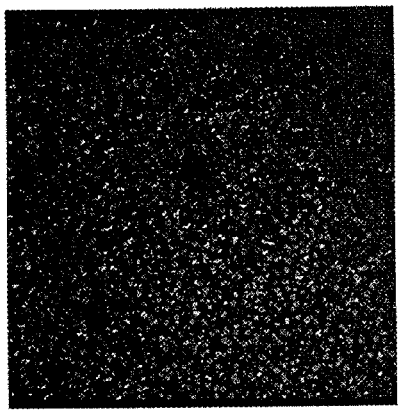 |
| i.v. | 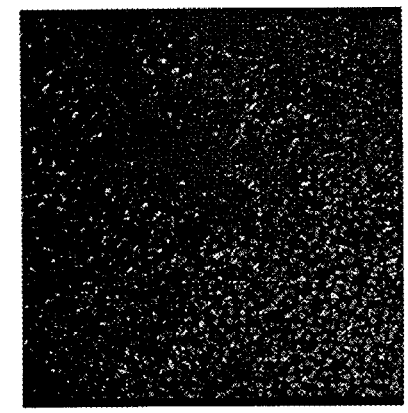 | 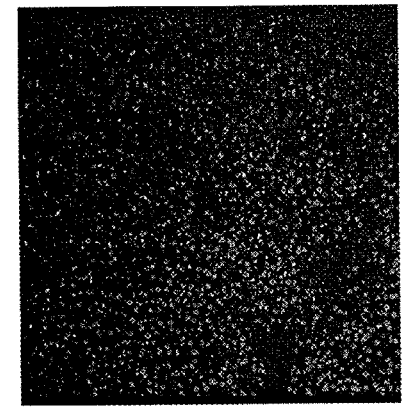 | 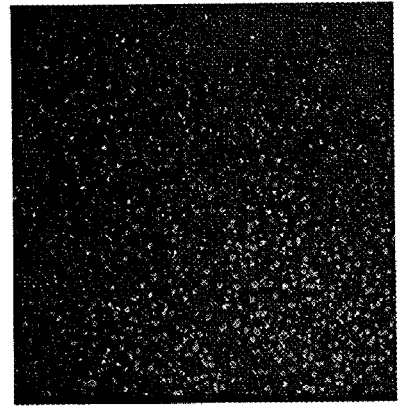 |
*All images taken using the 20X objective lens.*

Delivery Present Throughout Cells

Efficient Uptake of sd-rxRNA to Lung Macrophages

Visualization of sd-rxRNA-DY547 delivered by lung insufflation in isolated lung macrophages FIG. 17
Clinical Observations after Dosing to Rat Lung
Post-dose
24-hr, post-dose
Lungs
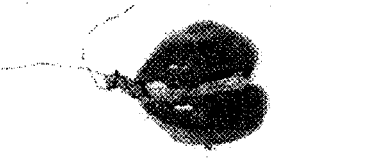
Peritoneum

FIG. 18

Examples of chemical modification patterns

MAP4K4

| Passenger | Guide |
|---|---|
| mC.#.G.#.G.G.A.A.G.#.mC.#.A.chl | P.#.A.G.A.fC.fU.#.fC.fC.A.mC.A.G*A*A*mC*#*mC*U |
| mC.#.G.#.G.G.A.A.G.#.mC.dT.A.chl | P.dT.A.G.A.fC.fU.#.fC.fC.A.mC.A.G*A*A*mC*#*mC*U |
| mC.#.G.#.G.G.A.A.G.#.mC.#.A | P.#.A.G.A.fC.fU.dT.fC.fC.A.mC.A.G*A*A*mC*#*mC*U |

PCSK9

| Passenger | Guide |
|---|---|
| G.G.A.G.#.mU.#.A.mU.#.mC.G.G.A.A.chl | P.#.#.fC.fC.G.A.A.#.A.A.A.fC.#*fC*fC*A*G*G*C |
| G.G.A.G.#.mU.#.A.mU.#.mC.G.G.A.A | P.dT.dT.fC.fC.G.A.A.#.A.A.A.fC.#*fC*fC*A*G*G*C |
|  | P.#.dT.fC.fC.G.A.A.dT.A.A.A.fC.#*fC*fC*A*G*G*C |
|  | P.#.#.fC.fC.G.A.A.#.A.A.A.fC.#*fC*fC*#*G*#*C |

5-uridyl modifications

FIG. 20 Long chain alkyl cholesterol analogs

Protonatable linkers 5 methyl 2' modified nucleosides

Universal support for conjugation with any chloroformate

Vitamin A and vitamin E conjugates for tissue targeting

Plasma Protein Binding Modifications

Increased protein binding modifications

Naturally occurring ribonucleotides (1)

Naturally occurring ribonucleotides

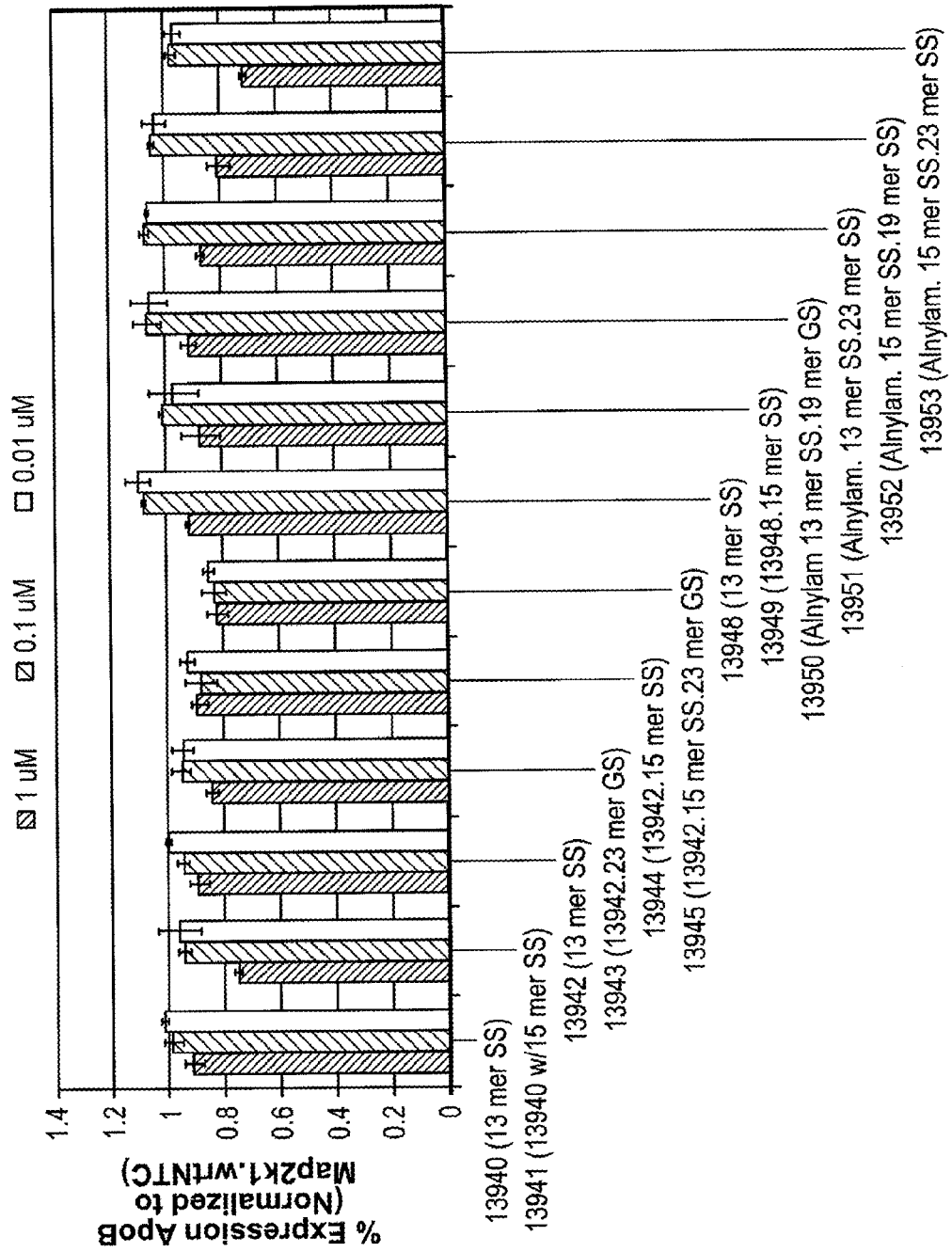

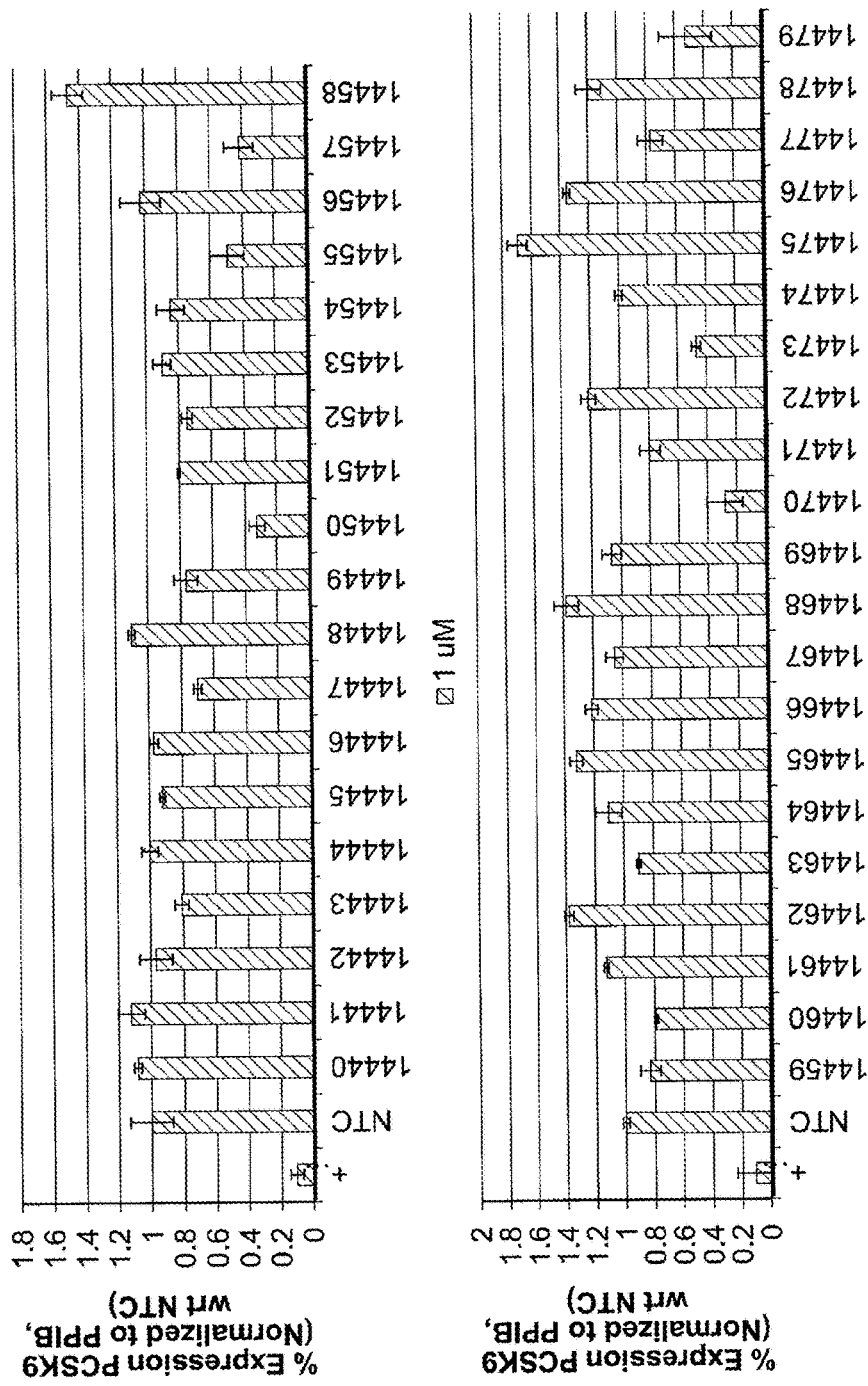
FIG. 32 PVSK9 sd-rxRNAs are Efficacious

PPIB Targeting sd-rxRNAs are Efficacious

FIG. 34B

| ID | Sequence |
|---|---|
| 17123 | G.G.A.mU.mU.mU.G.G.mC.mU.A.mC.A.A.A-chl |
| | P.mU.fU.fU.G.fU.A.G.fC.fC.A.A.A.fU*fC*fC*fU*fU*fU*C |
| | |
| 17124 | A.A.A.G.A.mC.mU.G.mU.mU.mC.mC.A.A.A-chl |
| | P.mU.fU.fU.G.G.A.A.fC.A.G.fU.fC.fU*fU*fU*fC*fC*G*A |
| | |
| 17125 | G.A.A.mC.mU.mU.mC.A.A.A.mC.mU.G.A.A-chl |
| | P.mU.fU.fC.A.G.fU.fU.fU.G.A.A.G.fU*fU*fC*fU*fC*A*U |
| | |
| 17126 | G.G.A.mC.mU.mU.mC.A.mU.G.A.mU.mC.mC.A-chl |
| | P.mU.G.G.A.fU.fC.A.fU.G.A.A.G.fU*fC*fC*fU*fU*G*A |
| | |
| 17127 | mC.mU.A.G.A.mU.G.G.mC.A.A.G.mC.A.mU-chl |
| | P.mA.fU.G.fC.fU.fU.G.fC.fC.A.fU.fC.fU*A*G*fC*fC*A*G |
| | |
| 17128 | mC.A.A.A.mU.mU.mC.mC.A.mU.mC.G.mU.G.mU-chl |
| | P.mA.fC.A.fC.G.A.fU.G.G.A.A.fU.fU*fU*G*fC*fU*G*U |
| | |
| 17129 | A.A.mU.mU.mC.mC.A.mU.mC.G.mU.G.mU-chl |
| | P.mA.fC.A.fC.G.A.fU.G.G.A.A.fU.fU*fU*G*fC*fU*G*U |
| | |
| 17130 | mU.A.G.mC.mU.A.mC.A.G.G.A.G.A.G.A-chl |
| | P.mU.fC.fU.fC.fU.fC.fC.fU.G.fU.A.G.fC*fU*A*A*G*G*C | sd-rxRNAs Containing RiboLinker are Efficacious

Old linker (hydroxyproline linker)

Ribo linker

FIG. 38

ApoB and PPIB sd-rxRNA Modification Scheme

| sd-rxRNA | Sequence | 2'Fluoro | >3 2'OH stretch | Silencing Levels (Liver, 50 mg/kg) |
|---|---|---|---|---|
| ApoB | P.mU.fU.G.A.fC.fU.fU.fU.A.fC.fU.fC.fU*A*A*fC*fU*fU*G | 12 | no | 77% |
| PPIB | P.mA.fC.A.fC.G.A.fU.G.G.A.A.fU.fU*fU*G*fC*fU*G*U | 8 | yes | 31% |

- ApoB:
  — Blue print modification scheme for designing stable sd-rxRNAs for systemic delivery
  — Data supports hypothesis that increasing stability of guide strand results in systemic efficacy

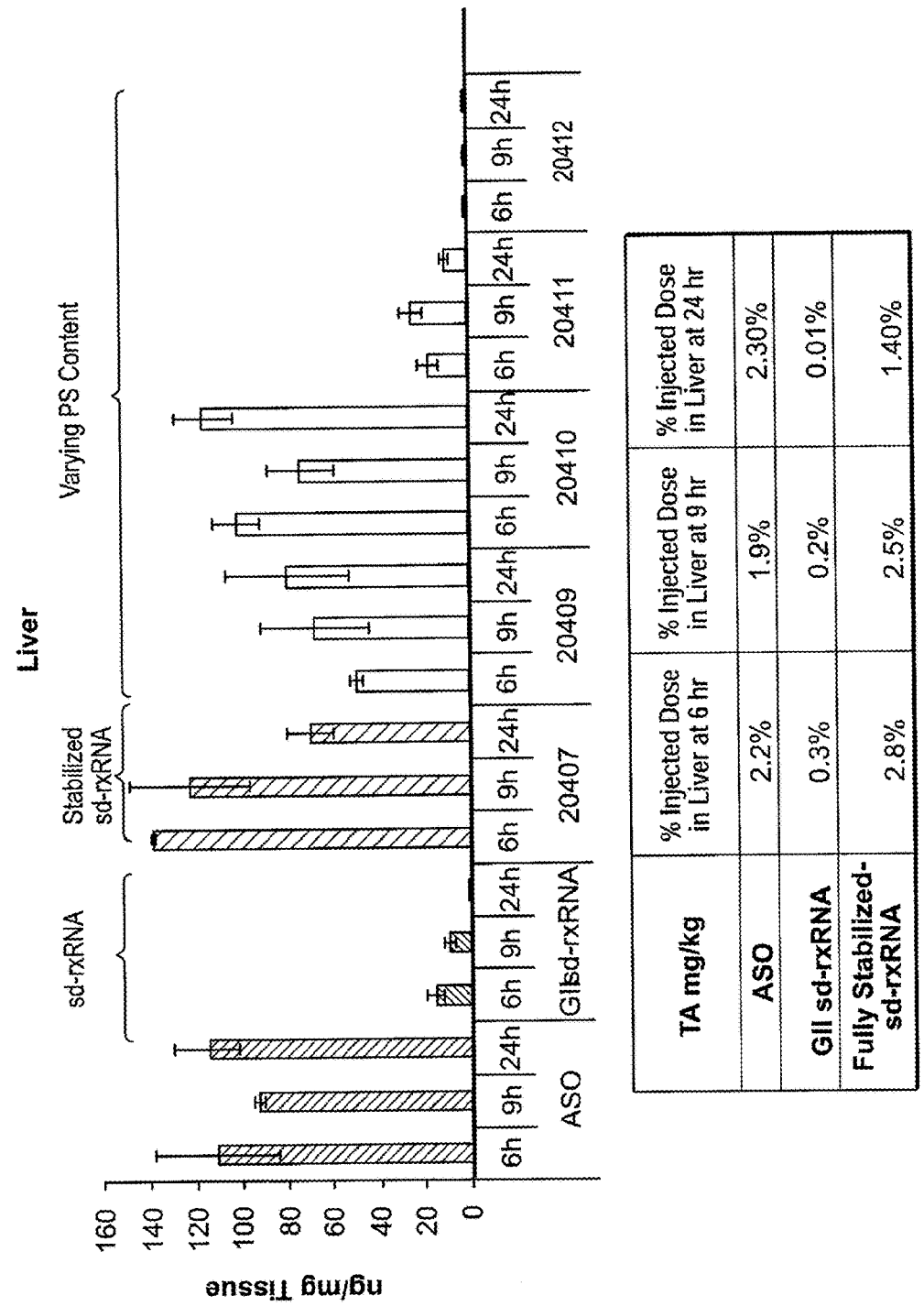

Certain Chemical Modification Patterns Result in Significant Distribution to Heart and Fat

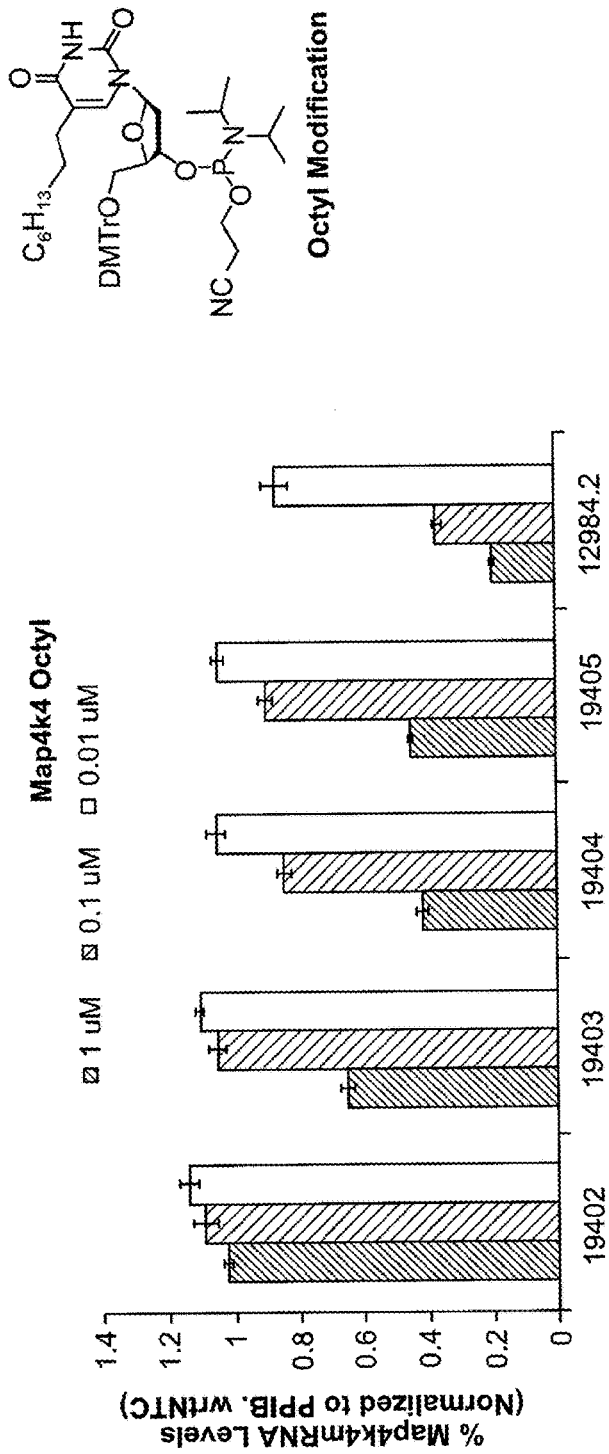
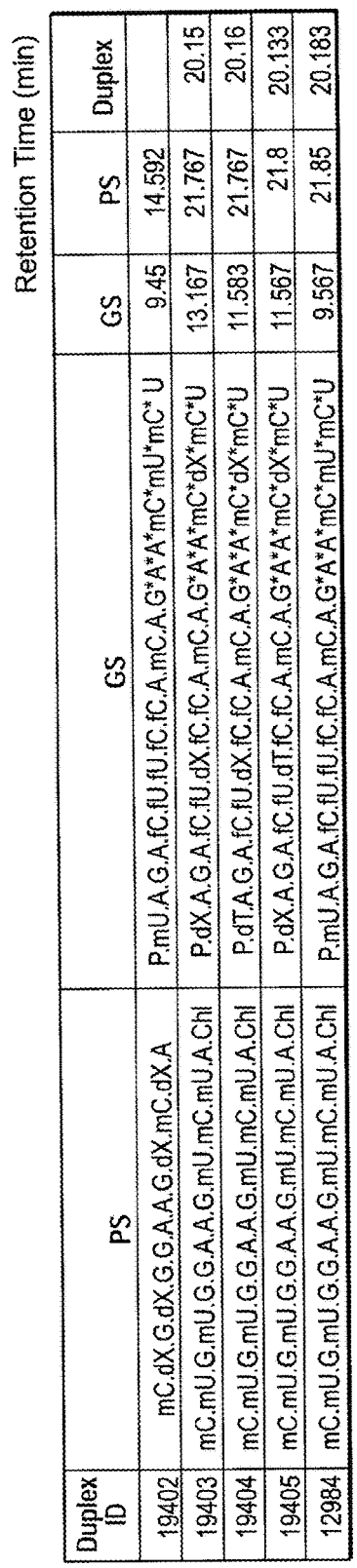
FIG. 41

FIG. 44 Map4k4

FIG. 55

5-Uridyl *in vitro* Screening Summary

| Gene | Thiophene | Octyl | Octyn-1-yl | Ethynyl | Pyridyl Amide | Phenyl |
|---|---|---|---|---|---|---|
| Map4k4 PS | ✓ | N/A | ✓ | ✓ | ✓ | ✓ |
| Map4k4 GS | marginal | marginal | marginal | ✓ | X | X |
| PCSK9 PS | N/A | ✓ | N/A | X | X | ✓ |
| PCSK9 GS | N/A | marginal | ✓ | ✓ | X | marginal |

- Toleration of 5-uridyl modifications is sequence specific
  - Map4k4 more amenable to 5-uridyl modification than PCSK9
- For Map4k4, 5-uridyl modifications better tolerated in SS than AS
- Incorporation of 5-uridyl modifications in the guide strand results in compounds with increased hydrophobicity (as seen by shift in retention times on HPLC)

FIG. 56

Modulation of Chemistry at Position 5 of Uridine Results in an Altered Tissue Distribution Profile - Liver

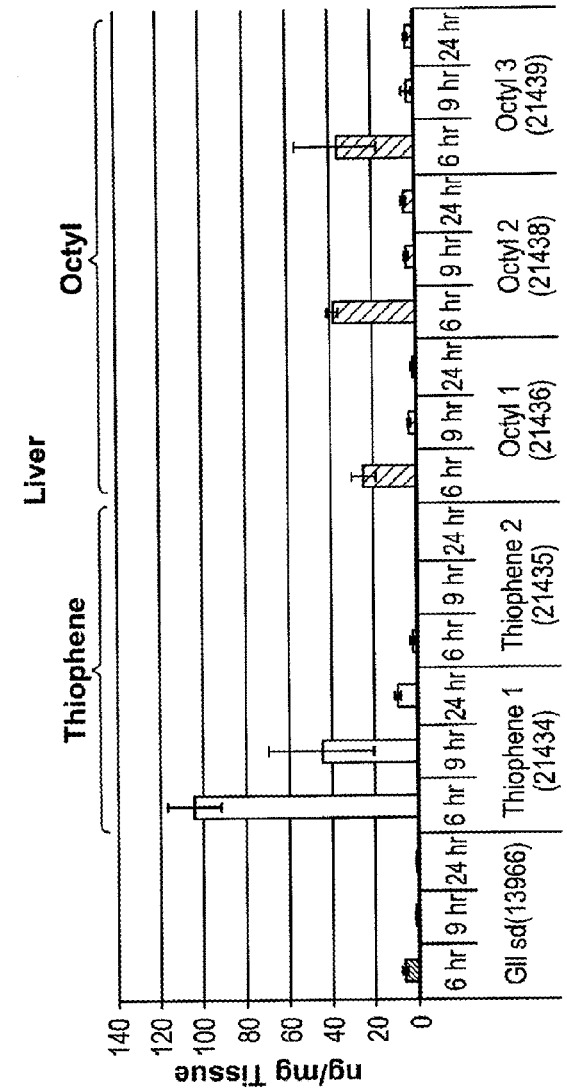

Conclusions:
1. Incorporation of uridyl modifications increase levels of compound in liver 24 hrs post dose.
2. Incorporation of Thiophene modifications increase sd-rxRNA levels in liver >10 fold
3. Octyl modifications on both PS and GS (without Chl) result in distribution of sd-rxRNA to liver

- BALB/c male mice; n=2/group
- single 50 mg/kg sd-rxRNA tail vein injection
- Uptake analyzed by hybridization assay

| DUPLEX ID | Description | PS | GS |
|---|---|---|---|
| 13966 | Gll sd-rxRNA | mC.mU.G.mU.G.G.A.A.G.mU.mC.mU.A.TEG-Chl | P.mU.A.G.A.fC.fU.fU.fC.A.mC.A.G*A*A*mC*mU*mC*U |
| 21434 | Thiophene 1(X= thiophene) | mC.dX.G.dX.G.G.A.A.G.dX.mC*dX* A.TEG-Chl | P.mU.A.G.A.fC.fU.dX.fC.fC.A.fC.mA.G*mA*mA*fC*dX*fC*U. |
| 21435 | Thiophene 2(X= thiophene) | mC.dX.G.dX.G.G.A.A.G.dX.mC*dX* A | P.mU.A.G.A.fC.fU.dX.fC.fC.A.fC.mA.mG*mA*mA*fC*dX*fC*U. |
| 21436 | Octyl 1(x=octyl) | mC.dX.G.dX.G.G.A.A.G.dX.mC*dX* A.TEG-Chl | P.dX.A.G.A.fC.fU.dX.fC.fC.A.fC.mA.mG*mA*mA*fC*dX*fC*U. |
| 21438 | Octyl 2(x=octyl) | mC.dX.G.dX.G.G.A.A.G.dX.mC*dX* A | P.dX.A.G.A.fC.fU.dX.fC.fC.A.fC.mA.mG*mA*mA*fC*dX*fC*U. |
| 21439 | Octyl 3(x=octyl) | mC.dX.G.dX.G.G.A.A.G.dX.mC*dX* A | P.mU.A.G.A.fC.fU.dX.fC.fC.A.fC.mA.mG*mA*mA*fC*dX*fC*U. |

FIG. 58
Synthons based on omethyl and 2' F
- Take GIII chemistries that show promise and replace the 2'-deoxy chemistry with 2'-O methyl and 2'-fluoro
- More complex sythetic route due to presence of 2' chemistry and different starting materials
- Initially start with thiophene and octyl
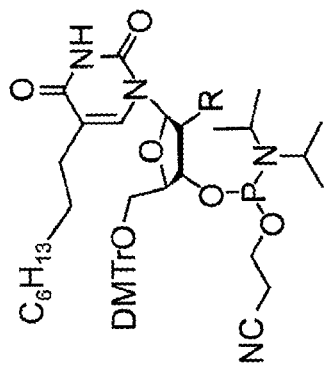
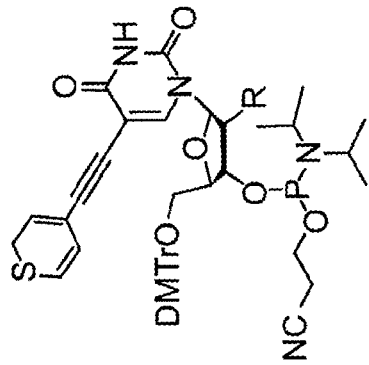

Synthons, GIV

Modifications to promote endosomal release

- Histidine spliced into existing TEG linker
- Between 2-5 protonatable amine containing chemistries (histidine as one of the class examples) might be required to promote endosomal escape.

Improving siRNA endosomal release by incorporating protonatable functionalities n = 1, 3 and 5; R = Me or tosylate protecting group where $R_{1,2}$ = H, Me or other inductively donating groups

GIV, "click" chemistry to access diversity rapidly

R-N₃ in aqueous phase

R = diversity

- One oligonucleotide can be diversified rapidly rather than having to manufacture different oligonucleotides from scratch
- Downside is that triazole functionality is always present, tolerance of RISC to this?

CTGF L2 Chemical Optimization (in vitro Stability)

sd-rxRNA: Pilot Studies Show Delivery to the Spinal Cord After CNS Injection

Indication of sd-rxRNA Delivery to the Brain Stem in a Pilot Study

SEQUENCE LISTING

<160> NUMBER OF SEQ ID NOS: 614

<210> SEQ ID NO 1
<211> LENGTH: 25
<212> TYPE: RNA

<213> ORGANISM: Homo sapiens

<400> SEQUENCE: 1
cccagcucug cagcuucauc cugaa                                                25

<210> SEQ ID NO 2
<211> LENGTH: 25
<212> TYPE: RNA
<213> ORGANISM: Homo sapiens

<400> SEQUENCE: 2
acccugaaag agguguaugg cuuca                                                25

<210> SEQ ID NO 3
<211> LENGTH: 25
<212> TYPE: RNA
<213> ORGANISM: Homo sapiens

<400> SEQUENCE: 3
cagccauguc cagguaugag cucaa                                                25

<210> SEQ ID NO 4
<211> LENGTH: 25
<212> TYPE: RNA
<213> ORGANISM: Homo sapiens

<400> SEQUENCE: 4
aaccuacuua cauccugaac aucaa                                                25

<210> SEQ ID NO 5
<211> LENGTH: 25
<212> TYPE: RNA
<213> ORGANISM: Homo sapiens

<400> SEQUENCE: 5
cccagagaca gaagaagcca agcaa                                                25

<210> SEQ ID NO 6
<211> LENGTH: 25
<212> TYPE: RNA
<213> ORGANISM: Homo sapiens

<400> SEQUENCE: 6
uguggcaaca gaaauaucca cugaa                                                25

<210> SEQ ID NO 7
<211> LENGTH: 25
<212> TYPE: RNA
<213> ORGANISM: Homo sapiens

<400> SEQUENCE: 7
guggcaacag aaauauccac ugaaa                                                25

<210> SEQ ID NO 8
<211> LENGTH: 25
<212> TYPE: RNA
<213> ORGANISM: Homo sapiens

<400> SEQUENCE: 8
caucagccca cuugcucuca ucaaa                                                25

<210> SEQ ID NO 9
<211> LENGTH: 25

```
<212> TYPE: RNA
<213> ORGANISM: Homo sapiens

<400> SEQUENCE: 9
aagugacaca gacuuugaaa cuuga                                              25

<210> SEQ ID NO 10
<211> LENGTH: 25
<212> TYPE: RNA
<213> ORGANISM: Homo sapiens

<400> SEQUENCE: 10
acagacuuug aaacuugaag acaca                                              25

<210> SEQ ID NO 11
<211> LENGTH: 25
<212> TYPE: RNA
<213> ORGANISM: Homo sapiens

<400> SEQUENCE: 11
acuuugaaac uugaagacac accaa                                              25

<210> SEQ ID NO 12
<211> LENGTH: 25
<212> TYPE: RNA
<213> ORGANISM: Homo sapiens

<400> SEQUENCE: 12
cuuugaaacu ugaagacaca ccaaa                                              25

<210> SEQ ID NO 13
<211> LENGTH: 25
<212> TYPE: RNA
<213> ORGANISM: Homo sapiens

<400> SEQUENCE: 13
aacuugaaga cacaccaaag aucaa                                              25

<210> SEQ ID NO 14
<211> LENGTH: 25
<212> TYPE: RNA
<213> ORGANISM: Homo sapiens

<400> SEQUENCE: 14
agcuguuuug aagacucucc aggaa                                              25

<210> SEQ ID NO 15
<211> LENGTH: 25
<212> TYPE: RNA
<213> ORGANISM: Homo sapiens

<400> SEQUENCE: 15
uuuugaagac ucuccaggaa cugaa                                              25

<210> SEQ ID NO 16
<211> LENGTH: 25
<212> TYPE: RNA
<213> ORGANISM: Homo sapiens

<400> SEQUENCE: 16
gcaaaauauc cagagagcua aucua                                              25

<210> SEQ ID NO 17
```

```
<211> LENGTH: 25
<212> TYPE: RNA
<213> ORGANISM: Homo sapiens

<400> SEQUENCE: 17
cacagcagcu gcgagagauc uucaa                                         25

<210> SEQ ID NO 18
<211> LENGTH: 25
<212> TYPE: RNA
<213> ORGANISM: Homo sapiens

<400> SEQUENCE: 18
ggagcugcug gacauugcua auuaa                                         25

<210> SEQ ID NO 19
<211> LENGTH: 25
<212> TYPE: RNA
<213> ORGANISM: Homo sapiens

<400> SEQUENCE: 19
cacuggggau gaagauuaca ccuaa                                         25

<210> SEQ ID NO 20
<211> LENGTH: 25
<212> TYPE: RNA
<213> ORGANISM: Homo sapiens

<400> SEQUENCE: 20
uggagcaguu aacuccagaa cucaa                                         25

<210> SEQ ID NO 21
<211> LENGTH: 25
<212> TYPE: RNA
<213> ORGANISM: Homo sapiens

<400> SEQUENCE: 21
caguuaacuc cagaacucaa gucua                                         25

<210> SEQ ID NO 22
<211> LENGTH: 25
<212> TYPE: RNA
<213> ORGANISM: Homo sapiens

<400> SEQUENCE: 22
uuaacuccag aacucaaguc uucaa                                         25

<210> SEQ ID NO 23
<211> LENGTH: 25
<212> TYPE: RNA
<213> ORGANISM: Homo sapiens

<400> SEQUENCE: 23
gaaauguguc caaaguacaa agcca                                         25

<210> SEQ ID NO 24
<211> LENGTH: 25
<212> TYPE: RNA
<213> ORGANISM: Homo sapiens

<400> SEQUENCE: 24
aggcucugcg gaaaauggag ccuaa                                         25
```

```
<210> SEQ ID NO 25
<211> LENGTH: 25
<212> TYPE: RNA
<213> ORGANISM: Homo sapiens

<400> SEQUENCE: 25
ggcucugcgg aaaauggagc cuaaa                                          25

<210> SEQ ID NO 26
<211> LENGTH: 25
<212> TYPE: RNA
<213> ORGANISM: Homo sapiens

<400> SEQUENCE: 26
uccuucacag gcagauauua acaaa                                          25

<210> SEQ ID NO 27
<211> LENGTH: 25
<212> TYPE: RNA
<213> ORGANISM: Homo sapiens

<400> SEQUENCE: 27
ccuucacagg cagauauuaa caaaa                                          25

<210> SEQ ID NO 28
<211> LENGTH: 25
<212> TYPE: RNA
<213> ORGANISM: Homo sapiens

<400> SEQUENCE: 28
caugggaaca gaaugagcaa gugaa                                          25

<210> SEQ ID NO 29
<211> LENGTH: 25
<212> TYPE: RNA
<213> ORGANISM: Homo sapiens

<400> SEQUENCE: 29
uguggcuucc cauauugcca auaua                                          25

<210> SEQ ID NO 30
<211> LENGTH: 25
<212> TYPE: RNA
<213> ORGANISM: Homo sapiens

<400> SEQUENCE: 30
aucuugaacu cagaagaauu ggaua                                          25

<210> SEQ ID NO 31
<211> LENGTH: 25
<212> TYPE: RNA
<213> ORGANISM: Homo sapiens

<400> SEQUENCE: 31
ugaacucaga agaauuggau aucca                                          25

<210> SEQ ID NO 32
<211> LENGTH: 25
<212> TYPE: RNA
<213> ORGANISM: Homo sapiens

<400> SEQUENCE: 32
guuagugaaa gaagcucuga aagaa                                          25
```

```
<210> SEQ ID NO 33
<211> LENGTH: 25
<212> TYPE: RNA
<213> ORGANISM: Homo sapiens

<400> SEQUENCE: 33
agcucugaaa gaaucucaac uucca                                         25

<210> SEQ ID NO 34
<211> LENGTH: 25
<212> TYPE: RNA
<213> ORGANISM: Homo sapiens

<400> SEQUENCE: 34
uggacuucag aaauucucu cggaa                                          25

<210> SEQ ID NO 35
<211> LENGTH: 25
<212> TYPE: RNA
<213> ORGANISM: Homo sapiens

<400> SEQUENCE: 35
uccaaauaac uaccuuccua aagaa                                         25

<210> SEQ ID NO 36
<211> LENGTH: 25
<212> TYPE: RNA
<213> ORGANISM: Homo sapiens

<400> SEQUENCE: 36
uaccuuccua aagaaagcau gcuga                                         25

<210> SEQ ID NO 37
<211> LENGTH: 25
<212> TYPE: RNA
<213> ORGANISM: Homo sapiens

<400> SEQUENCE: 37
accuuccuaa agaaagcaug cugaa                                         25

<210> SEQ ID NO 38
<211> LENGTH: 25
<212> TYPE: RNA
<213> ORGANISM: Homo sapiens

<400> SEQUENCE: 38
ugaccucauc gagauuggcu uggaa                                         25

<210> SEQ ID NO 39
<211> LENGTH: 25
<212> TYPE: RNA
<213> ORGANISM: Homo sapiens

<400> SEQUENCE: 39
cucaucgaga uuggcuugga aggaa                                         25

<210> SEQ ID NO 40
<211> LENGTH: 25
<212> TYPE: RNA
<213> ORGANISM: Homo sapiens

<400> SEQUENCE: 40
ucaucgagau uggcuuggaa ggaaa                                         25
```

```
<210> SEQ ID NO 41
<211> LENGTH: 25
<212> TYPE: RNA
<213> ORGANISM: Homo sapiens

<400> SEQUENCE: 41
uuggaaggaa aaggcuuuga gccaa                                              25

<210> SEQ ID NO 42
<211> LENGTH: 25
<212> TYPE: RNA
<213> ORGANISM: Homo sapiens

<400> SEQUENCE: 42
auuuuuccca gacaguguca acaaa                                              25

<210> SEQ ID NO 43
<211> LENGTH: 25
<212> TYPE: RNA
<213> ORGANISM: Homo sapiens

<400> SEQUENCE: 43
auggugucuc uaaggucuua gugga                                              25

<210> SEQ ID NO 44
<211> LENGTH: 25
<212> TYPE: RNA
<213> ORGANISM: Homo sapiens

<400> SEQUENCE: 44
aaagaugaua aacaugagca ggaua                                              25

<210> SEQ ID NO 45
<211> LENGTH: 25
<212> TYPE: RNA
<213> ORGANISM: Homo sapiens

<400> SEQUENCE: 45
ugauaaacau gagcaggaua uggua                                              25

<210> SEQ ID NO 46
<211> LENGTH: 25
<212> TYPE: RNA
<213> ORGANISM: Homo sapiens

<400> SEQUENCE: 46
acaugagcag gauaugguaa augga                                              25

<210> SEQ ID NO 47
<211> LENGTH: 25
<212> TYPE: RNA
<213> ORGANISM: Homo sapiens

<400> SEQUENCE: 47
auaugguaaa uggaauaaug cucaa                                              25

<210> SEQ ID NO 48
<211> LENGTH: 25
<212> TYPE: RNA
<213> ORGANISM: Homo sapiens

<400> SEQUENCE: 48
```
ugcucagugu ugagaagcug auuaa                                           25

<210> SEQ ID NO 49
<211> LENGTH: 25
<212> TYPE: RNA
<213> ORGANISM: Homo sapiens

<400> SEQUENCE: 49
gcucaguguu gagaagcuga uuaaa                                           25

<210> SEQ ID NO 50
<211> LENGTH: 25
<212> TYPE: RNA
<213> ORGANISM: Homo sapiens

<400> SEQUENCE: 50
caucuucaug gagaaugccu uugaa                                           25

<210> SEQ ID NO 51
<211> LENGTH: 25
<212> TYPE: RNA
<213> ORGANISM: Homo sapiens

<400> SEQUENCE: 51
ggagcuggau uacaguugca aauaa                                           25

<210> SEQ ID NO 52
<211> LENGTH: 25
<212> TYPE: RNA
<213> ORGANISM: Homo sapiens

<400> SEQUENCE: 52
ucccggagcc aaggcuggag uaaaa                                           25

<210> SEQ ID NO 53
<211> LENGTH: 25
<212> TYPE: RNA
<213> ORGANISM: Homo sapiens

<400> SEQUENCE: 53
gagccaaggc uggaguaaaa cugga                                           25

<210> SEQ ID NO 54
<211> LENGTH: 25
<212> TYPE: RNA
<213> ORGANISM: Homo sapiens

<400> SEQUENCE: 54
ccgugucugu ggaguuugug acaaa                                           25

<210> SEQ ID NO 55
<211> LENGTH: 25
<212> TYPE: RNA
<213> ORGANISM: Homo sapiens

<400> SEQUENCE: 55
ggcaacacau uacauuggu cucua                                            25

<210> SEQ ID NO 56
<211> LENGTH: 25
<212> TYPE: RNA
<213> ORGANISM: Homo sapiens

<400> SEQUENCE: 56
auuacauuug gucucuacca ccaaa                                         25

<210> SEQ ID NO 57
<211> LENGTH: 25
<212> TYPE: RNA
<213> ORGANISM: Homo sapiens

<400> SEQUENCE: 57
caguccuggu caguuugcaa gcaaa                                         25

<210> SEQ ID NO 58
<211> LENGTH: 25
<212> TYPE: RNA
<213> ORGANISM: Homo sapiens

<400> SEQUENCE: 58
ugaggccuac aggagagauu gagca                                         25

<210> SEQ ID NO 59
<211> LENGTH: 25
<212> TYPE: RNA
<213> ORGANISM: Homo sapiens

<400> SEQUENCE: 59
gccuacagga gagauugagc aguaa                                         25

<210> SEQ ID NO 60
<211> LENGTH: 25
<212> TYPE: RNA
<213> ORGANISM: Homo sapiens

<400> SEQUENCE: 60
uggauacccu gaaguuugua acuca                                         25

<210> SEQ ID NO 61
<211> LENGTH: 25
<212> TYPE: RNA
<213> ORGANISM: Homo sapiens

<400> SEQUENCE: 61
ccugaaguuu guaacucaag cagaa                                         25

<210> SEQ ID NO 62
<211> LENGTH: 25
<212> TYPE: RNA
<213> ORGANISM: Homo sapiens

<400> SEQUENCE: 62
gcagaguaug accuugucca gugaa                                         25

<210> SEQ ID NO 63
<211> LENGTH: 25
<212> TYPE: RNA
<213> ORGANISM: Homo sapiens

<400> SEQUENCE: 63
accucggaac aauccucaga guuaa                                         25

<210> SEQ ID NO 64
<211> LENGTH: 25
<212> TYPE: RNA
<213> ORGANISM: Homo sapiens

<400> SEQUENCE: 64
cggaacaauc cucagaguua augaa                                              25

<210> SEQ ID NO 65
<211> LENGTH: 25
<212> TYPE: RNA
<213> ORGANISM: Homo sapiens

<400> SEQUENCE: 65
gaacaauccu cagaguuaau gauga                                              25

<210> SEQ ID NO 66
<211> LENGTH: 25
<212> TYPE: RNA
<213> ORGANISM: Homo sapiens

<400> SEQUENCE: 66
aacaauccuc agaguuaaug augaa                                              25

<210> SEQ ID NO 67
<211> LENGTH: 25
<212> TYPE: RNA
<213> ORGANISM: Homo sapiens

<400> SEQUENCE: 67
agacucaccc uggacauuca gaaca                                              25

<210> SEQ ID NO 68
<211> LENGTH: 25
<212> TYPE: RNA
<213> ORGANISM: Homo sapiens

<400> SEQUENCE: 68
acccuggaca uucagaacaa gaaaa                                              25

<210> SEQ ID NO 69
<211> LENGTH: 25
<212> TYPE: RNA
<213> ORGANISM: Homo sapiens

<400> SEQUENCE: 69
cuucuccaaa uggacucauc ugcua                                              25

<210> SEQ ID NO 70
<211> LENGTH: 25
<212> TYPE: RNA
<213> ORGANISM: Homo sapiens

<400> SEQUENCE: 70
gaggguggca uggcauuaug augaa                                              25

<210> SEQ ID NO 71
<211> LENGTH: 25
<212> TYPE: RNA
<213> ORGANISM: Homo sapiens

<400> SEQUENCE: 71
aagauugaau uugaauggaa cacaa                                              25

<210> SEQ ID NO 72
<211> LENGTH: 25
<212> TYPE: RNA
<213> ORGANISM: Homo sapiens

```
<400> SEQUENCE: 72
auuugaaugg aacacaggca ccaaa                                              25

<210> SEQ ID NO 73
<211> LENGTH: 25
<212> TYPE: RNA
<213> ORGANISM: Homo sapiens

<400> SEQUENCE: 73
acacaggcac caauguagau accaa                                              25

<210> SEQ ID NO 74
<211> LENGTH: 25
<212> TYPE: RNA
<213> ORGANISM: Homo sapiens

<400> SEQUENCE: 74
cacaggcacc aauguagaua ccaaa                                              25

<210> SEQ ID NO 75
<211> LENGTH: 25
<212> TYPE: RNA
<213> ORGANISM: Homo sapiens

<400> SEQUENCE: 75
gagcuugcau auguaugcua auaga                                              25

<210> SEQ ID NO 76
<211> LENGTH: 25
<212> TYPE: RNA
<213> ORGANISM: Homo sapiens

<400> SEQUENCE: 76
uguaugcuaa uagacuccug gauca                                              25

<210> SEQ ID NO 77
<211> LENGTH: 25
<212> TYPE: RNA
<213> ORGANISM: Homo sapiens

<400> SEQUENCE: 77
cacaucccag aaaaccucuu cuuaa                                              25

<210> SEQ ID NO 78
<211> LENGTH: 25
<212> TYPE: RNA
<213> ORGANISM: Homo sapiens

<400> SEQUENCE: 78
gauuccuuug ccuuuuggug gcaaa                                              25

<210> SEQ ID NO 79
<211> LENGTH: 25
<212> TYPE: RNA
<213> ORGANISM: Homo sapiens

<400> SEQUENCE: 79
aaagauguua gagacuguua ggaca                                              25

<210> SEQ ID NO 80
<211> LENGTH: 25
<212> TYPE: RNA
```

```
<213> ORGANISM: Homo sapiens

<400> SEQUENCE: 80
accucuccac gaaugucuac agcaa                                              25

<210> SEQ ID NO 81
<211> LENGTH: 25
<212> TYPE: RNA
<213> ORGANISM: Homo sapiens

<400> SEQUENCE: 81
cuggagaaac aacauaugac cacaa                                              25

<210> SEQ ID NO 82
<211> LENGTH: 25
<212> TYPE: RNA
<213> ORGANISM: Homo sapiens

<400> SEQUENCE: 82
gaaacaacau augaccacaa gaaua                                              25

<210> SEQ ID NO 83
<211> LENGTH: 25
<212> TYPE: RNA
<213> ORGANISM: Homo sapiens

<400> SEQUENCE: 83
gaauaucaaa uucagucaug uagaa                                              25

<210> SEQ ID NO 84
<211> LENGTH: 25
<212> TYPE: RNA
<213> ORGANISM: Homo sapiens

<400> SEQUENCE: 84
aacccagucu caaaagguuu acuaa                                              25

<210> SEQ ID NO 85
<211> LENGTH: 25
<212> TYPE: RNA
<213> ORGANISM: Homo sapiens

<400> SEQUENCE: 85
cuggggacca cagaugucug cuuca                                              25

<210> SEQ ID NO 86
<211> LENGTH: 25
<212> TYPE: RNA
<213> ORGANISM: Homo sapiens

<400> SEQUENCE: 86
aaaagaaaca gcauuuguuu gucaa                                              25

<210> SEQ ID NO 87
<211> LENGTH: 25
<212> TYPE: RNA
<213> ORGANISM: Homo sapiens

<400> SEQUENCE: 87
gaaacagcau uuguuuguca aagaa                                              25

<210> SEQ ID NO 88
<211> LENGTH: 25
```

<212> TYPE: RNA
<213> ORGANISM: Homo sapiens

<400> SEQUENCE: 88
agcauuuguu ugucaaagaa gucaa                                        25

<210> SEQ ID NO 89
<211> LENGTH: 25
<212> TYPE: RNA
<213> ORGANISM: Homo sapiens

<400> SEQUENCE: 89
uguuugucaa agaagucaag auuga                                        25

<210> SEQ ID NO 90
<211> LENGTH: 25
<212> TYPE: RNA
<213> ORGANISM: Homo sapiens

<400> SEQUENCE: 90
auggagaguc caaccugagg uuuaa                                        25

<210> SEQ ID NO 91
<211> LENGTH: 25
<212> TYPE: RNA
<213> ORGANISM: Homo sapiens

<400> SEQUENCE: 91
auaacaggaa gauaugaaga uggaa                                        25

<210> SEQ ID NO 92
<211> LENGTH: 25
<212> TYPE: RNA
<213> ORGANISM: Homo sapiens

<400> SEQUENCE: 92
augagaacua cgagcugacu uuaaa                                        25

<210> SEQ ID NO 93
<211> LENGTH: 25
<212> TYPE: RNA
<213> ORGANISM: Homo sapiens

<400> SEQUENCE: 93
gaaguauaag aacuuugcca cuuca                                        25

<210> SEQ ID NO 94
<211> LENGTH: 25
<212> TYPE: RNA
<213> ORGANISM: Homo sapiens

<400> SEQUENCE: 94
auggauauga ccuucucuaa gcaaa                                        25

<210> SEQ ID NO 95
<211> LENGTH: 25
<212> TYPE: RNA
<213> ORGANISM: Homo sapiens

<400> SEQUENCE: 95
ucagccugcu uucuggauca cuaaa                                        25

<210> SEQ ID NO 96

```
<211> LENGTH: 25
<212> TYPE: RNA
<213> ORGANISM: Homo sapiens

<400> SEQUENCE: 96
ucuugaguua aaugcugaca ucuua                                    25

<210> SEQ ID NO 97
<211> LENGTH: 25
<212> TYPE: RNA
<213> ORGANISM: Homo sapiens

<400> SEQUENCE: 97
acaucuuagg cacugacaaa auuaa                                    25

<210> SEQ ID NO 98
<211> LENGTH: 25
<212> TYPE: RNA
<213> ORGANISM: Homo sapiens

<400> SEQUENCE: 98
ugacaaaauu aauaguggug cucaa                                    25

<210> SEQ ID NO 99
<211> LENGTH: 25
<212> TYPE: RNA
<213> ORGANISM: Homo sapiens

<400> SEQUENCE: 99
acaaaauuaa uaguggugcu cacaa                                    25

<210> SEQ ID NO 100
<211> LENGTH: 25
<212> TYPE: RNA
<213> ORGANISM: Homo sapiens

<400> SEQUENCE: 100
aggauuggcc aagauggaau aucua                                    25

<210> SEQ ID NO 101
<211> LENGTH: 25
<212> TYPE: RNA
<213> ORGANISM: Homo sapiens

<400> SEQUENCE: 101
agugcaacga ccaacuugaa gugua                                    25

<210> SEQ ID NO 102
<211> LENGTH: 25
<212> TYPE: RNA
<213> ORGANISM: Homo sapiens

<400> SEQUENCE: 102
aaauuaacaa caaauggccg cuuca                                    25

<210> SEQ ID NO 103
<211> LENGTH: 25
<212> TYPE: RNA
<213> ORGANISM: Homo sapiens

<400> SEQUENCE: 103
aaaaacauuu ucaacuucaa gguca                                    25
```

```
<210> SEQ ID NO 104
<211> LENGTH: 25
<212> TYPE: RNA
<213> ORGANISM: Homo sapiens

<400> SEQUENCE: 104
agucaagaag gacuuaagcu cucaa                                              25

<210> SEQ ID NO 105
<211> LENGTH: 25
<212> TYPE: RNA
<213> ORGANISM: Homo sapiens

<400> SEQUENCE: 105
gaugggcuca uaugcugaaa ugaaa                                              25

<210> SEQ ID NO 106
<211> LENGTH: 25
<212> TYPE: RNA
<213> ORGANISM: Homo sapiens

<400> SEQUENCE: 106
uaugcugaaa ugaaauuuga ccaca                                              25

<210> SEQ ID NO 107
<211> LENGTH: 25
<212> TYPE: RNA
<213> ORGANISM: Homo sapiens

<400> SEQUENCE: 107
aaacagucug aacauugcag gcuua                                              25

<210> SEQ ID NO 108
<211> LENGTH: 25
<212> TYPE: RNA
<213> ORGANISM: Homo sapiens

<400> SEQUENCE: 108
ggcuuaucac uggacuucuc uucaa                                              25

<210> SEQ ID NO 109
<211> LENGTH: 25
<212> TYPE: RNA
<213> ORGANISM: Homo sapiens

<400> SEQUENCE: 109
agcaaacugu uaauuuacag cuaca                                              25

<210> SEQ ID NO 110
<211> LENGTH: 25
<212> TYPE: RNA
<213> ORGANISM: Homo sapiens

<400> SEQUENCE: 110
aacuacuuua aacagugacc ugaaa                                              25

<210> SEQ ID NO 111
<211> LENGTH: 25
<212> TYPE: RNA
<213> ORGANISM: Homo sapiens

<400> SEQUENCE: 111
acuuuaaaca gugaccugaa auaca                                              25
```

```
<210> SEQ ID NO 112
<211> LENGTH: 25
<212> TYPE: RNA
<213> ORGANISM: Homo sapiens

<400> SEQUENCE: 112
cuuuaaacag ugaccugaaa uacaa                                              25

<210> SEQ ID NO 113
<211> LENGTH: 25
<212> TYPE: RNA
<213> ORGANISM: Homo sapiens

<400> SEQUENCE: 113
gguaaccuaa aaggagccua ccaaa                                              25

<210> SEQ ID NO 114
<211> LENGTH: 25
<212> TYPE: RNA
<213> ORGANISM: Homo sapiens

<400> SEQUENCE: 114
aaccuaaaag gagccuacca aaaua                                              25

<210> SEQ ID NO 115
<211> LENGTH: 25
<212> TYPE: RNA
<213> ORGANISM: Homo sapiens

<400> SEQUENCE: 115
aaaaggagcc uaccaaaaua augaa                                              25

<210> SEQ ID NO 116
<211> LENGTH: 25
<212> TYPE: RNA
<213> ORGANISM: Homo sapiens

<400> SEQUENCE: 116
aaugaaauaa aacacaucua ugcca                                              25

<210> SEQ ID NO 117
<211> LENGTH: 25
<212> TYPE: RNA
<213> ORGANISM: Homo sapiens

<400> SEQUENCE: 117
caaacuauaa uucagacuca cugca                                              25

<210> SEQ ID NO 118
<211> LENGTH: 25
<212> TYPE: RNA
<213> ORGANISM: Homo sapiens

<400> SEQUENCE: 118
cucucaugau uacaaaggcu ccaca                                              25

<210> SEQ ID NO 119
<211> LENGTH: 25
<212> TYPE: RNA
<213> ORGANISM: Homo sapiens

<400> SEQUENCE: 119
gcaucagugc agcucuugaa cacaa                                              25
```

```
<210> SEQ ID NO 120
<211> LENGTH: 25
<212> TYPE: RNA
<213> ORGANISM: Homo sapiens

<400> SEQUENCE: 120
agcucuugaa cacaaaguca gugca                                                25

<210> SEQ ID NO 121
<211> LENGTH: 25
<212> TYPE: RNA
<213> ORGANISM: Homo sapiens

<400> SEQUENCE: 121
aacaacaaug aauacagcca ggaca                                                25

<210> SEQ ID NO 122
<211> LENGTH: 25
<212> TYPE: RNA
<213> ORGANISM: Homo sapiens

<400> SEQUENCE: 122
cauuuuuuga gaccuugcaa gaaua                                                25

<210> SEQ ID NO 123
<211> LENGTH: 25
<212> TYPE: RNA
<213> ORGANISM: Homo sapiens

<400> SEQUENCE: 123
accuugcaag aauauuuuga gagga                                                25

<210> SEQ ID NO 124
<211> LENGTH: 25
<212> TYPE: RNA
<213> ORGANISM: Homo sapiens

<400> SEQUENCE: 124
cuggaaaacg uacagagaaa ccuga                                                25

<210> SEQ ID NO 125
<211> LENGTH: 25
<212> TYPE: RNA
<213> ORGANISM: Homo sapiens

<400> SEQUENCE: 125
ccugaagcac aucaauauug aucaa                                                25

<210> SEQ ID NO 126
<211> LENGTH: 25
<212> TYPE: RNA
<213> ORGANISM: Homo sapiens

<400> SEQUENCE: 126
ugggaaaacu cccacagcaa gcuaa                                                25

<210> SEQ ID NO 127
<211> LENGTH: 25
<212> TYPE: RNA
<213> ORGANISM: Homo sapiens

<400> SEQUENCE: 127
```

-continued acucccacag caagcuaaug auuaa                      25

<210> SEQ ID NO 128
<211> LENGTH: 25
<212> TYPE: RNA
<213> ORGANISM: Homo sapiens

<400> SEQUENCE: 128
ugggagagac aaguuucaca ugcca                      25

<210> SEQ ID NO 129
<211> LENGTH: 25
<212> TYPE: RNA
<213> ORGANISM: Homo sapiens

<400> SEQUENCE: 129
auugcauuag augaugccaa aauca                      25

<210> SEQ ID NO 130
<211> LENGTH: 25
<212> TYPE: RNA
<213> ORGANISM: Homo sapiens

<400> SEQUENCE: 130
cucaacugca gacauauaug auaca                      25

<210> SEQ ID NO 131
<211> LENGTH: 25
<212> TYPE: RNA
<213> ORGANISM: Homo sapiens

<400> SEQUENCE: 131
cuggauucaa aaugugggaua cuaaa                     25

<210> SEQ ID NO 132
<211> LENGTH: 25
<212> TYPE: RNA
<213> ORGANISM: Homo sapiens

<400> SEQUENCE: 132
aguaccaaau cagaauccag auaca                      25

<210> SEQ ID NO 133
<211> LENGTH: 25
<212> TYPE: RNA
<213> ORGANISM: Homo sapiens

<400> SEQUENCE: 133
aaaucagaau ccagauacaa gaaaa                      25

<210> SEQ ID NO 134
<211> LENGTH: 25
<212> TYPE: RNA
<213> ORGANISM: Homo sapiens

<400> SEQUENCE: 134
cagcuuaaga gacacauaca gaaua                      25

<210> SEQ ID NO 135
<211> LENGTH: 25
<212> TYPE: RNA
<213> ORGANISM: Homo sapiens

<400> SEQUENCE: 135

```
uuaagagaca cauacagaau auaga                                    25

<210> SEQ ID NO 136
<211> LENGTH: 25
<212> TYPE: RNA
<213> ORGANISM: Homo sapiens

<400> SEQUENCE: 136
gacacauaca gaauauagac aucca                                    25

<210> SEQ ID NO 137
<211> LENGTH: 25
<212> TYPE: RNA
<213> ORGANISM: Homo sapiens

<400> SEQUENCE: 137
auccagcacc uagcuggaaa guuaa                                    25

<210> SEQ ID NO 138
<211> LENGTH: 25
<212> TYPE: RNA
<213> ORGANISM: Homo sapiens

<400> SEQUENCE: 138
agcaccuagc uggaaaguua aaaca                                    25

<210> SEQ ID NO 139
<211> LENGTH: 25
<212> TYPE: RNA
<213> ORGANISM: Homo sapiens

<400> SEQUENCE: 139
aaguuaaaac aacacauuga ggcua                                    25

<210> SEQ ID NO 140
<211> LENGTH: 25
<212> TYPE: RNA
<213> ORGANISM: Homo sapiens

<400> SEQUENCE: 140
cuauugaugu uagagugcuu uuaga                                    25

<210> SEQ ID NO 141
<211> LENGTH: 25
<212> TYPE: RNA
<213> ORGANISM: Homo sapiens

<400> SEQUENCE: 141
uugauguuag agugcuuuua gauca                                    25

<210> SEQ ID NO 142
<211> LENGTH: 25
<212> TYPE: RNA
<213> ORGANISM: Homo sapiens

<400> SEQUENCE: 142
ugauguuaga gugcuuuuag aucaa                                    25

<210> SEQ ID NO 143
<211> LENGTH: 25
<212> TYPE: RNA
<213> ORGANISM: Homo sapiens
```

<400> SEQUENCE: 143 ugggggauuuu gaaguagcug agaaa                                              25

<210> SEQ ID NO 144
<211> LENGTH: 25
<212> TYPE: RNA
<213> ORGANISM: Homo sapiens

<400> SEQUENCE: 144
auuuugaagu agcugagaaa aucaa                                               25

<210> SEQ ID NO 145
<211> LENGTH: 25
<212> TYPE: RNA
<213> ORGANISM: Homo sapiens

<400> SEQUENCE: 145
uucagagcca aaguccauga guuaa                                               25

<210> SEQ ID NO 146
<211> LENGTH: 25
<212> TYPE: RNA
<213> ORGANISM: Homo sapiens

<400> SEQUENCE: 146
aaucgagagg uaugaaguag accaa                                               25

<210> SEQ ID NO 147
<211> LENGTH: 25
<212> TYPE: RNA
<213> ORGANISM: Homo sapiens

<400> SEQUENCE: 147
cgagagguau gaaguagacc aacaa                                               25

<210> SEQ ID NO 148
<211> LENGTH: 25
<212> TYPE: RNA
<213> ORGANISM: Homo sapiens

<400> SEQUENCE: 148
gagagguaug aaguagacca acaaa                                               25

<210> SEQ ID NO 149
<211> LENGTH: 25
<212> TYPE: RNA
<213> ORGANISM: Homo sapiens

<400> SEQUENCE: 149
ccaacaaauc cagguuuuaa uggaa                                               25

<210> SEQ ID NO 150
<211> LENGTH: 25
<212> TYPE: RNA
<213> ORGANISM: Homo sapiens

<400> SEQUENCE: 150
aggagacuau ucagaagcua agcaa                                               25

<210> SEQ ID NO 151
<211> LENGTH: 25
<212> TYPE: RNA
<213> ORGANISM: Homo sapiens

```
<400> SEQUENCE: 151
ggagacuauu cagaagcuaa gcaaa                                          25

<210> SEQ ID NO 152
<211> LENGTH: 25
<212> TYPE: RNA
<213> ORGANISM: Homo sapiens

<400> SEQUENCE: 152
agaagcuaag caauguccua caaca                                          25

<210> SEQ ID NO 153
<211> LENGTH: 25
<212> TYPE: RNA
<213> ORGANISM: Homo sapiens

<400> SEQUENCE: 153
ugaugcuguc aagaagcuua augaa                                          25

<210> SEQ ID NO 154
<211> LENGTH: 25
<212> TYPE: RNA
<213> ORGANISM: Homo sapiens

<400> SEQUENCE: 154
guuuguagau gaaaccaaug acaaa                                          25

<210> SEQ ID NO 155
<211> LENGTH: 25
<212> TYPE: RNA
<213> ORGANISM: Homo sapiens

<400> SEQUENCE: 155
aggugacuca gagacucaau gguga                                          25

<210> SEQ ID NO 156
<211> LENGTH: 25
<212> TYPE: RNA
<213> ORGANISM: Homo sapiens

<400> SEQUENCE: 156
cucagagacu caauggugaa auuca                                          25

<210> SEQ ID NO 157
<211> LENGTH: 25
<212> TYPE: RNA
<213> ORGANISM: Homo sapiens

<400> SEQUENCE: 157
gccacaguug caguguaucu ggaaa                                          25

<210> SEQ ID NO 158
<211> LENGTH: 25
<212> TYPE: RNA
<213> ORGANISM: Homo sapiens

<400> SEQUENCE: 158
aguugcagug uaucuggaaa gccua                                          25

<210> SEQ ID NO 159
<211> LENGTH: 25
<212> TYPE: RNA
```

<213> ORGANISM: Homo sapiens

<400> SEQUENCE: 159
gaaagccuac aggacaccaa aauaa    25

<210> SEQ ID NO 160
<211> LENGTH: 25
<212> TYPE: RNA
<213> ORGANISM: Homo sapiens

<400> SEQUENCE: 160
ccgaauguau caaauggaca uucaa    25

<210> SEQ ID NO 161
<211> LENGTH: 25
<212> TYPE: RNA
<213> ORGANISM: Homo sapiens

<400> SEQUENCE: 161
acauucagca ggaacuucaa cgaua    25

<210> SEQ ID NO 162
<211> LENGTH: 25
<212> TYPE: RNA
<213> ORGANISM: Homo sapiens

<400> SEQUENCE: 162
ucugguaggc cagguuuaua gcaca    25

<210> SEQ ID NO 163
<211> LENGTH: 25
<212> TYPE: RNA
<213> ORGANISM: Homo sapiens

<400> SEQUENCE: 163
agguuuauag cacacuuguc accua    25

<210> SEQ ID NO 164
<211> LENGTH: 25
<212> TYPE: RNA
<213> ORGANISM: Homo sapiens

<400> SEQUENCE: 164
gaaccuuacu gacuuugcag agcaa    25

<210> SEQ ID NO 165
<211> LENGTH: 25
<212> TYPE: RNA
<213> ORGANISM: Homo sapiens

<400> SEQUENCE: 165
acugacuuug cagagcaaua uucua    25

<210> SEQ ID NO 166
<211> LENGTH: 25
<212> TYPE: RNA
<213> ORGANISM: Homo sapiens

<400> SEQUENCE: 166
cuaaacguau gaaagcauug guaga    25

<210> SEQ ID NO 167
<211> LENGTH: 25

```
<212> TYPE: RNA
<213> ORGANISM: Homo sapiens

<400> SEQUENCE: 167
aacguaugaa agcauuggua gagca                                              25

<210> SEQ ID NO 168
<211> LENGTH: 25
<212> TYPE: RNA
<213> ORGANISM: Homo sapiens

<400> SEQUENCE: 168
aaggguucac uguuccugaa aucaa                                              25

<210> SEQ ID NO 169
<211> LENGTH: 25
<212> TYPE: RNA
<213> ORGANISM: Homo sapiens

<400> SEQUENCE: 169
uucacuguuc cugaaaucaa gacca                                              25

<210> SEQ ID NO 170
<211> LENGTH: 25
<212> TYPE: RNA
<213> ORGANISM: Homo sapiens

<400> SEQUENCE: 170
cagauuugag gauuccauca guuca                                              25

<210> SEQ ID NO 171
<211> LENGTH: 25
<212> TYPE: RNA
<213> ORGANISM: Homo sapiens

<400> SEQUENCE: 171
ugaggauucc aucaguucag auaaa                                              25

<210> SEQ ID NO 172
<211> LENGTH: 25
<212> TYPE: RNA
<213> ORGANISM: Homo sapiens

<400> SEQUENCE: 172
auuccaucag uucagauaaa cuuca                                              25

<210> SEQ ID NO 173
<211> LENGTH: 25
<212> TYPE: RNA
<213> ORGANISM: Homo sapiens

<400> SEQUENCE: 173
ccguuuacca gaaaucgcaa uucca                                              25

<210> SEQ ID NO 174
<211> LENGTH: 25
<212> TYPE: RNA
<213> ORGANISM: Homo sapiens

<400> SEQUENCE: 174
ucauaauccc aacucucaac cuuaa                                              25

<210> SEQ ID NO 175
```

```
<211> LENGTH: 25
<212> TYPE: RNA
<213> ORGANISM: Homo sapiens

<400> SEQUENCE: 175
cugaccuuca cauaccagaa uucca                                            25

<210> SEQ ID NO 176
<211> LENGTH: 25
<212> TYPE: RNA
<213> ORGANISM: Homo sapiens

<400> SEQUENCE: 176
cuucacauac cagaauucca gcuua                                            25

<210> SEQ ID NO 177
<211> LENGTH: 25
<212> TYPE: RNA
<213> ORGANISM: Homo sapiens

<400> SEQUENCE: 177
uuccccacau cucacacaca auuga                                            25

<210> SEQ ID NO 178
<211> LENGTH: 25
<212> TYPE: RNA
<213> ORGANISM: Homo sapiens

<400> SEQUENCE: 178
uggcaagcua uacaguauuc ugaaa                                            25

<210> SEQ ID NO 179
<211> LENGTH: 25
<212> TYPE: RNA
<213> ORGANISM: Homo sapiens

<400> SEQUENCE: 179
cacauuagau gcaaaugcug acaua                                            25

<210> SEQ ID NO 180
<211> LENGTH: 25
<212> TYPE: RNA
<213> ORGANISM: Homo sapiens

<400> SEQUENCE: 180
cgcagcuucc aucacugcca aagga                                            25

<210> SEQ ID NO 181
<211> LENGTH: 25
<212> TYPE: RNA
<213> ORGANISM: Homo sapiens

<400> SEQUENCE: 181
cuaagauuaa uccgcuggcu cugaa                                            25

<210> SEQ ID NO 182
<211> LENGTH: 25
<212> TYPE: RNA
<213> ORGANISM: Homo sapiens

<400> SEQUENCE: 182
aggagucagu gaaguucucc agcaa                                            25
```

```
<210> SEQ ID NO 183
<211> LENGTH: 25
<212> TYPE: RNA
<213> ORGANISM: Homo sapiens

<400> SEQUENCE: 183
gagggaaaau caaacacagu ggcaa                                      25

<210> SEQ ID NO 184
<211> LENGTH: 25
<212> TYPE: RNA
<213> ORGANISM: Homo sapiens

<400> SEQUENCE: 184
gaaaaucaaa cacaguggca aguua                                      25

<210> SEQ ID NO 185
<211> LENGTH: 25
<212> TYPE: RNA
<213> ORGANISM: Homo sapiens

<400> SEQUENCE: 185
aaaaucaaac acaguggcaa guuua                                      25

<210> SEQ ID NO 186
<211> LENGTH: 25
<212> TYPE: RNA
<213> ORGANISM: Homo sapiens

<400> SEQUENCE: 186
caguggcaag uuuacacaca gaaaa                                      25

<210> SEQ ID NO 187
<211> LENGTH: 25
<212> TYPE: RNA
<213> ORGANISM: Homo sapiens

<400> SEQUENCE: 187
agcuuaguaa uggagugauu gucaa                                      25

<210> SEQ ID NO 188
<211> LENGTH: 25
<212> TYPE: RNA
<213> ORGANISM: Homo sapiens

<400> SEQUENCE: 188
aguaauggag ugauugucaa gauaa                                      25

<210> SEQ ID NO 189
<211> LENGTH: 25
<212> TYPE: RNA
<213> ORGANISM: Homo sapiens

<400> SEQUENCE: 189
guaauggagu gauugucaag auaaa                                      25

<210> SEQ ID NO 190
<211> LENGTH: 25
<212> TYPE: RNA
<213> ORGANISM: Homo sapiens

<400> SEQUENCE: 190
agugauuguc aagauaaaca aucaa                                      25
```

```
<210> SEQ ID NO 191
<211> LENGTH: 25
<212> TYPE: RNA
<213> ORGANISM: Homo sapiens

<400> SEQUENCE: 191
auagcaacac uaaauacuuc cacaa                                          25

<210> SEQ ID NO 192
<211> LENGTH: 25
<212> TYPE: RNA
<213> ORGANISM: Homo sapiens

<400> SEQUENCE: 192
ucacuuccuu uggacugucc aauaa                                          25

<210> SEQ ID NO 193
<211> LENGTH: 25
<212> TYPE: RNA
<213> ORGANISM: Homo sapiens

<400> SEQUENCE: 193
gacuguccaa uaagaucaau agcaa                                          25

<210> SEQ ID NO 194
<211> LENGTH: 25
<212> TYPE: RNA
<213> ORGANISM: Homo sapiens

<400> SEQUENCE: 194
aggcaugaug cucauuuaaa uggaa                                          25

<210> SEQ ID NO 195
<211> LENGTH: 25
<212> TYPE: RNA
<213> ORGANISM: Homo sapiens

<400> SEQUENCE: 195
ucauuuaaau ggaaagguua uugga                                          25

<210> SEQ ID NO 196
<211> LENGTH: 25
<212> TYPE: RNA
<213> ORGANISM: Homo sapiens

<400> SEQUENCE: 196
gaucacggca uccacaaaca augaa                                          25

<210> SEQ ID NO 197
<211> LENGTH: 25
<212> TYPE: RNA
<213> ORGANISM: Homo sapiens

<400> SEQUENCE: 197
aaaguucguu uuccauuaag guuaa                                          25

<210> SEQ ID NO 198
<211> LENGTH: 25
<212> TYPE: RNA
<213> ORGANISM: Homo sapiens

<400> SEQUENCE: 198
uaacagggaa gauagacuuc cugaa                                          25
```

```
<210> SEQ ID NO 199
<211> LENGTH: 25
<212> TYPE: RNA
<213> ORGANISM: Homo sapiens

<400> SEQUENCE: 199
acagggaaga uagacuuccu gaaua                                      25

<210> SEQ ID NO 200
<211> LENGTH: 25
<212> TYPE: RNA
<213> ORGANISM: Homo sapiens

<400> SEQUENCE: 200
gauagacuuc cugaauaacu augca                                      25

<210> SEQ ID NO 201
<211> LENGTH: 25
<212> TYPE: RNA
<213> ORGANISM: Homo sapiens

<400> SEQUENCE: 201
gcccagcaag caaguuggca aguaa                                      25

<210> SEQ ID NO 202
<211> LENGTH: 25
<212> TYPE: RNA
<213> ORGANISM: Homo sapiens

<400> SEQUENCE: 202
cccagcaagc aaguuggcaa guaaa                                      25

<210> SEQ ID NO 203
<211> LENGTH: 25
<212> TYPE: RNA
<213> ORGANISM: Homo sapiens

<400> SEQUENCE: 203
aguuggcaag uaagugcuag guuca                                      25

<210> SEQ ID NO 204
<211> LENGTH: 25
<212> TYPE: RNA
<213> ORGANISM: Homo sapiens

<400> SEQUENCE: 204
guucaaucag uauaaguaca accaa                                      25

<210> SEQ ID NO 205
<211> LENGTH: 25
<212> TYPE: RNA
<213> ORGANISM: Homo sapiens

<400> SEQUENCE: 205
cauguaggaa uaaauggaga agcaa                                      25

<210> SEQ ID NO 206
<211> LENGTH: 25
<212> TYPE: RNA
<213> ORGANISM: Homo sapiens

<400> SEQUENCE: 206
```
auguaggaau aaauggagaa gcaaa                                                25

<210> SEQ ID NO 207
<211> LENGTH: 25
<212> TYPE: RNA
<213> ORGANISM: Homo sapiens

<400> SEQUENCE: 207
caauaaucac aacuccucca cugaa                                                25

<210> SEQ ID NO 208
<211> LENGTH: 25
<212> TYPE: RNA
<213> ORGANISM: Homo sapiens

<400> SEQUENCE: 208
ugggaaaaaa caggcuugaa ggaaa                                                25

<210> SEQ ID NO 209
<211> LENGTH: 25
<212> TYPE: RNA
<213> ORGANISM: Homo sapiens

<400> SEQUENCE: 209
aggaauucuu gaaaacgaca aagca                                                25

<210> SEQ ID NO 210
<211> LENGTH: 25
<212> TYPE: RNA
<213> ORGANISM: Homo sapiens

<400> SEQUENCE: 210
ggaauucuug aaaacgacaa agcaa                                                25

<210> SEQ ID NO 211
<211> LENGTH: 25
<212> TYPE: RNA
<213> ORGANISM: Homo sapiens

<400> SEQUENCE: 211
gauuuaagug uaaaagcuca guaua                                                25

<210> SEQ ID NO 212
<211> LENGTH: 25
<212> TYPE: RNA
<213> ORGANISM: Homo sapiens

<400> SEQUENCE: 212
ccuuuggcug ugcuuuguga guuua                                                25

<210> SEQ ID NO 213
<211> LENGTH: 25
<212> TYPE: RNA
<213> ORGANISM: Homo sapiens

<400> SEQUENCE: 213
gucaauguug aagugucucc auuca                                                25

<210> SEQ ID NO 214
<211> LENGTH: 25
<212> TYPE: RNA
<213> ORGANISM: Homo sapiens

<400> SEQUENCE: 214

```
cuuucucuuc cagauuucaa ggaaa                                      25

<210> SEQ ID NO 215
<211> LENGTH: 25
<212> TYPE: RNA
<213> ORGANISM: Homo sapiens

<400> SEQUENCE: 215
aauauuaccu augauuucuc cuuua                                      25

<210> SEQ ID NO 216
<211> LENGTH: 25
<212> TYPE: RNA
<213> ORGANISM: Homo sapiens

<400> SEQUENCE: 216
cuccuuuaaa ucaaguguca ucaca                                      25

<210> SEQ ID NO 217
<211> LENGTH: 25
<212> TYPE: RNA
<213> ORGANISM: Homo sapiens

<400> SEQUENCE: 217
uuaaaucaag ugucaucaca cugaa                                      25

<210> SEQ ID NO 218
<211> LENGTH: 25
<212> TYPE: RNA
<213> ORGANISM: Homo sapiens

<400> SEQUENCE: 218 caagucau cacacugaau accaa                                        25

<210> SEQ ID NO 219
<211> LENGTH: 25
<212> TYPE: RNA
<213> ORGANISM: Homo sapiens

<400> SEQUENCE: 219
ugucaucaca cugaauacca augca                                      25

<210> SEQ ID NO 220
<211> LENGTH: 25
<212> TYPE: RNA
<213> ORGANISM: Homo sapiens

<400> SEQUENCE: 220
caucacacug aauaccaaug cugaa                                      25

<210> SEQ ID NO 221
<211> LENGTH: 25
<212> TYPE: RNA
<213> ORGANISM: Homo sapiens

<400> SEQUENCE: 221
uaaccaguca gauauuguug cucaa                                      25

<210> SEQ ID NO 222
<211> LENGTH: 25
<212> TYPE: RNA
<213> ORGANISM: Homo sapiens
```

```
<400> SEQUENCE: 222
cuucaucugu cauugaugca cugca                                    25

<210> SEQ ID NO 223
<211> LENGTH: 25
<212> TYPE: RNA
<213> ORGANISM: Homo sapiens

<400> SEQUENCE: 223
cugucauuga ugcacugcag uacaa                                    25

<210> SEQ ID NO 224
<211> LENGTH: 25
<212> TYPE: RNA
<213> ORGANISM: Homo sapiens

<400> SEQUENCE: 224
auugaugcac ugcaguacaa auuaa                                    25

<210> SEQ ID NO 225
<211> LENGTH: 25
<212> TYPE: RNA
<213> ORGANISM: Homo sapiens

<400> SEQUENCE: 225
aauuuugaga augaauuuca agcaa                                    25

<210> SEQ ID NO 226
<211> LENGTH: 25
<212> TYPE: RNA
<213> ORGANISM: Homo sapiens

<400> SEQUENCE: 226
aauuucaagc aagaacuuaa uggaa                                    25

<210> SEQ ID NO 227
<211> LENGTH: 25
<212> TYPE: RNA
<213> ORGANISM: Homo sapiens

<400> SEQUENCE: 227
agaacuuaau ggaaauacca aguca                                    25

<210> SEQ ID NO 228
<211> LENGTH: 25
<212> TYPE: RNA
<213> ORGANISM: Homo sapiens

<400> SEQUENCE: 228
gaacuuaaug gaaauaccaa gucaa                                    25

<210> SEQ ID NO 229
<211> LENGTH: 25
<212> TYPE: RNA
<213> ORGANISM: Homo sapiens

<400> SEQUENCE: 229
cugucucuuc cuccauggaa uuuaa                                    25

<210> SEQ ID NO 230
<211> LENGTH: 25
<212> TYPE: RNA
<213> ORGANISM: Homo sapiens
```

```
<400> SEQUENCE: 230
aguugaccac aagcuuagcu uggaa                                              25

<210> SEQ ID NO 231
<211> LENGTH: 25
<212> TYPE: RNA
<213> ORGANISM: Homo sapiens

<400> SEQUENCE: 231
cuuuuccauu gagucaucua ccaaa                                              25

<210> SEQ ID NO 232
<211> LENGTH: 25
<212> TYPE: RNA
<213> ORGANISM: Homo sapiens

<400> SEQUENCE: 232
caggaacuau ugcuagugag gccaa                                              25

<210> SEQ ID NO 233
<211> LENGTH: 25
<212> TYPE: RNA
<213> ORGANISM: Homo sapiens

<400> SEQUENCE: 233
aacacuuacu ugaauuccaa gagca                                              25

<210> SEQ ID NO 234
<211> LENGTH: 25
<212> TYPE: RNA
<213> ORGANISM: Homo sapiens

<400> SEQUENCE: 234
augauaucug gaaccuugaa guaaa                                              25

<210> SEQ ID NO 235
<211> LENGTH: 25
<212> TYPE: RNA
<213> ORGANISM: Homo sapiens

<400> SEQUENCE: 235
uaucuggaac cuugaaguaa aagaa                                              25

<210> SEQ ID NO 236
<211> LENGTH: 25
<212> TYPE: RNA
<213> ORGANISM: Homo sapiens

<400> SEQUENCE: 236
ugaaugcuaa cacuaagaac cagaa                                              25

<210> SEQ ID NO 237
<211> LENGTH: 25
<212> TYPE: RNA
<213> ORGANISM: Homo sapiens

<400> SEQUENCE: 237
cuaagaacca gaagaucaga uggaa                                              25

<210> SEQ ID NO 238
<211> LENGTH: 25
<212> TYPE: RNA
```

```
<213> ORGANISM: Homo sapiens

<400> SEQUENCE: 238
gcuuuccaau gaccaagaaa aggca                                        25

<210> SEQ ID NO 239
<211> LENGTH: 25
<212> TYPE: RNA
<213> ORGANISM: Homo sapiens

<400> SEQUENCE: 239
caccaaaaac cccaauggcu auuca                                        25

<210> SEQ ID NO 240
<211> LENGTH: 25
<212> TYPE: RNA
<213> ORGANISM: Homo sapiens

<400> SEQUENCE: 240
ccaucccugu aaaguuuug gcuga                                         25

<210> SEQ ID NO 241
<211> LENGTH: 25
<212> TYPE: RNA
<213> ORGANISM: Homo sapiens

<400> SEQUENCE: 241
caaacuugac uucagagaaa uacaa                                        25

<210> SEQ ID NO 242
<211> LENGTH: 25
<212> TYPE: RNA
<213> ORGANISM: Homo sapiens

<400> SEQUENCE: 242
aaucuauaag aagcugagaa cuuca                                        25

<210> SEQ ID NO 243
<211> LENGTH: 25
<212> TYPE: RNA
<213> ORGANISM: Homo sapiens

<400> SEQUENCE: 243
uauucucaac cagaagacuc cuuga                                        25

<210> SEQ ID NO 244
<211> LENGTH: 25
<212> TYPE: RNA
<213> ORGANISM: Homo sapiens

<400> SEQUENCE: 244
auaaccgugc cugaaucuca guuaa                                        25

<210> SEQ ID NO 245
<211> LENGTH: 25
<212> TYPE: RNA
<213> ORGANISM: Homo sapiens

<400> SEQUENCE: 245
cauugcugcu uuggaucuaa augca                                        25

<210> SEQ ID NO 246
<211> LENGTH: 25
```

<212> TYPE: RNA
<213> ORGANISM: Homo sapiens

<400> SEQUENCE: 246
aaacaaagca gauuauguug aaaca                                            25

<210> SEQ ID NO 247
<211> LENGTH: 25
<212> TYPE: RNA
<213> ORGANISM: Homo sapiens

<400> SEQUENCE: 247
gaugguacgu uagccucuaa gacua                                            25

<210> SEQ ID NO 248
<211> LENGTH: 25
<212> TYPE: RNA
<213> ORGANISM: Homo sapiens

<400> SEQUENCE: 248
guuagccucu aagacuaaag gaaca                                            25

<210> SEQ ID NO 249
<211> LENGTH: 25
<212> TYPE: RNA
<213> ORGANISM: Homo sapiens

<400> SEQUENCE: 249
cagcccucag uccucuccag auaaa                                            25

<210> SEQ ID NO 250
<211> LENGTH: 25
<212> TYPE: RNA
<213> ORGANISM: Homo sapiens

<400> SEQUENCE: 250
aaaaacucac cauauucaaa acuga                                            25

<210> SEQ ID NO 251
<211> LENGTH: 25
<212> TYPE: RNA
<213> ORGANISM: Homo sapiens

<400> SEQUENCE: 251
cucacccuga gagaaguguc uucaa                                            25

<210> SEQ ID NO 252
<211> LENGTH: 25
<212> TYPE: RNA
<213> ORGANISM: Homo sapiens

<400> SEQUENCE: 252 aagucuuc aaagcugaga agaaa                                              25

<210> SEQ ID NO 253
<211> LENGTH: 25
<212> TYPE: RNA
<213> ORGANISM: Homo sapiens

<400> SEQUENCE: 253
cuucaaagcu gagaagaaau cugca                                            25

<210> SEQ ID NO 254

```
<211> LENGTH: 25
<212> TYPE: RNA
<213> ORGANISM: Homo sapiens

<400> SEQUENCE: 254
caaagcugag aagaaaucug cagaa                                              25

<210> SEQ ID NO 255
<211> LENGTH: 25
<212> TYPE: RNA
<213> ORGANISM: Homo sapiens

<400> SEQUENCE: 255
aucuguacca ggaacuguug acuca                                              25

<210> SEQ ID NO 256
<211> LENGTH: 25
<212> TYPE: RNA
<213> ORGANISM: Homo sapiens

<400> SEQUENCE: 256
uugacucacu cauugauuuu cugaa                                              25

<210> SEQ ID NO 257
<211> LENGTH: 25
<212> TYPE: RNA
<213> ORGANISM: Homo sapiens

<400> SEQUENCE: 257
uucgaaaguc cauaaugguu cagaa                                              25

<210> SEQ ID NO 258
<211> LENGTH: 25
<212> TYPE: RNA
<213> ORGANISM: Homo sapiens

<400> SEQUENCE: 258
ucgaaagucc auaaugguuc agaaa                                              25

<210> SEQ ID NO 259
<211> LENGTH: 25
<212> TYPE: RNA
<213> ORGANISM: Homo sapiens

<400> SEQUENCE: 259
augguucaga aauacuguuu uccua                                              25

<210> SEQ ID NO 260
<211> LENGTH: 25
<212> TYPE: RNA
<213> ORGANISM: Homo sapiens

<400> SEQUENCE: 260 guauaggaa cuguugaaag auuua                                               25

<210> SEQ ID NO 261
<211> LENGTH: 25
<212> TYPE: RNA
<213> ORGANISM: Homo sapiens

<400> SEQUENCE: 261
cauuaaacag cugaaagaga ugaaa                                              25
```

<210> SEQ ID NO 262
<211> LENGTH: 25
<212> TYPE: RNA
<213> ORGANISM: Homo sapiens

<400> SEQUENCE: 262
uuauauccaa gaugagauca acaca                                    25

<210> SEQ ID NO 263
<211> LENGTH: 25
<212> TYPE: RNA
<213> ORGANISM: Homo sapiens

<400> SEQUENCE: 263
augagaucaa cacaaucuuc aguga                                    25

<210> SEQ ID NO 264
<211> LENGTH: 25
<212> TYPE: RNA
<213> ORGANISM: Homo sapiens

<400> SEQUENCE: 264
cuucucaaga guuacagcag aucca                                    25

<210> SEQ ID NO 265
<211> LENGTH: 25
<212> TYPE: RNA
<213> ORGANISM: Homo sapiens

<400> SEQUENCE: 265
ucaagaguua cagcagaucc aucaa                                    25

<210> SEQ ID NO 266
<211> LENGTH: 25
<212> TYPE: RNA
<213> ORGANISM: Homo sapiens

<400> SEQUENCE: 266
caaguauagu uggcuggaca gugaa                                    25

<210> SEQ ID NO 267
<211> LENGTH: 25
<212> TYPE: RNA
<213> ORGANISM: Homo sapiens

<400> SEQUENCE: 267 uaguggcug gacagugaaa uauua                                     25

<210> SEQ ID NO 268
<211> LENGTH: 25
<212> TYPE: RNA
<213> ORGANISM: Homo sapiens

<400> SEQUENCE: 268
acuugaagaa aagauaguca gucua                                    25

<210> SEQ ID NO 269
<211> LENGTH: 25
<212> TYPE: RNA
<213> ORGANISM: Homo sapiens

<400> SEQUENCE: 269
ccauucugaa uauauuguca gugca                                    25

```
<210> SEQ ID NO 270
<211> LENGTH: 25
<212> TYPE: RNA
<213> ORGANISM: Homo sapiens

<400> SEQUENCE: 270
cuuuacuucc caacucucaa gucaa                                          25

<210> SEQ ID NO 271
<211> LENGTH: 25
<212> TYPE: RNA
<213> ORGANISM: Homo sapiens

<400> SEQUENCE: 271
uuucugcaca gaaauauuca ggaaa                                          25

<210> SEQ ID NO 272
<211> LENGTH: 25
<212> TYPE: RNA
<213> ORGANISM: Homo sapiens

<400> SEQUENCE: 272
agggaaagag aagauugcag agcua                                          25

<210> SEQ ID NO 273
<211> LENGTH: 25
<212> TYPE: RNA
<213> ORGANISM: Homo sapiens

<400> SEQUENCE: 273
aggccauugc gacgaagaaa auaaa                                          25

<210> SEQ ID NO 274
<211> LENGTH: 25
<212> TYPE: RNA
<213> ORGANISM: Homo sapiens

<400> SEQUENCE: 274
gaccaacucu cugauuacua ugaaa                                          25

<210> SEQ ID NO 275
<211> LENGTH: 25
<212> TYPE: RNA
<213> ORGANISM: Homo sapiens

<400> SEQUENCE: 275
cugaauccaa aagauugauu gacca                                          25

<210> SEQ ID NO 276
<211> LENGTH: 25
<212> TYPE: RNA
<213> ORGANISM: Homo sapiens

<400> SEQUENCE: 276
aagauugauu gaccugucca uucaa                                          25

<210> SEQ ID NO 277
<211> LENGTH: 25
<212> TYPE: RNA
<213> ORGANISM: Homo sapiens

<400> SEQUENCE: 277
aaaacuacca cacauuucug auaua                                          25
```

<210> SEQ ID NO 278
<211> LENGTH: 25
<212> TYPE: RNA
<213> ORGANISM: Homo sapiens

<400> SEQUENCE: 278
gaaccccuac augaagcuug cucca                                            25

<210> SEQ ID NO 279
<211> LENGTH: 25
<212> TYPE: RNA
<213> ORGANISM: Homo sapiens

<400> SEQUENCE: 279
ucucugaacu cagaaggaug gcaua                                            25

<210> SEQ ID NO 280
<211> LENGTH: 25
<212> TYPE: RNA
<213> ORGANISM: Homo sapiens

<400> SEQUENCE: 280
uaaagaaaau caggaucuga guuaa                                            25

<210> SEQ ID NO 281
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ggaucugagu uaa                                                         13

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uuaacucaga uccugauuu                                                   19

<210> SEQ ID NO 283
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gaaggauggc aua                                                         13

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 284
uaugccaucc uucugaguu                                                  19

<210> SEQ ID NO 285
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
acucucaagu caa                                                        13

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
uugacuugag aguugggaa                                                  19

<210> SEQ ID NO 287
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
uaaugguuca gaa                                                        13

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uucugaacca uuauggacu                                                  19

<210> SEQ ID NO 289
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gauagucagu cua                                                        13

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
```
uagacugacu aucuuuucu                                              19

<210> SEQ ID NO 291
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
cagugaaaua uua                                                    13

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
uaauauuuca cuguccagc                                              19

<210> SEQ ID NO 293
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uugauuuucu gaa                                                    13

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uucagaaaau caaugagug                                              19

<210> SEQ ID NO 295
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
aaugguucag aaa                                                    13

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296

```
uuucugaacc auuauggac                                              19
```

<210> SEQ ID NO 297
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297

```
gauuacuaug aaa                                                    13
```

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298

```
uuucauagua aucagagag                                              19
```

<210> SEQ ID NO 299
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299

```
gacuaaagga aca                                                    13
```

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300

```
uguuccuuua gucuuagag                                              19
```

<210> SEQ ID NO 301
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301

```
guugaaagau uua                                                    13
```

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302

```
uaaaucuuuc aacaguucc                                              19
```

<210> SEQ ID NO 303
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
gccucuaaga cua                                                      13

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uagucuuaga ggcuaacgu                                                19

<210> SEQ ID NO 305
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
accuugaagu aaa                                                      13

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
uuuacuucaa gguuccaga                                                19

<210> SEQ ID NO 307
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aguuggcaag uaa                                                      13

<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uuacuugcca acuugcuug                                                19

<210> SEQ ID NO 309
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
gagcaauauu cua                                                         13

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uagaauauug cucugcaaa                                                   19

<210> SEQ ID NO 311
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
agauaaacuu ca                                                          12

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ugaaguuuau cugaacuga                                                   19

<210> SEQ ID NO 313
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gaaucucagu uaa                                                         13

<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uuaacugaga uucaggcac                                                   19

```
<210> SEQ ID NO 315
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
aauaccaagu caa                                                          13

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uugacuuggu auuccauu                                                     19

<210> SEQ ID NO 317
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
gaauuccagc uua                                                          13

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uaagcuggaa uucugguau                                                    19

<210> SEQ ID NO 319
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aaagguuuac uaa                                                          13

<210> SEQ ID NO 320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uuaguaaacc uuuugagac                                                    19

<210> SEQ ID NO 321
```

```
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uacacacaga aaa                                                             13

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uuuucugugu guaaacuug                                                       19

<210> SEQ ID NO 323
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
caguacaaau uaa                                                             13

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uuaauuugua cugcagugc                                                       19

<210> SEQ ID NO 325
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
uuauguugaa aca                                                             13

<210> SEQ ID NO 326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uguuucaaca uaaucugcu                                                       19

<210> SEQ ID NO 327
<211> LENGTH: 13
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
aguuuauucg gaa                                                    13

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
uuccgaauaa acuccaggc                                              19

<210> SEQ ID NO 329
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
guuuauucgg aaa                                                    13

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uuuccgaaua aacuccagg                                              19

<210> SEQ ID NO 331
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
gaguuuauuc gga                                                    13

<210> SEQ ID NO 332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
uccgaauaaa cuccaggcc                                              19

<210> SEQ ID NO 333
<211> LENGTH: 13
<212> TYPE: RNA
```

<213> ORGANISM: Artificial Sequence
<220> FEATURE:
<223> OTHER INFORMATION: Description of Artificial Sequence: Synthetic
oligonucleotide
<400> SEQUENCE: 333
agugugacag uca 13

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 334
ugacugucac acuugcugg 19

<210> SEQ ID NO 335
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 335
uguggaccuc uuu 13

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 336
aaagaggucc acacagcgg 19

<210> SEQ ID NO 337
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 337
caagugugac agu 13

<210> SEQ ID NO 338
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<400> SEQUENCE: 338
acugucacac uugcuggcc 19

<210> SEQ ID NO 339
<211> LENGTH: 13
<212> TYPE: RNA
<213> ORGANISM: Artificial Sequence
```
<220> FEATURE:
<223> OTHER INFORMATION: Description of Artificial Sequence: Synthetic
      oligonucleotide

<400> SEQUENCE: 339
guggaccucu uug                                                          13

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
caaagagguc cacacagcg                                                    19

<210> SEQ ID NO 341
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
gcaaguguga cag                                                          13

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
cugucacacu ugcuggccu                                                    19

<210> SEQ ID NO 343
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
gcgugcucaa cug                                                          13

<210> SEQ ID NO 344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
caguugagca cgcgcaggc                                                    19

<210> SEQ ID NO 345
<211> LENGTH: 13
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 345
acugccaagg gaa                                                            13

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uucccuuggc aguugagca                                                      19

<210> SEQ ID NO 347
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
guuuauucgg aaa                                                            13

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uuuccgaaua aacuccagg                                                      19

<210> SEQ ID NO 349
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
gaguuuauuc gga                                                            13

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uccgaauaaa cuccaggcc                                                      19

<210> SEQ ID NO 351
<211> LENGTH: 13
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 351
agugugacag uca                                                              13

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
ugacugucac acuugcugg                                                        19

<210> SEQ ID NO 353
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uguggaccuc uuu                                                              13

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
aaagaggucc acacagcgg                                                        19

<210> SEQ ID NO 355
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
guggaccucu uug                                                              13

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
caaagagguc cacacagcg                                                        19

<210> SEQ ID NO 357
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 357
gcaaguguga cag                                                           13

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
cugucacacu ugcuggccu                                                     19

<210> SEQ ID NO 359
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gcgugcucaa cug                                                           13

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
caguugagca cgcgcaggc                                                     19

<210> SEQ ID NO 361
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
acugccaagg gaa                                                           13

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
uucccuuggc aguugagca                                                     19

<210> SEQ ID NO 363
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 363
ggaguuuauu cggaa                                                      15

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
uuccgaauaa acuccaggc                                                  19

<210> SEQ ID NO 365
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
gaguuuauuc ggaaa                                                      15

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366 uuccgaaua aacuccagg                                                   19

<210> SEQ ID NO 367
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uggaguuuau ucgga                                                      15

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uccgaauaaa cuccaggcc                                                  19

<210> SEQ ID NO 369
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
```
caagugugac aguca                                                        15

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
ugacugucac acuugcugg                                                    19

<210> SEQ ID NO 371
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
uguguggacc ucuuu                                                        15

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aaagaggucc acacagcgg                                                    19

<210> SEQ ID NO 373
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
agcaagugug acagu                                                        15

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
acugucacac uugcuggcc                                                    19

<210> SEQ ID NO 375
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375

```
guguggaccu cuuug                                                  15

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
caaagagguc cacacagcg                                              19

<210> SEQ ID NO 377
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
cagcaagugu gacag                                                  15

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
cugucacacu ugcuggccu                                              19

<210> SEQ ID NO 379
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
gcgcgugcuc aacug                                                  15

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
caguugagca cgcgcaggc                                              19

<210> SEQ ID NO 381
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
caacugccaa gggaa                                                  15
```

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 382
uucccuuggc aguugagca                                              19

<210> SEQ ID NO 383
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 383
gaguuuauuc ggaaa                                                  15

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 384
uuuccgaaua aacuccagg                                              19

<210> SEQ ID NO 385
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 385
uggaguuuau ucgga                                                  15

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 386
uccgaauaaa cuccaggcc                                              19

<210> SEQ ID NO 387
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 387
uguguggacc ucuuu                                                  15

```
<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aaagaggucc acacagcgg                                                  19

<210> SEQ ID NO 389
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
agcaagugug acagu                                                      15

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
acugucacac uugcuggcc                                                  19

<210> SEQ ID NO 391
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
guguggaccu cuuug                                                      15

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
caaagagguc cacacagcg                                                  19

<210> SEQ ID NO 393
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
cagcaagugu gacag                                                      15
```

```
<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
cugucacacu ugcuggccu                                                  19

<210> SEQ ID NO 395
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
gcgcgugcuc aacug                                                      15

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
caguugagca cgcgcaggc                                                  19

<210> SEQ ID NO 397
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
caacugccaa gggaa                                                      15

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uucccuuggc aguugagca                                                  19

<210> SEQ ID NO 399
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ggauuuggcu acaaa                                                      15

<210> SEQ ID NO 400
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uuuguagcca aauccuuuc                                                       19

<210> SEQ ID NO 401
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aaagacuguu ccaaa                                                           15

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uuuggaacag ucuuuccga                                                       19

<210> SEQ ID NO 403
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
gaacuucaaa cugaa                                                           15

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uucaguuuga aguucucau                                                       19

<210> SEQ ID NO 405
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ggacuucaug aucca                                                           15

<210> SEQ ID NO 406
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uggaucauga aguccuuga                                                      19

<210> SEQ ID NO 407
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
cuagauggca agcau                                                          15

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
augcuugcca ucuagccag                                                      19

<210> SEQ ID NO 409
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
caaauuccau cgugu                                                          15

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
acacgaugga auuugcugu                                                      19

<210> SEQ ID NO 411
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
aauuccaucg ugu                                                            13

<210> SEQ ID NO 412
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 412
acacgaugga auuugcugu                                                    19

<210> SEQ ID NO 413
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uagcuacagg agaga                                                        15

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
ucucuccugu agcuaaggc                                                    19

<210> SEQ ID NO 415
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
aaggauuugg cua                                                          13

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
uagccaaauc cuuucucuc                                                    19

<210> SEQ ID NO 417
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
auuuggcuac aaa                                                          13

<210> SEQ ID NO 418
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 418
uuuguagcca aauccuuuc                                                    19

<210> SEQ ID NO 419
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
auuuggcuac aaa                                                          13

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
uuuguagcca aauccuuuc                                                    19

<210> SEQ ID NO 421
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
auuuggcuac aaa                                                          13

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uuuguagcca aauccuuuc                                                    19

<210> SEQ ID NO 423
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
ggcuacaaaa aca                                                          13

<210> SEQ ID NO 424
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 424
uguuuuugua gccaaaucc                                                19

<210> SEQ ID NO 425
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
ggcuacaaaa aca                                                      13

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uguuuuugua gccaaaucc                                                19

<210> SEQ ID NO 427
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
aauuccaucg ugu                                                      13

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
acacgaugga auuugcugu                                                19

<210> SEQ ID NO 429
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uaaucaagga cuu                                                      13

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
```

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
aaguccuuga uuacacgau                                                19

<210> SEQ ID NO 431
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 431
aacuucaaac uga                                                      13

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 432
ucaguuugaa guucucauc                                                19

<210> SEQ ID NO 433
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 433
aacuucaaac uga                                                      13

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 434
ucaguuugaa guucucauc                                                19

<210> SEQ ID NO 435
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 435
aacaguggau a                                                        11

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 436
uauccacugu uuuuggaac                                                19

<210> SEQ ID NO 437
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
aggaaagagc auc                                                      13

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
gaugcucuuu ccuccugug                                                19

<210> SEQ ID NO 439
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
gcaccaagac aga                                                      13

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
ucugucuugg ugcucucca                                                19

<210> SEQ ID NO 441
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
gaacuucaaa cug                                                      13

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 442
caguuugaag uucucaucg                                        19

<210> SEQ ID NO 443
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
auuccaucgu gua                                              13

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uacacgaugg aauuugcug                                        19

<210> SEQ ID NO 445
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
aacuucaaac uga                                              13

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ucaguuugaa guucucauc                                        19

<210> SEQ ID NO 447
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
gauggcaagc aug                                              13

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
```

```
caugcuugcc aucuagcca                                              19
```

<210> SEQ ID NO 449
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449

```
gcaucuacgg uga                                                    13
```

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450

```
ucaccguaga ugcucuuuc                                              19
```

<210> SEQ ID NO 451
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451

```
aggaaagagc auc                                                    13
```

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452

```
gaugcucuuu ccuccugug                                              19
```

<210> SEQ ID NO 453
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453

```
gcaccaagac aga                                                    13
```

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
ucugucuugg ugcucucca                                              19

<210> SEQ ID NO 455
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
gaacuucaaa cug                                                    13

<210> SEQ ID NO 456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
caguuugaag uucucaucg                                              19

<210> SEQ ID NO 457
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
auuccaucgu gua                                                    13

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uacacgaugg aauuugcug                                              19

<210> SEQ ID NO 459
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
aacuucaaac uga                                                    13

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ucaguuugaa guucucauc                                              19

<210> SEQ ID NO 461
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
gauggcaagc aug                                                        13

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
caugcuugcc aucuagcca                                                  19

<210> SEQ ID NO 463
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
gcaucuacgg uga                                                        13

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
ucaccguaga ugcucuuuc                                                  19

<210> SEQ ID NO 465
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
agaguaaagu caa                                                        13

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
uugacuuuac ucuaacuug                                                  19

```
<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uugacuuuac ucuaacuug                                                    19

<210> SEQ ID NO 468
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
agaguaaagu caa                                                          13

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
uugacuuuac ucuaacuug                                                    19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uugacuuuac ucuaacuug                                                    19

<210> SEQ ID NO 471
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
gcaccuuucu aga                                                          13

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ucuagaaagg ugcaaacau                                                    19
```

```
<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
ucuagaaagg ugcaaacau                                                    19

<210> SEQ ID NO 474
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
gcaccuuucu aga                                                          13

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ucuagaaagg ugcaaacau                                                    19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ucuagaaagg ugcaaacau                                                    19

<210> SEQ ID NO 477
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
cuguggaagu cua                                                          13

<210> SEQ ID NO 478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
uagacuucca cagaacucu                                                    19

<210> SEQ ID NO 479
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
uagacuucca cagaacucu                                                19

<210> SEQ ID NO 480
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
cuguggaagu cua                                                      13

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uagacuucca cagaacucu                                                19

<210> SEQ ID NO 482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
uagacuucca cagaacucu                                                19

<210> SEQ ID NO 483
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
aaauuccauc gugu                                                     14

<210> SEQ ID NO 484
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
acacgaugga auuugcuguu                                               20

<210> SEQ ID NO 485
<211> LENGTH: 20
```

```
-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
acacgaugga auuugcuguu                                                   20

<210> SEQ ID NO 486
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
aaauuccauc gugu                                                         14

<210> SEQ ID NO 487
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
acacgaugga auuugcuguu                                                   20

<210> SEQ ID NO 488
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
acacgaugga auuugcuguu                                                   20

<210> SEQ ID NO 489
<211> LENGTH: 12
<212> TYPE: RNA
<213> ORGANISM: Artificial Sequence
<220> FEATURE:
<223> OTHER INFORMATION: Synthetic Oligonucleotide

<400> SEQUENCE: 489
ggaguaucgg aa                                                           12

<210> SEQ ID NO 490
<211> LENGTH: 16
<212> TYPE: RNA
<213> ORGANISM: Artificial Sequence
<220> FEATURE:
<223> OTHER INFORMATION: Synthetic Oligonucleotide

<400> SEQUENCE: 490
agacuccaca gaaccu                                                       16

<210> SEQ ID NO 491
<211> LENGTH: 17
<212> TYPE: DNA
<213> ORGANISM: Artificial Sequence
<220> FEATURE:
```

```
<223> OTHER INFORMATION: Synthetic Oligonucleotide

<400> SEQUENCE: 491
tagacuccac agaaccu                                                      17

<210> SEQ ID NO 492
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 492
agacutccac agaaccu                                                      17

<210> SEQ ID NO 493
<211> LENGTH: 15
<212> TYPE: RNA
<213> ORGANISM: Artificial Sequence
<220> FEATURE:
<223> OTHER INFORMATION: Synthetic Oligonucleotide

<400> SEQUENCE: 493
ccgaaaaacc caggc                                                        15

<210> SEQ ID NO 494
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 494
ttccgaaaaa cccaggc                                                      17

<210> SEQ ID NO 495
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 495
tccgaataaa cccaggc                                                      17

<210> SEQ ID NO 496
<211> LENGTH: 13
<212> TYPE: RNA
<213> ORGANISM: Artificial Sequence
<220> FEATURE:
<223> OTHER INFORMATION: Synthetic Oligonucleotide

<400> SEQUENCE: 496
ccgaaaaacc cgc                                                          13

<210> SEQ ID NO 497
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
```

```
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 497
nagacuncca cagaacncu                                              19

<210> SEQ ID NO 498
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 498
tagacuncca cagaacncu                                              19

<210> SEQ ID NO 499
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 499
nagacutcca cagaacncu                                              19

<210> SEQ ID NO 500
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl C

<400> SEQUENCE: 500
ggagnunaun cggaa                                                  15

<210> SEQ ID NO 501
<211> LENGTH: 19
<212> TYPE: RNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 501
nnccgaanaa acnccaggc                                                19

<210> SEQ ID NO 502
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 502
ttccgaanaa acnccaggc                                                19

<210> SEQ ID NO 503
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 503
ntccgaataa acnccaggc                                                19

<210> SEQ ID NO 504
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C
```

```
<220> FEATURE:
<221> NAME/KEY: misc_feature
<222> LOCATION: (16)..(16)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl C

<400> SEQUENCE: 504
nnccgaanaa acnccngnc                                                   19

<210> SEQ ID NO 505
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 505
nnccgaanaa acnccaggc                                                   19

<210> SEQ ID NO 506
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 506
ttccgaanaa acnccaggc                                                   19

<210> SEQ ID NO 507
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C

<400> SEQUENCE: 507
ntccgaataa acnccaggc                                                   19

<210> SEQ ID NO 508
```

```
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(2)
<223> OTHER INFORMATION: n is 5 methyl C
<220> FEATURE:
<221> NAME/KEY: misc_feature
<222> LOCATION: (8)..(8)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl C
<220> FEATURE:
<221> NAME/KEY: misc_feature
<222> LOCATION: (16)..(16)
<223> OTHER INFORMATION: n is 5 methyl C
<220> FEATURE:
<221> NAME/KEY: misc_feature
<222> LOCATION: (18)..(18)
<223> OTHER INFORMATION: n is 5 methyl C

<400> SEQUENCE: 508
nnccgaanaa acnccngnc                                              19

<210> SEQ ID NO 509
<211> LENGTH: 13
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl C

<400> SEQUENCE: 509
cngnggaagn cta                                                    13

<210> SEQ ID NO 510
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 510
nagacuncca cagaacncu                                              19
```

```
<210> SEQ ID NO 511
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 511
tagacuncca cagaacncu                                          19

<210> SEQ ID NO 512
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 512
nagacutcca cagaacncu                                          19

<210> SEQ ID NO 513
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 513
uagacuucca cagaacucu                                          19

<210> SEQ ID NO 514
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 514
nagacuncca cagaacncu                                          19

<210> SEQ ID NO 515
<211> LENGTH: 19
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 515
tagacuncca cagaacncu                                                19

<210> SEQ ID NO 516
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 516
nagacutcca cagaacncu                                                19

<210> SEQ ID NO 517
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 517
uagacuucca cagaacucu                                                19

<210> SEQ ID NO 518
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 518
nagacuncca cagaacncu                                                19

<210> SEQ ID NO 519
<211> LENGTH: 19
<212> TYPE: DNA
<213> ORGANISM: Artificial Sequence
<220> FEATURE:
<223> OTHER INFORMATION: Synthetic Oligonucleotide
```

-continued

```
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 519
tagacuncca cagaacncu                                                19

<210> SEQ ID NO 520
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 520
nagacutcca cagaacncu                                                19

<210> SEQ ID NO 521
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 521
uagacuucca cagaacucu                                                19

<210> SEQ ID NO 522
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 522
nagacuncca cagaacncu                                                19

<210> SEQ ID NO 523
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
```

```
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 523
tagacuncca cagaacncu                                                  19

<210> SEQ ID NO 524
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 524
nagacutcca cagaacncu                                                  19

<210> SEQ ID NO 525
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 525
uagacuucca cagaacucu                                                  19

<210> SEQ ID NO 526
<211> LENGTH: 13
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C

<400> SEQUENCE: 526
cngnggaagu cua                                                        13

<210> SEQ ID NO 527
<211> LENGTH: 13
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl C

<400> SEQUENCE: 527
```
cuguggaagn cna                                                    13

<210> SEQ ID NO 528
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl C

<400> SEQUENCE: 528
ggagnuuaun cggaa                                                  15

<210> SEQ ID NO 529
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: n is 5 methyl C

<400> SEQUENCE: 529
ggaguuuaun cggaa                                                  15

<210> SEQ ID NO 530
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (5)..(5)
<223> OTHER INFORMATION: n is 5 methyl C

<400> SEQUENCE: 530
ggagnuuauu cggaa                                                  15

<210> SEQ ID NO 531
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 531
uagacuncca cagaacncu                                              19

<210> SEQ ID NO 532
<211> LENGTH: 19
<212> TYPE: RNA

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 532
uagacuncca cagaacncu                                              19

<210> SEQ ID NO 533
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 533
nagacuncca cagaacncu                                              19

<210> SEQ ID NO 534
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C

<400> SEQUENCE: 534
nagacuncca cagaacncu                                              19

<210> SEQ ID NO 535
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (7)..(7)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl C
```

```
<400> SEQUENCE: 535
uagacuncca cagaacncu                                              19

<210> SEQ ID NO 536
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 536
uugacuuuac ucuaacuug                                              19

<210> SEQ ID NO 537
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 537
uugacuuuac ucuaacuug                                              19

<210> SEQ ID NO 538
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 538
uugacuuuac ucuaacuugu a                                           21

<210> SEQ ID NO 539
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 539
uugacuuuac ucuaacuugu a                                           21

<210> SEQ ID NO 540
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 540
uugacuuuac ucuaacuug                                              19

<210> SEQ ID NO 541
<211> LENGTH: 13
<212> TYPE: RNA
<213> ORGANISM: Artificial Sequence
<220> FEATURE:
<223> OTHER INFORMATION: Synthetic Oligonucleotide

<400> SEQUENCE: 541
agaguaaagu caa                                                    13

<210> SEQ ID NO 542
```

```
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 542
uugacuuuac ucuaacuug                                             19

<210> SEQ ID NO 543
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 543
uugacuuuac ucuaacuug                                             19

<210> SEQ ID NO 544
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 544
uugacuuuac ucuaacuugu a                                          21

<210> SEQ ID NO 545
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 545
uugacuuuac ucuaacuugu a                                          21

<210> SEQ ID NO 546
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 546
uugacuuuac ucuaacuug                                             19

<210> SEQ ID NO 547
<211> LENGTH: 13
<212> TYPE: RNA
<213> ORGANISM: Artificial Sequence
<220> FEATURE:
<223> OTHER INFORMATION: Synthetic Oligonucleotide

<400> SEQUENCE: 547
agaguaaagu caa                                                   13

<210> SEQ ID NO 548
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 548
```
uugacuuuac ucuaacuug                                                 19

<210> SEQ ID NO 549
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 549
uugacuuuac ucuaacuug                                                 19

<210> SEQ ID NO 550
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 550
uugacuuuac ucuaacuugu a                                              21

<210> SEQ ID NO 551
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 551
uugacuuuac ucuaacuugu a                                              21

<210> SEQ ID NO 552
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 552
uugacuuuac ucuaacuug                                                 19

<210> SEQ ID NO 553
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 553
aaaaaaagag uaaagucaa                                                 19

<210> SEQ ID NO 554
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 554
uugacuuuac ucuaacuug                                                 19

<210> SEQ ID NO 555
<211> LENGTH: 19
<212> TYPE: RNA

```
<213> ORGANISM: Artificial Sequence
<220> FEATURE:
<223> OTHER INFORMATION: Synthetic Oligonucleotide

<400> SEQUENCE: 555
uugacuuuac ucuaacuug                                              19

<210> SEQ ID NO 556
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 556
uugacuuuac ucuaacuugu a                                           21

<210> SEQ ID NO 557
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 557
uugacuuuac ucuaacuugu a                                           21

<210> SEQ ID NO 558
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 558
uugacuuuac ucuaacuug                                              19

<210> SEQ ID NO 559
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 559
aaaaaaagag uaaagucaaa aaaaa                                       25

<210> SEQ ID NO 560
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 560
acacgaugga auuugcuguu                                             20

<210> SEQ ID NO 561
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 561
acacgaugga auuugcuguu                                             20
```

<210> SEQ ID NO 562
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 562
acacgaugga auuugcuguu                                               20

<210> SEQ ID NO 563
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 563
acacgaugga auuugcuguu                                               20

<210> SEQ ID NO 564
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 564
acacgaugga auuugcuguu                                               20

<210> SEQ ID NO 565
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 565
acacgaugga auuugcuguu                                               20

<210> SEQ ID NO 566
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 566
acacgaugga auuugcuguu                                               20

<210> SEQ ID NO 567
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 567
acacgaugga auuugcuguu                                               20

<210> SEQ ID NO 568
<211> LENGTH: 20
<212> TYPE: RNA
<213> ORGANISM: Artificial Sequence
<220> FEATURE:

<223> OTHER INFORMATION: Synthetic Oligonucleotide

<400> SEQUENCE: 568
acacgaugga auuugcuguu                                                         20

<210> SEQ ID NO 569
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 569
acacgaugga auuugcuguu                                                         20

<210> SEQ ID NO 570
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 570
acacgaugga auuugcuguu                                                         20

<210> SEQ ID NO 571
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 571
acacgaugga auuugcuguu                                                         20

<210> SEQ ID NO 572
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 572
acacgaugga auuugcuguu                                                         20

<210> SEQ ID NO 573
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 573
acacgaugga auuugcuguu                                                         20

<210> SEQ ID NO 574
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 574
acacgaugga auuugcuguu                                                         20

```
<210> SEQ ID NO 575
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 575
aaauuccauc gugu                                                          14

<210> SEQ ID NO 576
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 576
aaauuccauc gugu                                                          14

<210> SEQ ID NO 577
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 577
aaauuccauc gugu                                                          14

<210> SEQ ID NO 578
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 578
aaauuccauc gugu                                                          14

<210> SEQ ID NO 579
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (12)..(14)
<223> OTHER INFORMATION: n is 5 methyl U
<220> FEATURE:
<221> NAME/KEY: misc_feature
<222> LOCATION: (16)..(16)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U
```

<400> SEQUENCE: 579
anangangga annngnnngu                    19

<210> SEQ ID NO 580
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (5)..(6)
<223> OTHER INFORMATION: n is 5 methyl U
<220> FEATURE:
<221> NAME/KEY: misc_feature
<222> LOCATION: (7)..(8)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (15)..(15)
<223> OTHER INFORMATION: n is 5 methyl U

<400> SEQUENCE: 580
naaannnnan ngngn                    15

<210> SEQ ID NO 581
<211> LENGTH: 15
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: n is 5 methyl C
<220> FEATURE:
<221> NAME/KEY: misc_feature
<222> LOCATION: (5)..(6)
<223> OTHER INFORMATION: n is 5 methyl U
<220> FEATURE:
<221> NAME/KEY: misc_feature
<222> LOCATION: (7)..(8)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl U
<220> FEATURE:
<221> NAME/KEY: misc_feature
<222> LOCATION: (11)..(11)
<223> OTHER INFORMATION: n is 5 methyl C
<220> FEATURE:
<221> NAME/KEY: misc_feature
<222> LOCATION: (13)..(13)
<223> OTHER INFORMATION: n is 5 methyl U
<220> FEATURE:
<221> NAME/KEY: misc_feature
<222> LOCATION: (15)..(15)
<223> OTHER INFORMATION: n is 5 methyl U -continued

<400> SEQUENCE: 581
naaannnnan ngngn                                                15

<210> SEQ ID NO 582
<211> LENGTH: 19
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (7)..(7)
<223> OTHER INFORMATION: n is 5 methyl U
<220> FEATURE:
<221> NAME/KEY: misc_feature
<222> LOCATION: (12)..(14)
<223> OTHER INFORMATION: n is 5 methyl U
<220> FEATURE:
<221> NAME/KEY: misc_feature
<222> LOCATION: (16)..(16)
<223> OTHER INFORMATION: n is 5 methyl C
<220> FEATURE:
<221> NAME/KEY: misc_feature
<222> LOCATION: (17)..(17)
<223> OTHER INFORMATION: n is 5 methyl U

<400> SEQUENCE: 582
anangangga annngnngu                                            19

<210> SEQ ID NO 583
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 583
aaauuccauc gugu                                                 14

<210> SEQ ID NO 584
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 584
acacgaugga auuugcuguu                                           20

<210> SEQ ID NO 585
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 585
aaauuccauc gugu                                                 14

<210> SEQ ID NO 586

```
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 586
acacgaugga auuugcuguu                                                   20

<210> SEQ ID NO 587
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 587
aaauuccauc gugu                                                         14

<210> SEQ ID NO 588
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 588
acacgaugga auuugcuguu                                                   20

<210> SEQ ID NO 589
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 589
aaauuccauc gugu                                                         14

<210> SEQ ID NO 590
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 590
acacgaugga auuugcuguu                                                   20

<210> SEQ ID NO 591
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 591
aaauuccauc gugu                                                         14

<210> SEQ ID NO 592
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 592
```

```
acacgaugga auuugcuguu                                              20

<210> SEQ ID NO 593
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 593
aaauuccauc gugu                                                    14

<210> SEQ ID NO 594
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 594
acacgaugga auuugcuguu                                              20

<210> SEQ ID NO 595
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 595
aaauuccauc gugu                                                    14

<210> SEQ ID NO 596
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 596
acacgaugga auuugcuguu                                              20

<210> SEQ ID NO 597
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 597
aaauuccauc gugu                                                    14

<210> SEQ ID NO 598
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 598
acacgaugga auuugcuguu                                              20

<210> SEQ ID NO 599
<211> LENGTH: 14
<212> TYPE: RNA
```

```
<213> ORGANISM: Artificial Sequence
<220> FEATURE:
<223> OTHER INFORMATION: Synthetic Oligonucleotide

<400> SEQUENCE: 599
aaauuccauc gugu                                                        14

<210> SEQ ID NO 600
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 600
acacgaugga auuugcuguu                                                  20

<210> SEQ ID NO 601
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 601
aaauuccauc gugu                                                        14

<210> SEQ ID NO 602
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 602
acacgaugga auuugcuguu                                                  20

<210> SEQ ID NO 603
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 603
aaauuccauc gugu                                                        14

<210> SEQ ID NO 604
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 604
acacgaugga auuugcuguu                                                  20

<210> SEQ ID NO 605
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 605
aaauuccauc gugu                                                        14
```

<210> SEQ ID NO 606
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 606
acacgaugga auuugcuguu                                               20

<210> SEQ ID NO 607
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 607
aaauuccauc gugu                                                     14

<210> SEQ ID NO 608
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 608
acacgaugga auuugcuguu                                               20

<210> SEQ ID NO 609
<211> LENGTH: 14
<212> TYPE: RNA
<213> ORGANISM: Artificial Sequence
<220> FEATURE:
<223> OTHER INFORMATION: Synthetic Oligonucleotide

<400> SEQUENCE: 609
aaauuccauc gugu                                                     14

<210> SEQ ID NO 610
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 610
acacgaugga auuugcuguu                                               20

<210> SEQ ID NO 611
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 611
uugacuuuac ucuaacuug                                                19

<210> SEQ ID NO 612
<211> LENGTH: 13
<212> TYPE: RNA
<213> ORGANISM: Artificial Sequence
<220> FEATURE:

```
<223> OTHER INFORMATION: Synthetic Oligonucleotide

<400> SEQUENCE: 612
agaguaaagu caa                                                          13

<210> SEQ ID NO 613
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 613
ucuagaaagg ugcaaacau                                                    19

<210> SEQ ID NO 614
<211> LENGTH: 13
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: n is 5 methyl C
<220> FEATURE:
<221> NAME/KEY: misc_feature
<222> LOCATION: (4)..(4)
<223> OTHER INFORMATION: n is 5 methyl C
<220> FEATURE:
<221> NAME/KEY: misc_feature
<222> LOCATION: (10)..(10)
<223> OTHER INFORMATION: n is 5 methyl C
<220> FEATURE:
<221> NAME/KEY: misc_feature
<222> LOCATION: (12)..(12)
<223> OTHER INFORMATION: n is 5 methyl C

<400> SEQUENCE: 614
cngnggaagn cna                                                          13
```

REDUCED SIZE SELF-DELIVERING RNAI COMPOUNDS

RELATED APPLICATIONS

This application is a continuation of U.S. patent application Ser. No. 13/636,728, now U.S. Pat. No. 9,080,171, entitled "REDUCED SIZE SELF-DELIVERING RNAI COMPOUNDS," which is a national stage filing under 35 U.S.C. § 371 of international application PCT/US2011/029824, filed on Mar. 24, 2011, which was published under PCT Article 21(2) in English and which claims the benefit under 35 U.S.C. § 119(e) of U.S. Provisional Application Ser. No. U.S. 61/317,261, entitled "REDUCED SIZE SELF-DELIVERING RNAI COMPOUNDS," filed on Mar. 24, 2010, and U.S. Provisional Application Ser. No. U.S. 61/317,597, entitled "REDUCED SIZE SELF-DELIVERING RNAI COMPOUNDS," filed on Mar. 25, 2010, the entire disclosures of which are incorporated by reference herein in their entireties.

FIELD OF INVENTION

The invention pertains to the field of RNA interference (RNAi). The invention more specifically relates to methods of administering nucleic acid molecules with improved in vivo delivery properties and their use in efficient gene silencing.

BACKGROUND OF INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of a delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oligonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds appears to be inhibited in the presence of biological fluids resulting in highly limited efficacy in gene silencing in vivo, limiting the applicability of these compounds in a clinical setting.

SUMMARY OF INVENTION

Aspects of the invention relate to modified polynucleotides that have increased stability and exhibit efficient systemic delivery. Polynucleotides associated with the invention include sd-rxRNA® molecules wherein at least 40% of the nucleotides are modified and wherein at least two Us and/or Cs include a hydrophobic modification selected from the group consisting of a methyl, octyl, thiophene, octyn-1-yl, ethynyl, pyridyl amide, isobutyl and phenyl modification. In some embodiments, at least 60% of the nucleotides are modified.

Modifications can include at least one 2'F or 2'O methyl modifications. In some embodiments, a plurality of U's and/or C's include a hydrophobic modification, optionally selected from the group consisting of a methyl octyl, thiophene, octyn-1-yl, ethynyl, pyridyl amide, isobutyl and phenyl modification.

The sd-rxRNA® can be attached to a linker. In some embodiments, the linker is protonatable. In certain embodiments, the sd-rxRNA® is attached to multiple linkers.

The sd-rxRNA® can be linked to a lipophilic group, such as at the 3' end of the sd-rxRNA®. In some embodiments, the sd-rxRNA® is linked to cholesterol. In certain embodiments, the sd-rxRNA® is attached to vitamin A or vitamin E.

The guide strand of the sd-rxRNA® can contain a single stranded region which contains at least 5 phosphorothioate modifications. In some embodiments, the sd-rxRNA® contains at least two single stranded regions.

In some embodiments, the sd-rxRNA® is formulated for intravenous, subcutaneous or intrathecal administration. The sd-rxRNA® can have a half-life in serum that is longer than 12 hours.

Aspects of the invention relate to compositions including any of the sd-rxRNA® molecules described herein. In some embodiments, the composition comprises two or more different sd-rxRNA®.

Aspects of the invention relate to double stranded RNAs (dsRNAs) wherein at least 40% of the nucleotides are modified and wherein at least two Us and/or Cs include a hydrophobic modification selected from the group consisting of a methyl, octyl, thiophene, octyn-1-yl, ethynyl, pyridyl amide, isobutyl and phenyl modification. In some embodiments, at least 60% of the nucleotides are modified.

Modifications can include at least one 2'F or 2'O methyl modifications. In some embodiments, a plurality of U's and/or C's include a hydrophobic modification, optionally selected from the group consisting of a methyl octyl, thiophene, octyn-1-yl, ethynyl, pyridyl amide, isobutyl and phenyl modification.

Aspects of the invention relate to single stranded RISC entering polynucleotides, wherein at least 40% of the nucleotides are modified and wherein at least two Us and/or Cs include a hydrophobic modification selected from the group consisting of a methyl, octyl, thiophene, octyn-1-yl, ethynyl, pyridyl amide, isobutyl and phenyl modification. In some embodiments, at least 60% of the nucleotides are modified.

Modifications can include at least one 2'F or 2'O methyl modifications. In some embodiments, a plurality of U's and/or C's include a hydrophobic modification, optionally selected from the group consisting of a methyl octyl, thiophene, octyn-1-yl, ethynyl, pyridyl amide, isobutyl and phenyl modification. In some embodiments, the single stranded RISC entering polynucleotide of any one of claims 23-26, wherein the isolated single stranded RISC entering polynucleotide is a miRNA inhibitor.

Aspects of the invention relate to methods for delivering a nucleic acid to a remote target tissue in a subject in need thereof, including systemically administering to the subject an sd-rxRNA® in an effective amount to promote RNA interference by the sd-rxRNA® in the remote target tissue. In some embodiments, at least 40%, or at least 60% of the nucleotides on the antisense strand of the sd-rxRNA® are modified.

Modifications can include at least one 2'F or 2'O methyl modifications. In some embodiments, at least one U or C includes a hydrophobic modification. In certain embodiments, a plurality of U's and/or C's includes a hydrophobic modification. The hydrophobic modification can be selected from the group consisting of an octyl, thiophene, octyn-1-yl, ethynyl, pyridyl amide, isobutyl and phenyl modification.

The sd-rxRNA® can be attached to a linker. In some embodiments, the linker is protonatable. In certain embodiments, the sd-rxRNA® is attached to multiple linkers.

The sd-rxRNA® can be linked to a lipophilic group, such as at the 3' end of the sd-rxRNA®. In some embodiments, the sd-rxRNA® is linked to cholesterol, vitamin A or vitamin E.

The guide strand of the sd-rxRNA® can contain a single stranded region which contains at least 5 phosphorothioate modifications. In some embodiments, the guide strand of the sd-rxRNA® contains at least two single stranded regions.

In some embodiments, the sd-rxRNA® is delivered to the liver, heart, brain, lung or fat. In certain embodiments, the sd-rxRNA® is delivered to a tumor. In some embodiments, the sd-rxRNA® is administered subcutaneously.

Aspects of the invention relate to methods including administering to a subject having a tumor an sd-rxRNA® in an effective amount to promote RNA interference by the sd-rxRNA® in the tumor. In some embodiments, the sd-rxRNA® is administered to the tumor through intravenous administration. In other embodiments, the sd-rxRNA® is administered to the tumor through direct injection into the tumor. In certain embodiments, the sd-rxRNA® is directed against a gene encoding for a protein selected from the group consisting of: VEGF/VEGFR, HER2, PDGF/PDGFR, HDAC, MET, c-kit, CDK, FLT-1, IGF/IGFR, FGF/FGFR, Ras/Raf, Abl, Bcl-2, Src, mTOR, PKC, MAPK, BRCS, FAS, HIF1A, CDH16, MYC, HRAS and CTNNB1, or a combination thereof.

Aspects of the invention relate to methods including administering an sd-rxRNA® to the central nervous system of a subject in need thereof. In some embodiments, the sd-rxRNA® is administered by intrathecal delivery.

Described herein are methods and compositions for efficient delivery of sd-rxRNA® molecules to remote target tissues. In some embodiments, the nucleic acid is delivered through intravenous administration. In certain embodiments, intravenous administration is a continuous infusion. In some embodiments, the nucleic acid is administered for 2-3 hours. The nucleic acid can be administered repetitively. In certain embodiments, the nucleic acid is administered subcutaneously. In some embodiments, the nucleic acid is administered daily, weekly or monthly. In certain embodiments, a second dose of the nucleic acid is administered 1-3 months after the first dose. In some embodiments, the nucleic acid is administered every 2-3 months.

In some embodiments, the sd-rxRNA® is linked to a long chain alkyl cholesterol analog, vitamin A or vitamin E. In some embodiments, the sd-rxRNA® is attached to chloroformate.

In some embodiments, methods associated with the invention include methods of treating lung conditions such as asthma, chronic obstructive pulmonary disease (COPD), lung cancer, lung metastasis, pulmonary fibrosis, infection and infectious disease, liver conditions such as cirrhosis and hepatitis (e.g., chronic hepatitis, acute hepatitis, lupoid hepatitis, autoimmune hepatitis, or viral hepatitis) or heart conditions such as ischemic heart diseases, cardiomyopathy, hypertensive heart diseases, valvular disease, congenital heart diseases, mayocarditis and arrhythmia.

Aspects of the invention relate to methods for delivering a nucleic acid to a remote target tissue, including subcutaneously administering to a subject an sd-rxRNA®, in an effective amount to promote RNA interference by the sd-rxRNA® in the remote target tissue. In some embodiments, the target tissue is lung and the sd-rxRNA® molecule is delivered to alveolar macrophage.

In some embodiments, the target tissue is heart, liver or fat. Methods associated with the invention can include methods for treating or preventing a lung condition, a heart condition or preventing a liver condition.

Aspects of the invention relate to methods for treating a lung condition, including: administering to a subject having a lung condition an sd-rxRNA® in an effective amount to promote RNA interference by the sd-rxRNA® in an alveolar macrophage in order to treat the lung condition. In some embodiments, the sd-rxRNA® is administered by insufflation or subcutaneously. In certain embodiments, the sd-rxRNA® is administered within a dry powder formulation and/or with a carrier. In some embodiments, the sd-rxRNA® is complexed with a glucan containing particle. In certain embodiments, the sd-rxRNA® is directed against a gene encoding for an alveolar macrophage specific protein. In some embodiments, the sd-rxRNA® is administered by intratracheal spray.

Further aspects of the invention relate to compositions comprising one or more double stranded nucleic acid molecules selected from the nucleic acid molecules contained in Tables 1-5 such that an antisense and a sense strand make up the double stranded nucleic acid molecule.

In some embodiments, an sd-rxRNA® associated with the invention is directed against ApoB, MAP4K4, PCSK9, PPIB, KSP, CTGF or VEGF.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 9 reveals distribution of sd-rxRNA® in the liver 24 hours following subcutaneous or intravenous administration.

FIG. 17 reveals clinical observations of rats following administration of sd-rxRNA® to the lung. No lethargy or dehydration was observed and lungs were observed to be normal and healthy.

FIG. 18 depicts example of chemical modification on passenger and guide strand sequences for MAP4K4 and PCSK9. The MAP4K4 guide strand sequences are SEQ ID NOs:490-492 from top to bottom. The passenger stands for PCSK9 are SEQ ID NO:489. The guide strands for PCSK9 are SEQ ID NOs:493-496 from top to bottom. The # symbol refers to modifications selected from the group shown in FIG. 19.

FIG. 31 demonstrates gene expression of ApoB in cells following administration of an sd-rxRNA® targeting ApoB.

FIG. 32 demonstrates gene expression of PCSK9 in cells following administration of an sd-rxRNA® targeting PCSK9.

FIG. 34B shows SEQ ID NOs:399-414 listed from top to bottom.

FIG. 38 provides non-limiting example of sequence modification schemes. SEQ ID NOs: 466 and 410 can be found from top to bottom respectively.

FIG. 38 provides non-limiting example of sequence modification schemes. SEQ ID NOs:466 and 410 can be found from top to bottom respectively.

FIGS. 39A-39B provide a summary of the impact of sd-rxRNA® chemistry and structure on tissue distribution.

FIG. 41 demonstrates the effects of octyl modification of sd-rxRNA® targeting MAP4K4. PS Duplex ID 19402 is SEQ ID NO:614. PS Duplex IDs 1903-19405 and 12984 are SEQ ID NO:477. GS Duplex IDs 19402-19405 and 12984 are SEQ ID NOs:478, 497, 498, 499, and 478 respectively.

FIG. 55 provides a summary of 5-uridyl modifications.

FIG. 56 demonstrates that modulation of chemistry at position 5 of uridine results in an altered tissue distribution of sd-rxRNA® in the liver. PS Duplex ID 13966 is SEQ ID NO:477. The remaining PS Duplex IDs are SEQ ID NO:614. GS Duplex IDs from top to bottom are SEQ ID NOs:478 and 531-535 respectively.

FIG. 58 summarizes construction of synthons.

DETAILED DESCRIPTION

Figure 1:
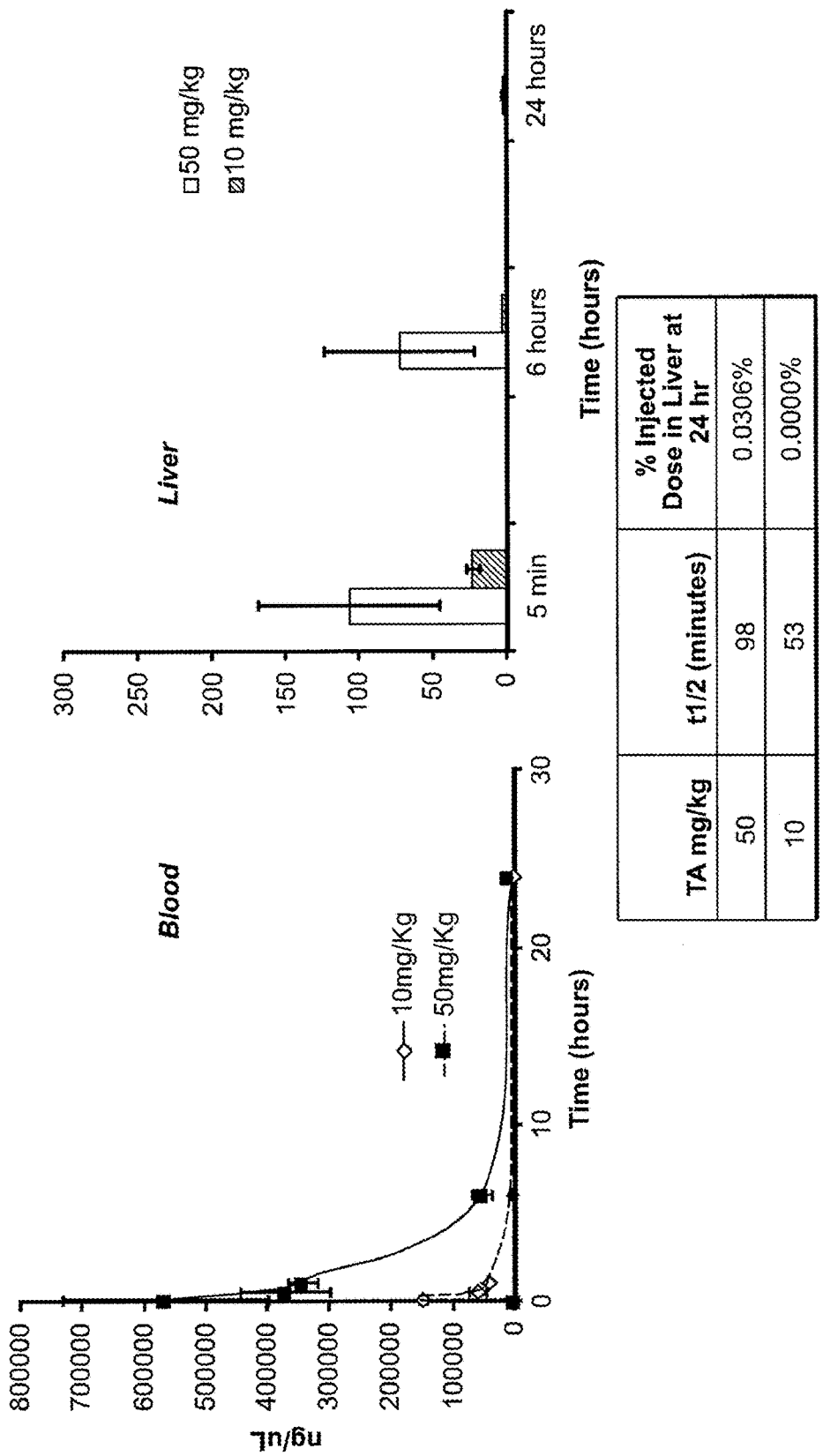
FIG. 1 demonstrates blood clearance rate and liver uptake of sd-rxRNA® following intravenous administration.

Aspects of the invention relate to methods and compositions involved in gene silencing. The invention is based at least in part on the surprising discovery that sd-rxRNA® molecules can be efficiently delivered to many different tissues. Intravenous administration is demonstrated herein to result in efficient distribution to tissues such as liver, spleen, heart and lung while subcutaneous delivery is shown to be highly effective for delivery to tissues such as liver and skin. Furthermore, efficient uptake and delivery of sd-rxRNA® molecules to the lungs, including alveolar macrophage, was achieved through insufflation. Methods and compositions described herein have widespread applications for improved in vivo nucleic acid delivery.

sd-rxRNA® Molecules

Aspects of the invention relate to sd-rxRNA® molecules. As used herein, an "sd-rxRNA®" or an "sd-rxRNA® molecule" refers to a self-delivering RNA molecule such as those described in and incorporated by reference from PCT Publication No. WO2010/033247 (Application No. PCT/US2009/005247), filed on Sep. 22, 2009, and entitled "REDUCED SIZE SELF-DELIVERING RNAI COMPOUNDS." Briefly, an sd-rxRNA®, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. sd-rxRNA® molecules can be optimized through chemical modification, and in some instances through attachment of hydrophobic conjugates.

In some embodiments, an sd-rxRNA® comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

The polynucleotides of the invention are referred to herein as isolated double stranded or duplex nucleic acids, oligonucleotides or polynucleotides, nano molecules, nano RNA, sd-rxRNA', sd-rxRNA® or RNA molecules of the invention.

sd-rxRNA® molecules are much more effectively taken up by cells compared to conventional siRNAs. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. sd-rxRNA® molecules however, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. This class of RNAi like compounds have superior efficacy in vitro and in vivo. It is believed that the reduction in the size of the rigid duplex region in combination with phosphorothioate modifications applied to a single stranded region contribute to the observed superior efficacy.

The invention is based at least in part on the surprising discovery that sd-rxRNA® molecules are compatible with multiple means of administration and are efficiently distributed to a variety of tissues. As presented in the Examples section, and as discussed further below, effective systemic administration of sd-rxRNA® was achieved through intravenous injection, including using a repetitive administration/short-term continuous infusion regimen. Surprisingly, efficient distribution of sd-rxRNA® was achieved in heart tissue using this method, even though the heart is traditionally not easily targeted by oligonucleotides. Distribution of sd-rxRNA® was also observed in tissues such as the liver, lung and spleen through intravenous administration.

Another surprising aspect of the invention was the efficiency by which sd-rxRNA® was delivered using subcutaneous administration. As presented in the Examples section, and as discussed further below, in some instances, a subcutaneous method of administration resulted in a higher concentration of an RNA molecule in a given tissue than did intravenous administration of the same dose of the same RNA molecule.

A further surprising aspect of the invention was the efficient delivery of sd-rxRNA® to the lungs, and in particular to alveolar macrophage cells, following administration by insufflation. Typical RNAi approaches have targeted epithelial cells, rather than alveolar macrophage cells. Delivery to alveolar macrophage cells is advantageous for treating lung conditions such as asthma.

A further surprising aspect of the invention was the discovery that delivery of sd-rxRNA® to target tissue can be substantially increased by stabilization of the sd-rxRNA® through chemical modification. For example, introduction of a stabilizing modification such as a 2'O methyl, 2' deoxy and/or a phosphorothioate can improved distribution to tissues. For example, in some instances, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 or more than 500 fold increase in tissue distribution. In some non-limiting examples, the sd-rxRNA® is distributed to the liver, heart, lung, brain or fat. As shown in the Examples, increasing the level of stabilizing modifications was found to lead to increased gene silencing compared to a less stable sd-rxRNA® and increased biodistribution to tissues such as liver, heart and fat.

Figure 57:
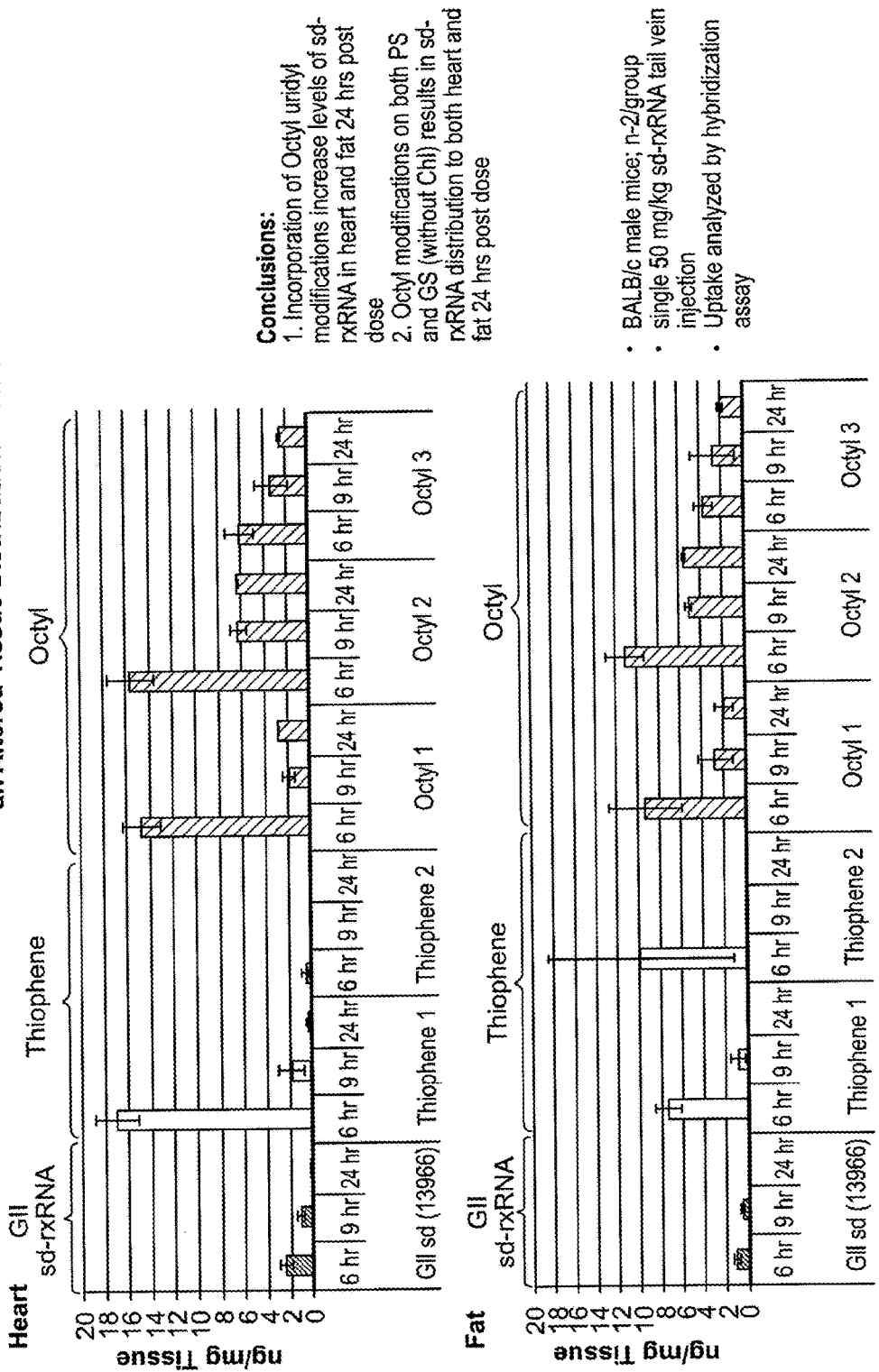
FIG. 57 demonstrates that modulation of chemistry at position 5 of uridine results in an altered tissue distribution of sd-rxRNA® in heart and fat.

Another surprising aspect of the invention was the demonstration that introducing hydrophobic modifications to sd-rxRNA® molecules enhances cellular uptake and tissue distribution. Several non-limiting examples of hydrophobic base modifications include: thiophene, octyl, octyn-1-yl, ethynyl, isobutyl, methyl, pyridyl amide and phenyl. FIG. 57 shows that incorporation of hydrophobic modifications into sd-rxRNA® results in altered tissue distribution.

In some instances, at least one of the C or U residues includes a hydrophobic modification. In some instances, a plurality of Cs and Us contain a hydrophobic modification. For example, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

Another surprising aspect of the invention was the development of highly phosphorothioated RNA molecules that maintain the ability to enter RISC. Several past groups have tried to develop completely phosphorothoiated RNAi compounds, however, these compounds did not demonstrate the correct pharmacokinetic profile. Completely phosphorothioated single stranded RNAi compounds have also been designed previously, however, these compounds did not efficiently enter RISC. Significantly, herein hybrid RNAi compounds have been developed that efficiently enter RISC and contain complete phosphorothioate backbones. In some instances, at least 10%, 15%, 20%, 30%, 40%, 50%, 55%, 60% 65%, 70%, 75%, 80%, 85%, 90% or at least 95% of the nucleotides on the guide strand and/or the passenger strand are phosphorothioate modified. In certain embodiments, all of the nucleotides on the guide strand and/or the passenger strand are phophorothioate modified. In some embodiments, the RNA molecule is single stranded and at least 10%, 15%, 20%, 30%, 40%, 50%, 55%, 60% 65%, 70%, 75%, 80%, 85%, 90% or at least 95% of the nucleotides of the single stranded molecule are phosphorothioate modified. In certain embodiments, all of the nucleotides in the single stranded molecule are phosphorothioate modified.

A further aspect of the invention relates to the enhancement of endosomal release of sd-rxRNA® molecules through the incorporation of protonatable amines. In some embodiments, protonatable amines are incorporated in the sense strand (in the part of the molecule which is discarded after RISC loading).

In a preferred embodiment, the RNAi compounds of the invention comprise an asymmetric compound comprising a duplex region (required for efficient RISC entry of 10-15 bases long) and single stranded region of 4-12 nucleotides long; with a 13 nucleotide duplex. A 6 nucleotide single stranded region is preferred in some embodiments. The single stranded region of the new RNAi compounds also comprises 2-12 phosphorothioate internucleotide linkages (referred to as phosphorothioate modifications). 6-8 phosphorothioate internucleotide linkages are preferred in some embodiments. Additionally, the RNAi compounds of the invention also include a unique chemical modification pattern, which provides stability and is compatible with RISC entry. The combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes Omethyl modification of C and U nucleotides within the passenger strand or alternatively the passenger strand may be completely Omethyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2'Omethyl modification of position 1 and C/U in positions 11-18 and 5' end chemical phosphorylation. Yet another preferred chemical modification pattern in the guide strand includes 2'Omethyl modification of position 1 and C/U in positions 11-18 and 5' end chemical phosphorylation and 2'F modification of C/U in positions 2-10. In some embodiments the passenger strand and/or the guide strand contains at least one 5-methyl C or U modifications.

In some embodiments, at least 30% of the nucleotides in the sd-rxRNA® are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-rxRNA® are modified. In some embodiments, 100% of the nucleotides in the sd-rxRNA® are modified.

dsRNA formulated according to the invention also includes rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA® are modified. In some embodiments, only the passenger strand of the rxRNAori contains modifications.

The above-described chemical modification patterns of the oligonucleotides of the invention are well tolerated and actually improved efficacy of asymmetric RNAi compounds. The combination of modifications to RNAi when used together in a polynucleotide results in the achievement of optimal efficacy in passive uptake of the RNAi. Elimination of any of the described components (Guide strand stabilization, phosphorothioate stretch, sense strand stabilization and hydrophobic conjugate) or increase in size in some instances results in sub-optimal efficacy and in some instances complete lost of efficacy. The combination of elements results in development of a compound, which is fully active following passive delivery to cells such as HeLa cells.

The data in the Examples presented below demonstrates high efficacy of the oligonucleotides of the invention in vivo upon local and systemic administration. The sd-rxRNA® can be further improved in some instances by improving the hydrophobicity of compounds using of novel types of chemistries. For example one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. A version of sd-rxRNA® compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake prosperities in vivo.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is 6 or 7 nucleotides long.

RNAi constructs associated with the invention can have a thermodynamic stability (ΔG) of less than −13 kkal/mol. In some embodiments, the thermodynamic stability (ΔG) is less than −20 kkal/mol. In some embodiments there is a loss of efficacy when (ΔG) goes below −21 kkal/mol. In some embodiments a (ΔG) value higher than −13 kkal/mol is compatible with aspects of the invention. Without wishing to be bound by any theory, in some embodiments a molecule with a relatively higher (ΔG) value may become active at a relatively higher concentration, while a molecule with a relatively lower (ΔG) value may become active at a relatively lower concentration. In some embodiments, the (ΔG) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Aspects of the invention relate to chemically modified RNA molecules that have increased stability. In some instances, a chemically modified sd-rxRNA® molecule has a half-life in serum that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In certain embodiments, the sd-rxRNA® has a half-life in serum that is longer than 12 hours.

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. The Examples section presents molecules in which 2'F modifications have been eliminated, offering an advantage over previously described RNAi compounds due to a predicted reduction in toxicity. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. As demonstrated in the Examples, chemical modification patterns on both the guide and passenger strand are well tolerated and a combination of chemical modifications is shown herein to lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications. In some embodiments, the sd-rxRNA® molecule has more than one single stranded region.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. Based on the data described herein, molecules that have a double stranded region of 8-15 nucleotides can be selected for use in RNAi. In some embodiments, molecules are selected based on their thermodynamic stability ($\Delta G$). In some embodiments, molecules will be selected that have a ($\Delta G$) of less than −13 kkal/mol. For example, the ($\Delta G$) value may be −13, −14, −15, −16, −17, −18, −19, −21, −22 or less than −22 kkal/mol. In other embodiments, the ($\Delta G$) value may be higher than −13 kkal/mol. For example, the ($\Delta G$) value may be −12, −11, −10, −9, −8, −7 or more than −7 kkal/mol. It should be appreciated that $\Delta G$ can be calculated using any method known in the art. In some embodiments $\Delta G$ is calculated using Mfold, available through the Mfold internet site (mfold.bioinfo.rpi.edu/cgi-bin/rna-form1.cgi). Methods for calculating $\Delta G$ are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101: 7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

Aspects of the invention relate to using nucleic acid molecules described herein, with minimal double stranded regions and/or with a ($\Delta G$) of less than −13 kkal/mol, for gene silencing. RNAi molecules can be administered in vivo or in vitro, and gene silencing effects can be achieved in vivo or in vitro.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the miniRNA polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

In some embodiments, the 5'-stem sequence may comprise a 2'-modified ribose sugar, such as 2'-O-methyl modified nucleotide, at the $2^{nd}$ nucleotide on the 5'-end of the polynucleotide and, in some embodiments, no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the miniRNA structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA® compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly Omethyl modified with the PS content described previously. For these types of compounds the 5' phosphorilation is not necessary. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the over-expression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent.

Another aspect of the invention provides a method for inhibiting the expression of a target gene in a mammalian cell, comprising contacting the mammalian cell with any of the subject RNAi constructs.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 6 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

Figure 19:
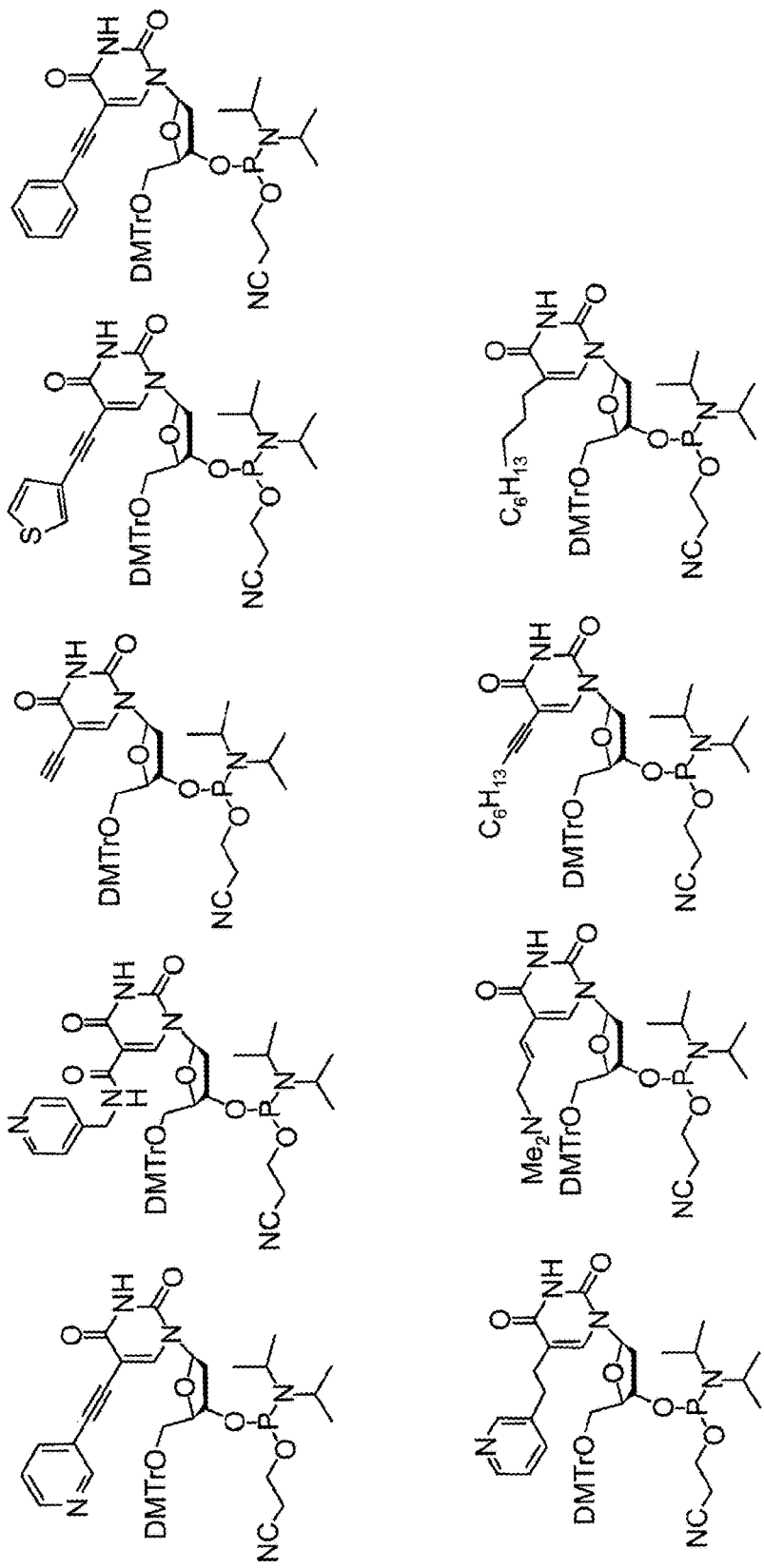
FIG. 19 depicts examples of 5-uridyl modifications.
Figure 20:
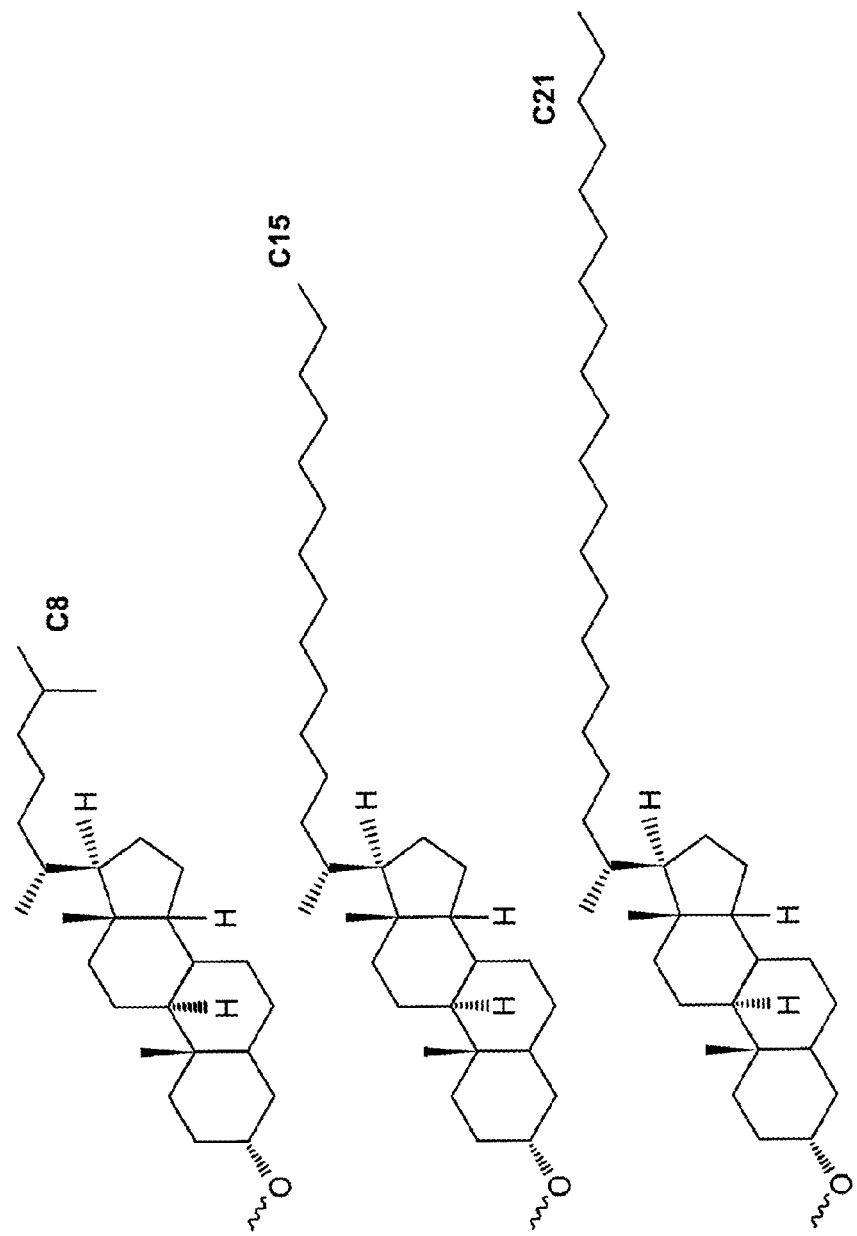
FIG. 20 depicts examples of long chain alkyl cholesterol analogs.
Figure 29A:
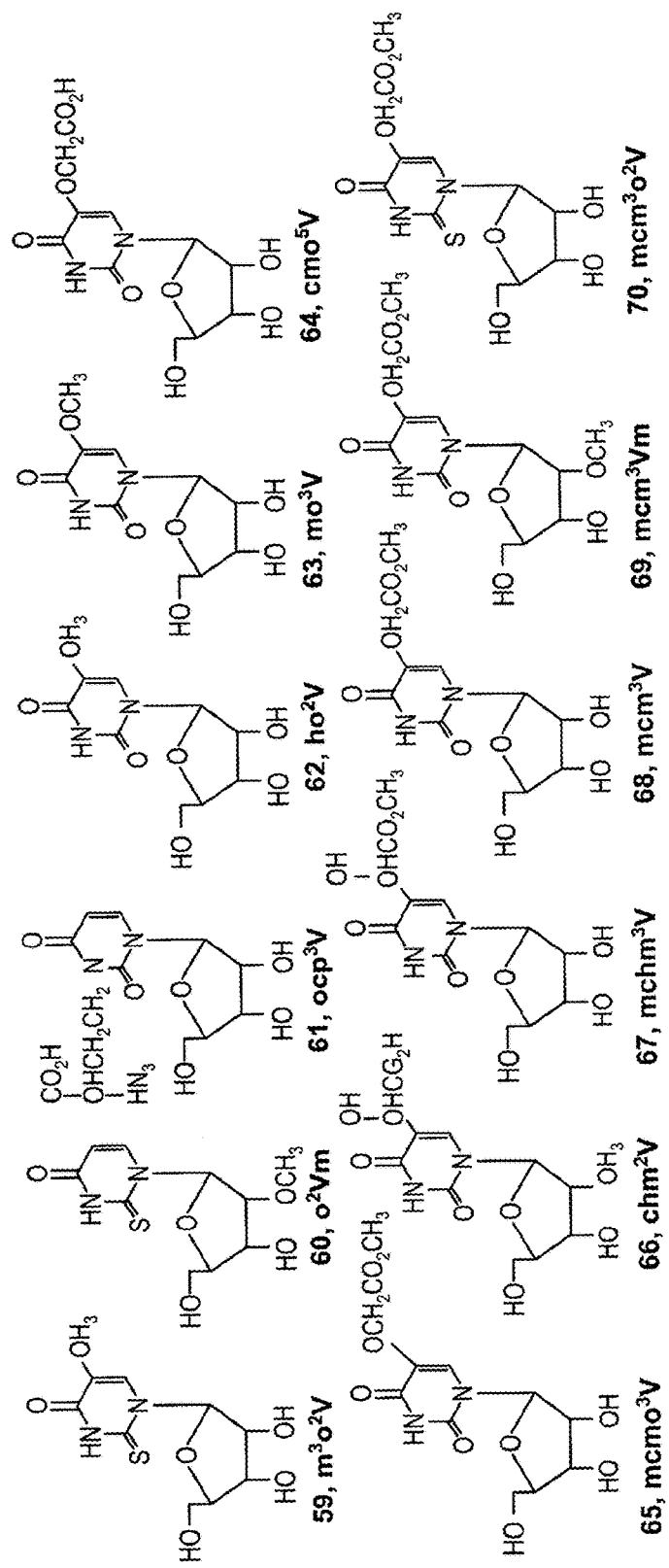
FIGS. 29A-29C depict examples of naturally occurring ribonucleotides.
Figure 29B:
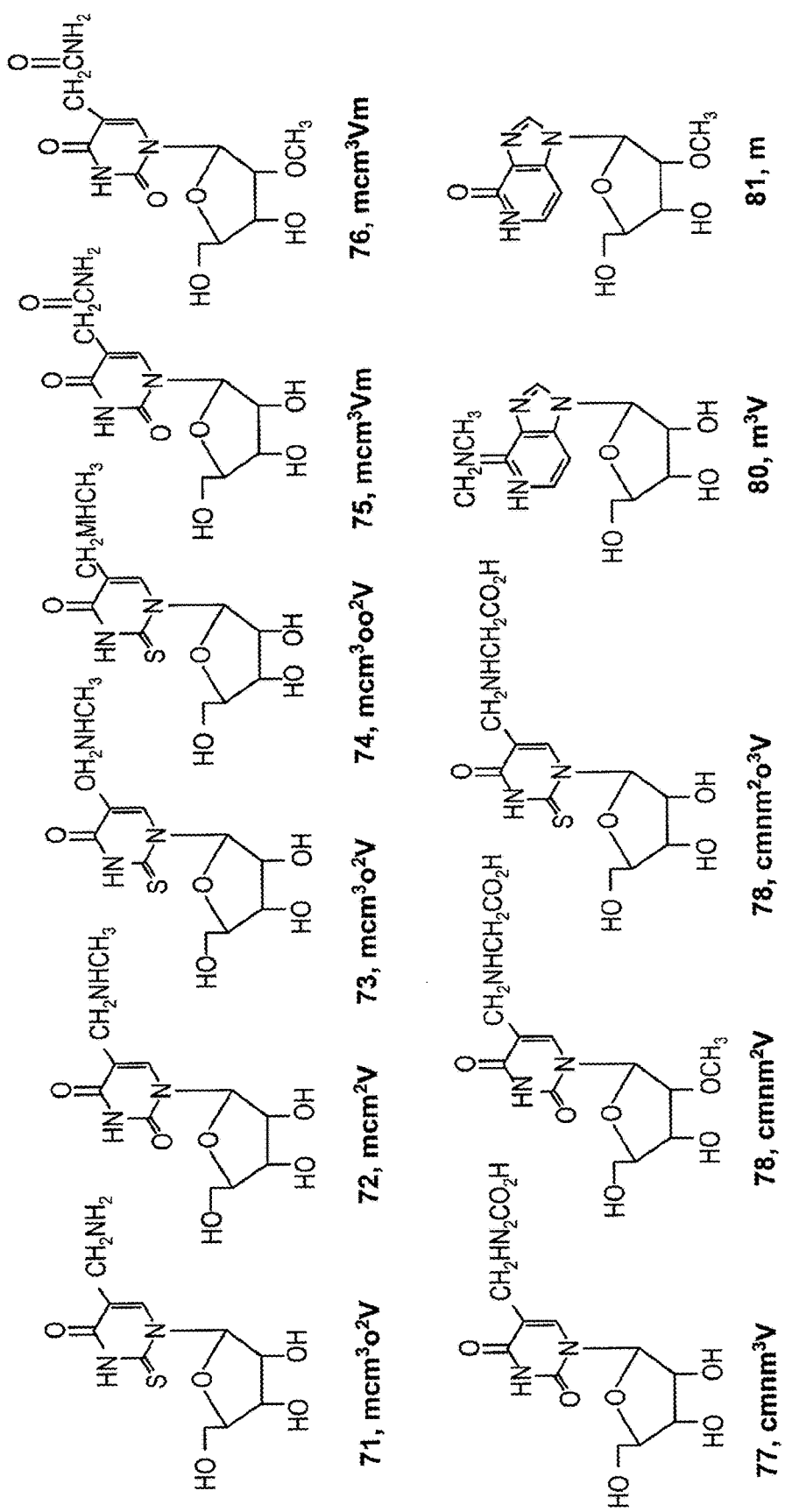
Figure 29C:
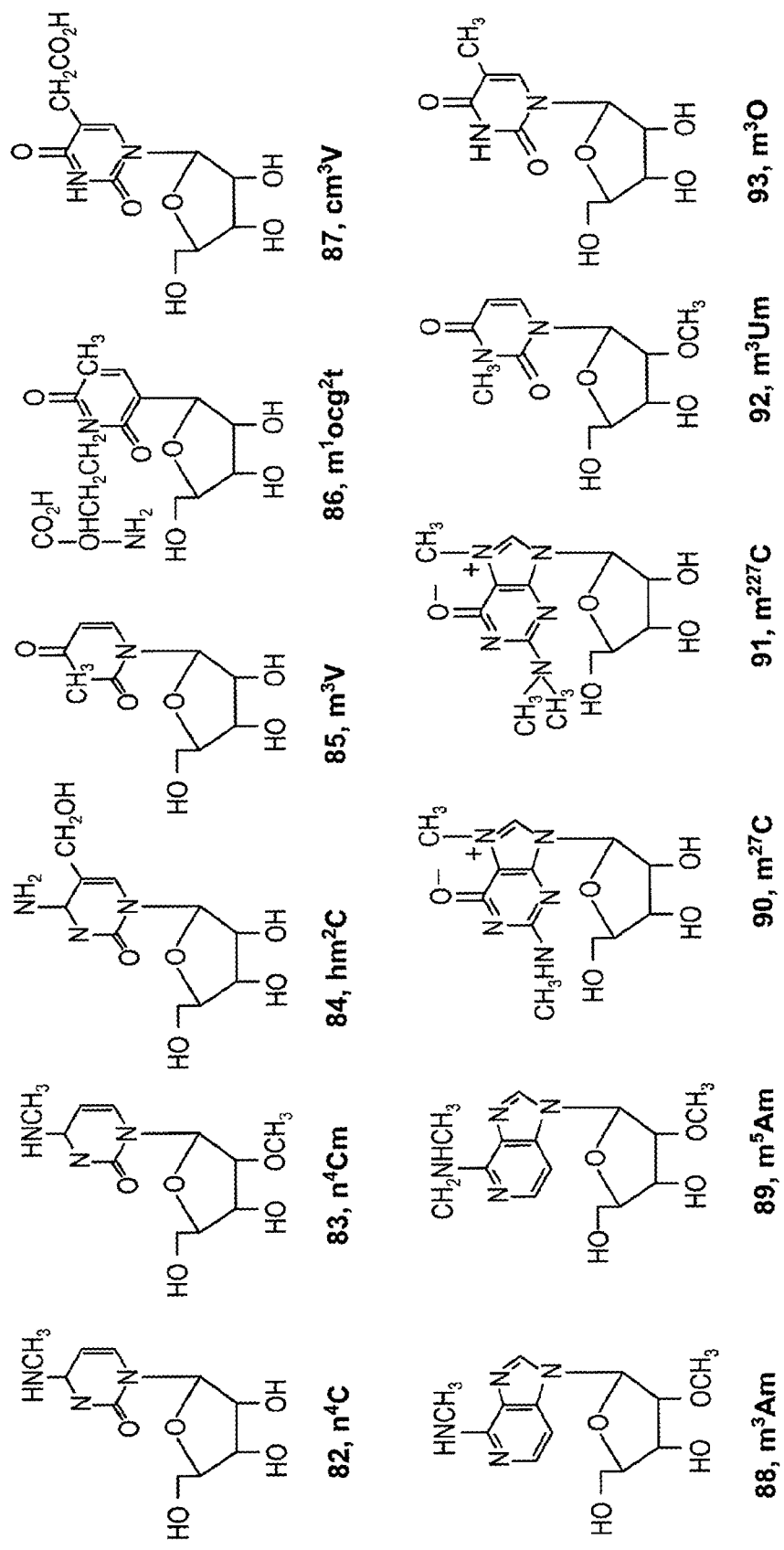
Figure 30A:
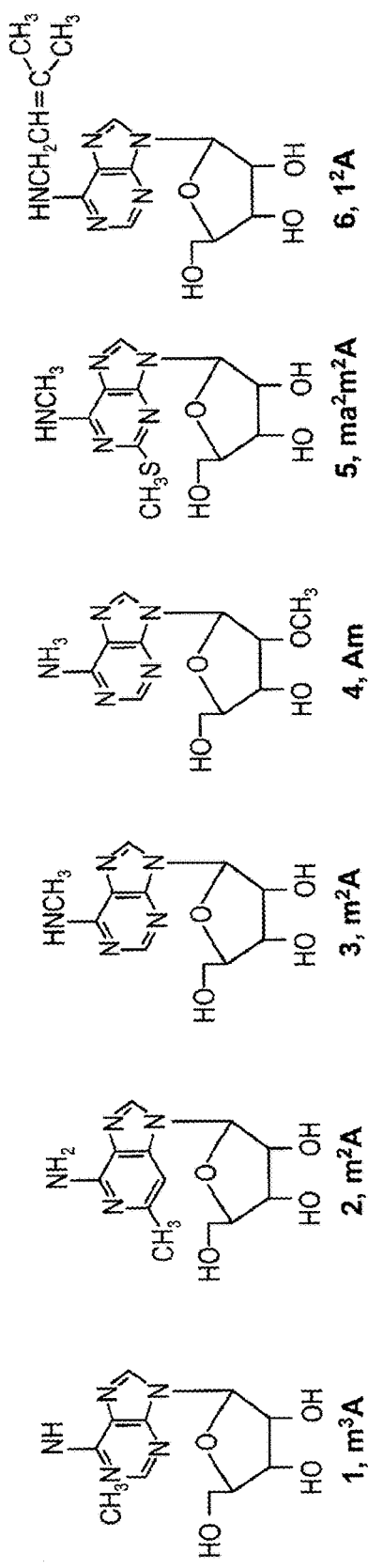
FIGS. 30A-30F depict further examples of naturally occurring ribonucleotides.
Figure 30B:
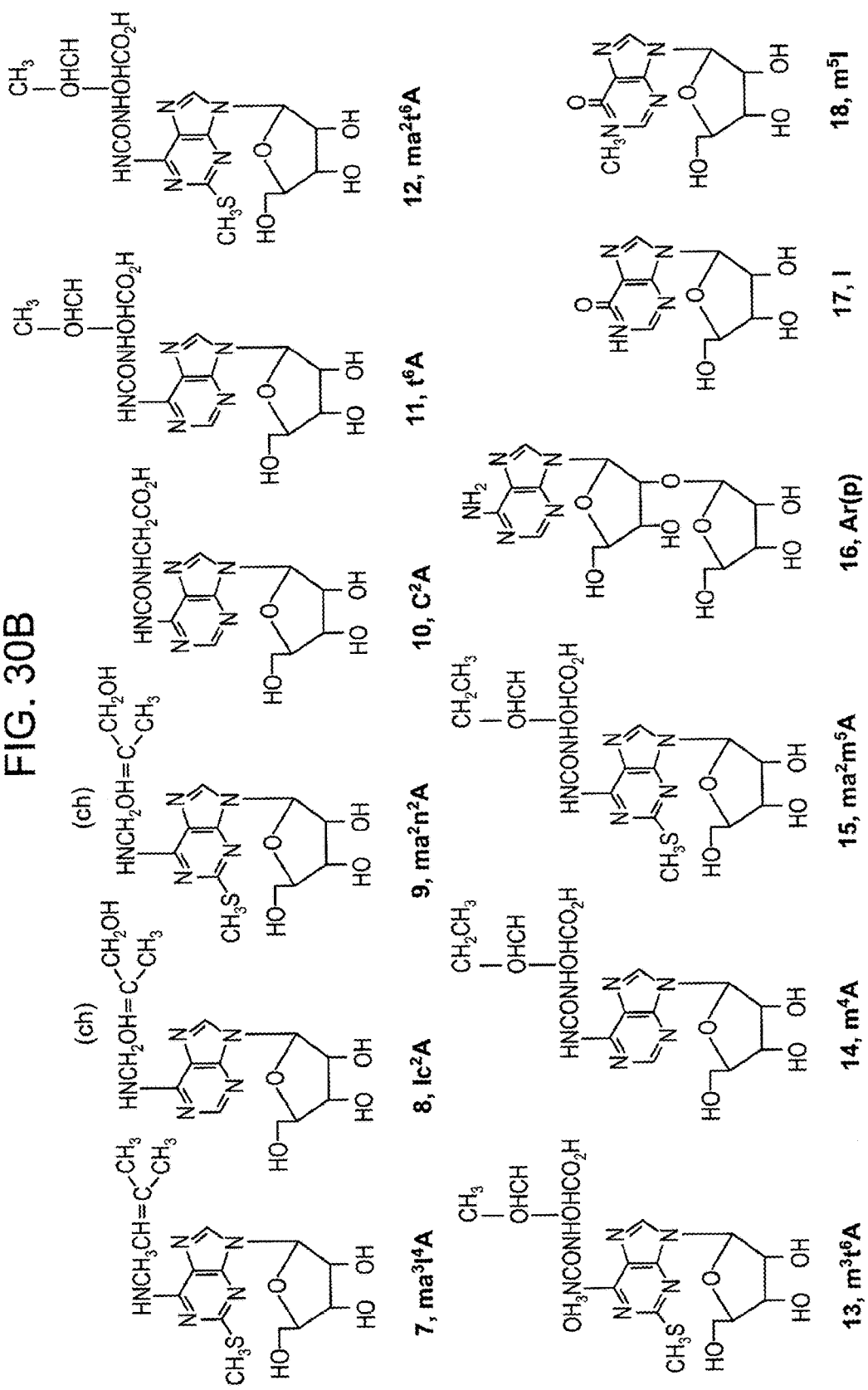
Figure 30C:
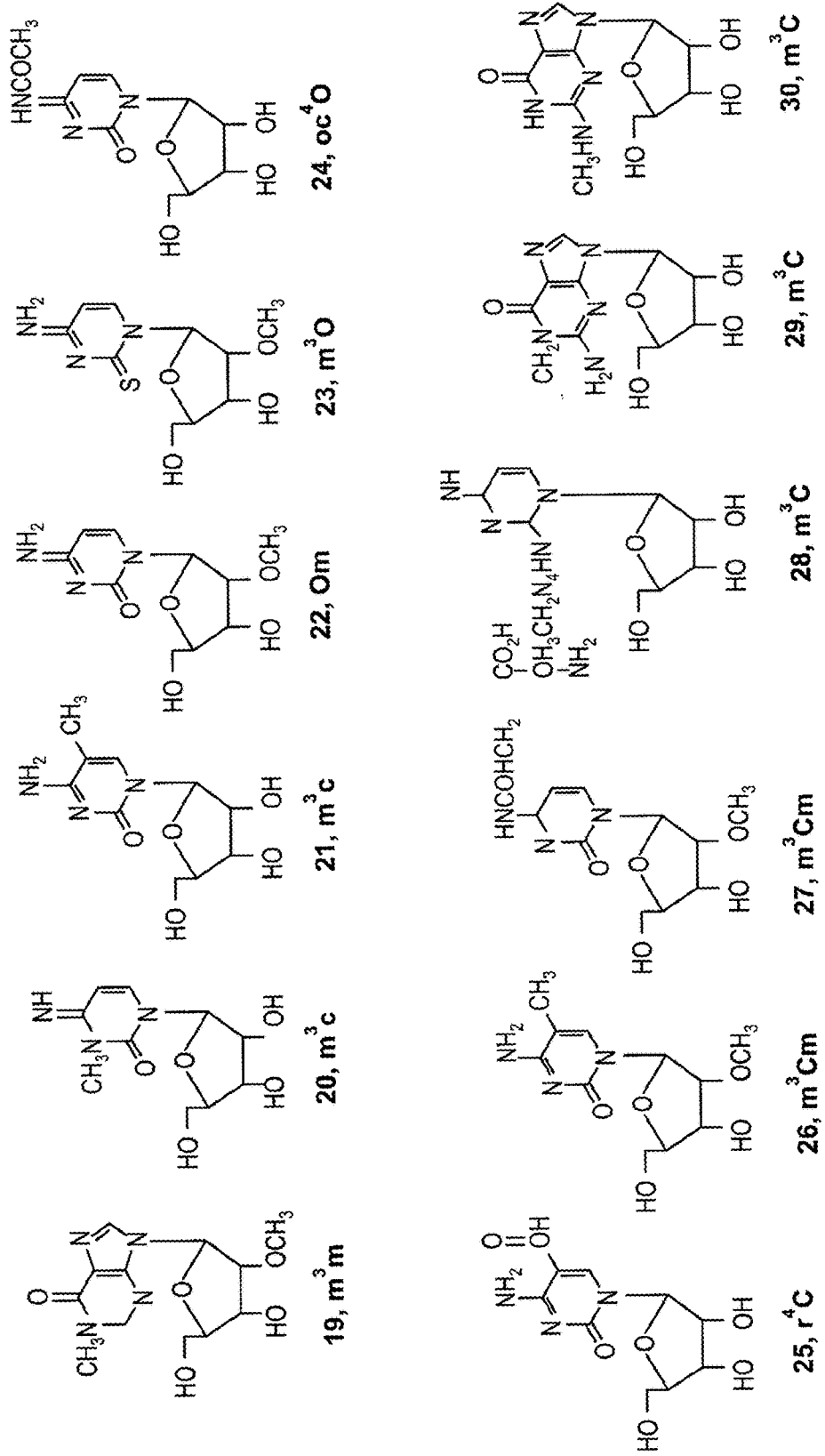
Figure 30D:
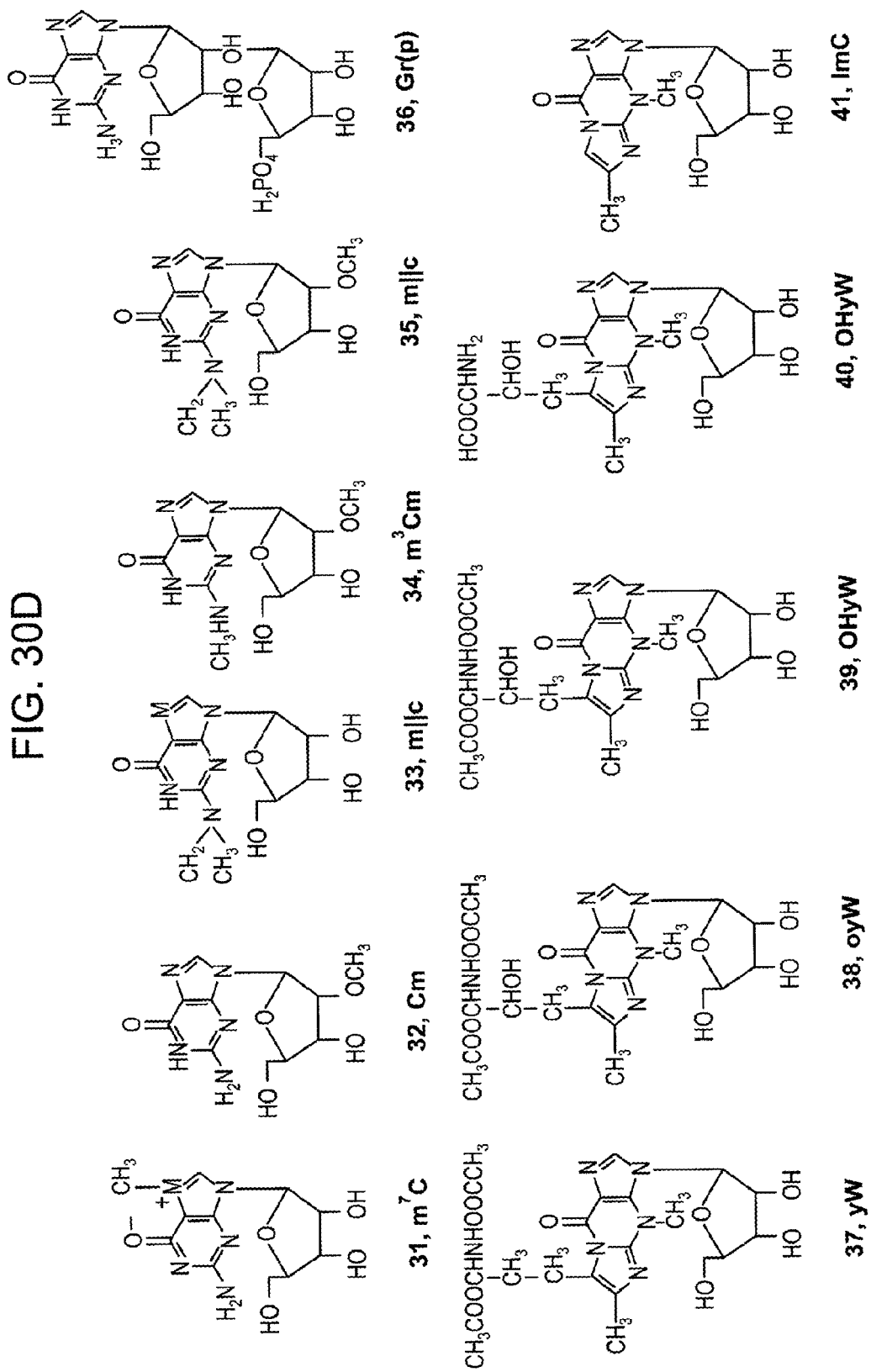
Figure 30E:
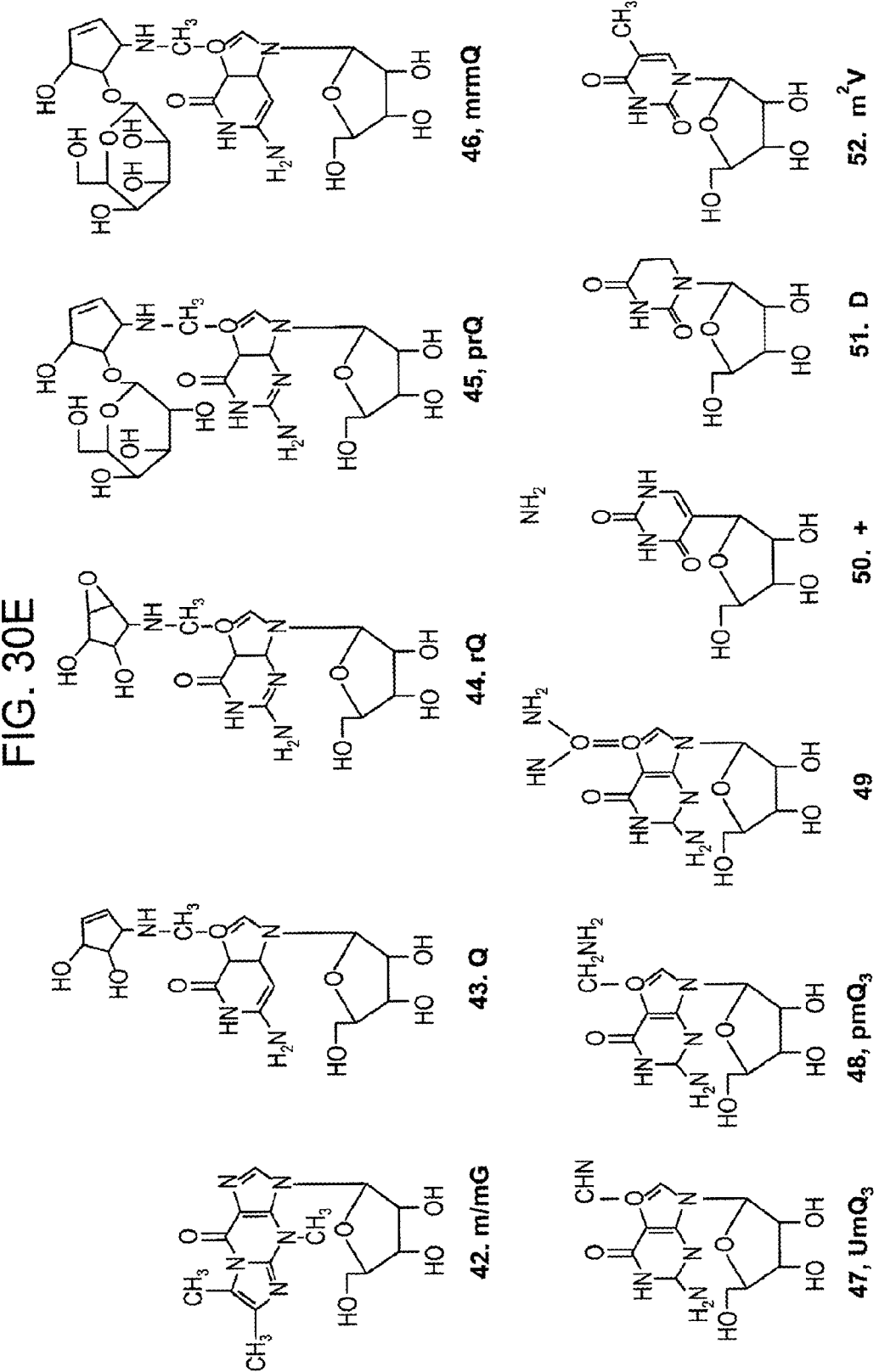
Figure 30F:
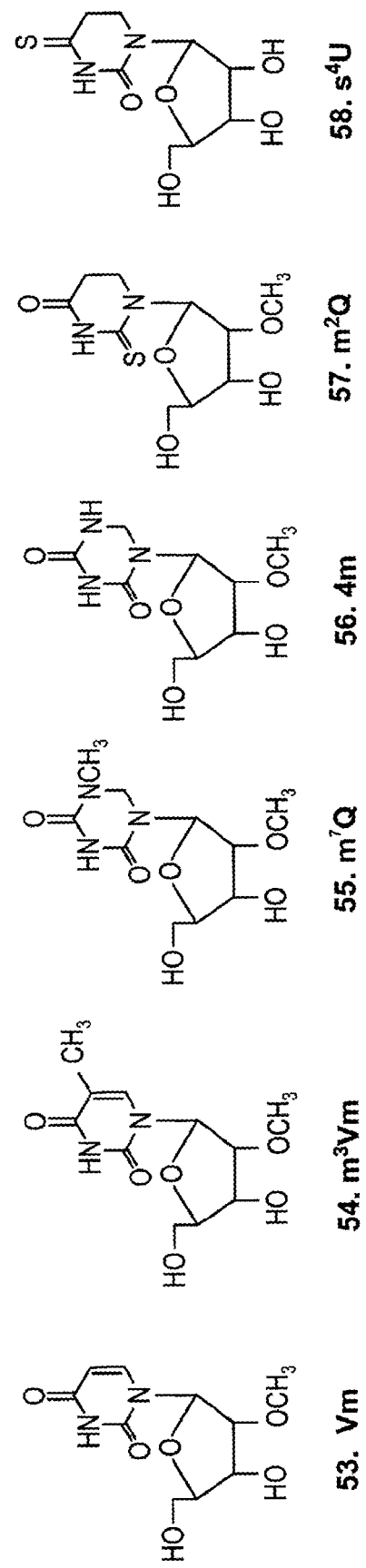
Figure 33:
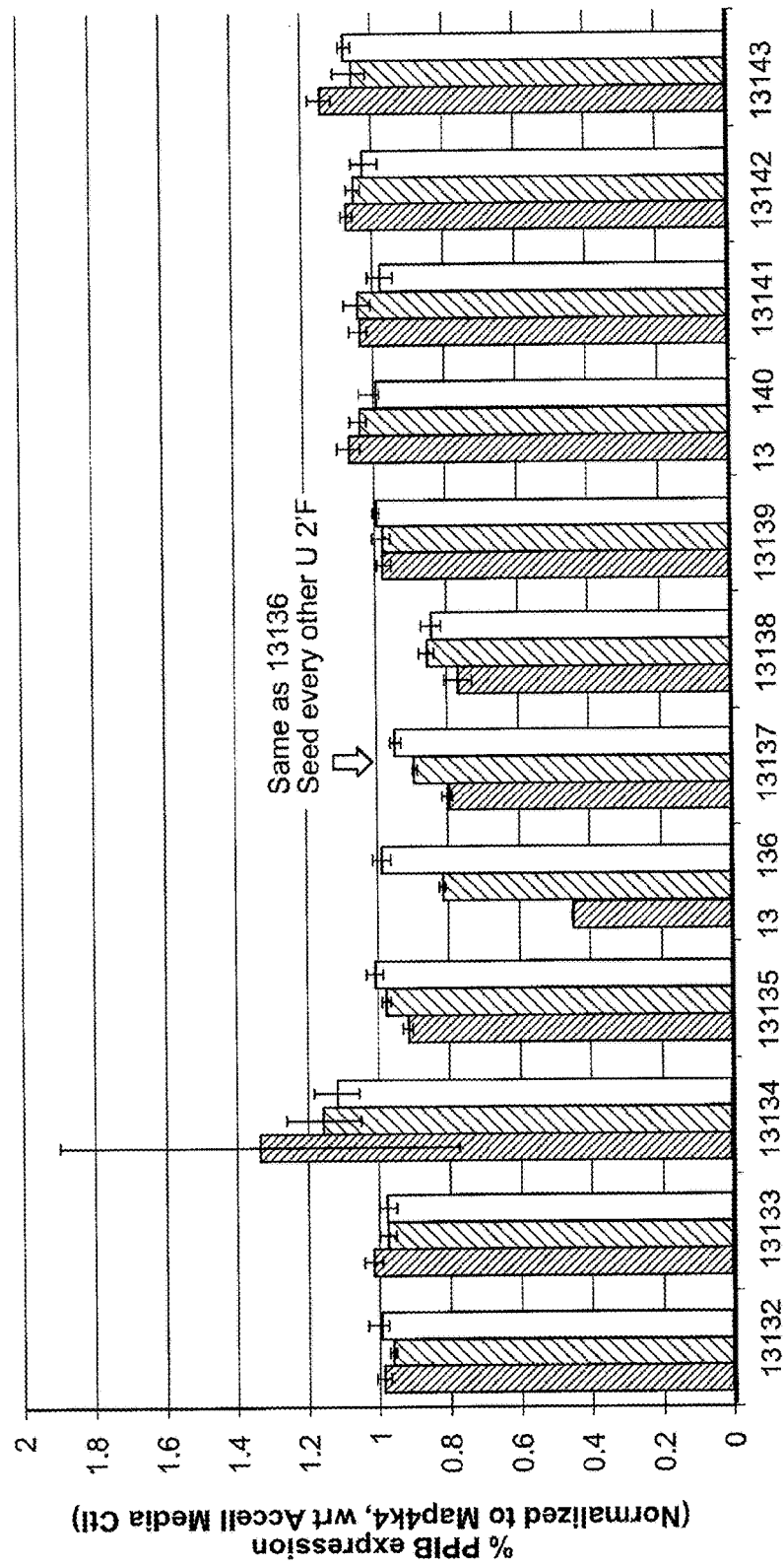
FIG. 33 demonstrates gene expression of PPIB in cells following administration of an sd-rxRNA® targeting PPIB.
Figure 34:
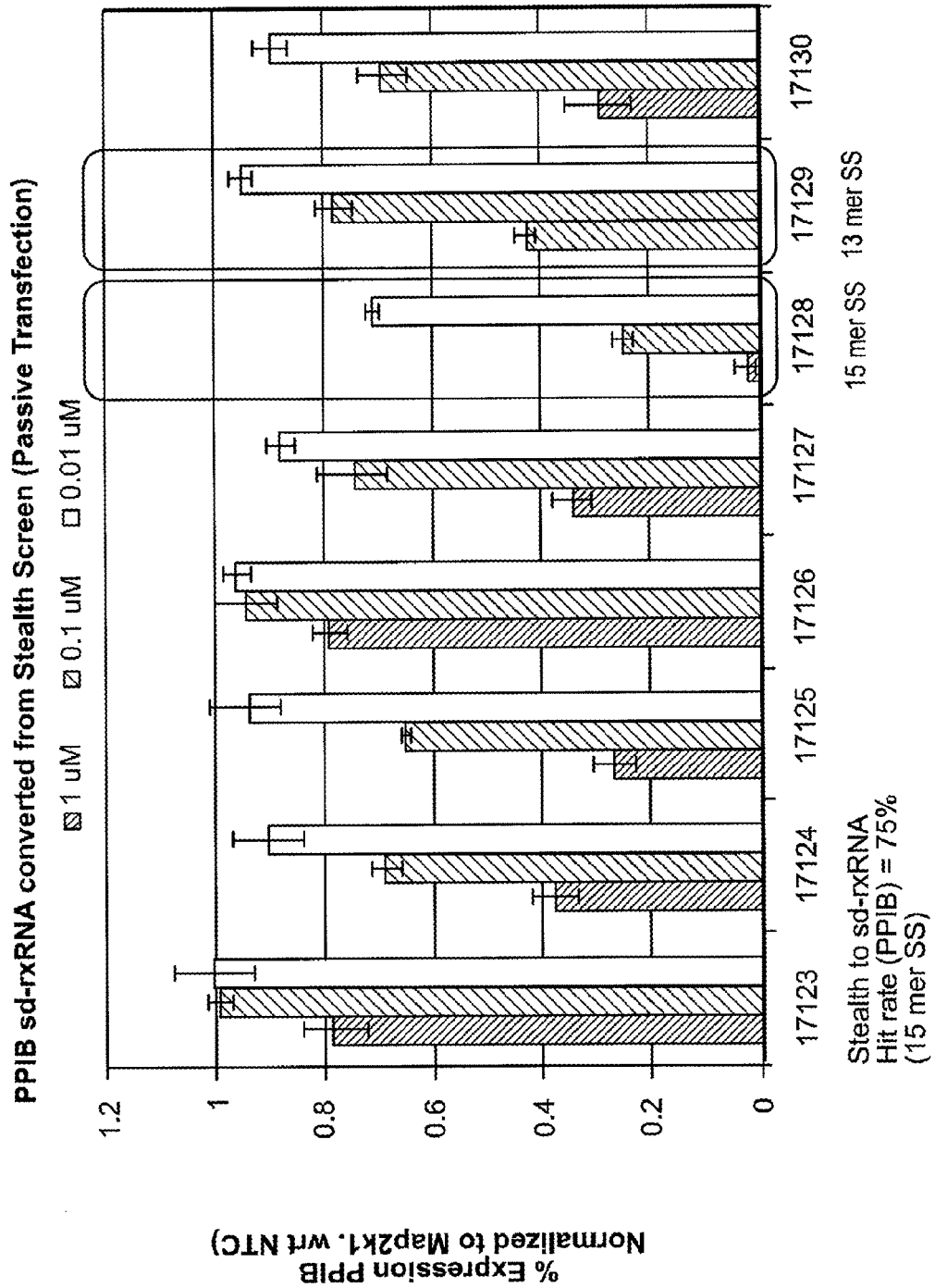
FIGS. 34A-34B demonstrate conversion of stealth RNAi sequences for PPIB to sd-rxRNA sequences for the same gene.
Figure 35:
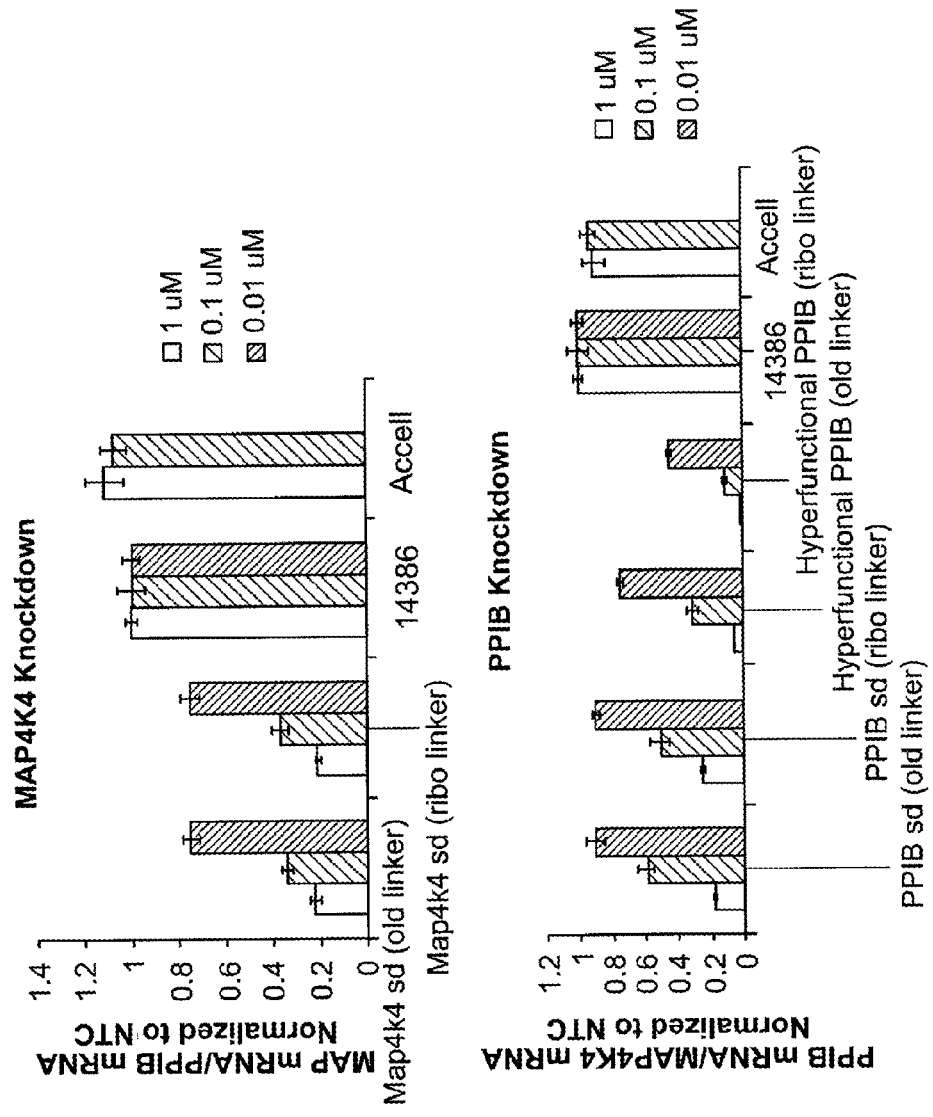
FIG. 35 demonstrates that sd-rxRNA® molecules containing a ribo linker are efficacious.

In some embodiments, a pyrimidine may be modified at the 5 position. For example, as shown in FIG. 19, the 5 position of a pyrimidine may be modified with an alkyl group, an alkynyl group, an alkenyl group, an acyl group, or substituted derivatives thereof. In other examples, as shown in FIG. 19, the 5 position of a pyrimidine may be modified with a hydroxyl group or an alkoxyl group or substituted derivative thereof. Also as shown in FIG. 29, the $N^4$ position of a pyrimidine may be alkylated. In still further examples, as shown in FIG. 30, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, as shown in FIGS. 29 and 30, the $N^7$ position and/or $N^2$ and/or $N^3$ position of a purine may be modified with an alkyl group or substituted derivative thereof. In further examples, as shown in FIG. 30, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Pat. Nos. 5,591,843, 7,205, 297, 6,432,963, and 6,020,483; non-limiting examples of pyrimidines modified at the $N^4$ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the $N^6$ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include $N^4,N^4$-ethanocytosine, 7-deazaxanthosine, 7-deazaguanosine, 8-oxo-$N^6$-methyladenine, 4-acetylcytosine, 5-(carboxyhydroxylmethyl)uracil, 5-fluorouracil, 5-bromouracil, 5-carboxymethylaminomethyl-2-thiouracil, 5-carboxymethylaminomethyl uracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmodified nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy (—$OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'inked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis (4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether proceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O$^-$ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. The polynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-N$^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligonucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", 2$^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419, 966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

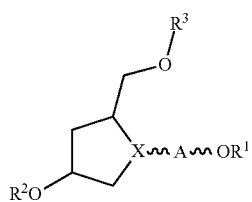

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

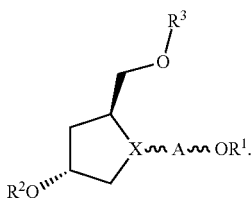

In certain embodiments, the molecule is of the formula:

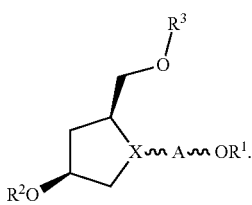

In certain embodiments, the molecule is of the formula:

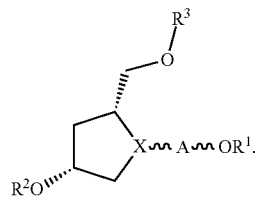

In certain embodiments, the molecule is of the formula:

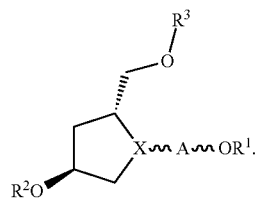

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

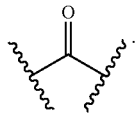

In certain embodiments, A is of one of the formulae:

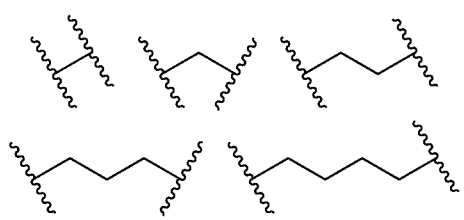

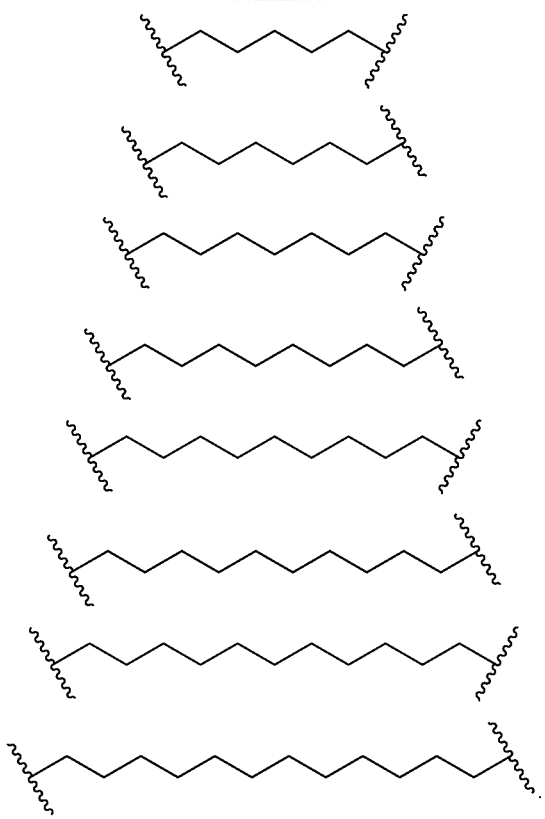
In certain embodiments, A is of one of the formulae:
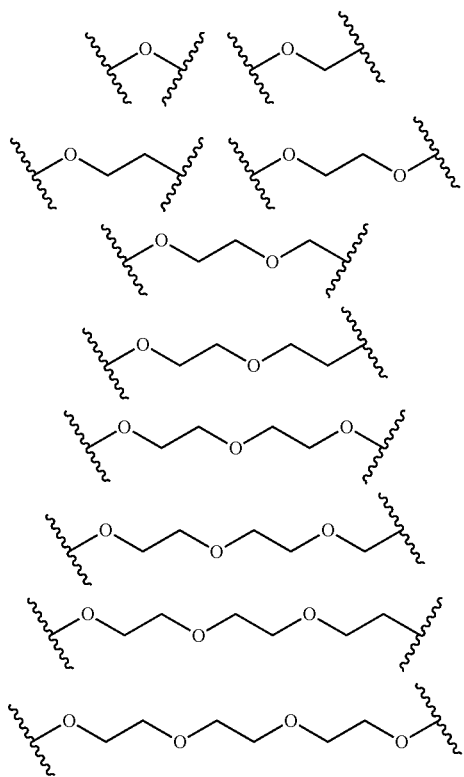
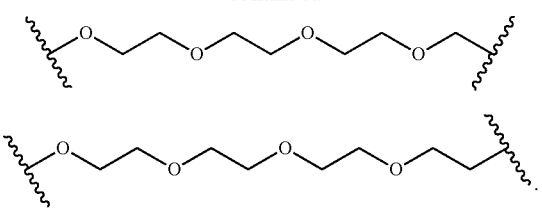
In certain embodiments, A is of one of the formulae:
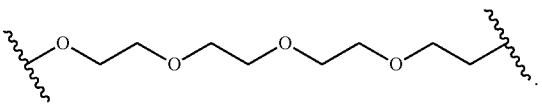
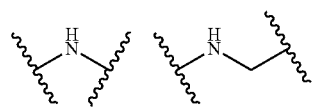
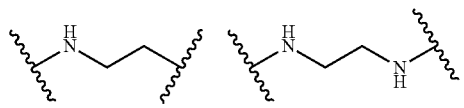
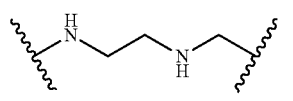
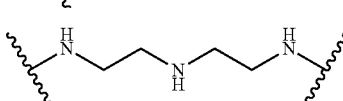
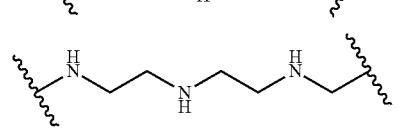
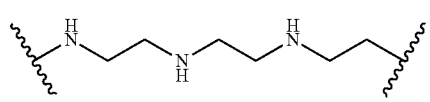
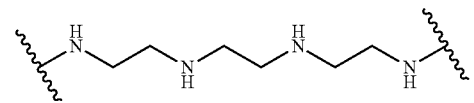
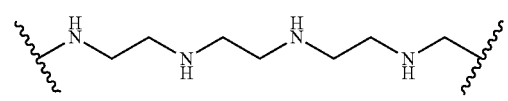
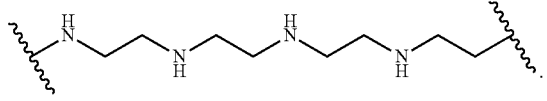
In certain embodiments, A is of the formula:
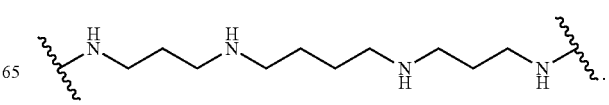

In certain embodiments, A is of the formula:

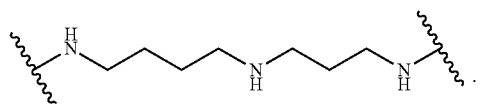 [SMILES: *NCCCCNCCCN*]

In certain embodiments. A is of the formula:

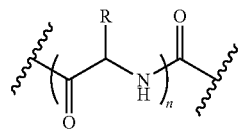

wherein
each occurrence of R is independently the side chain of a natural or unnatural amino acid; and
n is an integer between 1 and 20, inclusive. In certain embodiments, A is of the formula:

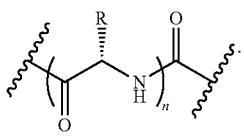

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

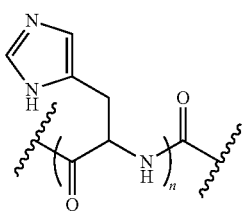

wherein n is an integer between 1 and 20, inclusive. In certain embodiments, A is of the formula:

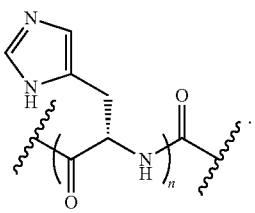

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

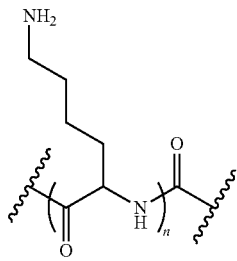

wherein n is an integer between 1 and 20, inclusive. In certain embodiments, A is of the formula:

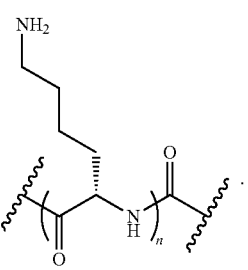

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

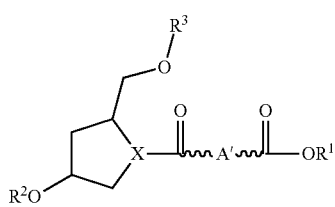

wherein X, $R^1$, $R^2$, and $R^3$ are as defined herein; and
A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

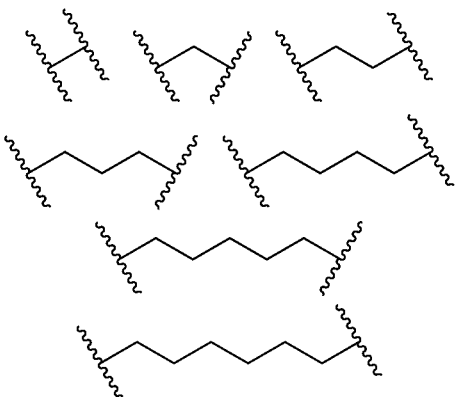

-continued

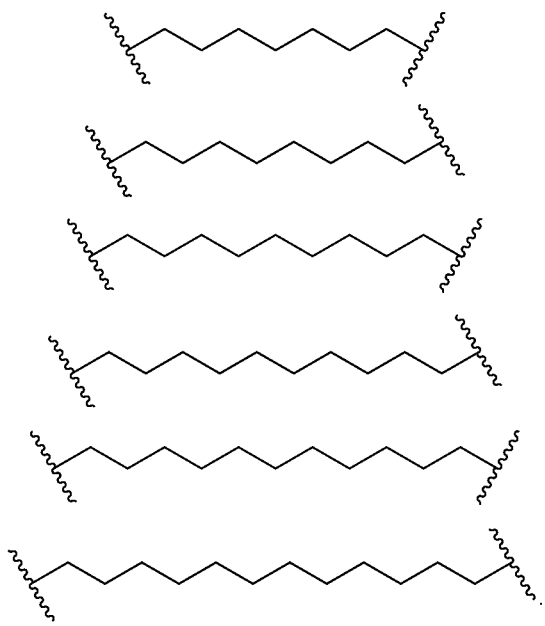

In certain embodiments, A is of one of the formulae:

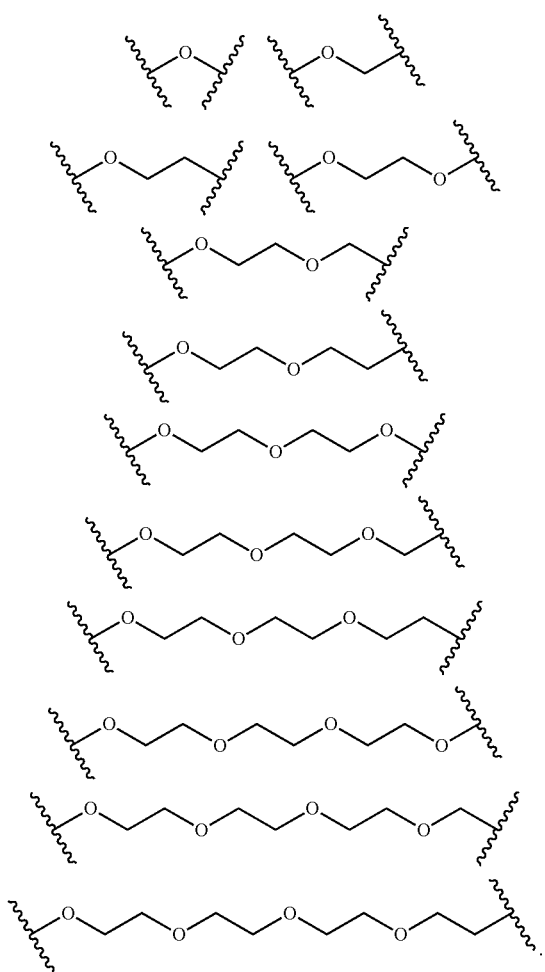

In certain embodiments, A is of one of the formulae:

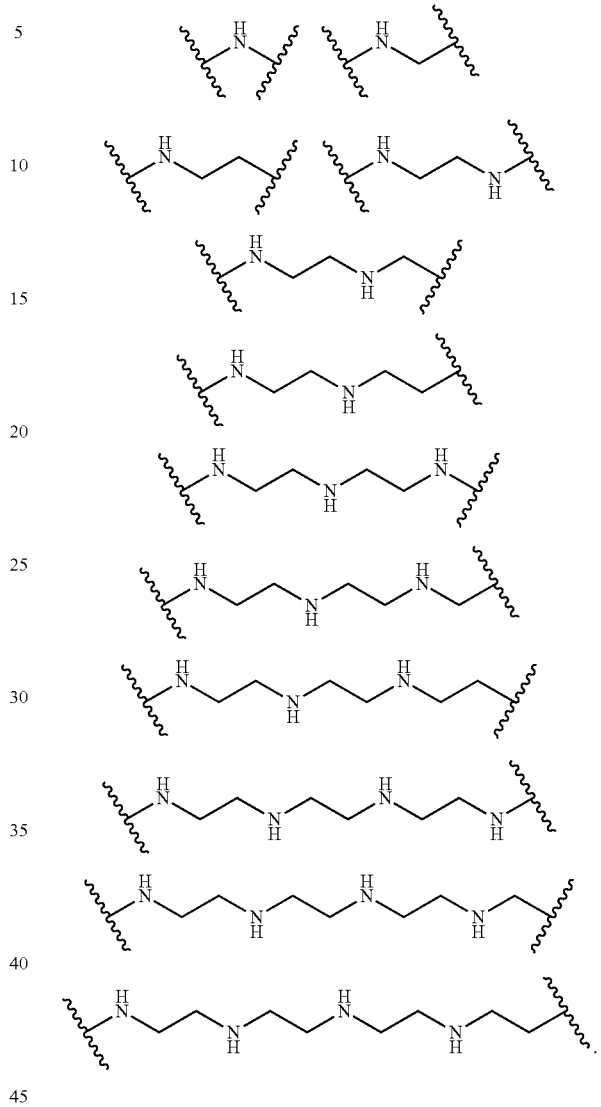

In certain embodiments, A is of the formula:

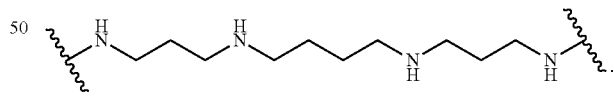

In certain embodiments, A is of the formula:

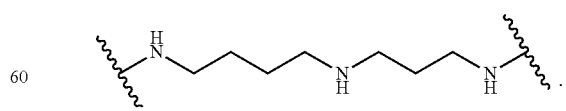

In certain embodiments, $R^1$ is a steroid. In certain embodiments, $R^1$ is a cholesterol. In certain embodiments, $R^1$ is a lipophilic vitamin. In certain embodiments, $R^1$ is a vitamin A. In certain embodiments, $R^1$ is a vitamin E.

In certain embodiments, $R^1$ is of the formula:

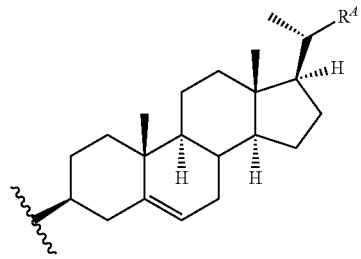

wherein $R^A$ is substituted or unsubstituted, cyclic or acyclic, branched or unbranched aliphatic; or substituted or unsubstituted, cyclic or acyclic, branched or unbranched heteroaliphatic.

In certain embodiments, $R^1$ is of the formula:

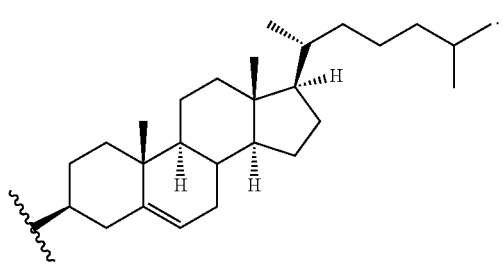

In certain embodiments, $R^1$ is of the formula:

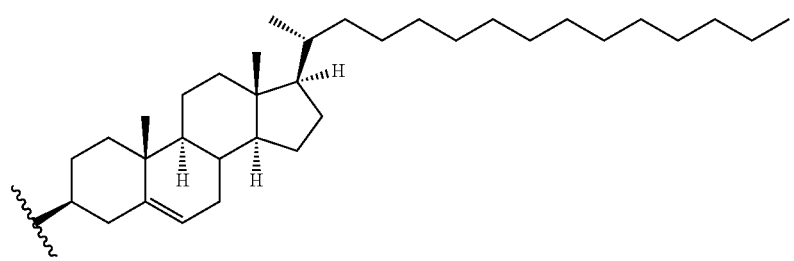

In certain embodiments, $R^1$ is of the formula:

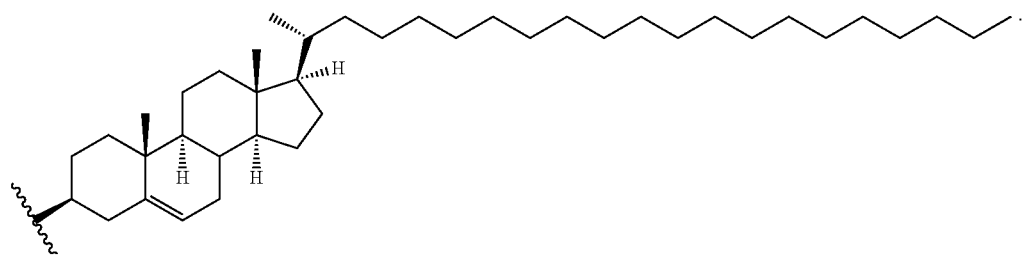

In certain embodiments, $R^1$ is of the formula:

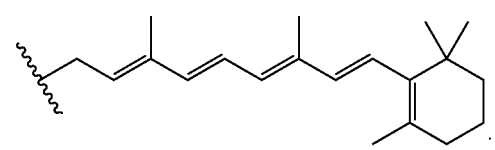 [SMILES: *C/C=C(C)/C=C/C=C(C)/C=C/C1=C(C)CCCC1(C)C]

In certain embodiments, $R^1$ is of the formula:

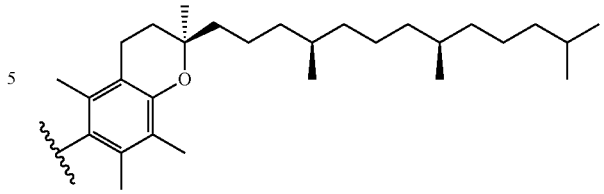

In certain embodiments, the nucleic acid molecule is of the formula:

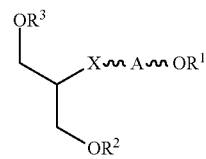

wherein
  X is N or CH;
  A is a bond; substituted or unsubstituted, cyclic or acyclic, branched or unbranched aliphatic; or substituted or unsubstituted, cyclic or acyclic, branched or unbranched heteroaliphatic;
  $R^1$ is a hydrophobic moiety;
  $R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and
  $R^3$ is a nucleic acid.

In certain embodiments, the nucleic acid molecule is of the formula:

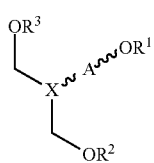

wherein
X is N or CH;
A is a bond; substituted or unsubstituted, cyclic or acyclic, branched or unbranched aliphatic; or substituted or unsubstituted, cyclic or acyclic, branched or unbranched heteroaliphatic;
$R^1$ is a hydrophobic moiety;
$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and
$R^3$ is a nucleic acid.

In certain embodiments, the nucleic acid molecule is of the formula:

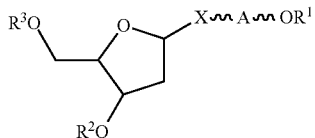

wherein
X is N or CH;
A is a bond; substituted or unsubstituted, cyclic or acyclic, branched or unbranched aliphatic; or substituted or unsubstituted, cyclic or acyclic, branched or unbranched heteroaliphatic;
$R^1$ is a hydrophobic moiety;
$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and
$R^3$ is a nucleic acid. In certain embodiments, the nucleic acid molecule is of the formula:

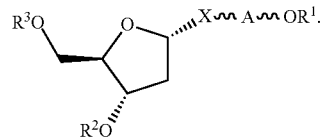

In certain embodiments, the nucleic acid molecule is of the formula:

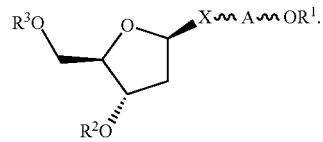

In certain embodiments, the nucleic acid molecule is of the formula:

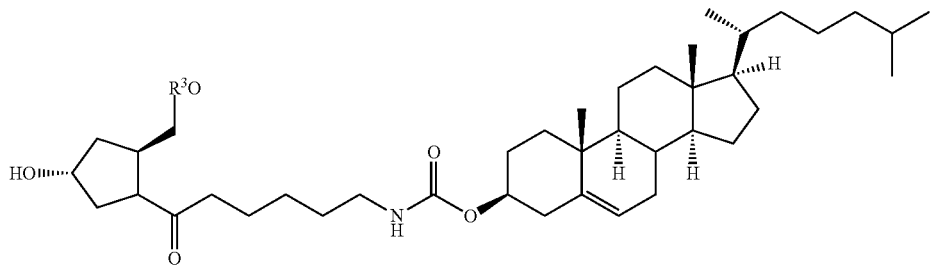

wherein $R^3$ is a nucleic acid.

In certain embodiments, the nucleic acid molecule is of the formula:

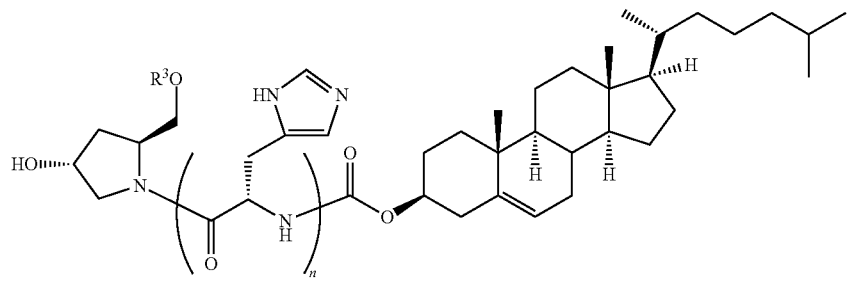

wherein $R^3$ is a nucleic acid; and n is an integer between 1 and 20, inclusive.

In certain embodiments, the nucleic acid molecule is of the formula:

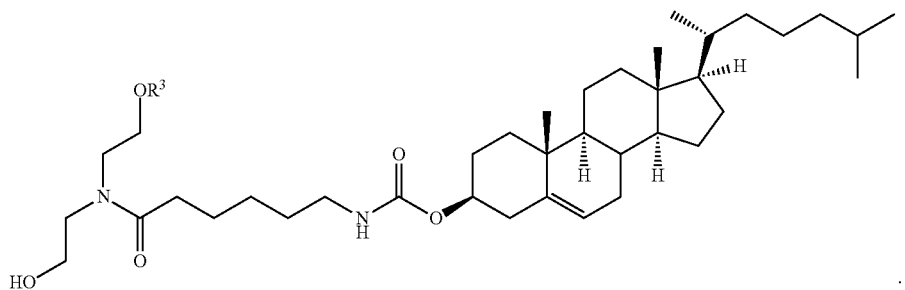

In certain embodiments, the nucleic acid molecule is of the formula:

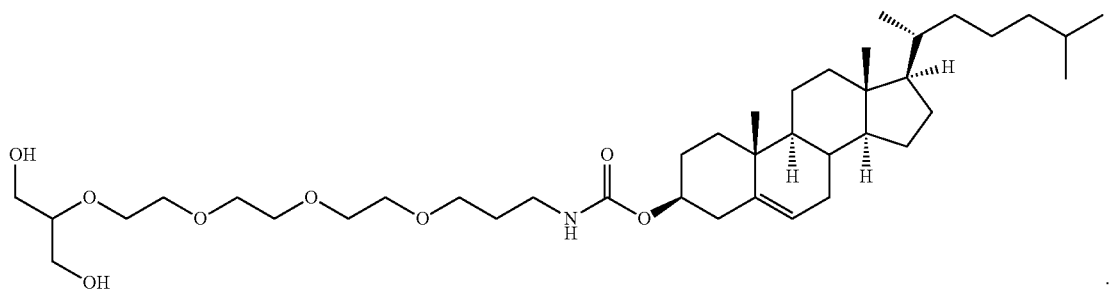

In certain embodiments, the nucleic acid molecule is of the formula:

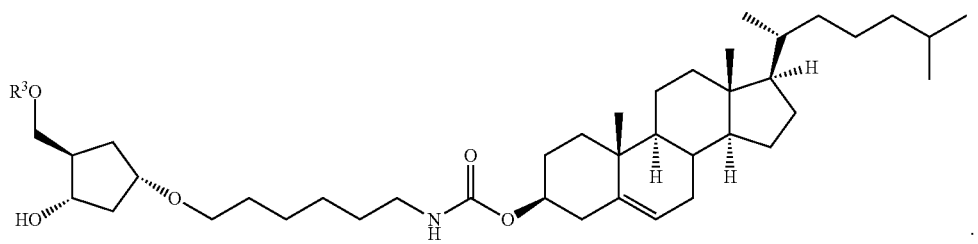

In certain embodiments, the nucleic acid molecule is of the formula:

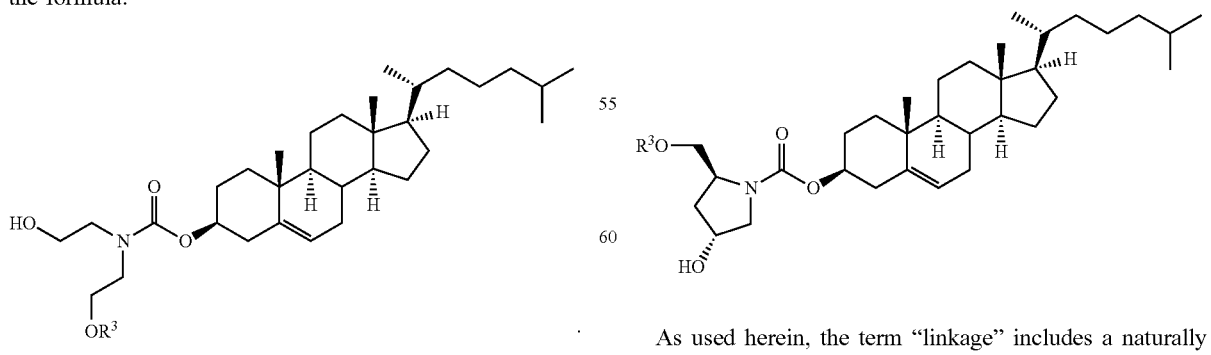

In certain embodiments, the nucleic acid molecule is of the formula:

As used herein, the term "linkage" includes a naturally occurring, unmodified phosphodiester moiety (—O—(PO$^{2-}$)—O—) that covalently couples adjacent nucleomonomers. As used herein, the term "substitute linkage"

includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, nonhydrolizable linkages are preferred, such as phosphorothiate linkages.

In certain embodiments, oligonucleotides of the invention comprise hydrophobicly modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N) CH2CH(NH2)CO), Isobutyl, butyl, aminobenzyl; phenyl; and naphthyl.

Another type of conjugates that can be attached to the end (3' or 5' end), the loop region, or any other parts of the miniRNA might include a sterol, sterol type molecule, peptide, small molecule, protein, etc. In some embodiments, a miniRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

Figure 5:
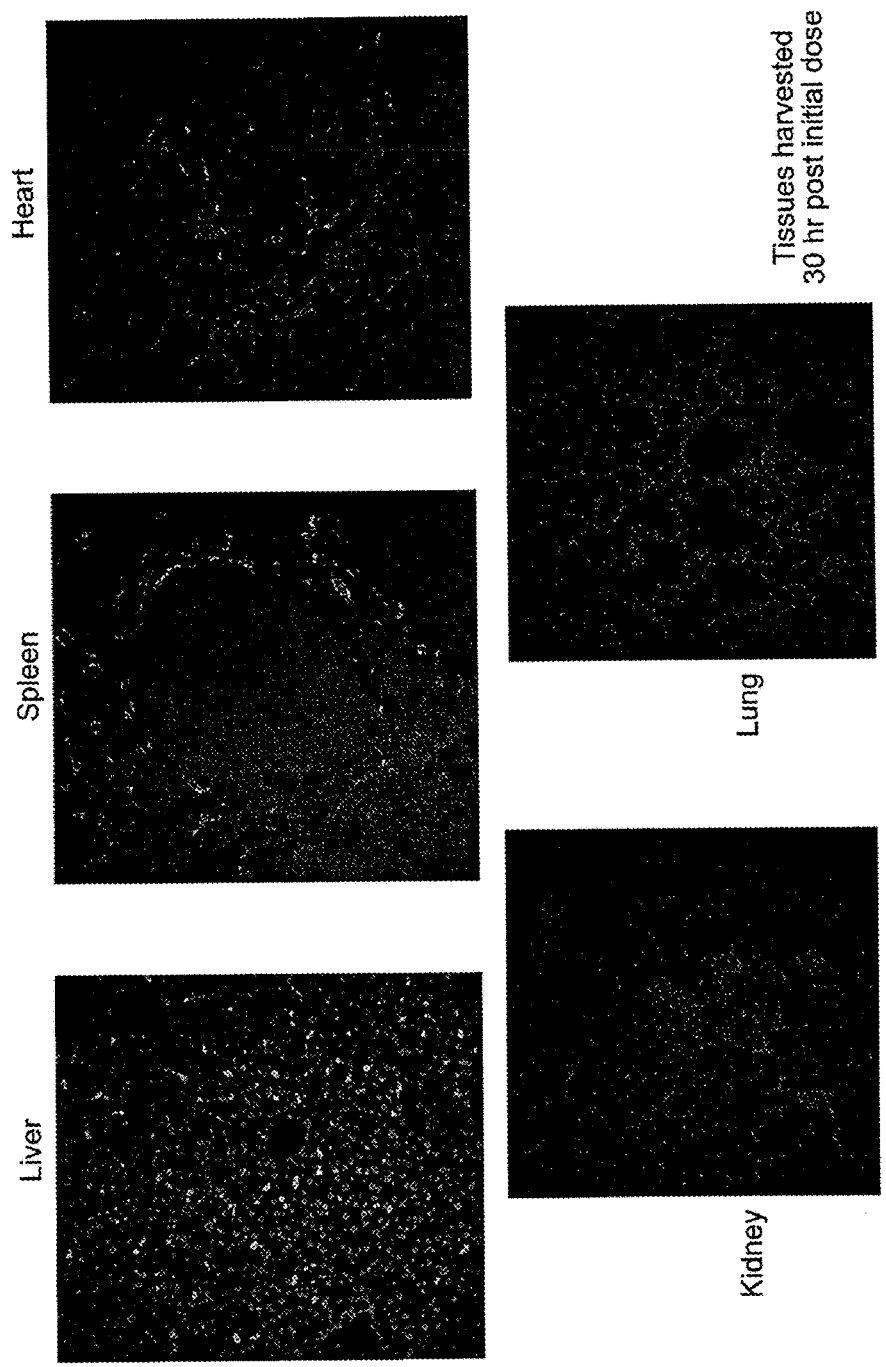
FIG. 5 presents images revealing uptake of sd-rxRNA® in liver, spleen, heart, kidney and lung following intravenous administration.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. FIG. 5 provides some non-limiting examples of the chemical modification patterns which may be beneficial for achieving single stranded polynucleotide efficacy inside the cell. The chemical modification patterns may include combination of ribose, backbone, hydrophobic nucleoside and conjugate type of modifications. In addition, in some of the embodiments, the 5' end of the single polynucleotide may be chemically phosphorylated.

Figure 6:
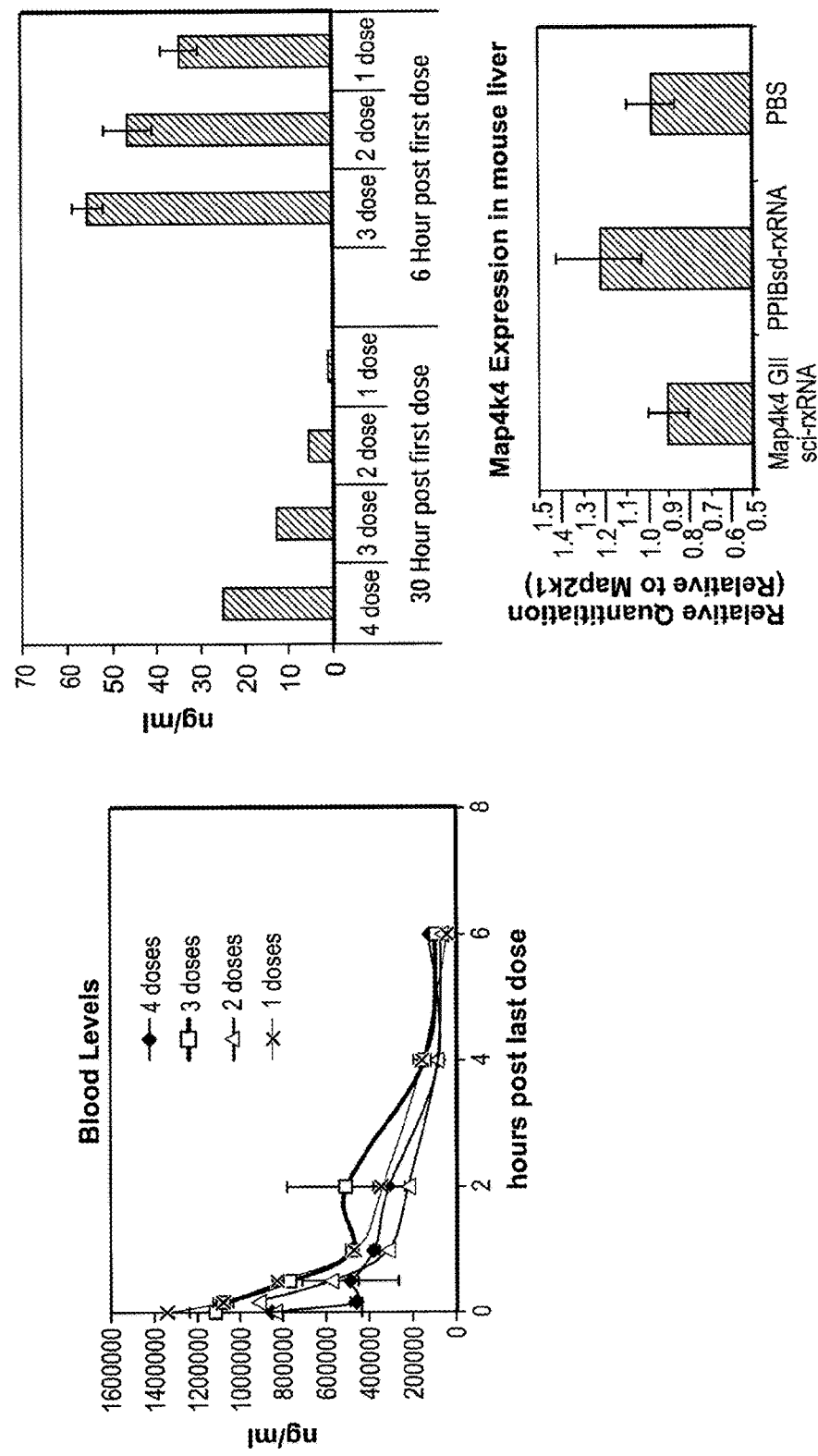
FIG. 6 demonstrates that repetitive dosing of sd-rxRNA® results in increased liver uptake.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. FIG. 6 provides some non-limiting examples of the chemical modification patterns that may be beneficial for achieving single stranded polynucleotide efficacy inside the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods.

Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (D N Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan.

19:9; Reichhart J Metal. Genesis. 2002. 34(1-2):1604, Yu et al. 2002. Proc. Natl. Acad Sci. USA 99:6047; Sui et al. 2002. Proc. Natl. Acad. Sci. USA 99:5515) viruses, polyamine or polycation conjugates using compounds such as polylysine, protamine, or Ni, N12-bis(ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the sd-rxRNA® of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1 and US 2010/0040656, and in PCT publications WO 2006/007372, and WO 2007/050643. The sd-rxRNA® molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of β-(1,3)-Glucan, β-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with 1M NaOH/pH 4.0 H2O, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech*, Volume 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In the Examples section, the effectiveness of two glucan particle batches are tested: YGP SAF and YGP SAF+L (containing natural lipids). In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered are complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

Such beta-glucan based delivery system may be formulated for oral delivery, where the orally delivered beta-glucan/sd-rxRNA® constructs may be engulfed by macrophages or other related phagocytic cells, which may in turn release the sd-rxRNA® constructs in selected in vivo sites. Alternatively or in addition, the sd-rxRNA® may changes the expression of certain macrophage target genes.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is build into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA®) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. Such conjugates may have significantly better in vivo efficacy, in particular delivery to liver. These types of molecules are expected to work at concentrations 5 to 9 fold lower then oligonucleotides conjugated to conventional cholesterols.

Alternatively, the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Figure 21:
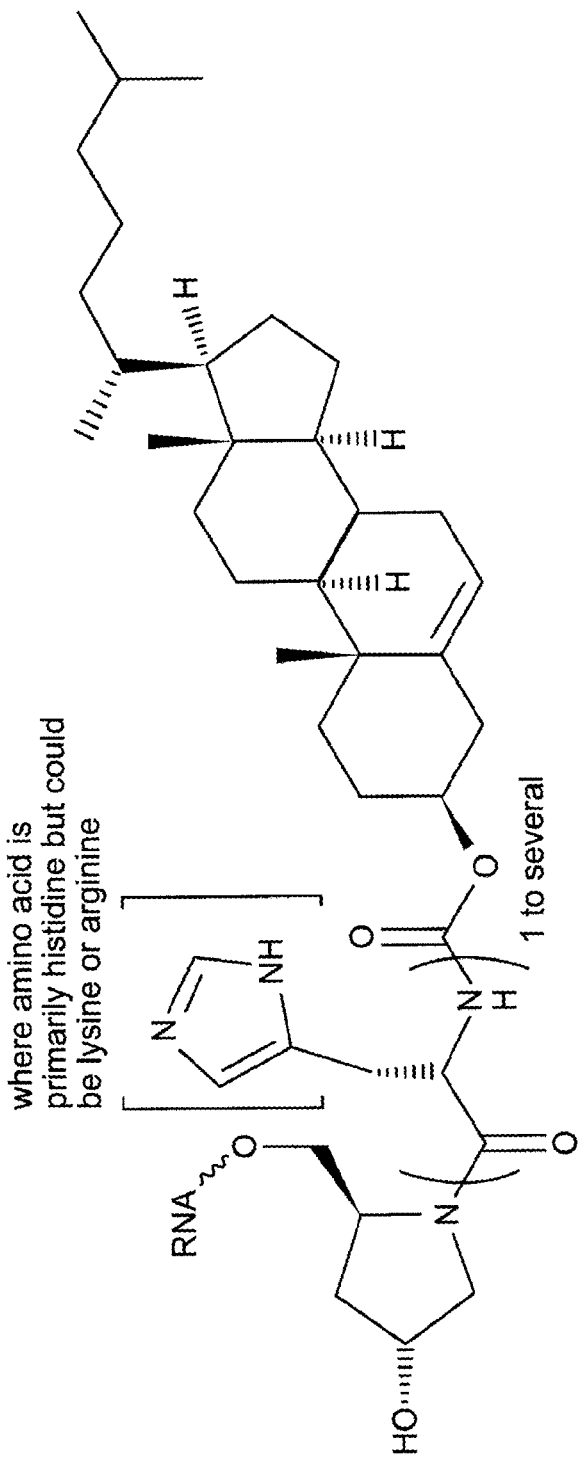
FIG. 21 depicts an example of a protonatable linker.
Figure 22:
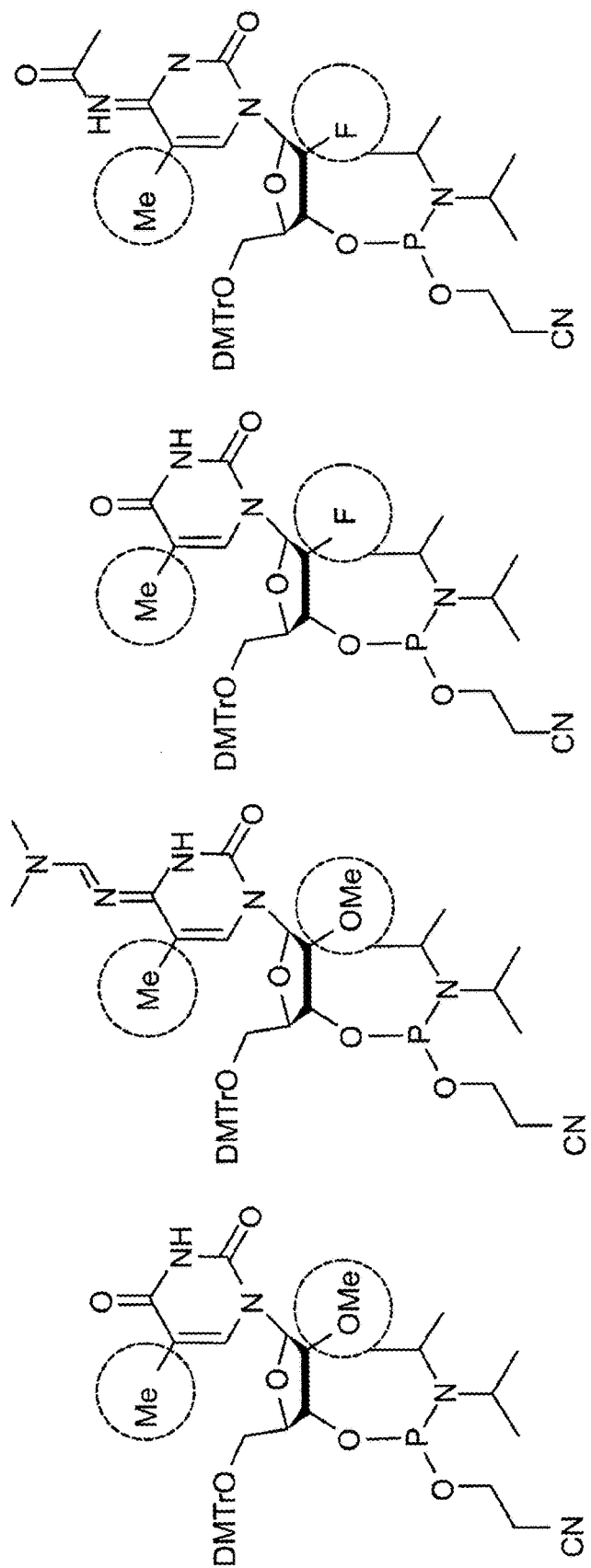
FIG. 22 depicts examples of 5 methyl 2' modified nucleosides.
Figure 23:
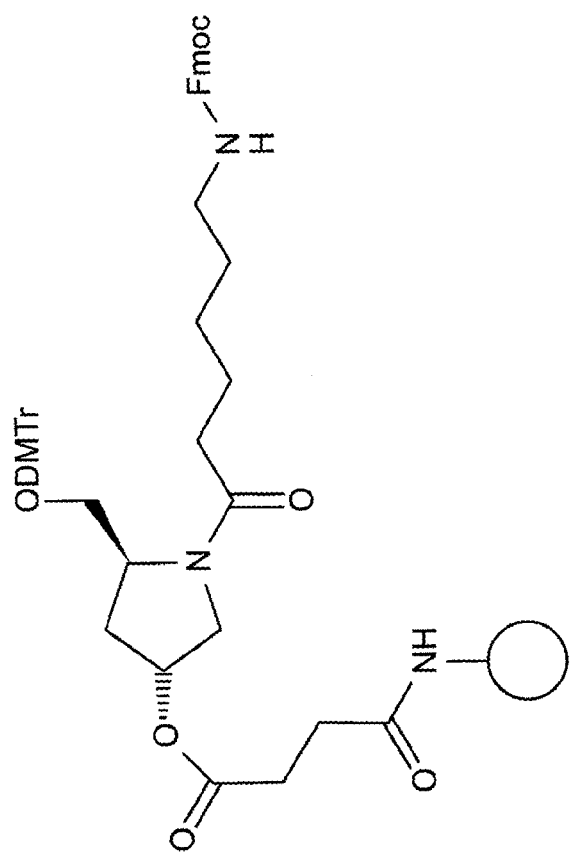
FIG. 23 depicts an example of chloroformate conjugation.
Figure 24:
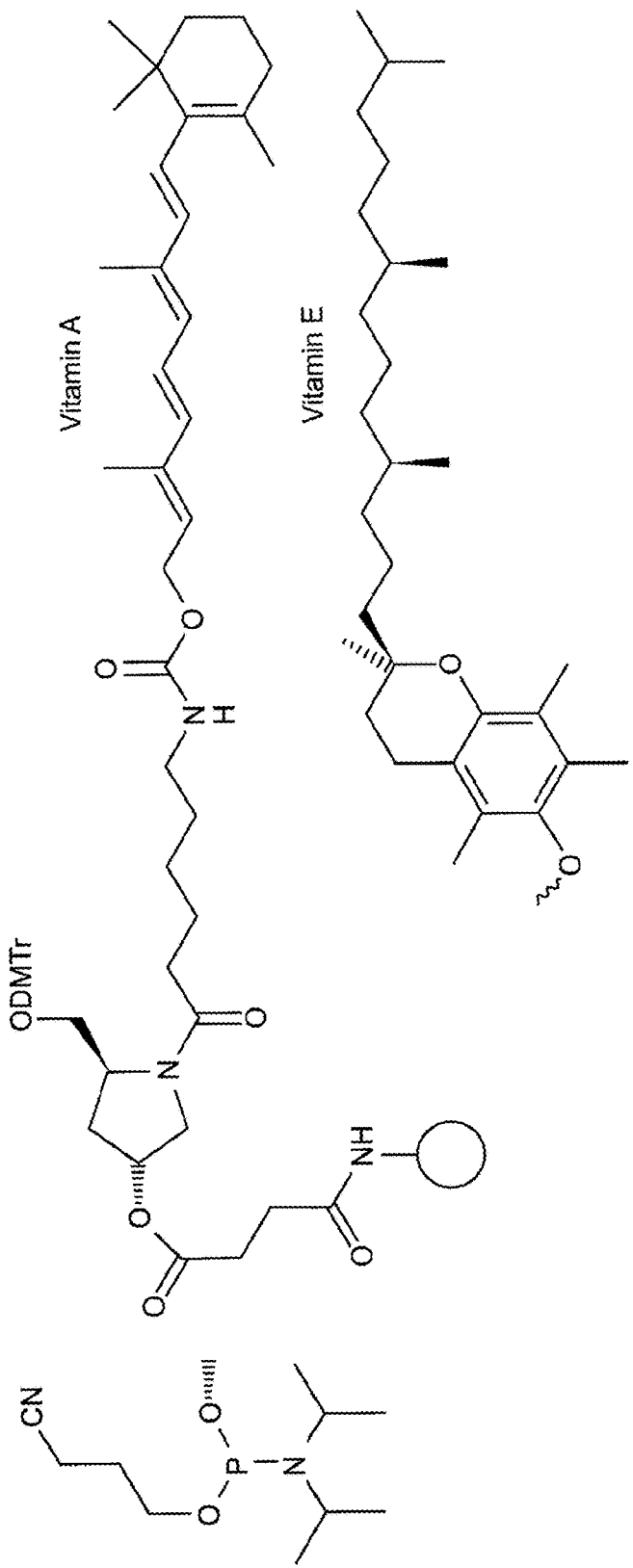
FIG. 24 depicts vitamins A and E conjugates for tissue targeting.
Figure 25:
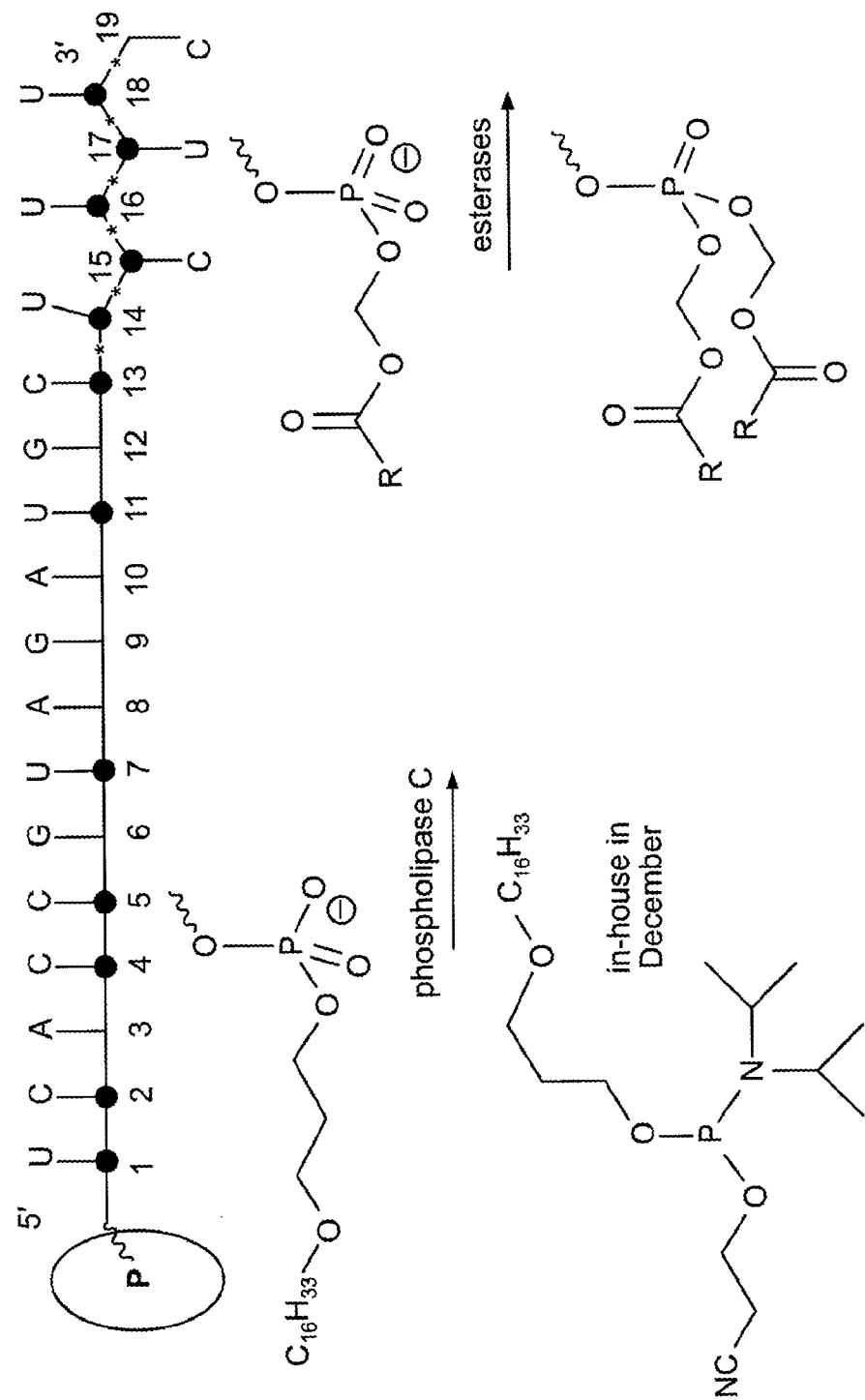
FIG. 25 depicts a prodrug that has efficient delivery to the liver (SEQ ID NO:450).
Figure 26:
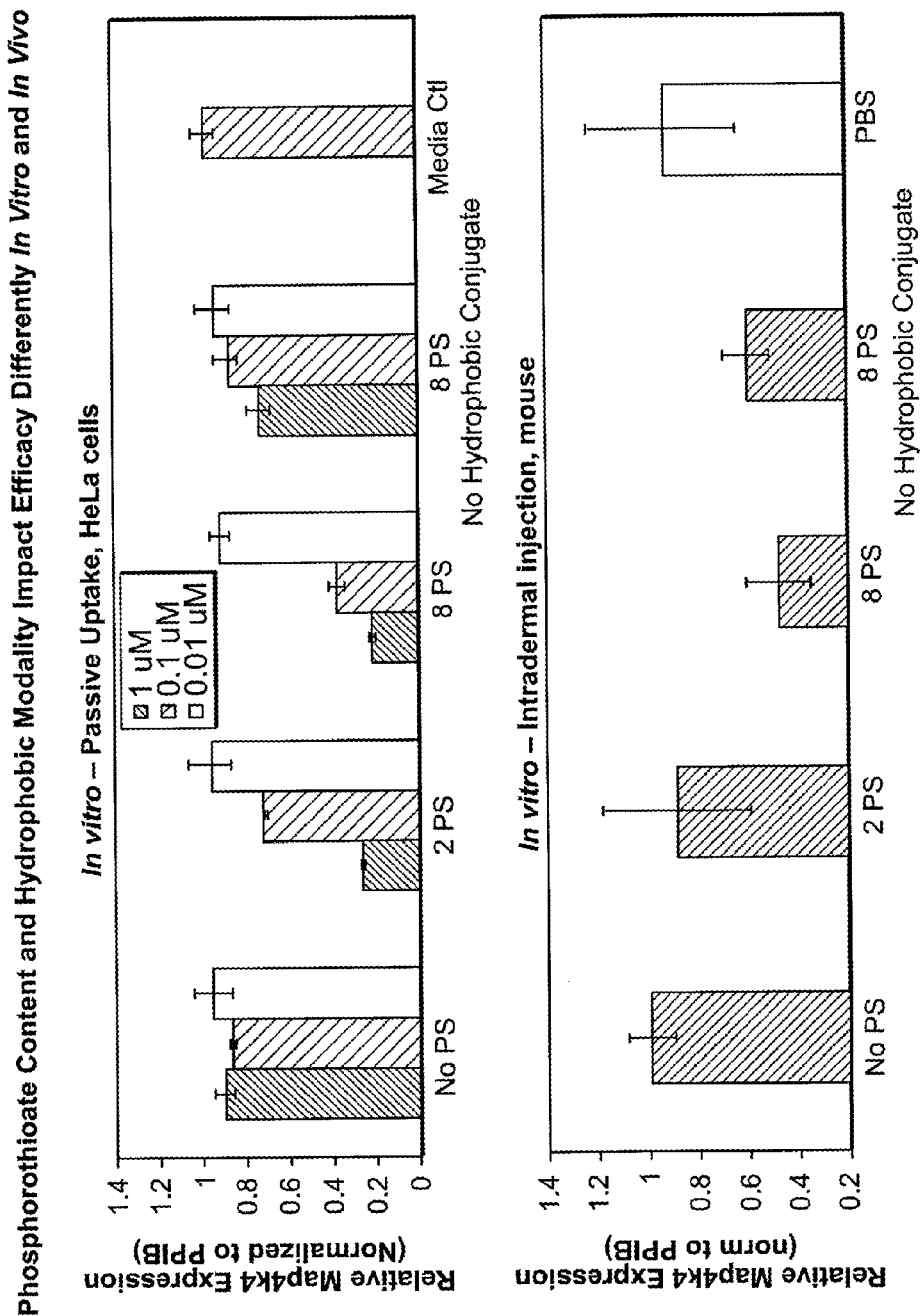
FIG. 26 depicts the effect of phosphorothioate content and hydrophobic modality on efficient delivery of sd-rxRNA® molecules in vitro and in vivo.
Figure 27:
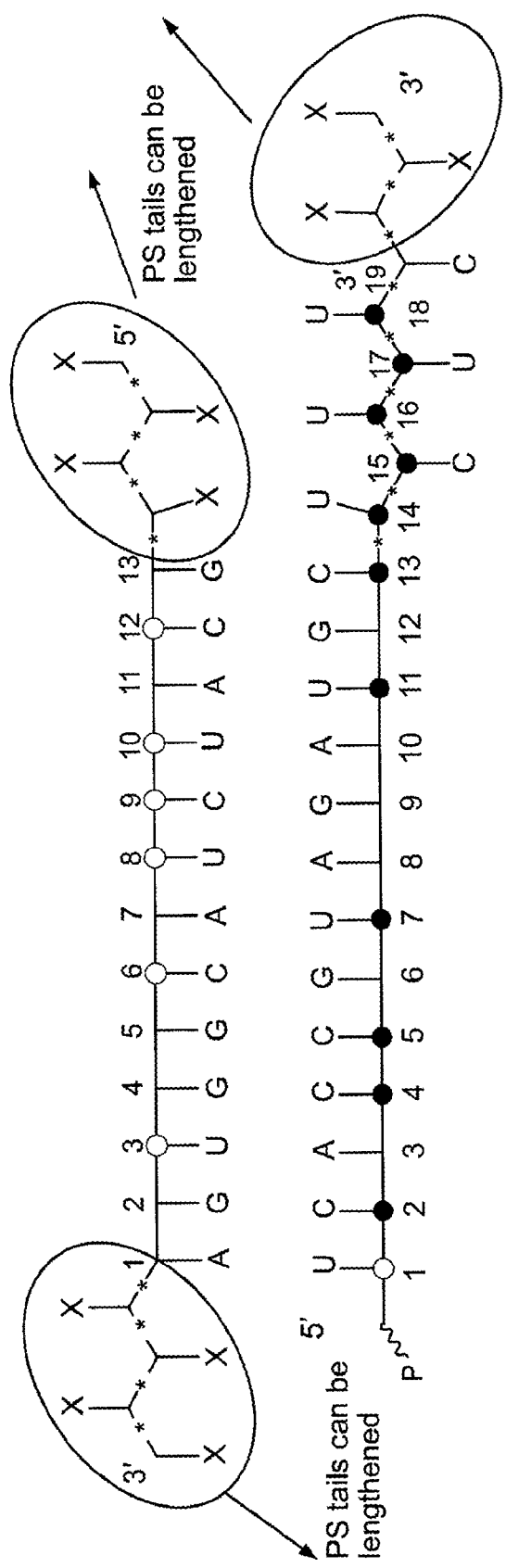
FIG. 27 is a schematic depicting addition and lengthening of multiple phosphorothioate tail regions on one or both strands of the sd-rxRNA® molecule (SEQ ID NOs:449-450 from top to bottom).
Figure 28:
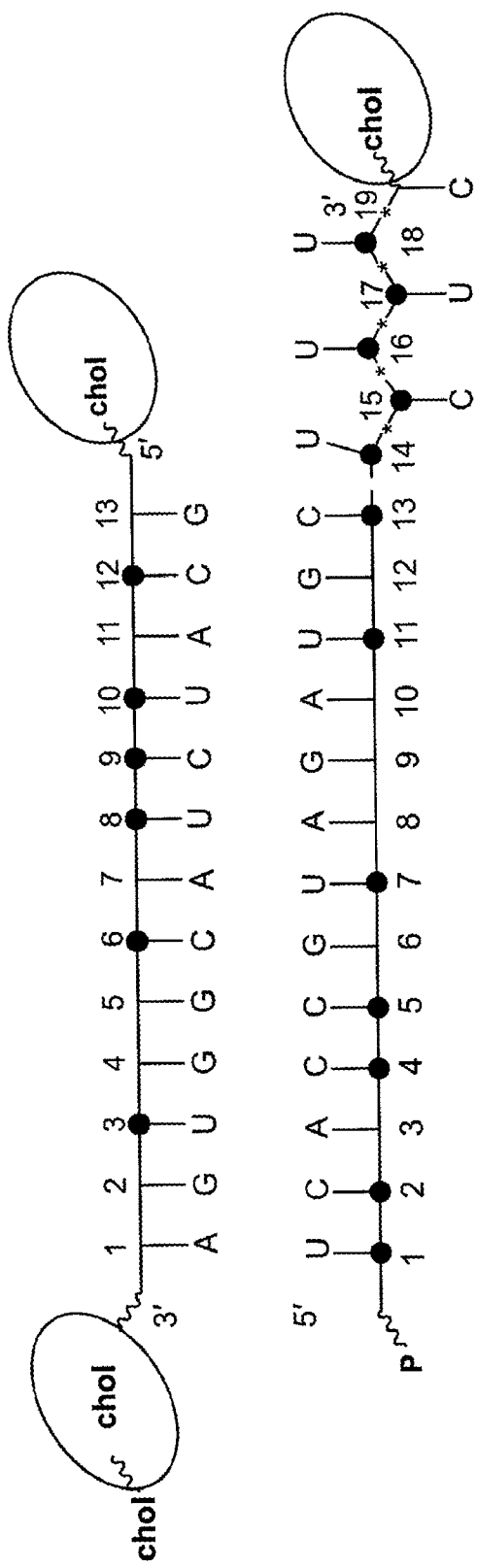
FIG. 28 depicts the addition of multiple cholesterol moieties on an sd-rxRNA® molecule (SEQ ID NOs:449-450 from top to bottom).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. Complexes are formed at different oligonucleotide concentrations, with higher concentrations favoring more efficient complex formation (FIGS. 21-22).

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

Figure 12:
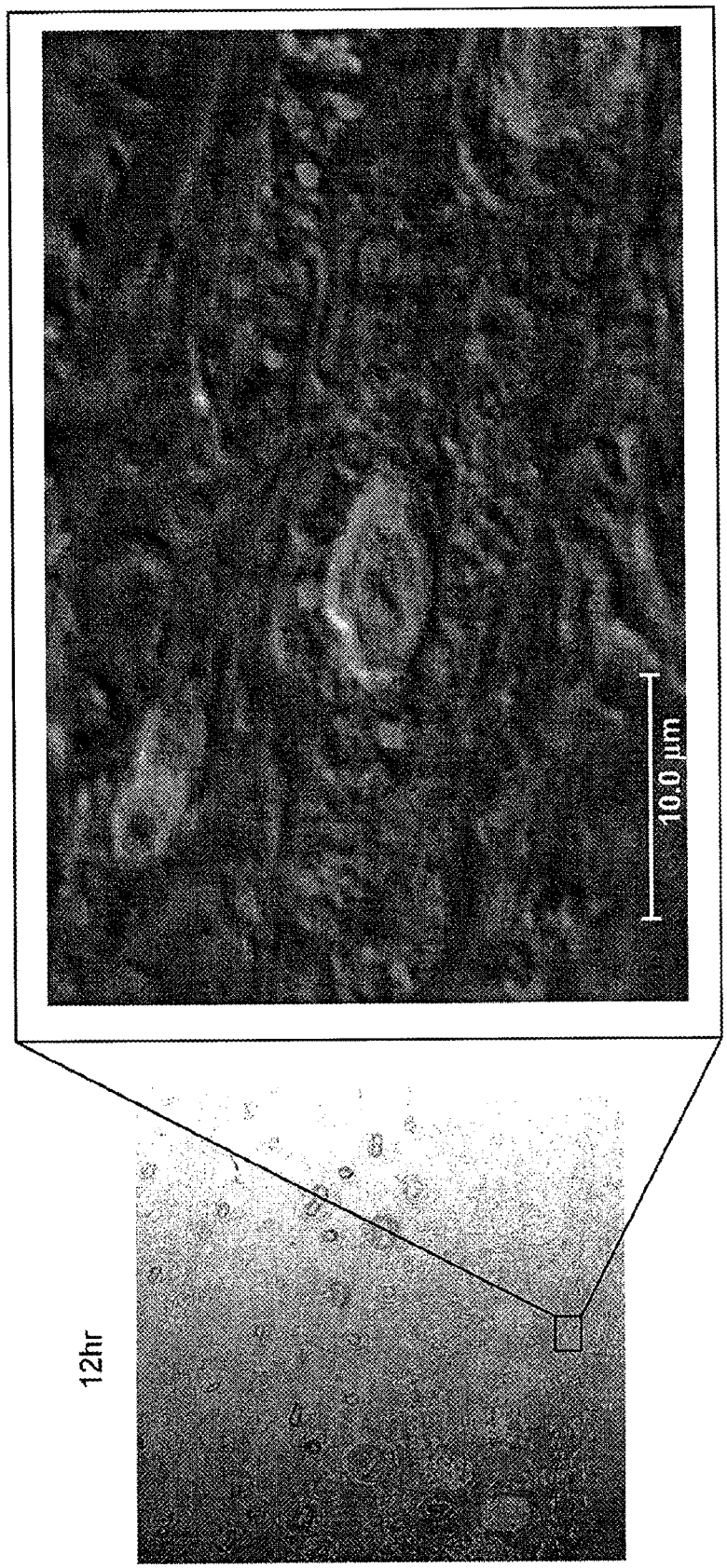
FIG. 12 reveals presence of the sd-rxRNA® throughout cells following subcutaneous injection.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues (FIG. 12).

In another embodiment the fat emulsions of the cargo molecule contain more then 70% of Linoleic acid ($C_{18}H_{32}O_2$) and/or cardiolipin are used for specifically delivering RNAi to heart muscle.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound(s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl—, Br—, I—, F—, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly(L-lysine) or avidin and lipids may, or may not, be included in this mixture, e.g., steryl-poly(L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. USA.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. Cell 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. *J Cell Biol.* 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991.276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in aveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

Moreover, the present invention provides for administering the subject oligonucleotides with an osmotic pump providing continuous infusion of such oligonucleotides, for example, as described in Rataiczak et al. (1992 Proc. Natl. Acad. Sci. USA 89:11823-11827). Such osmotic pumps are commercially available, e.g., from Alzet Inc. (Palo Alto, Calif.). In some instances, topical administration and parenteral administration in a cationic lipid carrier are preferred.

With respect to in vivo applications, the formulations of the present invention can be administered to a patient in a variety of forms adapted to the chosen route of administration, e.g., parenterally, orally, or intraperitoneally. Parenteral administration, which in some instances is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. As demonstrated in the Examples section, sd-rxRNA® molecules can be effectively administered through a variety of methods including intravenous injection, subcutaneous administration and insufflation.

The sd-rxRNA® molecules, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

Pharmaceutical preparations for topical administration include transdermal patches, ointments, lotions, creams, gels, drops, sprays, suppositories, liquids and powders. In addition, conventional pharmaceutical carriers, aqueous, powder or oily bases, or thickeners may be used in pharmaceutical preparations for topical administration.

Pharmaceutical preparations for oral administration include powders or granules, suspensions or solutions in water or non-aqueous media, capsules, sachets or tablets. In addition, thickeners, flavoring agents, diluents, emulsifiers, dispersing aids, or binders may be used in pharmaceutical preparations for oral administration.

For transmucosal or transdermal administration, penetrants appropriate to the barrier to be permeated are used in the formulation. Such penetrants are known in the art, and include, for example, for transmucosal administration bile salts and fusidic acid derivatives, and detergents. Transmucosal administration may be through nasal sprays or using suppositories. For oral administration, the oligonucleotides are formulated into conventional oral administration forms such as capsules, tablets, and tonics. For topical administration, the oligonucleotides of the invention are formulated into ointments, salves, gels, or creams as known in the art.

For administration by inhalation, such as by insufflation, the sd-rxRNA® molecules for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the sd-rxRNA® molecules. The sd-rxRNA® molecule is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656

(granulocyte colony stimulating factor). A method and composition for pulmonary delivery of drugs for systemic effect is described in, and incorporated by reference from, U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of oligonucleotide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified oligonucleotide may also be prepared in different formulations depending on the type of chemical modification or the type of device employed.

Formulations suitable for use with a nebulizer, either jet or ultrasonic, will typically comprise oligonucleotide (or derivative) dissolved in water at a concentration of about 0.1 to 25 mg of biologically active oligonucleotide per mL of solution. The formulation may also include a buffer and a simple sugar (e.g., for oligonucleotide stabilization and regulation of osmotic pressure). The nebulizer formulation may also contain a surfactant, to reduce or prevent surface induced aggregation of the oligonucleotide caused by atomization of the solution in forming the aerosol.

Formulations for use with a metered-dose inhaler device will generally comprise a finely divided powder, such as a dry powder formulation, containing the sd-rxRNA® molecule suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing oligonucleotide (or derivative) and may also include a bulking agent, such as lactose, sorbitol, sucrose, or mannitol in amounts which facilitate dispersal of the powder from the device, e.g., 50 to 90% by weight of the formulation. The sd-rxRNA® molecule can be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The described oligonucleotides may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., J. Pharm. Sci., 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

In an embodiment, the present invention employs various penetration enhancers to affect the efficient delivery of nucleic acids, particularly oligonucleotides, to the skin of animals. Even non-lipophilic drugs may cross cell membranes if the membrane to be crossed is treated with a penetration enhancer. In addition to increasing the diffusion of non-lipophilic drugs across cell membranes, penetration enhancers also act to enhance the permeability of lipophilic drugs.

Five categories of penetration enhancers that may be used in the present invention include: surfactants, fatty acids, bile salts, chelating agents, and non-chelating non-surfactants. Other agents may be utilized to enhance the penetration of the administered oligonucleotides include: glycols such as ethylene glycol and propylene glycol, pyrrols such as 2-15 pyrrol, azones, and terpenes such as limonene, and menthone.

The oligonucleotides, especially in lipid formulations, can also be administered by coating a medical device, for example, a catheter, such as an angioplasty balloon catheter, with a cationic lipid formulation. Coating may be achieved, for example, by dipping the medical device into a lipid formulation or a mixture of a lipid formulation and a suitable solvent, for example, an aqueous-based buffer, an aqueous solvent, ethanol, methylene chloride, chloroform and the like. An amount of the formulation will naturally adhere to the surface of the device which is subsequently administered to a patient, as appropriate. Alternatively, a lyophilized mixture of a lipid formulation may be specifically bound to the surface of the device. Such binding techniques are described, for example, in K. Ishihara et al., Journal of Biomedical Materials Research, Vol. 27, pp. 1309-1314 (1993), the disclosures of which are incorporated herein by reference in their entirety.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

As described in the Examples section, intravenous administration of sd-rxRNA® molecules can be optimized through testing of dosing regimens. In some instances, intravenous administration is achieved through infusion, for example through the use of an infusion pump to infuse molecules into the circulatory system of a subject. The infusion can be continuous or intermittent. In some instances, it is preferred if the dosing regimen involves repetitive administration of a short-term continuous infusion. For example, the continuous infusion can last for approximately 5 min, 10 min, 20 min, 30 min, 40 min, 50 min, 1.0 hour, 1.1 hours, 1.2 hours, 1.3 hours, 1.4 hours, 1.5 hours, 1.6 hours, 1.7 hours, 1.8 hours, 1.9 hours, 2.0 hours, 2.1 hours, 2.2 hours, 2.3 hours, 2.4 hours, 2.5 hours, 2.6 hours, 2.7 hours, 2.8 hours, 2.9 hours, 3.0 hours, 3.1 hours, 3.2 hours, 3.3 hours, 3.4 hours, 3.5 hours, 3.6 hours, 3.7 hours, 3.8 hours, 3.9 hours, 4.0 hours, 4.1 hours, 4.2 hours, 4.3 hours, 4.4 hours, 4.5 hours, 4.6 hours, 4.7 hours, 4.8 hours, 4.9 hours, 5.0 hours, 5.1 hours, 5.2 hours, 5.3 hours, 5.4 hours, 5.5 hours, 5.6 hours, 5.7 hours, 5.8 hours, 5.9 hours, 6.0 hours, or more than 6.0 hours, including any intermediate values.

The infusion can be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Aspects of the invention relate to administering sd-rxRNA® molecules to a subject. In some instances the subject is a patient and administering the sd-rxRNA® molecule involves administering the sd-rxRNA® molecule through continuous infusion in a doctor's office. Without wishing to be bound by any theory, a continuous infusion may saturate the normal clearance mechanism and maintain relatively high compound levels in the blood to ensure tissue distribution. sd-rxRNA® are well suited to such an approach due to their low levels of toxicity.

Figure 2:
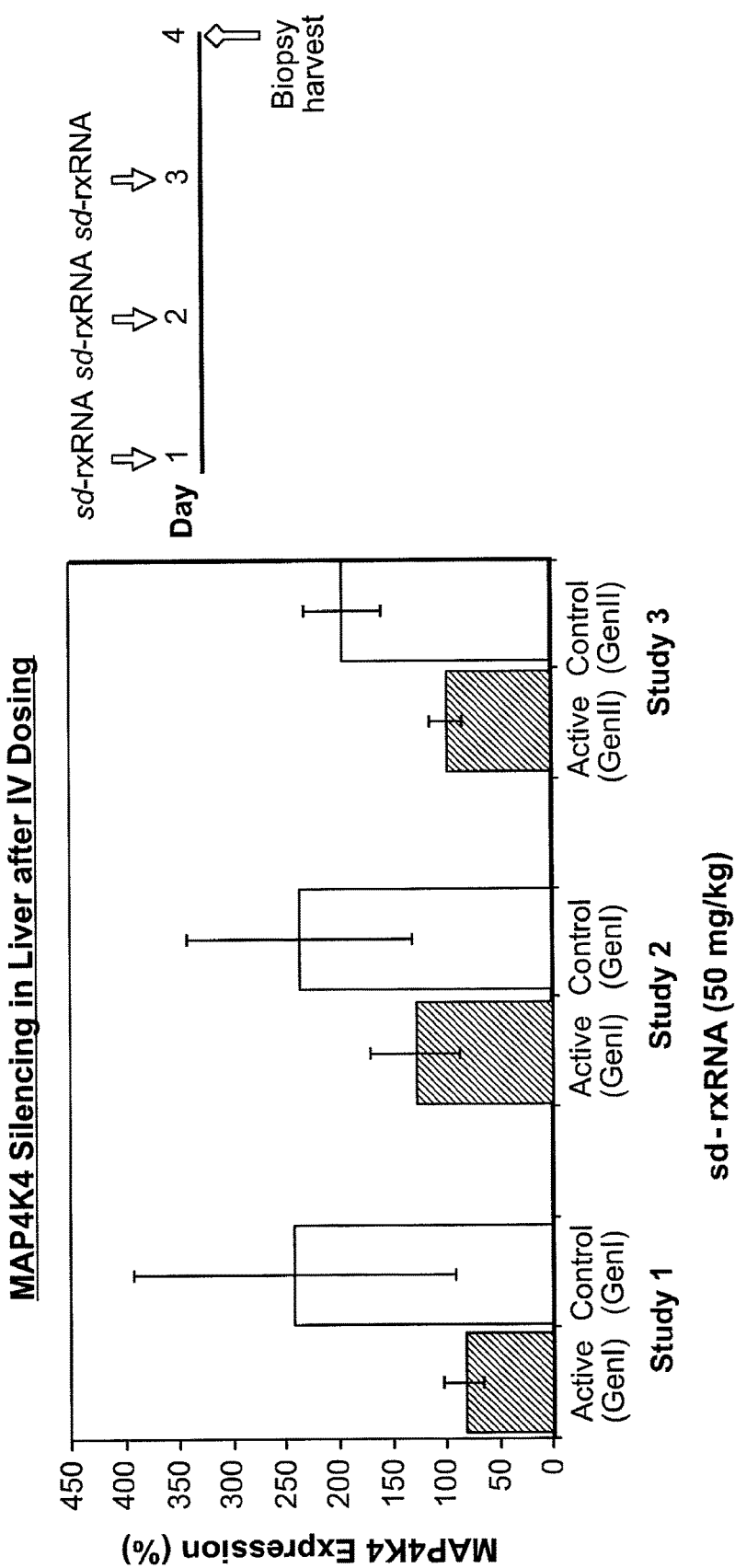
FIG. 2 demonstrates silencing of MAP4K4 in the liver following daily intravenous administration of sd-rxRNA®.
Figure 3:
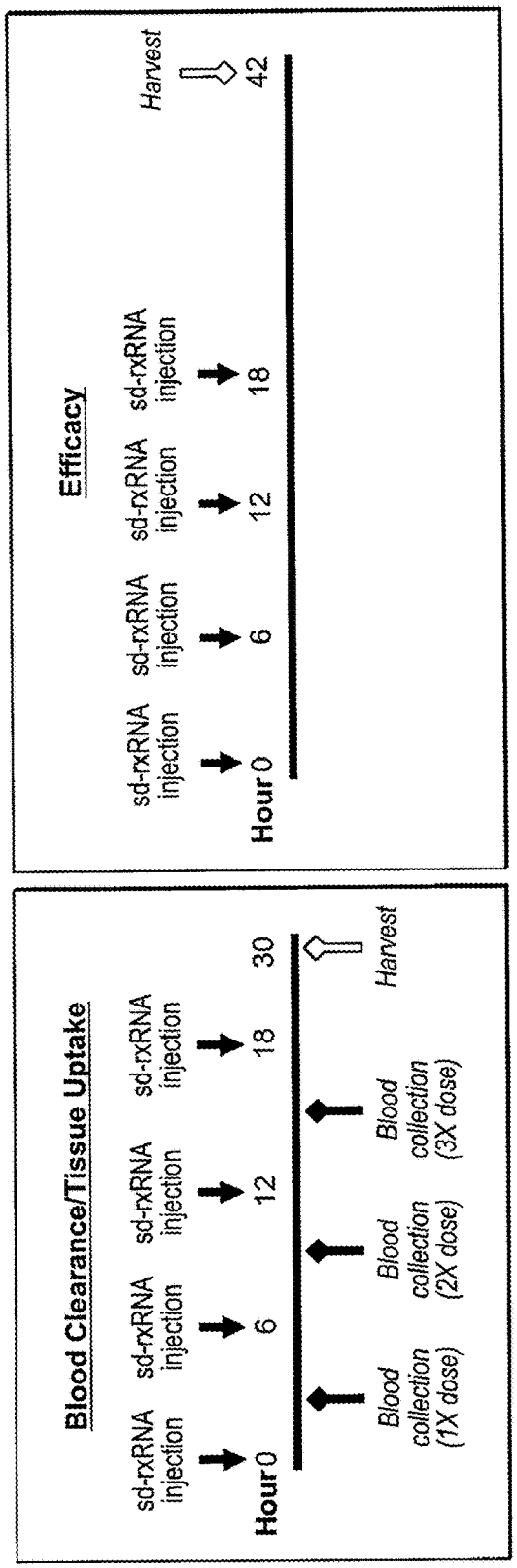
FIG. 3 presents a schematic of a repetitive dosing regimen for sd-rxRNA® administration.
Figure 4:
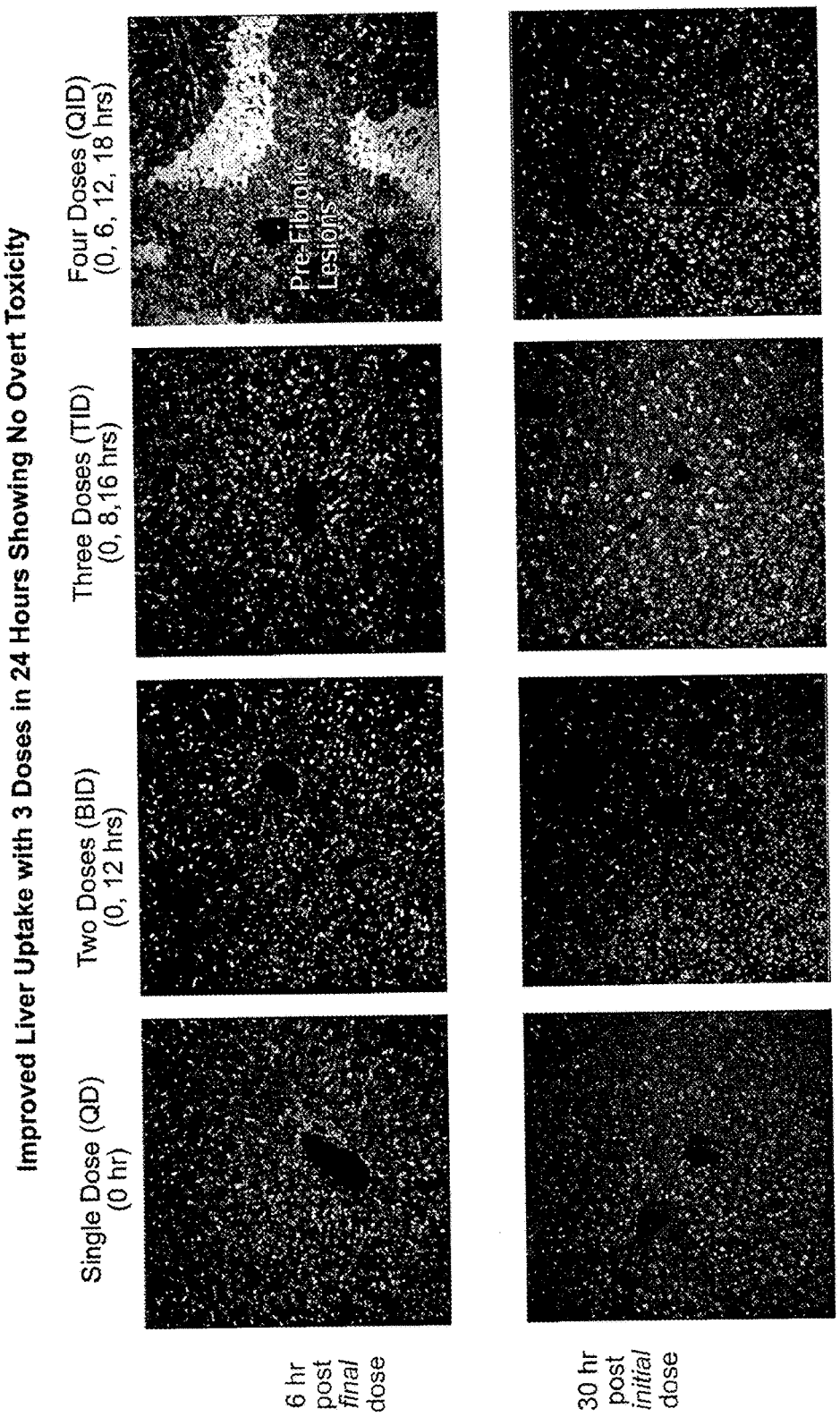
FIG. 4 presents images revealing liver uptake of sd-rxRNA® in mice. Mice were dosed 1, 2, 3, or 4 times with 50 mg/kg within 24 hours.

FIG. 1 reveals blood clearance and liver uptake of sdRNA following sd-rxRNA® intravenous administration at 50 mg/kg and 10 mg/kg. FIGS. 2 and 3 demonstrate dosing regimens. FIGS. 4 and 5 reveal distribution of sd-rxRNA® in tissues including liver, spleen, heart and lung following intravenous administration. FIG. 6 demonstrates increased sd-rxRNA® expression in the liver following administration of multiple doses within 24 hours.

Figure 7:
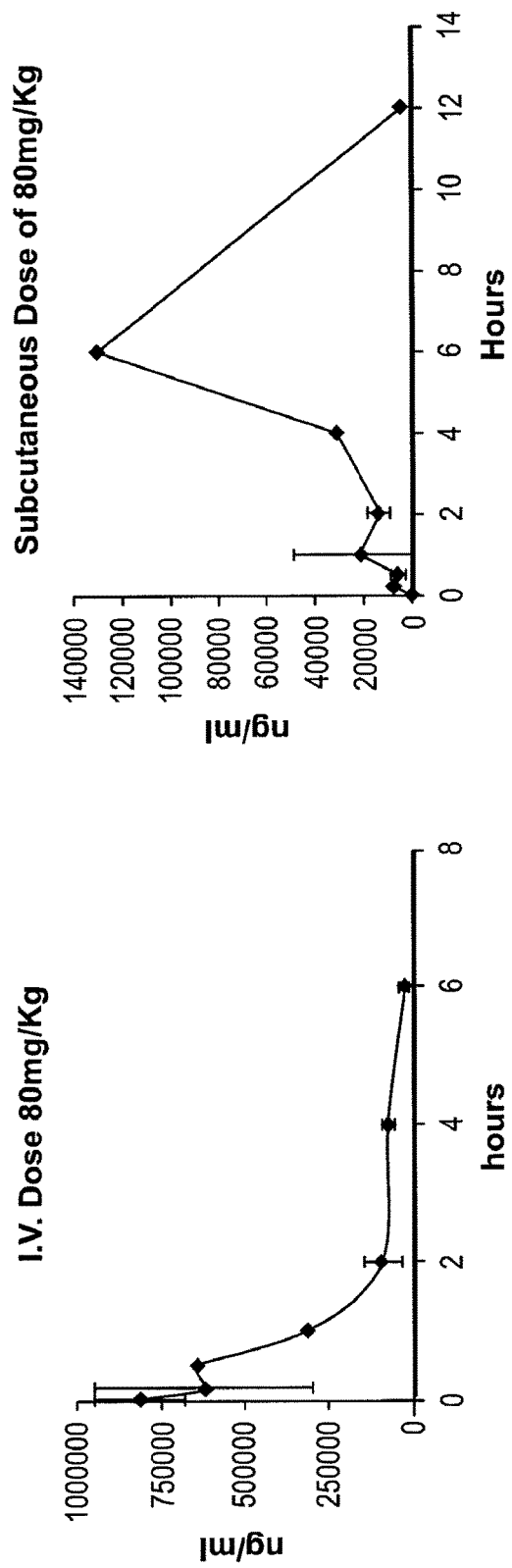
FIG. 7 presents a comparison of subcutaneous and intravenous administration for efficacy in the liver. A single bolus of 80 mg/kg sd-rxRNA® was delivered for both samples.
Figure 8:
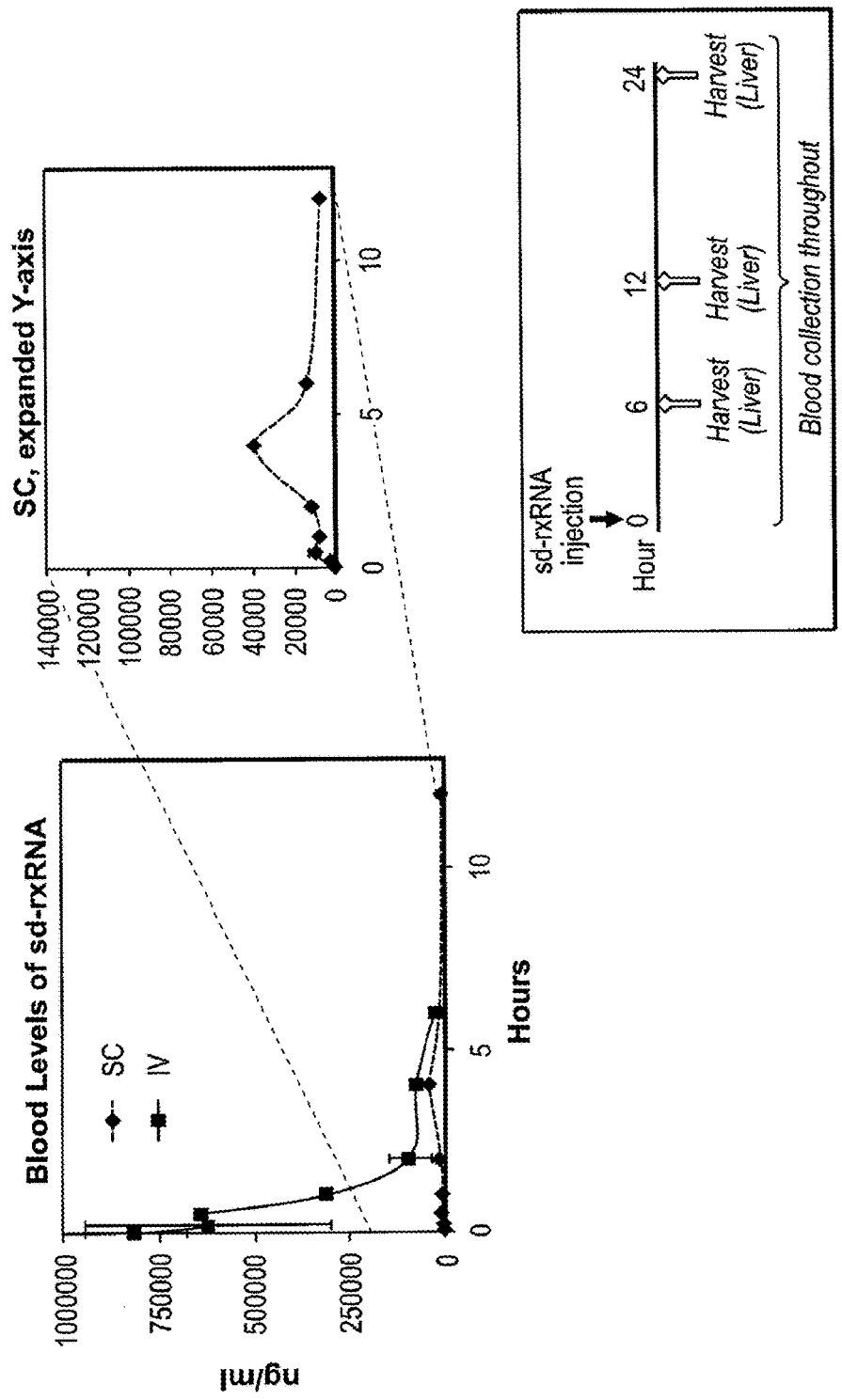
FIG. 8 demonstrates that the route of administration of sd-rxRNA® has an impact on clearance kinetics, blood levels and tissue uptake. A single bolus of 80 mg/kg sd-rxRNA® was delivered.
Figure 10:
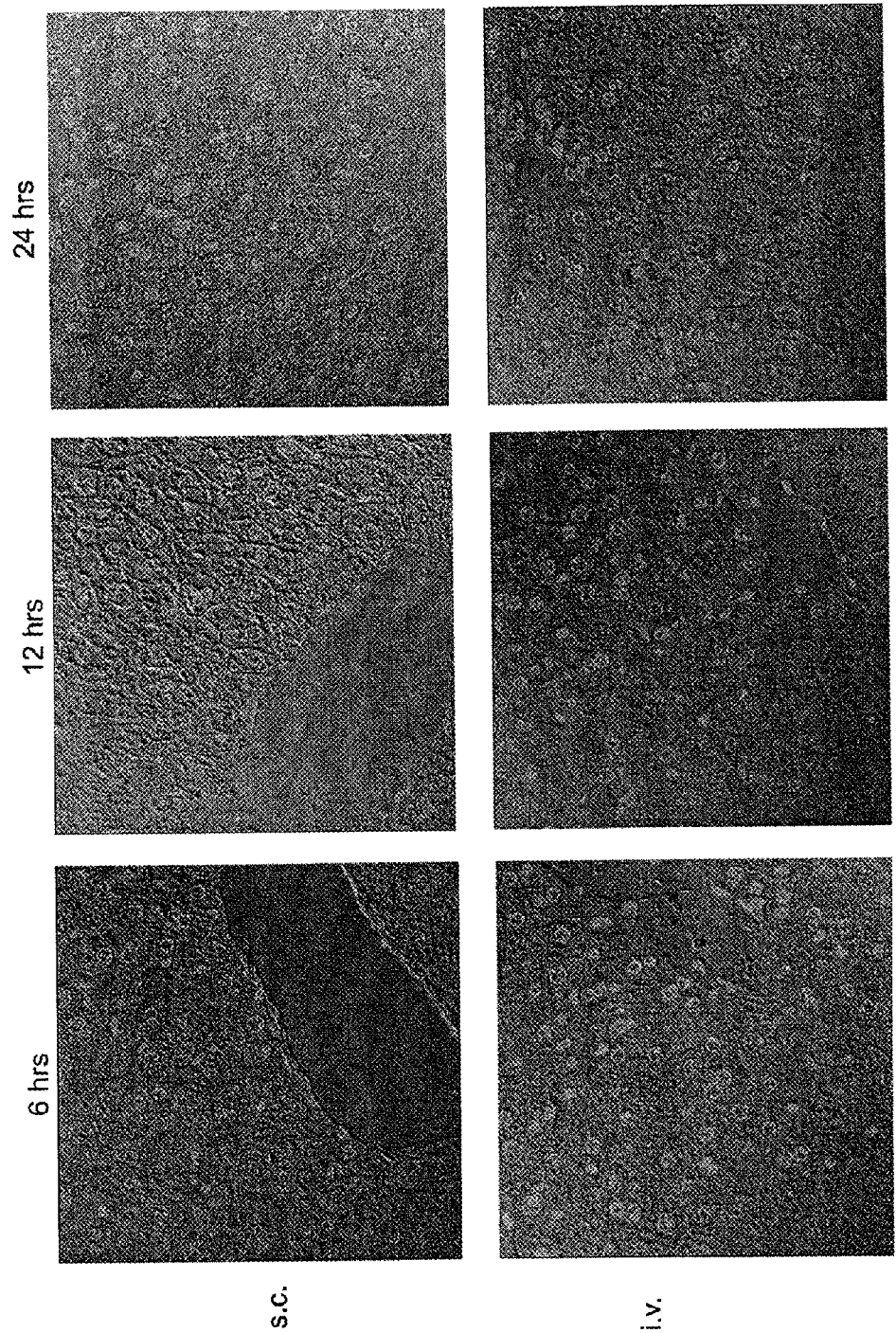
FIG. 10 reveals distribution of sd-rxRNA® in the liver 24 hours following subcutaneous or intravenous administration.
Figure 11:
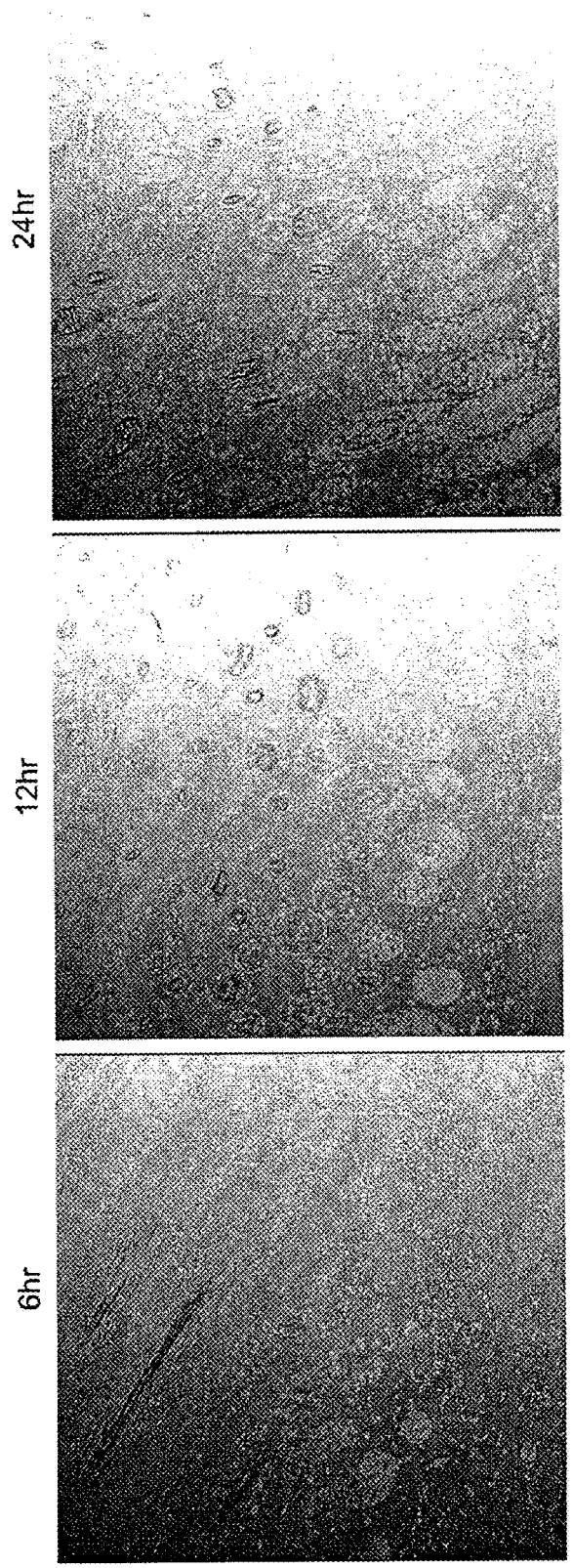
FIG. 11 reveals delivery of sd-rxRNA® to skin following subcutaneous injection.

FIG. 7 reveals that when equivalent doses of 80 mg/kg of sd-rxRNA® were administered by intravenous and subcutaneous methods, in some instances, subcutaneous administration resulted in higher efficacy of sd-rxRNA® expression in the liver than intravenous administration. FIG. 8 summarizes the effect of route of administration on clearance kinetics and blood levels. FIGS. 9 and 10 reveal that 24 hours after dosing, more sd-rxRNA® was detectable in the liver following subcutaneous administration than following intravenous administration. Efficient delivery of sd-rxRNA® to the skin through subcutaneous administration was also demonstrated (FIG. 11).

In some instances, the effective amount of sd-rxRNA® that is delivered by intravenous or subcutaneous administration is at least approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

Subcutaneous administration can also be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Figure 13:
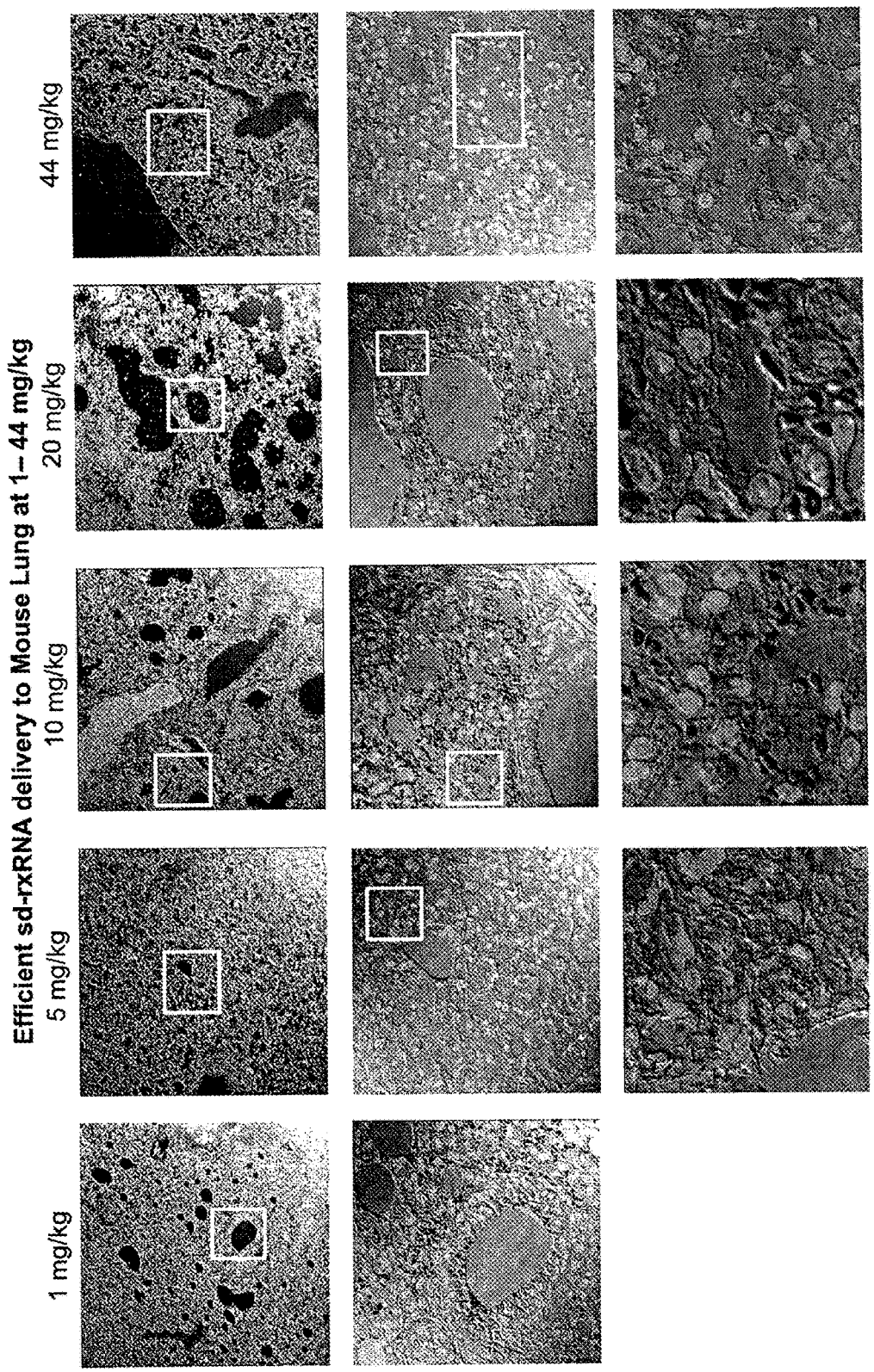
FIG. 13 reveals uptake of sd-rxRNA® in the mouse lung following administration by insufflation of dosages ranging from 1 mg/kg to 44 mg/kg.
Figure 14:
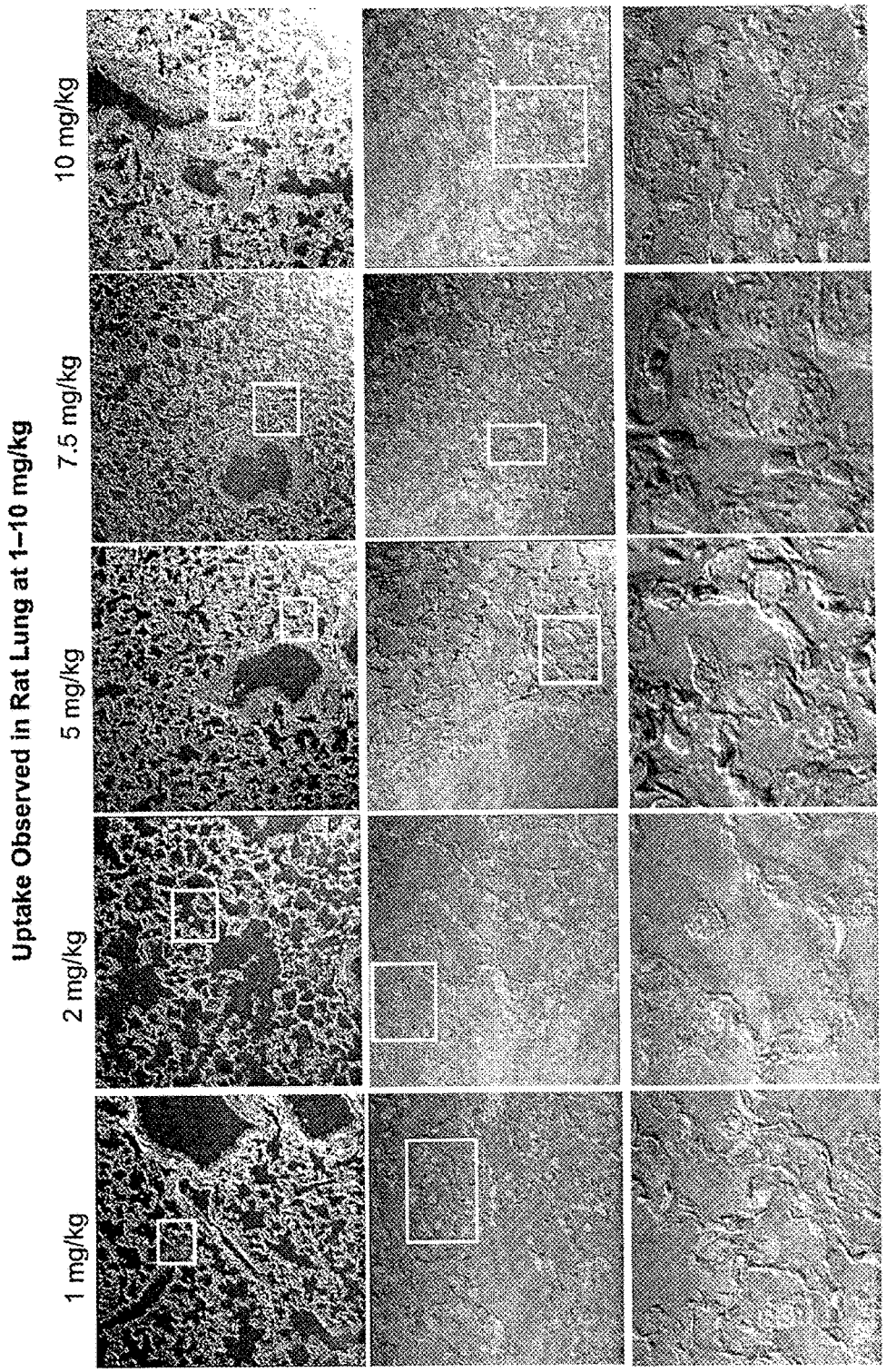
FIG. 14 reveals uptake of sd-rxRNA® in the rat lung following administration by insufflation of dosages ranging from 1 mg/kg to 10 mg/kg.

In some instances, sd-rxRNA® is administered through insufflation. FIGS. 13-14 reveal that sd-rxRNA® is efficiently delivered to mouse lung at 1-44 mg/kg and to rat lung at 1-10 mg/kg. In some instances, the effective amount of sd-rxRNA® that is delivered by insufflation is at least approximately 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 mg/kg including any intermediate values.

Administration by insufflation can also be repetitive. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

sd-rxRNA® molecules administered by methods described herein including intravenous, subcutaneous and insufflation, can be targeted to a variety of remote tissues in the body including liver, heart, lung, kidney, spleen and skin.

Physical methods of introducing nucleic acids include injection of a solution containing the nucleic acid, bombardment by particles covered by the nucleic acid, soaking the cell or organism in a solution of the nucleic acid, or electroporation of cell membranes in the presence of the nucleic acid. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or other-wise increase inhibition of the target gene.

Nucleic acid may be directly introduced into the cell (i.e., intracellularly); or introduced extracellularly into a cavity, interstitial space, into the circulation of an organism, introduced orally or by inhalation, or may be introduced by bathing a cell or organism in a solution containing the nucleic acid. Vascular or extravascular circulation, the blood or lymph system, and the cerebrospinal fluid are sites where the nucleic acid may be introduced.

The cell with the target gene may be derived from or contained in any organism. The organism may a plant, animal, protozoan, bacterium, virus, or fungus. The plant may be a monocot, dicot or gymnosperm; the animal may be a vertebrate or invertebrate. Preferred microbes are those used in agriculture or by industry, and those that are pathogenic for plants or animals.

Alternatively, vectors, e.g., transgenes encoding a siRNA of the invention can be engineered into a host cell or transgenic animal using art recognized techniques.

Another use for the nucleic acids of the present invention (or vectors or transgenes encoding same) is a functional analysis to be carried out in eukaryotic cells, or eukaryotic non-human organisms, preferably mammalian cells or organisms and most preferably human cells, e.g. cell lines such as HeLa or 293 or rodents, e.g. rats and mice. By administering a suitable nucleic acid of the invention which is sufficiently complementary to a target mRNA sequence to direct target-specific RNA interference, a specific knockout or knockdown phenotype can be obtained in a target cell, e.g. in cell culture or in a target organism.

Thus, a further subject matter of the invention is a eukaryotic cell or a eukaryotic non-human organism exhibiting a target gene-specific knockout or knockdown phenotype comprising a fully or at least partially deficient expression of at least one endogenous target gene wherein said cell or organism is transfected with at least one vector comprising DNA encoding an RNAi agent capable of inhibiting the expression of the target gene. It should be noted that the present invention allows a target-specific knockout or knockdown of several different endogenous genes due to the specificity of the RNAi agent.

Gene-specific knockout or knockdown phenotypes of cells or non-human organisms, particularly of human cells or non-human mammals may be used in analytic to procedures, e.g. in the functional and/or phenotypical analysis of complex physiological processes such as analysis of gene expression profiles and/or proteomes. Preferably the analysis is carried out by high throughput methods using oligonucleotide based chips.

Assays of Oligonucleotide Stability

In some embodiments, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

The target RNA cleavage reaction achieved using the siRNAs of the invention is highly sequence specific. Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10. Additionally, numerous commercial entities, such as Dharmacon, and Invitrogen provide access to algorithms on their website. The Whitehead Institute also offers a free siRNA Selection Program. Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA may be defined functionally as a nucleotide sequence (or oligonucleotide sequence) that is capable of hybridizing with a portion of the target gene transcript. Examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

As discussed above, sd-rxRNA® molecules administered by methods described herein including intravenous, subcutaneous and insufflation, can be targeted to a variety of remote tissues in the body including liver, heart, lung, kidney, spleen, skin and fat.

In some instances, an sd-rxRNA® is targeted to the liver and is used to ameliorate at least one symptom of a condition or disorder associated with the liver. Several non-limiting examples of conditions or disorders associated with the liver include: cirrhosis, liver disease caused by alcohol use, drug use, hepatotoxic medication, radiation, physical injury, exposure to a hepatotoxic substance, traumatic injury to the liver, infection (including viral, bacterial, mycoplasmal, fungal, protozoan, parasitic, or helminthian infections), hypertrophy of the liver (hepatomegaly), hepatic steatosis, non-alcoholic steatohepatitis, primary biliary cirrhosis, biliary atresia, hemochromatosis, alpha-1-antitrypsin deficiency, type-1 glycogen storage disease, porphyria, tyrosinemia, Wilson's disease, autoimmune hepatitis, neonatal hepatitis, Reye's syndrome, sarcoidosis, cystic liver disease (including choledochal cysts, Caroli's syndrome, congenital hepatic fibrosis, and polycystic liver disease), inflammatory liver disease (e.g., primary sclerosing cholangitis); cystic fibrosis, tuberculosis, Byler's disease, Niemann-Pick disease, hepatitis (e.g., chronic hepatitis, acute hepatitis, lupoid hepatitis, autoimmune hepatitis, or viral hepatitis), hepatitis caused by a virus selected from the group consisting of hepatitis A, hepatitis B, hepatitis C, hepatitis D, hepatitis E, hepatitis non A-E, cytomegalovirus, Epstein-Barr virus, and combinations thereof, hepatitis caused by a bacterial infection, e.g., caused by a bacterium selected from the group consisting of *leptospira, rickettsia*, and *streptococcus* species, and combinations thereof, a mycoplasmal infection, a protistal infection, or a helminthian infection. Non-limiting examples of conditions or disorders affecting the liver are incorporated by reference from US Patent Publications US2002/0142986 and US2007/0128294.

The sd-rxRNA® that is targeted to the liver may, in some instances target a liver-specific gene or a gene that is expressed at higher levels in the liver than in other tissues. In some instances, an sd-rxRNA® can target a gene involved in liver development. Non-limiting examples of genes involved in liver development are incorporated by reference from U.S. Pat. No. 5,955,594, and include for example elf 1-3, liyor-1 (145), pk, protein 106 and praja-1. As one of ordinary skill in the art would appreciate, publicly accessible databases can be used to identify genes that have liver-specific expression or increased expression in the liver relative to other tissues. Non-limiting examples of liver-specific genes are incorporated by reference from US Patent Publication US 2004/0229233.

In some instances, an sd-rxRNA® is targeted to the heart and is used to ameliorate at least one symptom of a condition or disorder associated with the heart. Several non-limiting examples of conditions or disorders associated with the heart include: diseases causative of heart failure, ischemic heart diseases, cardiomyopathy, hypertensive heart diseases, valvular disease, congenital heart diseases, mayocarditis, arrhythmia and diseases associated with cardiac hypertrophy and/or tachycardia, ischemic heart diseases (for example, myocardial infarction), cardiomyopathy (for example, congestive cardiomyopathy, hypertrophic cardiomyopathy, restrictive cardiomyopathy), hypertensive heart diseases, valvular disease (for example, atresia of aorta valve, mitral valve and the like, or stenosis thereof), congenital heart diseases, mayocarditis and the like, arrhythmia includes bradyarrhythmia and tachyarrhythmia, and examples of tachyarrhythmia includes superventricular arrhythmia (for example, sinus tachycardia, superventricular extrasystole, atrial fibrillation, artial flutter, superventricular tachycardia), ventricular arrhythmia (for example, ventricular extrasystole, ventricular tachycardia, ventricular fibrillation, torsade de pointes), WPW syndrome, long QT syndrome, Brugada syndrome, arrhythmia-inducing right ventricular dysplasia (ARVD, ARVC). Non-limiting examples of conditions or disorders affecting the heart are incorporated by reference from US Patent Publication 2007/0161584.

The sd-rxRNA® that is targeted to the heart may, in some instances target a heart-specific gene or a gene that is expressed at higher levels in the heart than in other tissues. Non-limiting examples of heart-specific genes are incorporated by reference from US Patent Publication US 2004/0229233, and include for example myosin light chain 2a, troponin I, cardiac, natriuretic peptide precursor B, troponin T2, cardiac, and neural cell adhesion molecule 1. As one of ordinary skill in the art would appreciate, publicly accessible databases can be used to identify genes that have heart-specific expression or increased expression in the heart relative to other tissues.

In some instances, an sd-rxRNA® is targeted to the lung and is used to ameliorate at least one symptom of a condition or disorder associated with the lung. Non-limiting examples of conditions or disorders associated with the lung, incorporated by reference from US Patent Publication 20090325958, include: asthma, chronic obstructive pulmonary disease; respiratory tract illness caused by respiratory syncytial virus; pulmonary arterial hypertension, acute respiratory distress syndrome and ventilator induced lung injury; cystic fibrosis; bronchiectasis; alpha-1-antitrypsin deficiency; rhinitis; rhinosinusitis; primary ciliary dyskinesia; pneumonia; bronchiolitis caused by agents other than respiratory syncytial virus; interstitial lung disease including lymphangioleiomyomatosis; idiopathic pulmonary fibrosis; obliterative bronchiolitis or bronchiolitis obliterans organizing pneumonia due to lung transplantation or HSCT; non-specific interstitial pneumonia; cryptogenic organizing pneumonia; acute interstitial pneumonia; respiratory bronchiolitis-associated interstitial lung disease; or pulmonary sarcoidosis.

The sd-rxRNA® that is targeted to the lung may, in some instances target a lung-specific gene or a gene that is expressed at higher levels in the lung than in other tissues. Non-limiting examples of lung-specific genes are incorporated by reference from US Patent Publication US 2004/0229233. As one of ordinary skill in the art would appreciate, publicly accessible databases can be used to identify genes that have heart-specific expression or increased expression in the heart relative to other tissues.

In some instances, an sd-rxRNA® is targeted to the spleen and is used to ameliorate at least one symptom of a condition or disorder associated with the spleen. Non-limiting examples of conditions or disorders associated with the spleen are incorporated by reference from US Patent Publication 2006/0134109 and include: abnormal immunoblastic proliferations of unknown origin, acute infections, acute parasitemias, agnogenic myeloid metaplasia, amyloidosis, angioimmunoblastic lymphadenopathy, antibody-coated cells, asplenia, autoimmune diseases, autoimmune hemolytic anemias, B-cell chronic lymphocytic leukemia and prolymphocytic leukemia, babesiosis, bone marrow involvement by carcinoma, brucellosis, carcinoma, ceroid histiocytosis, chronic alcoholism, chronic granulomatous disease, chronic hemolytic anemias, chronic hemolytic disorders, chronic immunologic inflammatory disorders, chronic infections, chronic lymphocytic leukemia, chronic myelogenous leukemia, chronic parasitemias, chronic uremia, cirrhosis, cold agglutinin disease, congestive splenomegaly, cryoglobulinemia, disseminated tuberculosis, dysproteinemias, endocrine disorders, erythroblastic leukemia, erythropoiesis; essential thrombocythemia, extramedullary hematopoiesis, Felty syndrome, fibrocongestive splenomegaly, fungal infections, gamm heavy-chain disease, Gaucher's disease, graft rejection, granulomatous infiltration, hairy cell leukemia, hamartomas, Hand-Schuller-Christian disease, hemangiomas, hemangiosarcomas, hematologic disorders, hemoglobinopathies, hemolytic anemias, hereditary elliptocytosis, hereditary spherocytosis, histiocytic medullary reticulosis, histiocytosis X, Hodgkin's disease, hypersensitivity reactions, hypersplenism, hyposplenism, idiopathic thrombocytopenic purpura, IgA deficiency, immune granulomas, immune thrombocytopenia, immune thrombocytopenic purpura, immunodeficiency disorders, infection associated hemophagocytic syndrome, infectious granulomas, infectious mononucleosis, infective endocarditis, infiltrative splenomegaly, inflammatory pseudotumors, leishmaniasis, Leterer-Siwe disease, leukemia, lipogranulomas, lymphocytic leukemias, lymphoma, malabsorption syndromes, malaria, malignant lymphoma, megakaryoblastic leukemia, metastatic tumor, monocytic leukemias, mucopolysaccharidoses, multicentric Castleman's disease, multiple myeloma, myelocytic leukemias, myelofibrosis, myeloproliferative syndromes, neoplasms, Niemann-Pick disease, non-Hodgkin's lymphoma, parasitic disorders, parasitized red blood cells, peliosis, polycythemia rubra vera, portal vein congestion, portal vein stenosis, portal vein thrombosis, portal venous hypertension, rheumatoid arthritis, right-sided cardiac failure, sarcoidosis, sarcoma, secondary amyloidosis, secondary myeloid metaplasia, serum sickness, sickle-cell disease, splenic cysts, splenic infarction, splenic vein hypertension, splenic vein stenosis, splenic vein thrombosis, splenomegaly, storage diseases, systemic lupus erythematosus, systemic vasculitides, T-cell chronic lymphocytic leukemia, thalasemia, thrombocytopenic purpura, thyrotoxicosis, trapping of immature hematologic cells, tuberculosis, tumorlike conditions, typhoid fever, vascular tumors, vasculitis, and viral infections.

The sd-rxRNA® that is targeted to the spleen may, in some instances target a spleen-specific gene or a gene that is expressed at higher levels in the spleen than in other tissues. Non-limiting examples of spleen-specific genes are incorporated by reference from US Patent Publication US 2004/0229233. As one of ordinary skill in the art would appreciate, publicly accessible databases can be used to identify genes that have spleen-specific expression or increased expression in the spleen relative to other tissues.

In some embodiments, the sd-rxRNA® is targeted to fat.

In some embodiments, the sd-rxRNA® is directed against MAP4K4, PCSK9, ApoB, PPIB, KSP or VEGF.

MAP4K4 is a mammalian serine/threonine protein kinase that belongs to a group of protein kinases related to *Saccharomyces cerevisiae* Sterile 20 (STE20). MAP4K4 (also known as NIK for Nck interacting kinase) was first identified in a mouse screen for proteins that interact with the SH3 domain of Nck (Su et al. (1997). Since its discovery, MAP4K4 has been and continues to be linked to wide range of physiological functions.

MAP4K4 is proposed to link protein tyrosine kinase signals to JNK activation and may play a role in cytoskeletal regulation (Xue et al., *Development* (2000), 128, 1559-1572). MAP4K4 has been found to be essential for development in mammalian cells. Nik$^{-/-}$ mouse embryos have been show to die postgastrulation. Patterning experiments in mice have suggested that NIK plays a critical and specific role in regulating the migration of cells that arise from the region of the primitive streak just posterior to the node (Xue et al., *Development* (2000), 128, 1559-1572). These experiments also led to the suggestion that MAP4K4 may regulate the mesodermal migration that contributes to the elongation of the body axis. Xue et al. have further speculated that a NCK/MAP4K4 complex may be required for segmentation of presomitic mesoderm into somites.

More recently, MAP4K4 has also been shown to be involved in metabolic disorders. For example, silencing of MAP4K4 resulted in an increase in the expression of a nuclear hormone receptor, PPARγ, that regulates the expression of genes responsible for adipocyte differentiation (Tang et al., *Proc. Natl. Acad. Sci.* (2006), 103, 2087-2092). Such genes include, for example, the insulin-responsive facilitative glucose transporter isoform 4 (GLUT4), which mediates insulin-dependent glucose transport into both muscle and adipose tissue. Indeed, several studies have revealed that a MAP4K4-dependent signaling pathway potently inhibits PPARγ-responsive gene expression, adipogenesis, and insulin-stimulated glucose transport. Further discussion of RNAi directed at MAP4K4 is described in, and incorporated by reference from U.S. Provisional Application Ser. No. 61/199,661, entitled "Inhibition of MAP4K4 through RNAi," filed on Nov. 19, 2008, and PCT Application PCT/US2009/006211, filed on Nov. 19, 2009 and entitled "Inhibition of MAP4K4 Through RNAi."

Proprotein convertase subtilisin kexin 9 (PCSK9) is a member of the subtilisin serine protease family. The other eight mammalian subtilisin proteases, PCSK1-PCSK8 (also called PC1/3, PC2, furin, PC4, PC5/6, PACE4, PC7, and S1P/SKI-1) are proprotein converges that process a wide variety of proteins in the secretory pathway and play roles in diverse biological processes (Bergeron, F. (2000) *J. Mol. Endocrinol.* 24, 1-22, Gensberg, K., (1998) *Semin. Cell Dev. Biol.* 9, 11-17, Seidah, N. G. (1999) *Brain Res.* 848, 45-62, Taylor, N. A., (2003) *FASEB J.* 17, 1215-1227, and Zhou, A., (1999) *J. Biol. Chem.* 274, 20745-20748). PCSK9 has been proposed to play a role in cholesterol metabolism. PCSK9 mRNA expression is down-regulated by dietary cholesterol feeding in mice (Maxwell, K, N., (2003) *J. Lipid Res.* 44, 2109-2119), up-regulated by statins in HepG2 cells (Dubuc, G., (2004) *Arterioscler. Thromb. Vasc. Biol.* 24, 1454-1459), and up-regulated in sterol regulatory element binding protein (SREBF) transgenic mice (Horton, J, D., (2003) *Proc. Natl. Acad. Sci. USA* 100, 12027-12032), similar to the cholesterol biosynthetic enzymes and the low-density lipoprotein receptor (LDLR). Furthermore, PCSK9 missense mutations have been found to be associated with a form of autosomal dominant hypercholesterolemia (Hchola3) (Abifadel, M., et at (2003) *Nat. Genet,* 34, 154-156, Timms, K. M., (2004) *Hum. Genet* 114, 349-353, Leren, T. P. (2004) *Clin. Genet.* 65, 419-422), PCSK9 may also play a role in determining LDL cholesterol levels in the general population, because single-nucleotide polymorphisms (SNPs) have been associated with cholesterol levels in a Japanese population (Shioji, K., (2004) *J. Hum. Genet.* 49, 109-114).

Autosomal dominant hypercholesterolemias (ADHs) are monogenic diseases in which patients exhibit elevated total and LDL cholesterol levels, tendon xanthomas, and premature atherosclerosis (Rader, D. J., (2003) *J. Clin. Invest.* 111, 1795-1803). The pathogenesis of ADHs and a recessive form, autosomal recessive hypercholesterolemia (ARH)

(Cohen, J. C., (2003) *Curr. Opin. Lipidol.* 14, 121-127), is due to defects in LDL uptake by the liver, ARH may be caused by LDLR mutations, which prevent LDL uptake, or by mutations in the protein on LDL, apolipoprotein B, which binds to the LDLR. ARH is caused by mutations in the ARM protein that are necessary for endocytosis of the LDLR-LDL complex via its interaction with clathrin. Therefore, if PCSK9 mutations are causative in Hchola3 families, it seems likely that PCSK9 plays a role in receptor-mediated LDL uptake.

Overexpression studies point to a role for PCSK9 in controlling LDLR levels and, hence, LDL uptake by the liver (Maxwell K. N. (2004) *Proc. Natl. Acad. Sci. USA* 101, 7100-7105, Benjannet, S., et al. (2004) *J. Biol. Chem.* 279, 48865-18875, Park, S. W., (2004) *J. Biol. Chem.* 279, 50630-50638). Adenoviral-mediated overexpression of mouse or human PCSK9 for 3 or 4 days in mice results in elevated total and LDL cholesterol levels; this effect is not seen in LDLR knockout animals (Maxwell K. N. (2004) *Proc. Natl. Acad. Sci. USA* 101, 7100-7105, Benjannet, S., et al. (2904) *J. Biol. Chem.* 279, 48865-48875, Park, S. W., (2004) *J. Biol. Chem.* 279, 50630-50638). In addition, PCSK9 overexpression results in a severe reduction in hepatic LDLR protein, without affecting IDLE mRNA levels, SREBP protein levels, or SREBP protein nuclear to cytoplasmic ratio. These results indicate that PCSK9, either directly or indirectly, reduces LDLR protein levels by a post transcriptional mechanism Loss of function mutations in PCSK9 have been designed in mouse models (Rashid et al., (2005) *PNAS*, 102, 5374-5379, and identified in human individuals Cohen et al., (2005), *Nature Genetics.*, 37.161-165. In both cases loss of PCSK9 function lead to lowering of total and LDLc cholesterol. In a retrospective outcome study over 15 years, loss of one copy of PCSK9 was shown to shift LDLc lower and to lead to an increased risk-benefit protection from developing cardiovascular heart disease (Cohen et al. 2006 *N. Engl. J. Med.*, 354, 1264-1272.). Clearly the evidence to date indicates that lowering of PCSK9 levels will lower LDLc.

Despite significant advances in the field of RNAi and advances in the treatment of pathological processes which can be mediated by down regulating PCSK9 gene expression, there remains a need for agents that can inhibit PCSK9 gene expression and that can treat diseases associated with PCSK9 gene expression.

Further discussion of RNAi targeted to PCSK9 is described in, and incorporated by reference from U.S. Provisional Application Ser. No. 61/204,348, entitled "INHIBITION OF PCSK9 THROUGH RNAI," filed on Jan. 5, 2009, and PCT application PCT/US2010/000019, filed on Jan. 5, 2010, and entitled "Inhibition of PCSK9 Through RNAi."

ApoB (Apolipoprotein B) is an apolipoprotein involved in cholesterol transport. Human ApoB is represented by GenBank number NM_000384.2. ApoB has been associated with coronary heart disease, atherosclerosis, metabolic disorders and hypercholesterolemia. PPIB (peptidyl-prolyl cis-trans isomerase B) is associated with the secretory system and has been linked to cancer and immunosuppression. PPIB is represented by GenBank number NM_000942. KSP (Kinesin spindle protein, also called Kinesin Family Member 11 (KIF11), EG5, HKSP, KNSL1, and TRIPS) is associated with cancer. Targeting KSP represents antimitotic approach to targeting cancer. VEGF (Vascular endothelial growth factor) belongs to the platelet-derived family of growth factors. It is associated with angiogenesis and vasculogenesis.

In some instances, an sd-rxRNA® is targeted to a neoplasm or a neoplastic tissue and is used to ameliorate at least one symptom of a condition or disorder associated with neoplasia. Neoplasia refers to the abnormal proliferation of cells, often resulting in an abnormal mass of tissue (i.e., a neoplasm). Neoplasm may be benign, pre-malignant (e.g., a carcinoma in situ), or malignant (cancerous). Benign neoplasms include uterine fibroids and melanocytic nevi (i.e., skin moles) that do not transform into cancer. Potentially malignant, or pre-cancerous, neoplasms include carcinoma in situ, which is a early form of carcinoma that does not invade surrounding tissue, but rather proliferate in their normal environment. Malignant neoplasms are commonly referred to as cancer, and they invade and destroy surrounding tissue, may form metastases, and eventually may be fatal to the host.

In some instances, the sd-rxRNA® is targeted to a neoplasm or neoplastic cells of epithelial origin. Epithelial cells reside in one or more layers which cover the entire surface of the body and which line most of the hollow structures of the body, excluding the blood vessels, lymph vessels, and the heart interior, which are lined with endothelium, and the chest and abdominal cavities which are lined with mesothelium.

Epithelial neoplasms include, but are not limited to, benign and premalignant epithelial tumors, such as breast fibroadenoma and colon adenoma, and malignant epithelial tumors. Malignant epithelial tumors include primary tumors, also referred to as carcinomas, and secondary tumors, also referred to as metastases of epithelial origin. Carcinomas include, but are not limited to, acinar carcinoma, acinous carcinoma, alveolar adenocarcinoma (also called adenocystic carcinoma, adenomyoepithelioma, cribriform carcinoma and cylindroma), carcinoma adenomatosum, adenocarcinoma, carcinoma of adrenal cortex, alveolar carcinoma, alveolar cell carcinoma (also called bronchiolar carcinoma, alveolar cell tumor and pulmonary adenomatosis), basal cell carcinoma, carcinoma basocellulare (also called basaloma, or basiloma, and hair matrix carcinoma), basaloid carcinoma, basosquamous cell carcinoma, breast carcinoma, bronchioalveolar carcinoma, bronchiolar carcinoma, bronchogenic carcinoma, cerebriform carcinoma, cholangiocellular carcinoma (also called cholangioma and cholangiocarcinoma), chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epibulbar carcinoma, epidermoid carcinoma, carcinoma epitheliale adenoides, carcinoma exulcere, carcinoma fibrosum, gelatiniform carcinoma, gelatinous carcinoma, giant cell carcinoma, gigantocellulare, glandular carcinoma, granulosa cell carcinoma, hair-matrix carcinoma, hematoid carcinoma, hepatocellular carcinoma (also called hepatoma, malignant hepatoma and hepatocarcinoma), Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, lenticular carcinoma, carcinoma lenticulare, lipomatous carcinoma, lymphoepithelial carcinoma, carcinoma mastitoides, carcinoma medullare, medullary carcinoma, carcinoma melanodes, melanotic carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, carcinoma nigrum, oat cell carcinoma, carcinoma ossificans, osteoid carcinoma, ovarian carcinoma, papillary carcinoma, periportal carcinoma, preinvasive carcinoma, prostate carcinoma, renal cell carcinoma of kidney (also called adenocarcinoma of kidney and hypernephoroid carcinoma), reserve cell carcinoma, carcinoma sarcomatodes, scheinderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma vilosum.

In other instances, the sd-rxRNA® is targeted to a neoplasm or neoplastic cells of mesenchymal origin, for example, neoplastic cells forming a sarcoma. Sarcomas are rare mesenchymal neoplasms that arise in bone and soft tissues. Different types of sarcomas are recognized, including liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal [not bone] Ewing's sarcoma, and primitive neuroectodermal tumor [PNET]), synovial sarcoma, angiosarcomas, hemangiosarcomas, lymphangiosarcomas, Kaposi's sarcoma, hemangioendothelioma, fibrosarcoma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST) (also known as GI stromal sarcoma), osteosarcoma (also known as osteogenic sarcoma)-skeletal and extraskeletal, and chondrosarcoma.

In yet other instances, the sd-rxRNA® targets neoplasms or neoplastic cells of melanocytic origin. Melanomas are tumors arising from the melanocytic system of the skin and other organs. Examples of melanoma include lentigo maligna melanoma, superficial spreading melanoma, nodular melanoma, and acral lentiginous melanoma.

In still other instances, the sd-rxRNA® targets malignant neoplasms or neoplastic cells including, but not limited to, those found in biliary tract cancer, endometrial cancer, esophageal cancer, gastric cancer, intraepithelial neoplasms, including Bowen's disease and Paget's disease, liver cancer, oral cancer, including squamous cell carcinoma, sarcomas, including fibrosarcoma and osteosarcoma, skin cancer, including melanoma, Kaposi's sarcoma, testicular cancer, including germinal tumors (seminoma, non-seminoma (teratomas, choriocarcinomas)), stromal tumors and germ cell tumors, thyroid cancer, including thyroid adenocarcinoma and medullar carcinoma, and renal cancer including adenocarcinoma and Wilms tumor.

In other instances, the sd-rxRNA® targets neoplasms or neoplastic cells originating in bone, muscle or connective tissue. The neoplastic cells may be found in primary tumors (e.g., sarcomas) of bone and connective tissue.

In some instances, the sd-rxRNA® is delivered directly to a neoplasm, for example, by injection using a needle and syringe. Injection into the neoplasm permits large quantities of the sd-rxRNA® to be delivered directly to the target cells while minimizing delivery to systemic sites. By direct injection into the neoplasm, an effective amount to promote RNA interference by the sd-rxRNA® is distributed throughout at least a substantial volume of the neoplasm. In some instances, delivery of the sd-rxRNA® requires a single injection into the neoplasm. In other instances, delivery of the sd-rxRNA® requires multiple injections into separate regions of the neoplasm such that the entire mass of the neoplasm is invested with an effective amount to promote RNA interference by the sd-rxRNA®. See U.S. Pat. Nos. 5,162,115 and 5,051,257, and Livraghi et al, *Tumori* 72 (1986), pp. 81-87, each of which is incorporated herein by reference.

The total dose, concentration, volume of the sd-rxRNA® delivered, and rate of delivery can be optimized for a given neoplasm type, size and architecture. The zone of RNA interference can be controlled by optimizing these parameters. The volume and concentration of the sd-rxRNA® delivered into the neoplasm must be sufficient to promote RNA interference throughout the tumor. Depending on the number of injections, and their placement with respect to neoplasm architecture, it can be useful to administer total sd-rxRNA® volumes less than the neoplasm volume, greater than the neoplasm volume, or approximately equal to the neoplasm volume.

In some instances, the sd-rxRNA® is delivered directly to the neoplasm using an implantable device.

In some instances sd-rxRNA® injection into a neoplasm can be accompanied by ultrasound guidance.

In other instances, the sd-rxRNA® is administered systemically, for example, intravenously, intraarterially, intramuscularly, or subcutaneously.

The sd-rxRNA® that is targeted to a neoplasm, in some instances target a proliferative gene or a gene that is expressed at higher levels in a neoplastic tissue than in other tissues. A "proliferative gene," as referred to herein, can be any gene that promotes, directly or indirectly, increased rate of growth or replication of cells, resulting in formation of a neoplasm or neoplastic cells. Increase rate of growth or replication resulting from expression/function of a proliferative gene is relative to the rate of growth or replication of non-neoplastic tissue of similar origin (e.g., neoplasms of the skin v. non-neoplastic skin). Several non-limiting examples of proliferative genes or genes that are expressed at higher levels in a neoplastic tissue than in other tissues include VEGF/VEGFR, HER2, PDGF/PDGFR, HDAC, MET, c-kit, CDK, FLT-1, IGF/IGFR, FGF/FGFR, Ras/Raf, Abl, Bcl-2, Src, mTOR, PKC, MAPK, BIRC5, FAS, HIF1A, CDH16, MYC, HRAS, and CTNNB1.

Vascular endothelial growth factor (VEGF) is a member of the PDGF/VEGF growth factor family and encodes a protein that is often found as a disulfide linked homodimer. This protein is a glycosylated mitogen that specifically acts on endothelial cells and has various effects, including mediating increased vascular permeability, inducing angiogenesis, vasculogenesis and endothelial cell growth, promoting cell migration, and inhibiting apoptosis. Elevated levels of this protein is linked to POEMS syndrome, also known as Crow-Fukase syndrome. Mutations in this gene have been associated with proliferative and nonproliferative diabetic retinopathy. Alternatively spliced transcript variants, encoding either freely secreted or cell-associated isoforms, have been characterized, and can be targeted with sd-rxRNA® molecules of the present invention. There is also evidence for the use of non-AUG (CUG) translation initiation sites upstream of, and in-frame with the first AUG, leading to additional isoforms. A representative example of a transcript variant of human VEGFA is Genbank accession number NM_001025366.2. Its corresponding protein is Genbank accession number NP_001020537.2.

Platelet-derived growth factor (PDGFA/PDGFB) is a member of the platelet-derived growth factor family. The four members of this family are mitogenic factors for cells of mesenchymal origin and are characterized by a motif of eight cysteines. The PDGF gene product can exist either as a homodimer or as a heterodimer with the platelet-derived growth factor beta polypeptide, where the dimers are connected by disulfide bonds. Studies using knockout mice have shown cellular defects in oligodendrocytes, alveolar smooth muscle cells, and Leydig cells in the testis; knockout mice die either as embryos or shortly after birth. Two splice variants have been identified for PDGF, and can be targeted by the sd-rxRNA® of the present invention. Representative examples of human PDGF transcripts are GenBank accession numbers NM_002607.5 and NM_011057.3. Their corresponding proteins are Genbank accession numbers NP_002598.4 and NP_03187.2, respectively. PDGF binds to its receptor, PDGFR. A representative example of human PDGFR transcript is Genbank accession number NM_006206.4, and its corresponding protein is NP_006197.1.

Human epidermal growth factor 2 (HER2, also referred to as HER-2, NEU, NGL, TKR1, CD340, MLN 19, and ERBB2) encodes a member of the epidermal growth factor (EGF) receptor family of receptor tyrosine kinases. This protein has no ligand binding domain of its own and therefore cannot bind growth factors. However, it does bind tightly to other ligand-bound EGF receptor family members to form a heterodimer, stabilizing ligand binding and enhancing kinase-mediated activation of downstream signaling pathways, such as those involving mitogen-activated protein kinase and phosphatidylinositol-3 kinase. Allelic variations at amino acid positions 654 and 655 of isoform a (positions 624 and 625 of isoform b) have been reported, with the most common allele being Ile654/Ile655. Amplification and/or overexpression of this gene has been reported in numerous cancers, including breast and ovarian tumors. Alternative splicing results in several additional transcript variants, some encoding different isoforms. Each transcript variant can be a target of the sd-rxRNA® of the present invention. A representative example of a transcript variant of HER2 is GenBank accession number NM_004448.2. Its corresponding protein is Genbank accession number NP_004439.2.

Histone deacetylase 1 (HDAC1), belongs to the histone deacetylase/acuc/alpha family and is a component of the histone deacetylase complex. It interacts with retinoblastoma tumor-suppressor protein and this complex is a key element in the control of cell proliferation and differentiation. Together with metastasis-associated protein-2, it deacetylates p53 and modulates its effect on cell growth and apoptosis. In some instances, the sd-rxRNA® molecules can target HDAC1, retinoblastoma tumor-suppressor protein, and/or metastasis-associated protein-2. In other instances, the sd-rxRNA® can target p53. A representative example of human HDAC1 transcript is Genbank accession number NM_004964.2, and its corresponding protein is Genbank accession number NP_004955.2.

Met proto-oncogene (MET), is a hepatocyte growth factor receptor and encodes tyrosine-kinase activity. The primary single chain precursor protein is post-translationally cleaved to produce the alpha and beta subunits, which are disulfide linked to form the mature receptor. Various mutations in the MET gene are associated with papillary renal carcinoma. Two transcript variants encoding different isoforms have been found for this gene, each of which can be targeted by the sd-rxRNA®. A representative example of human MET transcript is Genbank accession number NM_000245.2, and its corresponding protein is Genbank accession number NP_000236.2.

V-kit Hardy-Zuckerman 4 feline sarcoma viral oncogene (KIT, also referred to as PBT, SCFR, C-Kit, or CD117), encodes the human homolog of the proto-oncogene c-kit. C-kit was first identified as the cellular homolog of the feline sarcoma viral oncogene v-kit. This protein is a type 3 transmembrane receptor for MGF (mast cell growth factor, also known as stem cell factor). Mutations in this gene are associated with gastrointestinal stromal tumors, mast cell disease, acute myelogenous leukemia, and piebaldism. Multiple transcript variants encoding different isoforms have been found for this gene, each of which can be targeted by the sd-rxRNA® molecules. A representative example of human KIT transcript is Genbank accession number NM_000222.2, and its corresponding protein is NP_000213.1.

Cyclin-dependent kinases (CDKs) play an essential role in cell cycle control of eukaryotic cells, are phosphorylated, and thus activated by the CDK-activating kinase (CAK). CAK is a multisubunit protein that includes CDK7 (MIM 601955), cyclin H (CCNH; MIM 601953), and MAT1. MAT1 (for 'menage a trois-1') is involved in the assembly of the CAK complex. A representative example of a human CDK transcript is Genbank accession number NM_001177963.1, and its corresponding protein is NP_001171434.1.

Fms-related tyrosine kinase 1 (FLT-1, also referred to as FLT, VEGFR1, FLT1) encodes a member of the vascular endothelial growth factor receptor (VEGFR) family. VEGFR family members are receptor tyrosine kinases (RTKs) which contain an extracellular ligand-binding region with seven immunoglobulin (Ig)-like domains, a transmembrane segment, and a tyrosine kinase (TK) domain within the cytoplasmic domain. This protein binds to VEGFR-A, VEGFR-B and placental growth factor and plays an important role in angiogenesis and vasculogenesis. Expression of this receptor is found in vascular endothelial cells, placental trophoblast cells and peripheral blood monocytes. Multiple transcript variants encoding different isoforms have been found for this gene. Isoforms include a full-length transmembrane receptor isoform and shortened, soluble isoforms. The soluble isoforms are associated with the onset of pre-eclampsia. Each transcript variant of FLT-1 can be a target of the sd-rxRNA®. A representative example of human FLT-1 transcript is Genbank accession number NM_001159920.1, and its corresponding protein is NP_00115392.1.

Insulin-like growth factors (IGFs) are similar to insulin in function and structure and are members of a family of proteins involved in mediating growth and development. IGFI protein, for example, is processed from a precursor, bound by a specific receptor, and secreted. Defects in this gene are a cause of insulin-like growth factor I deficiency. Several transcript variants encoding different isoforms have been found for these genes, each of which can be a target of the sd-rxRNA®. A representative example of human IGF transcript is Genbank accession number NM_000618.3, and its corresponding protein is NP_000609.1.

Fibroblast growth factor (FGF) family members possess broad mitogenic and cell survival activities, and are involved in a variety of biological processes, including embryonic development, cell growth, morphogenesis, tissue repair, tumor growth, and invasion. FGF1, for example, functions as a modifier of endothelial cell migration and proliferation, as well as an angiogenic factor. It acts as a mitogen for a variety of mesoderm- and neuroectoderm-derived cells in vitro, thus is thought to be involved in organogenesis. Alternatively spliced transcript variants encoding distinct isoforms of several FGFs have been reported, each of which may be a target of the sd-rxRNA®. A representative example of human FGF1 transcript s Genbank accession number NM_000800.3, and its corresponding protein is NP_000791.1.

Fibroblast growth factor receptor (FGFR) family members, having highly conserved amino acid sequences between members and throughout evolution, differ from one another in their ligand affinities and tissue distribution. A full-length representative protein consists of an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation. FGFR1, for example, binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome 2. Chromosomal aberrations involving FGFR1 are associated with stem cell myeloproliferative disorder and stem cell leukemia lymphoma syndrome. Alternatively spliced variants which encode different protein isoforms of FGFR1 family members have been described, each of which may be a target of the sd-rxRNA®. A representative example of a human FGFR1 is Genbank accession number NM_001174063.1, and its corresponding protein is NP_001167534.1.

The Ras subfamily (an abbreviation of RAt Sarcoma) is a protein subfamily of small GTPases that are involved in cellular signal transduction, and is also used to designate gene subfamily of the genes encoding those proteins. Activation of Ras signaling causes cell growth, differentiation and survival. Ras is the prototypical member of the Ras superfamily of proteins which are all related in structure and regulate diverse cell behaviors. Since Ras communicates signals from outside the cell to the nucleus, mutations in ras genes can permanently activate it and cause inappropriate transmission inside the cell, even in the absence of extracellular signals. Because these signals result in cell growth and division, dysregulated Ras signaling can ultimately lead to oncogenesis and cancer. Activating mutations in Ras are found in 20-25% of all human tumors and up to 90% in specific tumor types.

KRAS, a Kirsten ras oncogene homolog from the mammalian ras gene family, encodes a protein that is a member of the small GTPase superfamily. A single amino acid substitution is responsible for an activating mutation. The transforming protein that results is implicated in various malignancies, including lung adenocarcinoma, mucinous adenoma, ductal carcinoma of the pancreas and colorectal carcinoma. Alternative splicing leads to variants encoding two isoforms that differ in the C-terminal region. Each KRAS gene variant can be a target of the sd-rxRNA®. A representative example of human KRAS transcript is Genbank accession number NM_004985.3, and its corresponding protein is NP_04976.2.

HRAS, a v-HA-ras Harvey rat sarcoma viral oncogene homolog from the mammalian ras gene family, encodes a protein that undergoes a continuous cycle of de- and re-palmitoylation, which regulates its rapid exchange between the plasma membrane and the Golgi apparatus. Mutations in this gene cause Costello syndrome, a disease characterized by increased growth at the prenatal stage, growth deficiency at the postnatal stage, predisposition to tumor formation, mental retardation, skin and musculoskeletal abnormalities, distinctive facial appearance and cardiovascular abnormalities. Defects in this gene are implicated in a variety of cancers, including bladder cancer, follicular thyroid cancer, and oral squamous cell carcinoma. Multiple transcript variants, which encode different isoforms, have been identified for this gene. Each transcript variant can be a target of the sd-rxRNA®. A representative example of human HRAS transcript is Genbank accession number NM_001130442.1, and its corresponding protein is NP_001123914.1.

RAF proto-oncogene serine/threonine-protein kinase also known as proto-oncogene c-RAF or simply c-Raf is an enzyme that in humans is encoded by the RAF1 gene. The c-Raf protein functions in the MAPK/ERK signal transduction pathway as part of a protein kinase cascade. c-Raf is a member of the Raf kinase family of serine/threonine-specific protein kinases, and is a MAP kinase kinase kinase (MAP3K) that functions downstream of the Ras subfamily of membrane associated GTPases to which it binds directly. Once activated, Raf-1 can phosphorylate to activate the dual specificity protein kinases MEK1 and MEK2, which, in turn, phosphorylate to activate the serine/threonine-specific protein kinases ERK1 and ERK2. Activated ERKs are pleiotropic effectors of cell physiology and play an important role in the control of gene expression involved in the cell division cycle, apoptosis, cell differentiation, and cell migration. Any one or more of c-Raf (RAF1), MEK1, MEK2, ERK1, and ERK2 may be targets of the sd-rxRNA®. A representative example of human RAF1 transcript is NM_002880.3, and its corresponding protein is NP_00287.1.

Mitogen-activated protein kinase 1 (MAPK1) (also referred to as ERK, p38, p40, p41, ERK2, ERT1, MAPK2, PRKM1, PRKM2, P42MAPK, or p41mapk) encodes a member of the MAP kinase family. MAP kinases, also known as extracellular signal-regulated kinases (ERKs), act as an integration point for multiple biochemical signals, and are involved in a wide variety of cellular processes such as proliferation, differentiation, transcription regulation and development. The activation of this kinase requires its phosphorylation by upstream kinases. Upon activation, this kinase translocates to the nucleus of the stimulated cells, where it phosphorylates nuclear targets. Two alternatively spliced transcript variants encoding the same protein, but differing in the UTRs, have been reported for this gene. Each transcript variant of MAPK1 can be a target of the sd-rxRNA®. A representative example of human MAPK1 transcript is NM_002745.4, and its corresponding protein is NP_002736.3.

C-abl oncogene 1, non-receptor tyrosine kinase (ABL1) encodes a cytoplasmic and nuclear protein tyrosine kinase that has been implicated in processes of cell differentiation, cell division, cell adhesion, and stress response. Activity of c-Abl protein is negatively regulated by its SH3 domain, and deletion of the SH3 domain turns ABL1 into an oncogene. The t(9;22) translocation results in the head-to-tail fusion of the BCR (MIM:151410) and ABL1 genes present in many cases of chronic myelogeneous leukemia. The DNA-binding activity of the ubiquitously expressed ABL1 tyrosine kinase is regulated by CDC2-mediated phosphorylation, suggesting a cell cycle function for ABL1. The ABL1 gene is expressed as either a 6- or 7-kb mRNA transcript, with alternatively spliced first exons spliced to the common exons 2-11. Each transcript variant of ABL1 can be a target of the sd-rxRNA®. A representative example of human ABL1 transcript is Genbank accession number NM_005057.4, and its corresponding protein is NP_005148.2.

B-cell CLL/lymphoma 2 (Bcl-2) encodes an integral outer mitochondrial membrane protein that blocks the apoptotic death of some cells such as lymphocytes. Constitutive expression of BCL2, such as in the case of translocation of BCL2 to Ig heavy chain locus, is thought to be the cause of follicular lymphoma. Two transcript variants, produced by alternate splicing, differ in their C-terminal ends, each of which can be a target of the sd-rxRNA®. A representative example of a human Bcl-2 transcript is NM_000633.2, and its corresponding protein is NP_00624.2.

V-src sarcoma viral oncogene homolog (SRC) is highly similar to the v-src gene of Rous sarcoma virus. This proto-oncogene may play a role in the regulation of embryonic development and cell growth. The protein encoded by this gene is a tyrosine-protein kinase whose activity can be inhibited by phosphorylation by c-SRC kinase. Mutations in this gene could be involved in the malignant progression of colon cancer. Two transcript variants encoding the same protein have been found for this gene, each of which may be a target of the sd-rxRNA®. A representative example of a human SRC transcript is NM_005417.3, and its corresponding protein is NP_005408.1.

Mechanistic target of rapamycin (serine/threonine kinase) (mTOR) encodes a protein belonging to a family of phosphatidylinositol kinase-related kinases. These kinases mediate cellular responses to stresses such as DNA damage and nutrient deprivation. This protein acts as the target for the cell-cycle arrest and immunosuppressive effects of the FKBP12-rapamycin complex. A representative example of a human mTOR transcript is NM_004958.3, and its corresponding protein is NP_004949.1.

Protein kinase C (PKC) encodes a family of enzymes that are involved in controlling the function of other proteins through the phosphorylation of hydroxyl groups of serine and threonine amino acid residues on these proteins. PKC enzymes in turn are activated by signals such as increases in the concentration of diacylglycerol or Ca2+. Hence PKC enzymes play important roles in several signal transduction cascades. The PKC family consists of about ten isozymes. They are divided into three subfamilies, based on their second messenger requirements: conventional (or classical), novel, and atypical. Conventional (c)PKCs contain the isoforms α, βI, βII, and γ. These require Ca2+, diacylglycerol (DAG), and a phospholipid such as phosphatidylserine for activation. Novel (n)PKCs include the δ, ε, η, and θ isoforms, and require DAG, but do not require Ca2+ for activation. Thus, conventional and novel PKCs are activated through the same signal transduction pathway as phospholipase C. On the other hand, atypical (a)PKCs (including protein kinase Mζ and ι/λ isoforms) require neither Ca2+ nor diacylglycerol for activation. The term "protein kinase C" refers to the entire family of isoforms. Any one or more of conventional, novel, and atypical PKC genes can be a target of the sd-rxRNA®. A representative example of human PKC transcript is NM_005400.2, and its corresponding protein NP_005391.1.

Baculoviral IAP repeat containing 5 (BIRC5) (also referred to as API4 or EPR-1) is a member of the inhibitor of apoptosis (IAP) gene family, which encode negative regulatory proteins that prevent apoptotic cell death. IAP family members usually contain multiple baculovirus IAP repeat (BIR) domains, but this gene encodes proteins with only a single BIR domain. The encoded proteins also lack a C-terminus RING finger domain. Gene expression is high during fetal development and in most tumors yet low in adult tissues. Antisense transcripts are involved in the regulation of this gene's expression. At least four transcript variants encoding distinct isoforms have been found for this gene, each of which may be a target of the sd-rxRNA®. A representative example of human BRCS transcript is NM_001012270.1, and its corresponding protein NP_001012270.1.

Fas (TNF receptor superfamily, member 6) (FAS, also referred to as APT1, CD95, FAS 1, APO-1, FASTM, ALPS 1A, or TNFRSF6) encodes a member of the TNF-receptor superfamily. This receptor contains a death domain. It has been shown to play a central role in the physiological regulation of programmed cell death, and has been implicated in the pathogenesis of various malignancies and diseases of the immune system. The interaction of this receptor with its ligand allows the formation of a death-inducing signaling complex that includes Fas-associated death domain protein (FADD), caspase 8, and caspase 10. The autoproteolytic processing of the caspases in the complex triggers a downstream caspase cascade, and leads to apoptosis. This receptor has been also shown to activate NF-kappaB, MAPK3/ERK1, and MAPK8/JNK, and is found to be involved in transducing the proliferating signals in normal diploid fibroblast and T cells. Several alternatively spliced transcript variants have been described, some of which are candidates for nonsense-mediated mRNA decay (NMD). The isoforms lacking the transmembrane domain may negatively regulate the apoptosis mediated by the full length isoform. Each transcript variant may be a target of the sd-rxRNA®. In some instances, the sd-rxRNA® target is FADD, caspase 8, and/or caspase 10. In other instances, the sd-rxRNA® target is NF-kappaB, MAPK3/ERK1 and/or MAPK8/JNK. A representative example of human BRCS transcript is NM_001012270.1, and its corresponding protein NP_001012270.1.

Hypoxia inducible factor 1, alpha subunit (HIF1A), is a transcription factor found in mammalian cells cultured under reduced oxygen tension that plays an essential role in cellular and systemic homeostatic responses to hypoxia. HIF1 is a heterodimer composed of an alpha subunit and a beta subunit. The beta subunit has been identified as the aryl hydrocarbon receptor nuclear translocator (ARNT). This gene encodes the alpha subunit of HIF-1. Overexpression of a natural antisense transcript (aHIF) of this gene has been shown to be associated with nonpapillary renal carcinomas. Two alternative transcripts encoding different isoforms have been identified. Each transcript variant and/or the natural antisense transcript can be a target of the sd-rxRNA®. A representative example of human HIF1A transcript is NM_001530.3, and its corresponding protein NP_001521.1.

Cadherin 16, KSP-cadherin (CDH16) is a member of the cadherin superfamily, genes encoding calcium-dependent, membrane-associated glycoproteins. Mapped to a previously identified cluster of cadherin genes on chromosome 16q22.1, the gene localizes with superfamily members CDH1, CDH3, CDH5, CDH8 and CDH11. The protein consists of an extracellular domain containing 6 cadherin domains, a transmembrane region and a truncated cytoplasmic domain but lacks the prosequence and tripeptide HAV adhesion recognition sequence typical of most classical cadherins. Expression is exclusively in kidney, where the protein functions as the principal mediator of homotypic cellular recognition, playing a role in the morphogenic direction of tissue development. Alternatively spliced transcript variants encoding distinct isoforms have been identified, each of which can be a target of the sd-rxRNA®. A representative example of human CDH16 transcript is NM_004062.3, and its corresponding protein NP_004053.1.

Catenin (cadherin-associated protein), beta 1 (CTNNB1) encodes a protein that is part of a complex of proteins that constitute adherens junctions (AJs). AJs are necessary for the creation and maintenance of epithelial cell layers by regulating cell growth and adhesion between cells. The encoded protein also anchors the actin cytoskeleton and may be responsible for transmitting the contact inhibition signal that causes cells to stop dividing once the epithelial sheet is complete. This protein binds to the product of the APC gene, which is mutated in adenomatous polyposis of the colon. Mutations in this gene are a cause of colorectal cancer (CRC), pilomatrixoma (PTR), medulloblastoma (MDB), and ovarian cancer. Three transcript variants encoding the same protein have been found for this gene, each of which can be a target of the sd-rxRNA®. A representative example of human CTNNB1 transcript is NM_001098209.1, and its corresponding protein NP_001091679.1.

V-myc myelocytomatosis viral oncogene homolog (MYC) encodes a multifunctional, nuclear phosphoprotein that plays a role in cell cycle progression, apoptosis and cellular transformation. It functions as a transcription factor that regulates transcription of specific target genes. Mutations, overexpression, rearrangement and translocation of this gene have been associated with a variety of hematopoietic tumors, leukemias and lymphomas, including Burkitt lymphoma. There is evidence to show that alternative translation initiations from an upstream, in-frame non-AUG (CUG) and a downstream AUG start site result in the production of two isoforms with distinct N-termini. The synthesis of non-AUG initiated protein is suppressed in Burkitt's lymphomas, suggesting its importance in the normal function of this gene. Each transcript variant, including mutant variants, can be a target of the sd-rxRNA®. A representative example of human MYC transcript is NM_002467.4, and its corresponding protein NP_002458.2.

Further aspects of the invention relate to delivery of sd-rxRNA® to the nervous system. For example, an sd-rxRNA® can be delivered to the brain or to the spinal cord. Any appropriate delivery mechanism for delivering an sd-rxRNA® to the brain or spinal cord can be applied. In some embodiments, delivery to the brain or spinal cord occurs by infusion, intrathecal delivery, parenchymal delivery, intravenous delivery or direct injection into the brain or spinal cord. In some embodiments, an sd-rxRNA® is delivered to a specific region of the brain. An sd-rxRNA® can be modified or formulated appropriately to pass the blood-brain barrier. In other embodiments, an sd-rxRNA® is administered in such a way that it does not need to cross the blood-brain barrier.

In some embodiments, the sd-rxRNA® is delivered by a pump or catheter system into the brain or spinal cord. Examples of such delivery are incorporated by reference from U.S. Pat. No. 6,093,180 (Elsberry). Techniques for infusing drugs into the brain are also incorporated by reference from U.S. Pat. No. 5,814,014 (Elsberry et al.).

Aspects of the invention relate to the use of sd-rxRNA® in treatment of disorders affecting the nervous system. In some embodiments, the sd-rxRNA® is used to treat a neurodegenerative disorder. As used herein, the term "neurodegenerative disorder" refers to disorders, diseases or conditions that are caused by the deterioration of cell and tissue components of the nervous system. Some non-limiting examples of neurodegenerative disorders include stroke, Alzheimer's disease, Parkinson's disease, Huntington's disease, Periventricular leukomalacia (PVL), amyotrophic lateral sclerosis (ALS, "Lou Gehrig's disease"), ALS-Parkinson's-Dementia complex of Guam, Friedrich's Ataxia, Wilson's disease, multiple sclerosis, cerebral palsy, progressive supranuclear palsy (Steel-Richardson syndrome), bulbar and pseudobulbar palsy, diabetic retinopathy, multi-infarct dementia, macular degeneration, Pick's disease, diffuse Lewy body disease, prion diseases such as Creutzfeldt-Jakob, Gerstmann-Straussler-Scheinker disease, Kuru and fatal familial insomnia, primary lateral sclerosis, degenerative ataxias, Machado-Joseph disease/spinocerebellar ataxia type 3 and olivopontocerebellar degenerations, spinal and spinobulbar muscular atrophy (Kennedy's disease), familial spastic paraplegia, Wohlfart-Kugelberg-Welander disease, Tay-Sach's disease, multisystem degeneration (Shy-Drager syndrome), Gilles De La Tourette's disease, familial dysautonomia (Riley-Day syndrome), Kugelberg-Welander disease, subacute sclerosing panencephalitis, Werdnig-Hoffmann disease, synucleinopathies (including multiple system atrophy), Sandhoff disease, cortical basal degeneration, spastic paraparesis, primary progressive aphasia, progressive multifocal leukoencephalopathy, striatonigral degeneration, familial spastic disease, chronic epileptic conditions associated with neurodegeneration, Binswanger's disease, and dementia (including all underlying etiologies of dementia).

In some embodiments, the disorder is Parkinson's disease Huntington's or ALS. In certain embodiments, the disorder is ALS and the sd-rxRNA® targets SOD1, a superoxide dismutase.

Neurodegenerative disorders may also be the result of a brain injury or trauma including that which is caused by a stroke, an injury to the head or spinal cord, or acute ischemic injury. Ischemic injuries refer to conditions that arise when the brain receives insufficient blood flow. In some embodiments, injury to the brain or nervous system can result from a traumatic injury, or could be the result of infection, radiation, chemical or toxic damage. Injury within the brain and nervous system, which may be diffuse or localized, includes an intracranial or intravertebral lesion or hemorrhage, cerebral ischemia or infarction including embolic occlusion and thrombotic occlusion, perinatal hypoxic-ischemic injury, whiplash, shaken infant syndrome, reperfusion following acute ischemia, or cardiac arrest.

In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. There are numerous medical conditions for which antisense therapy is reported to be suitable (see, e.g., U.S. Pat. No. 5,830,653) as well as respiratory syncytial virus infection (WO 95/22,553) influenza virus (WO 94/23,028), and malignancies (WO 94/08, 003). Other examples of clinical uses of antisense sequences are reviewed, e.g., in Glaser. 1996. *Genetic Engineering News* 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia.

The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for inhibiting or preventing in a subject, a disease or condition associated with an aberrant or unwanted target gene expression or activity, by administering to the subject a nucleic acid of the invention. If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays known in the art. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the methods of the invention involve contacting a cell capable of expressing target gene with a nucleic acid of the invention that is specific for the target gene or protein (e.g., is specific for the mRNA encoded by said gene or specifying the amino acid sequence of said protein) such that expression or one or more of the activities of target protein is modulated. These methods can be performed in vitro (e.g., by culturing the cell with the agent), in vivo (e.g., by administering the agent to a subject), or ex vivo. The subjects may be first treated with a priming agent so as to be more responsive to the subsequent RNAi therapy if desired. As such, the present invention provides methods of treating a subject afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Thus the therapeutic agents of the invention can be administered to subjects to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Systemic Delivery of Sd-rxRNA® Through Intravenous Administration sd-rxRNA® molecules were efficiently delivered systemically to remote target tissues such as the liver and heart using intravenous administration. Systemic delivery resulted in efficient compound uptake and silencing in target tissues. As shown in FIG. 1, blood clearance of the sd-rxRNA® molecule is affected by the concentration of the molecule. Half-lives of sd-rxRNA® molecules, delivered at 10 mg/kg or 50 mg/kg are shown in FIG. 1. sd-rxRNA® was detected in the liver after 6 hours but no significant signal was detected after 24 hours.

Daily dosing schedules were tested for intravenous delivery of sd-rxRNA® targeting MAP4K4 and silencing of MAPK4K in the liver was determined (FIG. 2). Male BALB/c6J mice, 6-8 weeks of age were used, with 5 mice in each test group. 50 mg/kg of sd-rxRNA® was administered via tail vain injection daily for 3 days and then samples were harvested on day 4.

sd-rxRNA® molecules with generation I and II chemistry were tested, including active molecules and mismatch or non-targeting controls. Expression of MAP4K4 was determined by QPCR and normalized to expression of a housekeeping gene. Expression was also normalized relative to a control PBS-treated group.

One of the goals of this work was to determine whether repetitive dosing over a 24 hour period enhances uptake in liver. Examples of repetitive dosing regimens tested for sd-rxRNA® delivery are shown in FIG. 3. sd-rxRNA®

(targeting MAP4K4) was dosed 1-4 times over a 24 hour period. sd-rxRNA® molecules were administered through intravenous tail injection at 50 mg/kg per injection. Samples were analyzed at several time points including 6 hours post final dose and 30 hours post first dose. Confocal microscopy and hybridization assays were performed. Concentration in blood was determined through a hybridization assay. Samples were analyzed at several time points including 24 hours post final dose.

FIG. 4 reveals liver uptake following 1-4 doses of sd-rxRNA®. Mice were administered doses of sd-rxRNA® 1, 2, 3, or 4 times with 50 mg/kg within 24 hours. Images were taken using a 20× objective lens. Improved liver uptake was seen with multiple doses within 24 hours. No overt toxicity was seen. Significantly, efficient delivery was also seen in spleen and heart following multiple doses of sd-rxRNA® within a 24 hour period (FIG. 5). Repetitive dosing resulted in increased liver uptake of sd-rxRNA® without accumulation in the blood (FIG. 6)

Figure 37:
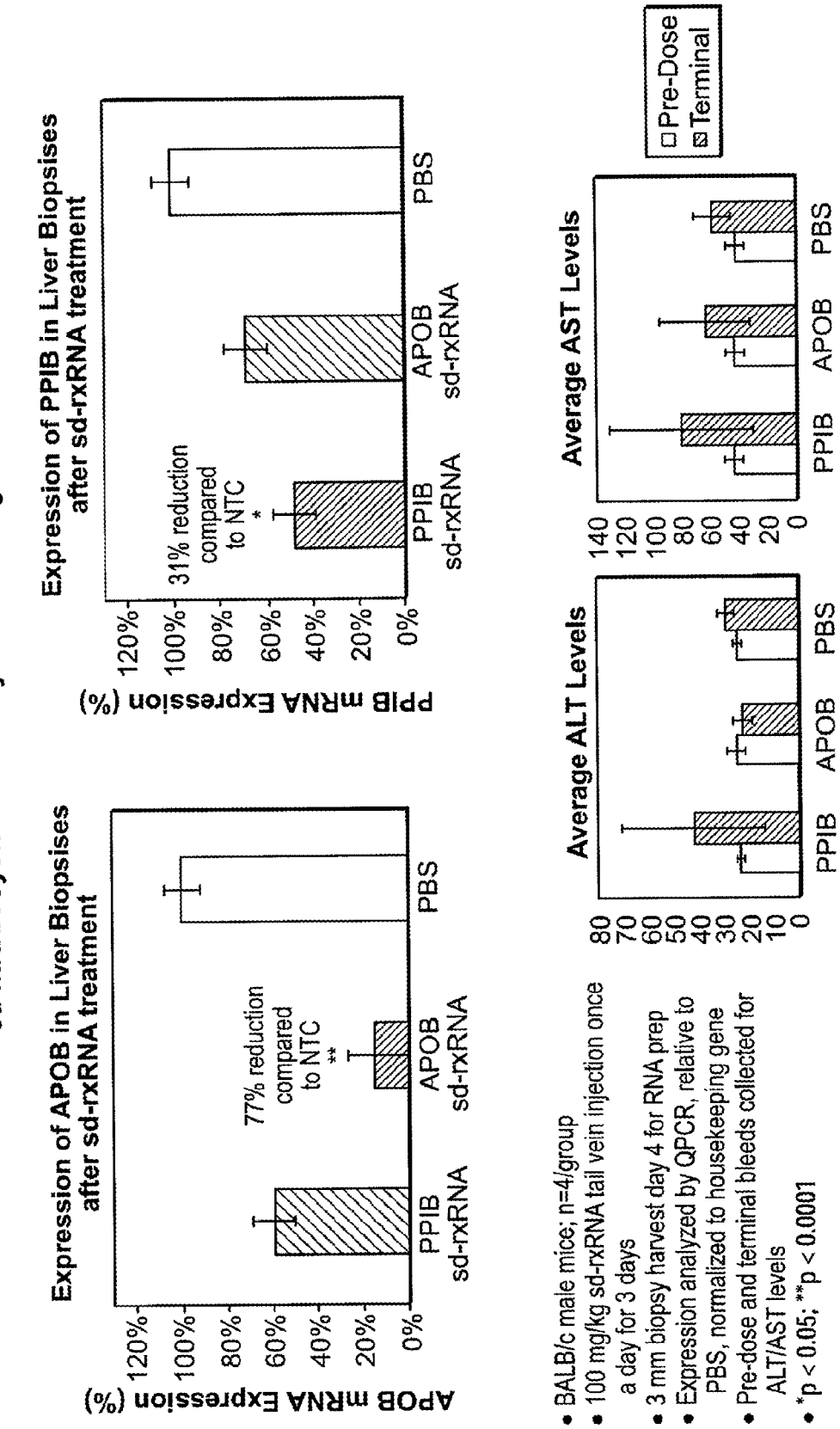
FIG. 37 reveals silencing in the liver following systemic delivery of sd-rxRNA®.

FIG. 37 also reveals efficient systemic sd-rxRNA® delivery to the liver. BALB/c male mice (n=4/group) received 100 mg/kg tail vein injections of sd-rxRNA® once a day for 3 days. On day 4, a 3 mm biopsy was harvested for RNA preparation. Gene expression was analyzed by QPCR, relative to PBS, normalized to housekeeping gene. Statistically significant silencing of target genes was observed in the liver, as measured by qPCR 24 hrs post final dose. These data demonstrate the potential of the sd-rxRNA® molecules for use in systemic clinical indications. Pre-dose and terminal bleeds were also collected for ALT/AST levels. Importantly, systemic administration of sd-rxRNA® molecules does not result in elevated liver enzyme function, e.g., ALT and AST.

Example 2: Subcutaneous Administration of sd-rxRNA®

Efficient delivery of sd-rxRNA® molecules was also achieved through subcutaneous delivery. In conditions described herein, equal dosages of subcutaneously administered sd-rxRNA® molecules resulted in higher sd-rxRNA® presence in target tissues than achieved through intravenous administration. FIG. 7 reveals a comparison of subcutaneous and intravenous administration for efficacy in liver. For both intravenous and subcutaneous administration, a single bolus of 80 mg/kg sd-rxRNA® was administered. Blood levels were determined by a hybridization assay and fluorescence visualization was conducted by confocal microscopy.

The route of administration was found to have an impact on clearance kinetics, blood levels and tissue uptake (FIG. 8). Compound clearance (indicated by pink urine) was detected for 30 minutes past intravenous administration and for 6-8 hours past subcutaneous administration. Blood concentration increases for at least 4 hours after subcutaneous injection. Subcutaneous administration resulted in higher sd-rxRNA® levels in the liver at 24 hours than intravenous administration (FIGS. 9-10).

sd-rxRNA® was also efficiently delivered to the skin using subcutaneous administration. A single subcutaneous injection resulted in sd-rxRNA® delivery at the injection site. Presence of sd-rxRNA® expression was detected 24 hours after injection (FIG. 11). The subcutaneous area of the skin at the site of injection retained integrity for at least 24 hours post injection and the sd-rxRNA® was detected throughout the cells (FIG. 12).

Figure 15:
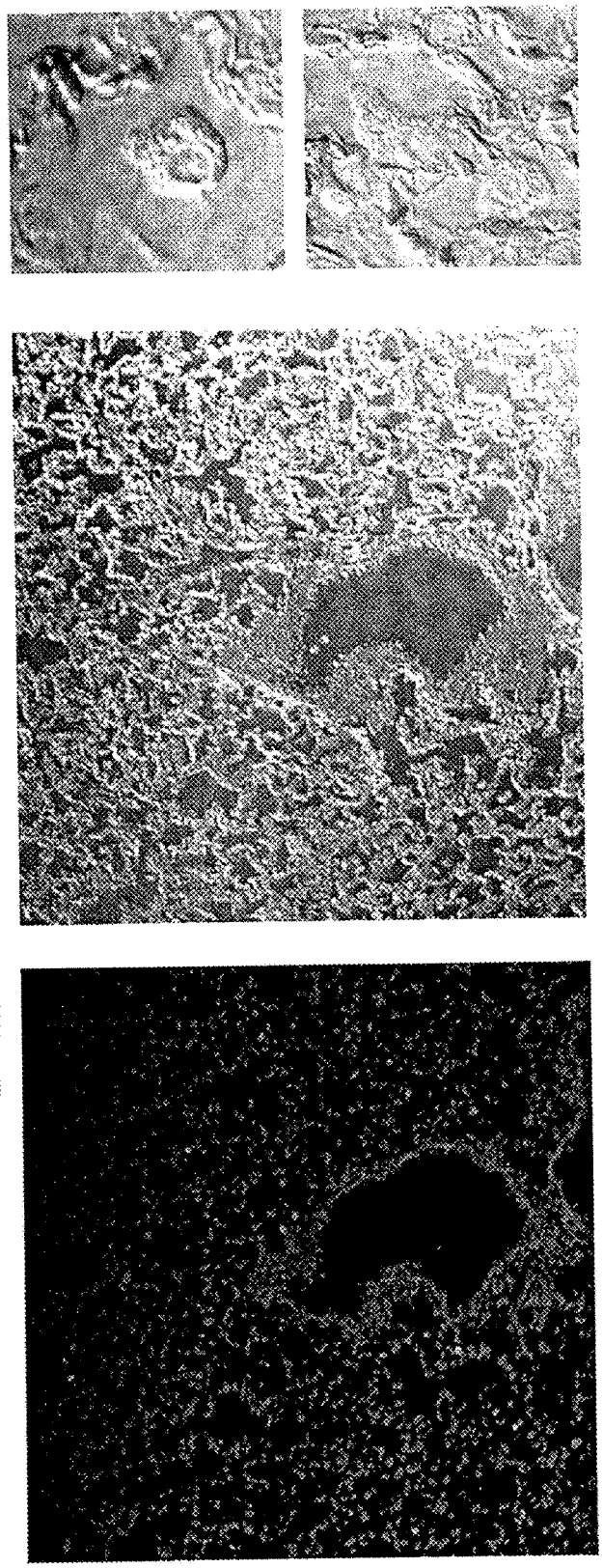
FIG. 15 reveals uptake of d-rxRNA in different cell types following insufflation.

Example 3: Respiratory Applications of sd-rxRNA® sd-rxRNA® molecules were found to be efficiently delivered to a variety of cell types in the lung through insufflation. FIGS. 13-14 reveal efficient delivery of sd-rxRNA® to mouse lungs at 1-44 mg/kg and to rat lungs at 1-10 mg/kg. sd-rxRNA® are preferentially taken up by alveolar macrophages. In mouse tissue, the fluorescent signal was detected primarily in macrophages at up to 20 mg/kg, but in tissue and macrophages at 44 mg/kg. FIG. 15 reveals efficient delivery of sd-rxRNA® compounds to alveolar macrophages. Cell type identification was based on visualization. Some delivery to other cell types was also observed, but under tested conditions, no visible delivery to ciliated epithelial cells was observed.

Figure 16:
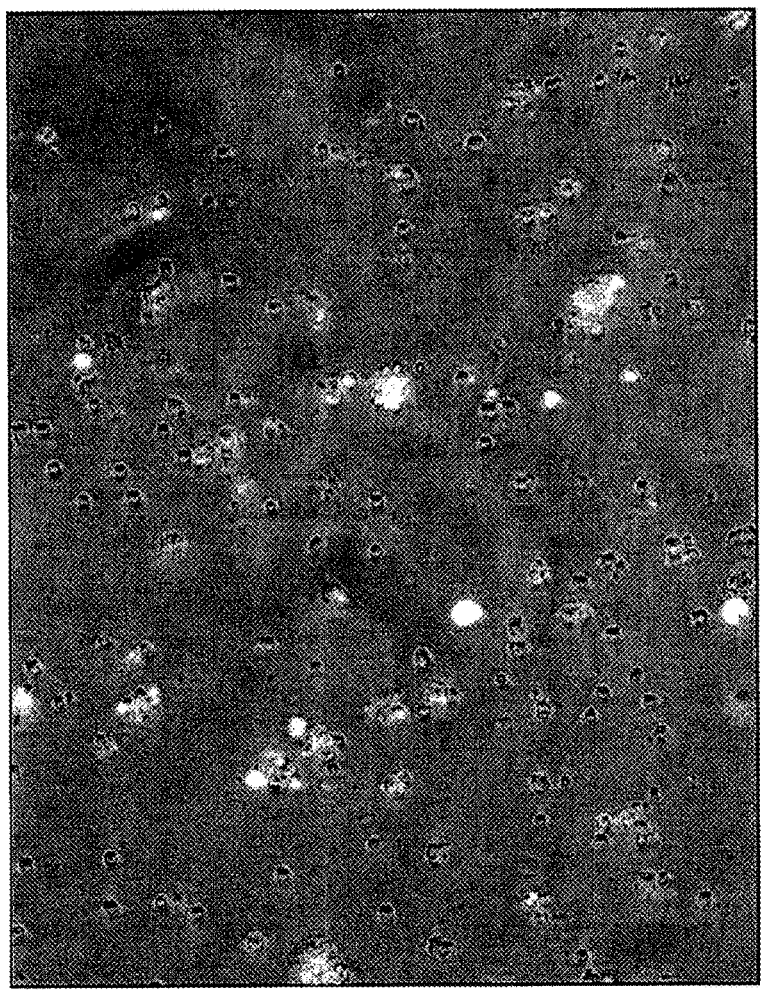
FIG. 16 reveals efficient uptake of sd-rxRNA® in alveolar macrophages following insufflation.

Visualization of sd-rxRNA®-DY547 delivered by insufflation in isolated lung macrophages is demonstrated in FIG. 16. Male BALB/c mouse lungs were minced and incubated in collagenase for 30 minutes. Cells were strained through a 70 micron filter, washed in PBS and plated in 10 cm dishes in DMEM. After 3 hours, the cells were rinsed to remove red blood cells. Animals were observed following dosing and exhibited no lethargy or dehydration (FIG. 17). Lungs appeared normal and healthy.

Methods

Tracheal Insufflation Procedure

Animals were anaesthetized by aerosol isoflurane (5% at induction with 2 L/m $O_2$ flow) through a nose cone. Animals were recumbent, thorax upward. The thorax was elevated at approximately a 45° angle by placement of rolled gauze behind the neck. A light source equipped with flexible fiber-optics arm was adjusted to provide optimal illumination of the trachea. A small sterile q-tip was used to open the lower jaw of the animal and blunted forceps were used to help displace the tongue for maximal oropharyngeal exposure. After a clear view of the trachea was obtained, the MicroSprayer (Penn Century MSA-250) tip was endotracheally inserted and maximum volume 50 ml (mice) or 250 ml (rat) of TA (test article) was delivered via spray down from the trachea into the pulmonary space. Once dosing was accomplished, the tip was immediately withdrawn and the animal was removed from anesthesia. A stethoscope was used to confirm the presence of liquid in the lung and the animal was moved to a clean cage placed upon a heating pad for observation and recovery. Post-dose observation period was a minimum of 1 hour, post-dose.

Male SD rats were dosed via pulmonary insufflation with 250 μl of DY547 labeled sd-rxRNA® (oligonucleotide number 13766.3) at 0.1-10 mpk. Samples were harvested for visualization at 24 or 48 hours. At 5 and 7.7 mpk doses, significant sd-rxRNA® lung uptake was observed, including preferential compound delivery to alveolar macrophages. Under some test conditions, dose levels of 5-7.5 mpk were found to be preferred.

Example 4: Identification of sd-rxRNA® Sequences Targeting hApoB, PCSK9 and PPIB Optimal sequences in ApoB, PCSK9 and PPIB for sd-rxRNA® development were identified using a sequence selection algorithm. The algorithm selects sequences based on the following criteria: a GC content greater than 32% but less than 47%, homology to specific animal models (e.g., mouse or rat), avoidance of 5 or more U/U stretches and/or 2 or more G/C stretches, an off-target hit score of less than 500, and avoidance of sequences contained within the 5' UTR.

The sequences were developed initially as 25 nucleotide blunt-ended duplexes with O-methyl modification. These sequences were screened in various cell lines to identify those that were most efficient in reducing gene expression. Several concentrations of the RNA molecules, such as 0.025, 0.1 and 0.25 nM, were tested, and suitable concentrations were determined. A full screen was then run at a desirable concentration. Dose response curves were generated to determine the most potent sequences. Hits considered hyperfunctional were those that had EC50 values of less than 100 pM in lipid transfection. Optimal sequences were then developed into sd-rxRNA® molecules based on parameters described throughout the application. sd-rxRNA® molecules were used for secondary screening.

Table 1 reflects sequences identified in ApoB using an algorithm as described above. Percent expression data for each sequence, indicating effectiveness at achieving gene silencing, when used at a concentration of 0.1 nM is provided. Table 2 presents ApoB sd-rxRNA® sequences. Table 3 presents PCSK9 sd-rxRNA® sequences and Table 4 presents PPIB sd-rxRNA® sequences.

Example 5: Linker Chemistry

Figure 36A:
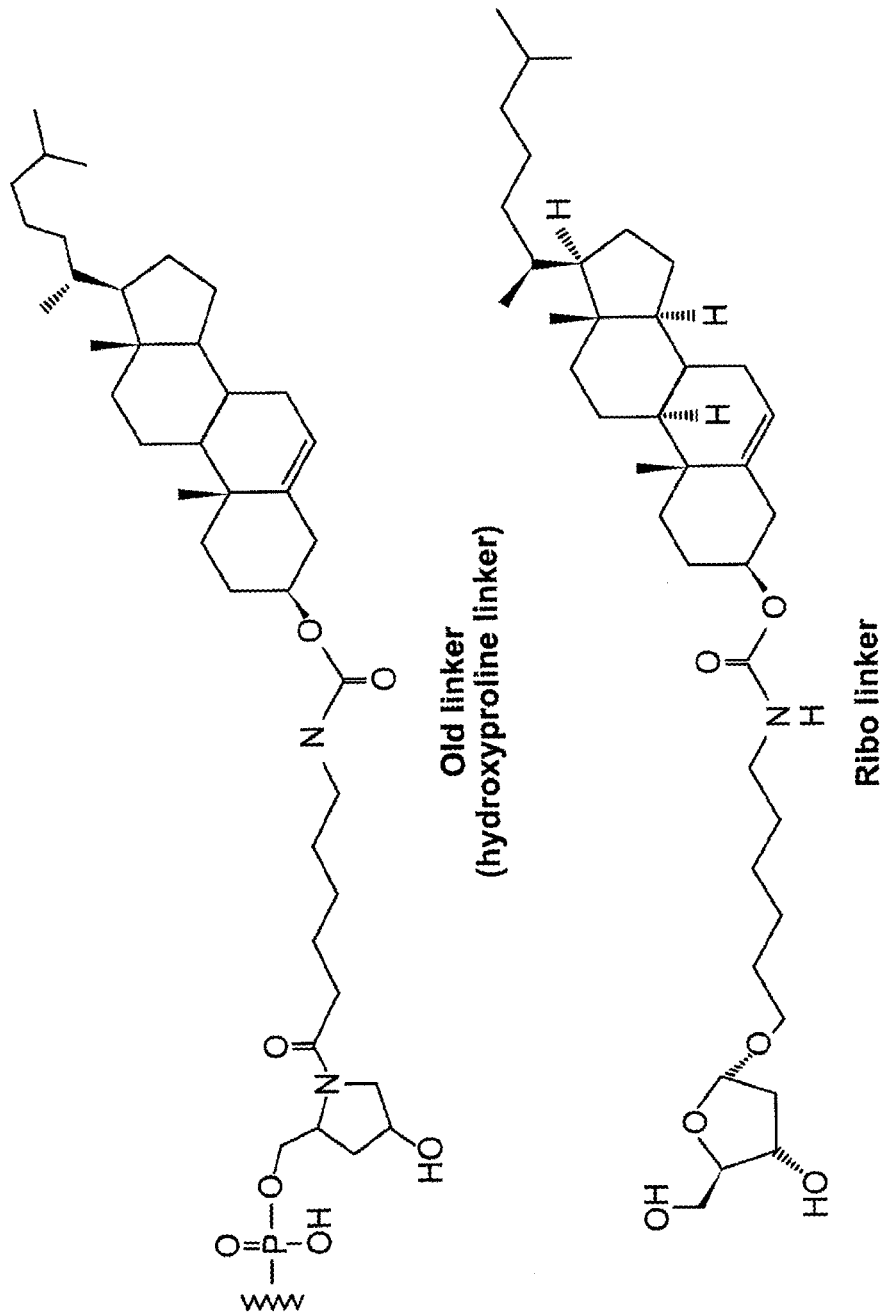
FIGS. 36A-36B demonstrate that variation of linker chemistry does not influence silencing activity of sd-rxRNA® molecules in vitro. Two different linker chemistries were evaluated, a hydroxyproline linker and ribo linker, on multiple sd-rxRNA® molecules (targeting Map4k4 or PPIB) in passive uptake assays to determine linkers which favor self delivery. HeLa cells were transfected in the absence of a delivery vehicle (passive transfection) with sd-rxRNA® molecules at 1 uM, 0.1 uM or 0.01 uM for 48 hrs. Use of either linker results in an efficacious delivery of sd-rxRNA®.
Figure 36B:
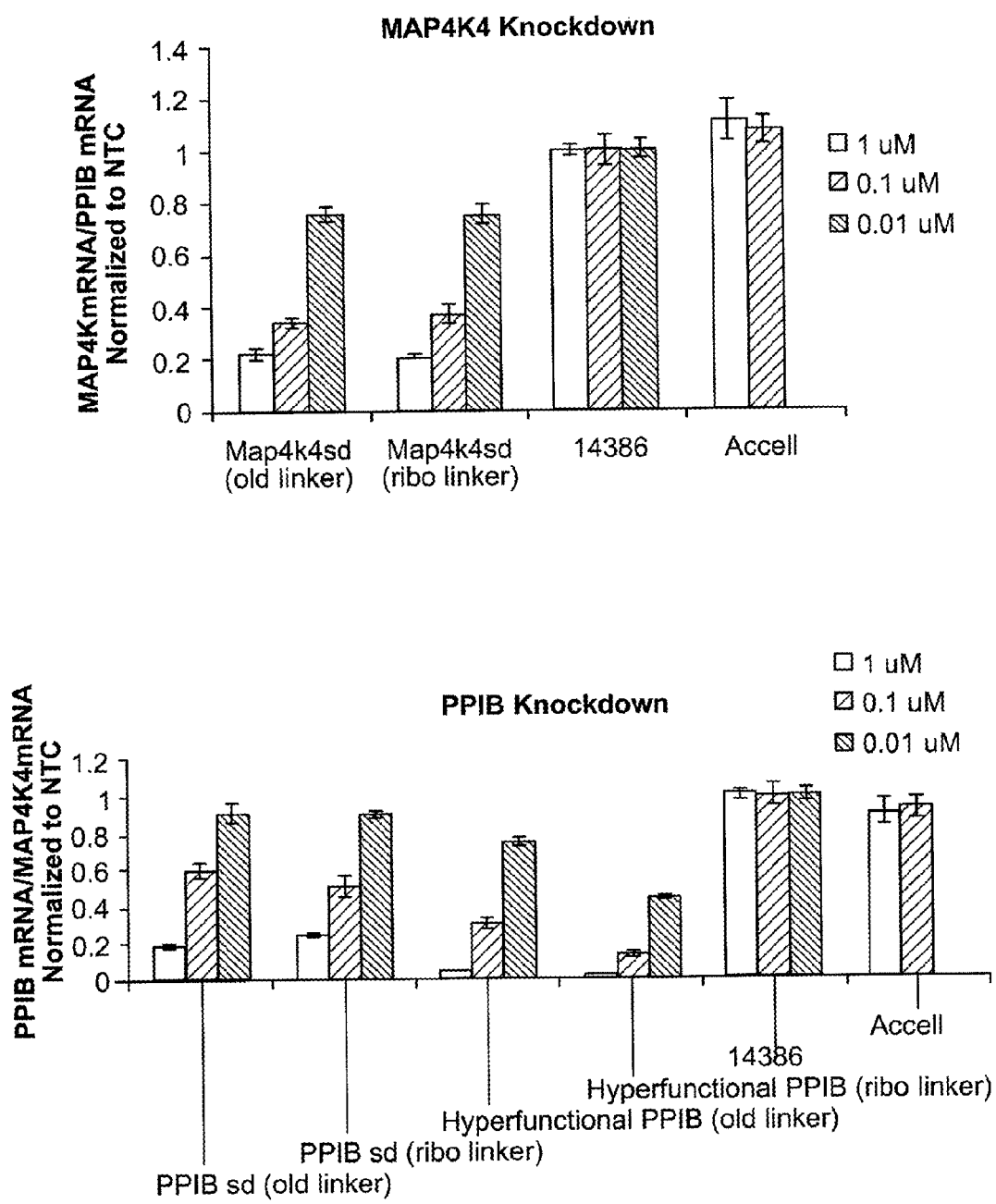

FIG. 36 demonstrates that variation of linker chemistry does not influence silencing activity of sd-rxRNA® molecules in vitro. Two different linker chemistries were evaluated, a hydroxyproline linker and ribo linker, on multiple sd-rxRNA® molecules (targeting Map4k4 or PPIB) in passive uptake assays to determine linkers which favor self delivery. HeLa cells were transfected in the absence of a delivery vehicle (passive transfection) with sd-rxRNA® molecules at 1 uM, 0.1 uM or 0.01 uM for 48 hrs. Use of either linker results in an efficacious delivery of sd-rxRNA®.

The ribo linker used in Example 5 had the following structure:

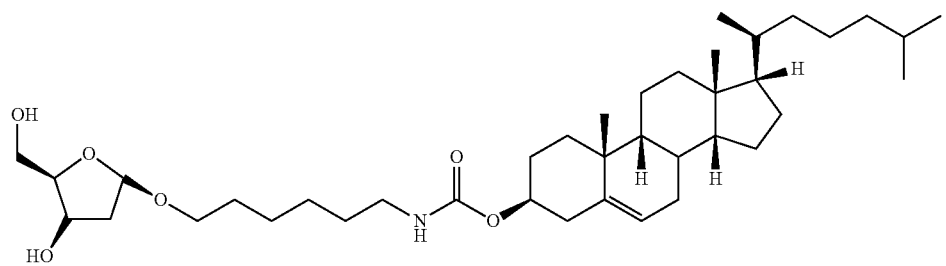

Example 6: Chemical Optimization of sd-rxRNA® Molecules for Optimal Delivery

The effect of chemical modification on stability and systemic delivery of sd-rxRNA® was evaluated. FIG. 38 presents non-limiting examples of modified sequences for ApoB and PPIB sd-rxRNA® molecules. Significantly, through extensive investigation of chemical modification patterns, it was found that increasing the stability of the guide strand through chemical modifications resulted in increased systemic efficacy. In the examples shown in FIG. 38, the ApoB sd-rxRNA® was more highly modified compared to the PPIB sequence (12 2'F vs 8, respectively).

Furthermore, the PPIB sequence contained a stretch of >3 2'OH in a row, a potential site for endonucleases. The increased modification scheme of the ApoB sd-rxRNA® imparts stability to the compound and ensures the maximum compound is delivered to the target of interest, which in this example was the liver. Increasing the stability of the oligonucleotide, via chemical modification of the 2'OH (2'F or 2'OMe), resulted in greater silencing after systemic administration to the liver.

Figure 39A:
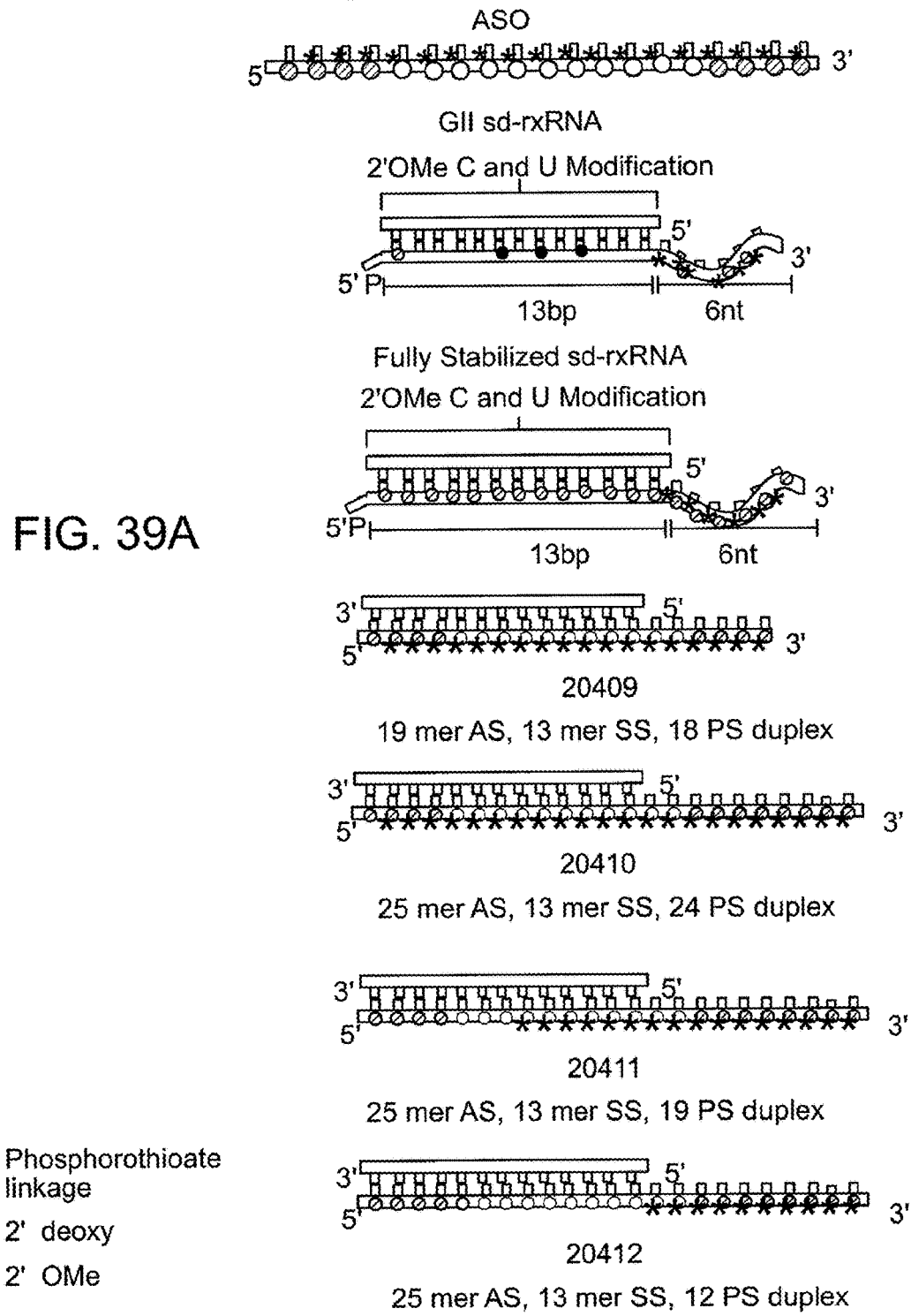

In an effort to improve the biodistribution of sd-rxRNA® molecules upon systemic administration, a panel of chemical and structural modifications were investigated. Chemistries known to impart stability were employed throughout the sd-rxRNA® chemical variant structures; 2'Ome, 2' deoxy and phosphorothioates. As shown in FIG. 39, increasing stability of the sd-rxRNA® leads to greater than 140 fold improvement in sd-rxRNA® distribution to the liver compared to the normal sd-rxRNA®. (In some instances, chemical variants are not active compounds due to modification schemes employed to greatly enhance stability.) It was also observed that varying the phosphorothioate content significantly affected distribution to the liver.

Figure 40:
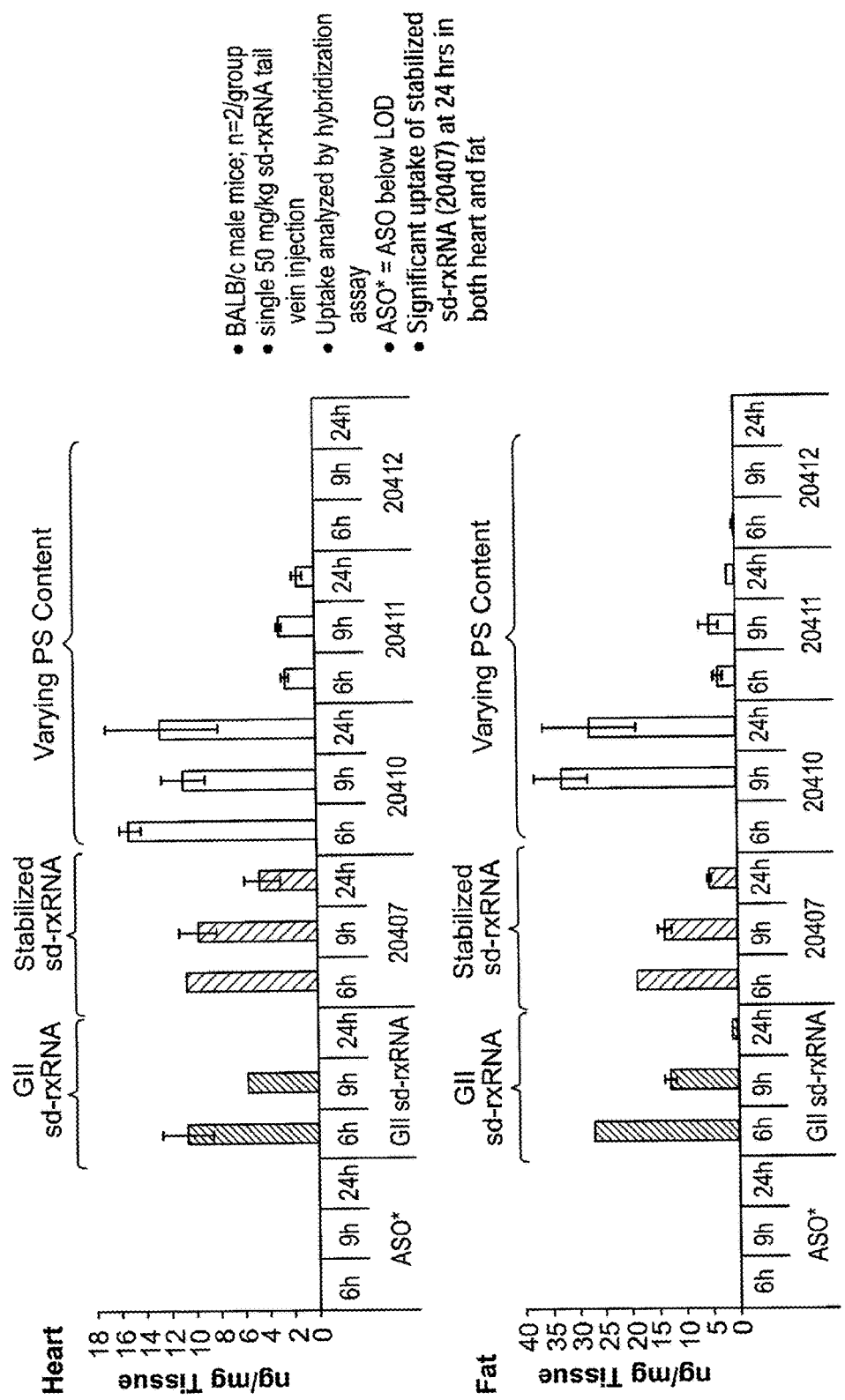
FIG. 40 reveals that certain chemical modification patterns result in significant distribution to heart and fat.

Stabilization of the sd-rxRNA® variants also led to distribution of the compound in other tissues such as the heart and fat, as shown in FIG. 40. Overall, increasing the level of stabilizing modifications was found to lead to: i) increased silencing (mApoB sd liver silencing) compared to less stable sd-rxRNA® (PPIB); ii) increased biodistribution in the liver; and distribution to other tissues such as the heart and fat.

Generation III Compounds

The goal in creating a new generation of sd-rxRNA® was to modulate the PK/PD behavior of sd-rxRNA® molecules by incorporating hydrophobic moieties at position 5 of uridines.

Increasing hydrophobicity is known to enhance cellular uptake (e.g., addition of cholesterol to siRNA compounds). Thus, it was hypothesized that incorporating hydrophobic moieties into the sd-rxRNA® may confer additional stability while retaining potent sd-rxRNA® activity.

FIG. 41 demonstrates that addition of Octyl modifications to the guide strand of sd-rxRNA® targeting Map4k4 resulted in an increase in retention time of 2 minutes or greater (19403-19405) compared to the unmodified guide strand (12984). This shift signifies that the compounds are more hydrophobic than the unmodified compound. Due to the increased hydrophobic character of the passenger strand, incorporation of GIII moieties to this strand does not result in changes in retention time.

Figure 42:
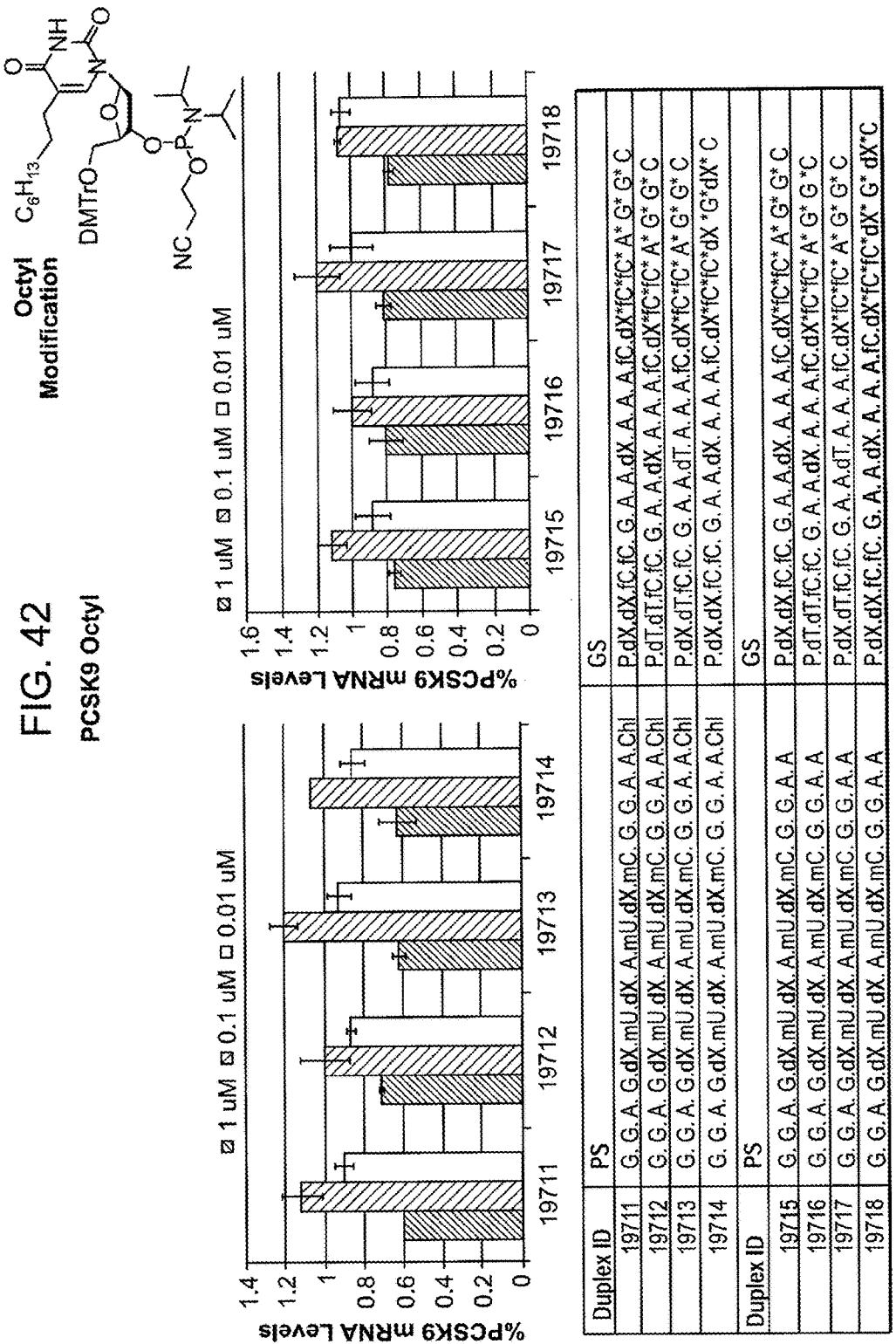
FIG. 42 demonstrates the effects of octyl modification of sd-rxRNA® targeting PCSK9. PS Duplex IDs 19711-18 are SEQ ID NO:500. GS Duplex IDs 19711-18 are SEQ ID NOs: 501-508 respectively.
Figure 43:
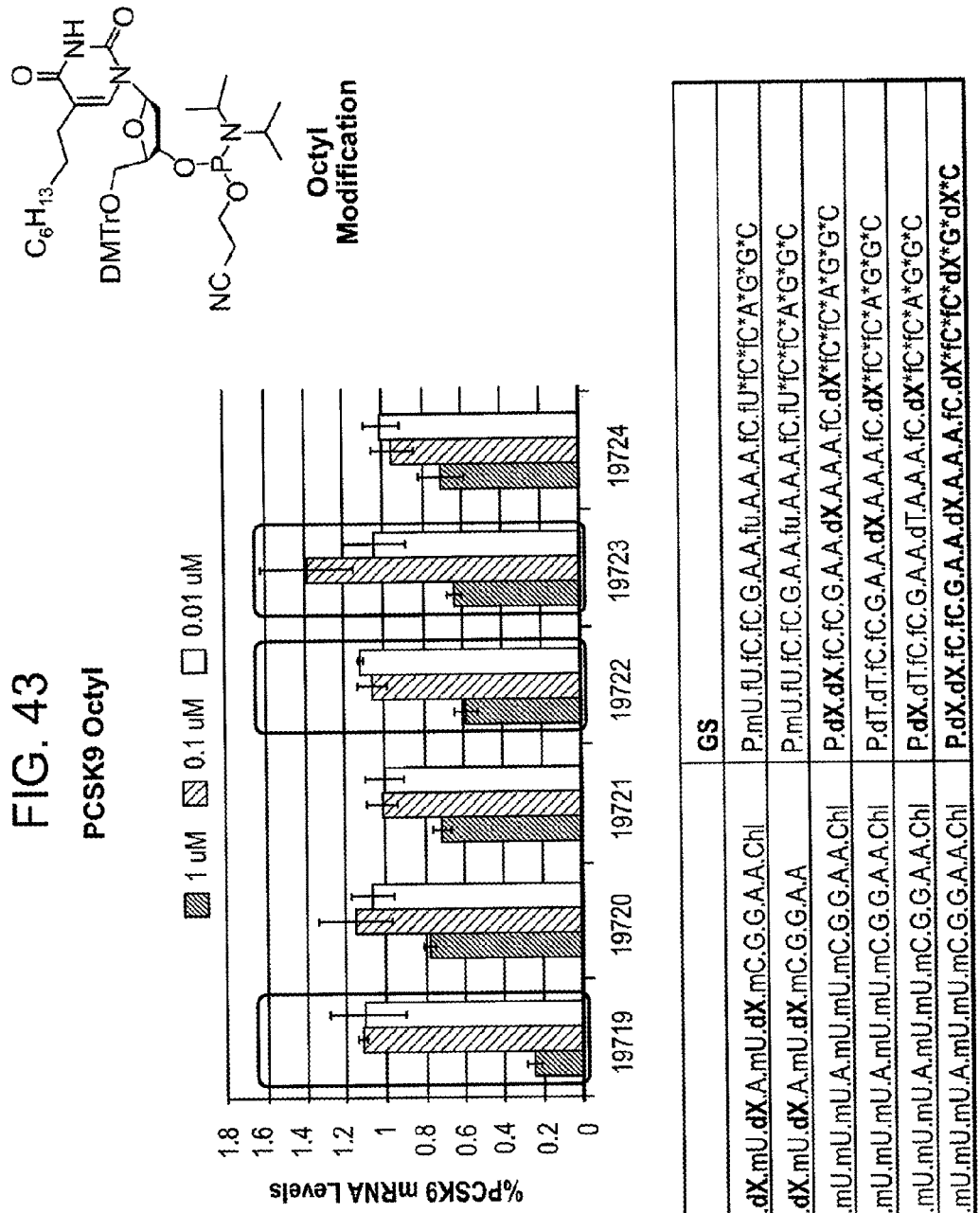
FIG. 43 demonstrates the effects of octyl modification of sd-rxRNA® targeting PCSK9. PS Duplex IDs 1919-24 are SEQ ID NOs:500, 500, 363, 363, 363, and 363 respectively. GS Duplex IDs 1919-24 are SEQ ID NOs:328, 328, 501, 502, 502, and 504 respectively.

FIG. 42 shows that for PCSK9, octyl modifications were not well tolerated when incorporated on both the passenger and guide strand simultaneously. FIG. 43 shows that for PCSK9, octyl modifications were tolerated in the passenger strand (19719 and 20333) when duplexed with a non-octyl-modified guide strand. Octyl modifications to the guide strand were not well tolerated; two octyl modified guide strands demonstrated significantly reduced activity (19722 and 19723).

Figure 44:
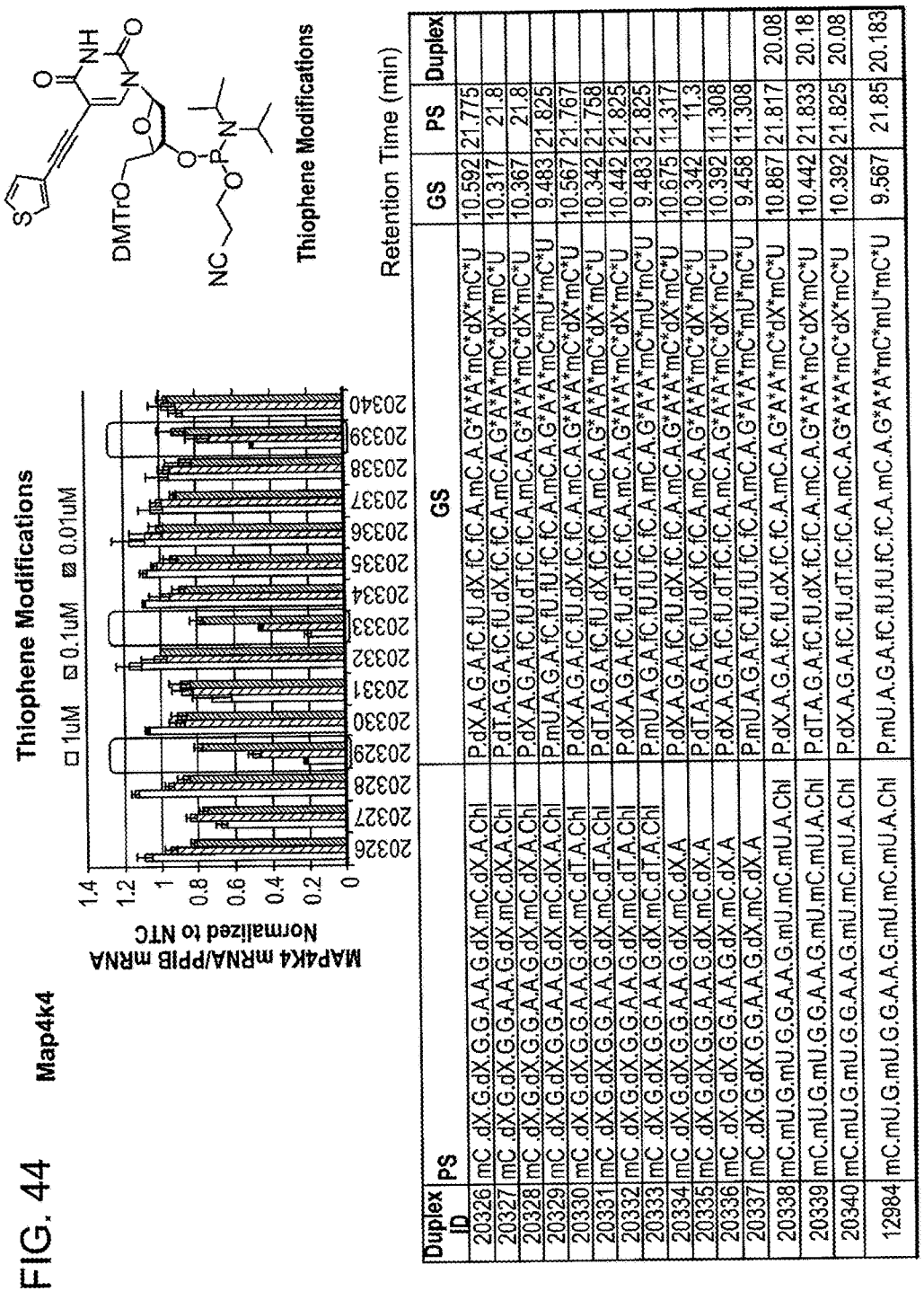
FIG. 44 demonstrates the effects of thiophene modification of sd-rxRNA® targeting MAP4K4. PS Duplex IDs 20326-29 and 20334-37 are SEQ ID NO:614. PS Duplex IDs 20330-33 are SEQ ID NO:509. PS Duplex IDs 2035-40 and 12984 are SEQ ID NO:480. GS Duplex IDs from top to bottom are SEQ ID NOs:510-525 respectively.

FIG. 44 shows that thiophene modifications were well tolerated in the passenger strand (20329 and 20333) when duplexed with a non-thiophene-modified guide strand. Thiophene modifications to the guide strand were not well tolerated. Only one thiophene modified guide strand demonstrated significantly reduced activity (20339).

Figure 45:
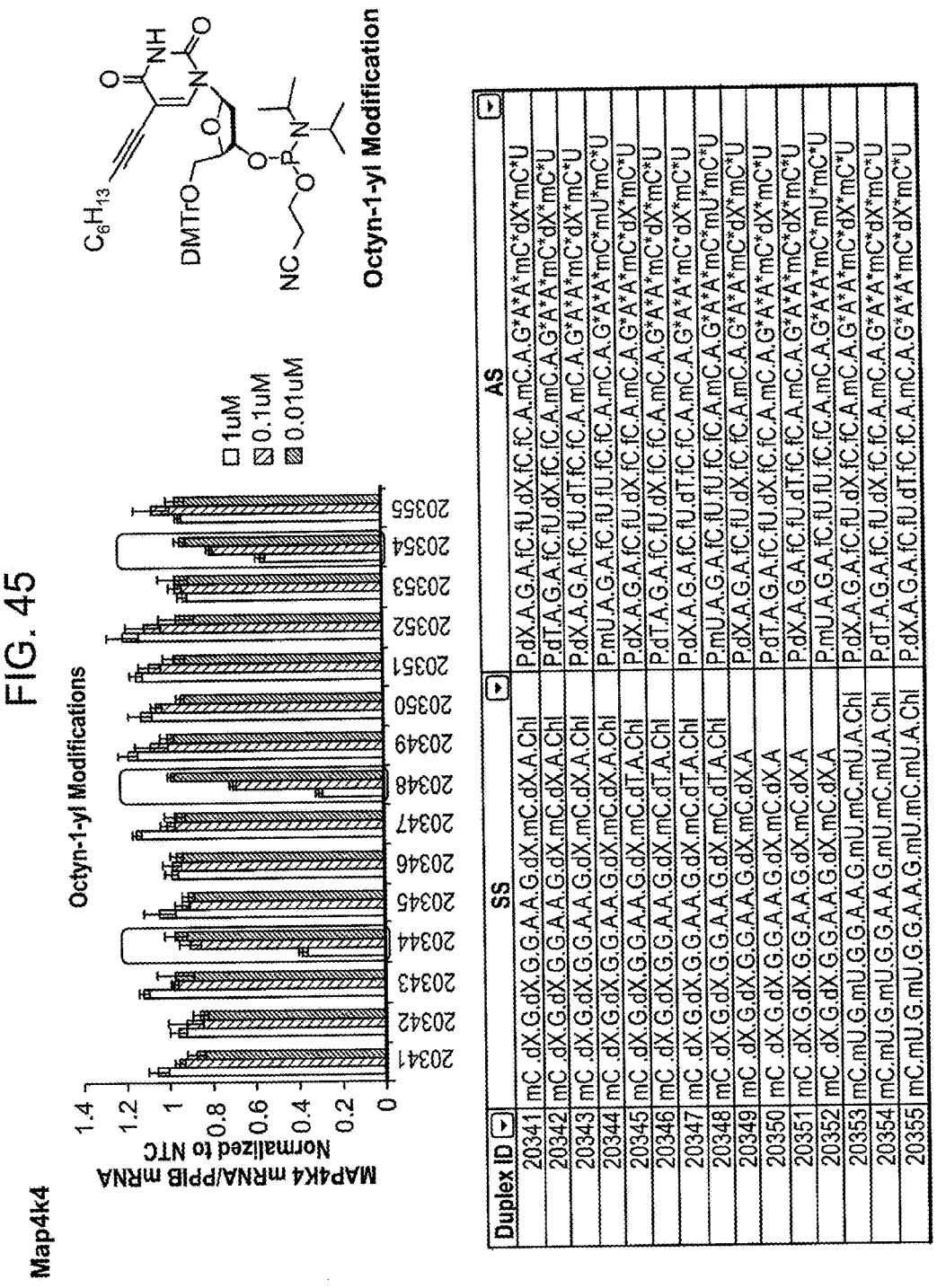
FIG. 45 demonstrates the effects of octyn-1-yl modification of sd-rxRNA® targeting MAP4K4. SS Duplex IDs 20341-44 and 20349-52 are SEQ ID NO:614. SS Duplex IDs 20345-48 are SEQ ID NO:509. SS Duplex IDs 20353-55 are SEQ ID NO:480. AS Duplex IDs from top to bottom are SEQ ID NOs:510-524 respectively.
Figure 46:
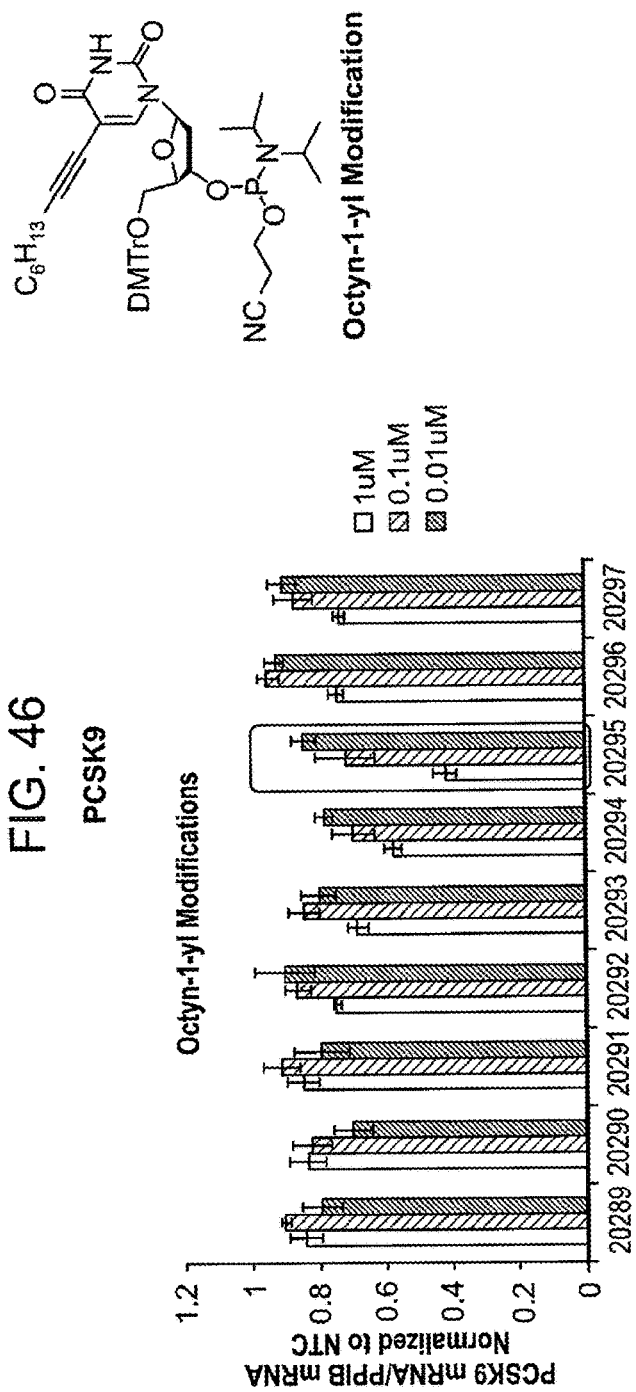
FIG. 46 demonstrates the effects of octyn-1-yl modification of sd-rxRNA® targeting PCSK9. PS Duplex IDs 20289-93 are SEQ ID NO:500. PS Duplex IDs 20294-97 are SEQ ID NO:363. GS Duplex IDs from top to bottom are SEQ ID NOs:501-504, 328, 501, 502, 503, and 504 respectively.

FIG. 45 shows that Octyn-1-yl modifications were well tolerated in the passenger strand (20344 and 20348) when duplexed with a non-octyn-1-yl-modified guide strand. Octyn-1-yl modifications to the guide strand were not well tolerated. Only one Octyn-1-yl modified guide strand demonstrated significantly reduced activity (20354). FIG. 46 also reveals that Octyn-1-yl modifications to the guide strand were not well tolerated for PCSK9 (20295).

Figure 47:
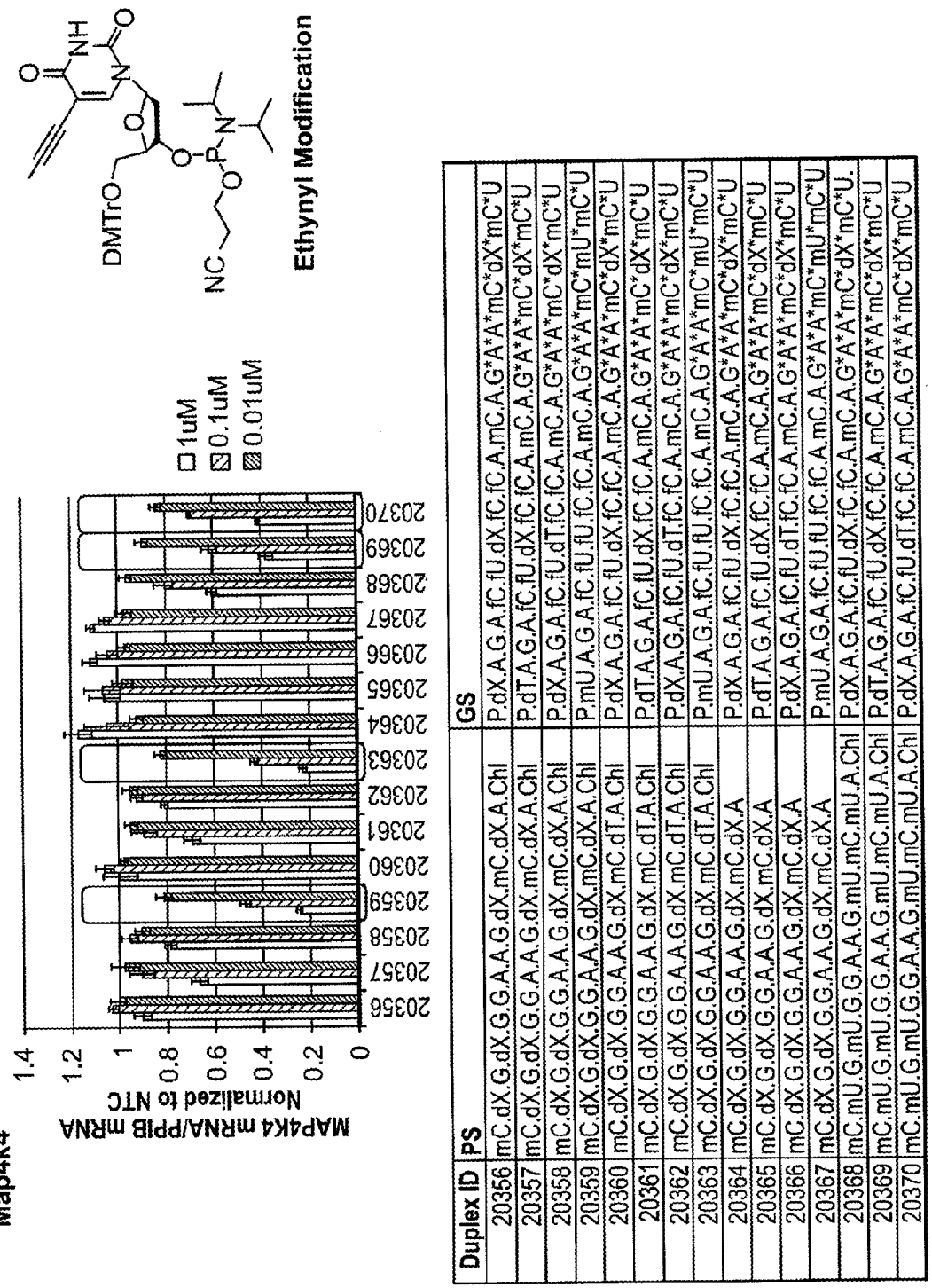
FIG. 47 demonstrates the effects of ethynyl modification of sd-rxRNA® targeting MAP4K4. PS Duplex IDs 20356-59 and 20364-67 are SEQ ID NO:614. PS Duplex IDs 20360-63 are SEQ ID NO:509. PS Duplex IDs 20368-70 are SEQ ID NO:477. GS Duplex IDs from top to bottom are SEQ ID NOs:510-524 respectively.

FIG. 47 reveals that ethynyl modifications were well tolerated in the passenger strand (20344 and 20348) for MAP4K4 when duplexed with a non-ethynyl-modified guide strand. Incorporation of 2 ethynyl modifications in the guide strand was tolerated and demonstrated only a marginal reduction in activity (20369 and 20370). Incorporation of 3 ethynyl modifications in the guide strand was not well tolerated and resulted in a significant reduction in activity (20368).

Figure 48:
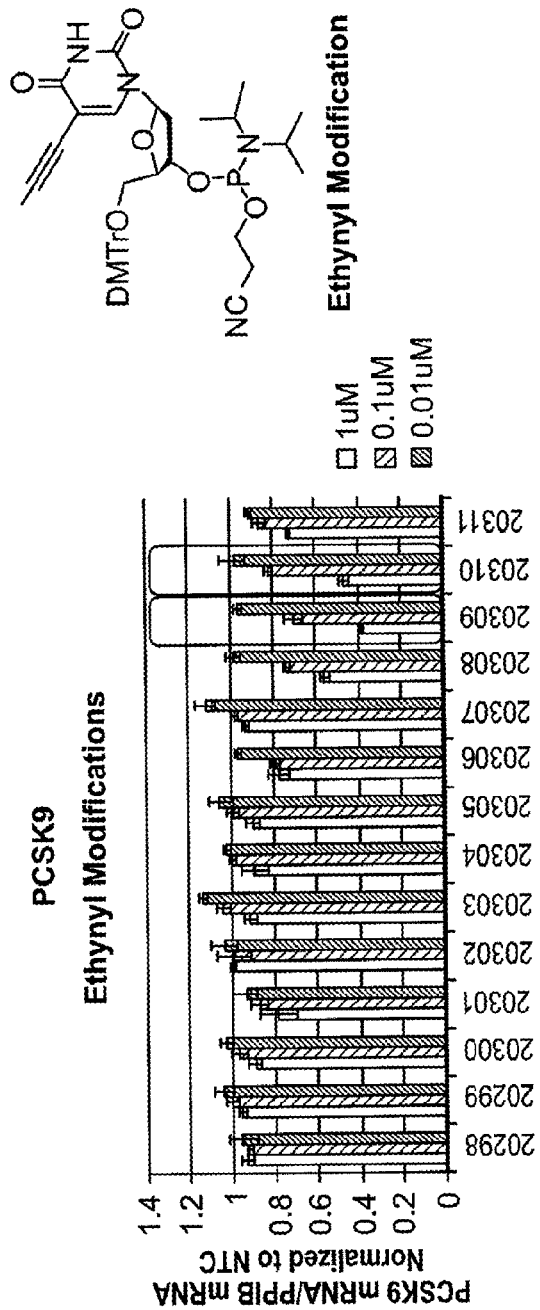
FIG. 48 demonstrates the effects of ethynyl modification of sd-rxRNA® targeting PCSK9. PS Duplex IDs 20298-307 are SEQ ID NO:500. PS Duplex IDs 20308-11 are SEQ ID NO:363. GS Duplex IDs from top to bottom are SEQ ID NOs:501-504, 328, 501-504, 328, 501, 502, 503, and 504 respectively.

FIG. 48 reveals that Ethynyl modifications were not tolerated in the passenger strand (20298 through 20302) for PCSK9 when duplexed with a modified or non-ethynyl-modified guide strand. Incorporation of 2 ethynyl modifications in the guide strand was tolerated and demonstrated only a marginal reduction in activity (20309 and 20310).

Figure 49:
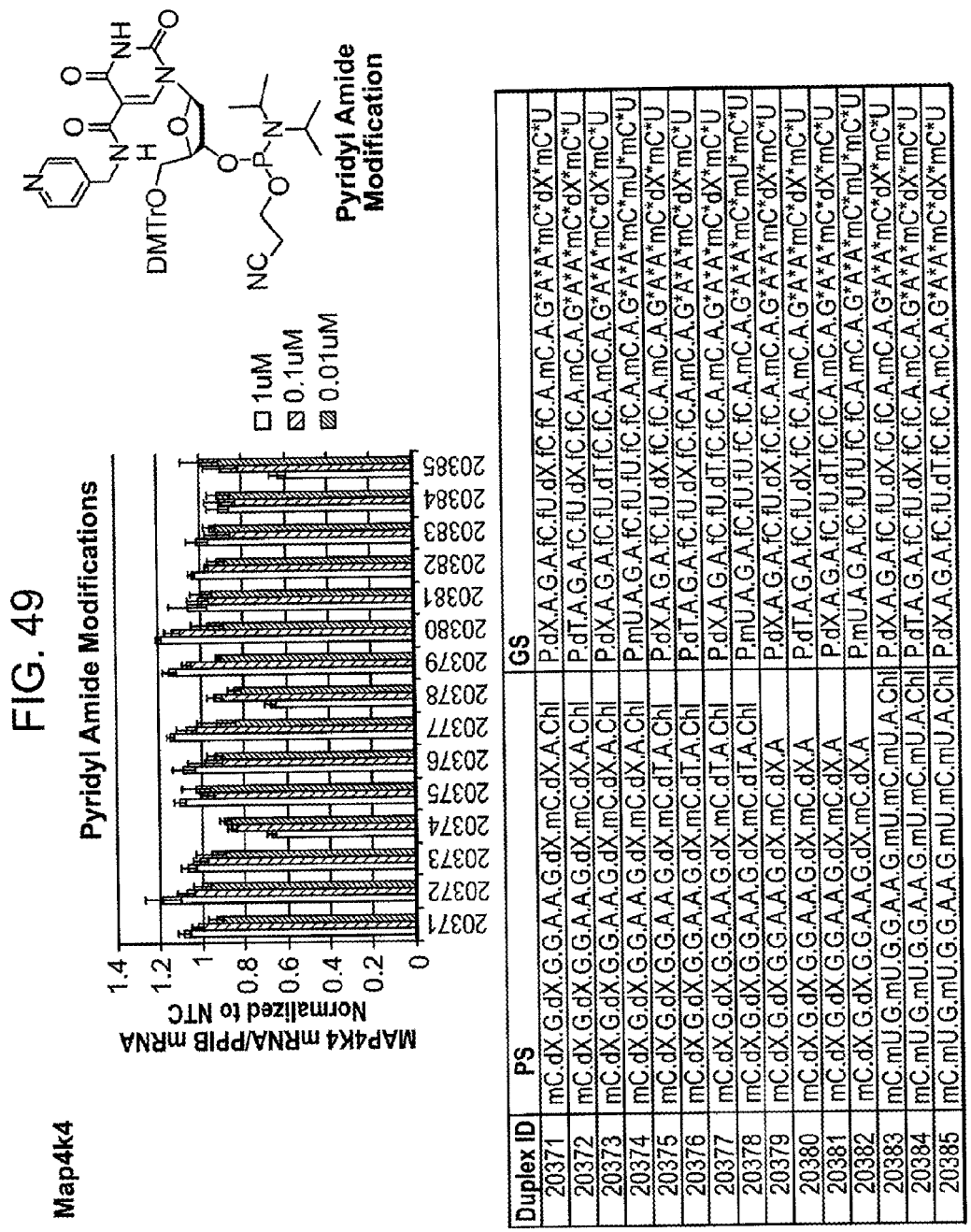
FIG. 49 demonstrates the effects of pyridyl amide modification of sd-rxRNA® targeting PCSK9. PS Duplex IDs 20371-74 and 20379-82 are SEQ ID NO:614. PS Duplex IDs 20375-78 are SEQ ID NO:509. PS Duplex IDs 20383-85 are SEQ ID NO:477. GS Duplex IDs from top to bottom are SEQ ID NOs:510-524 respectively.
Figure 50:
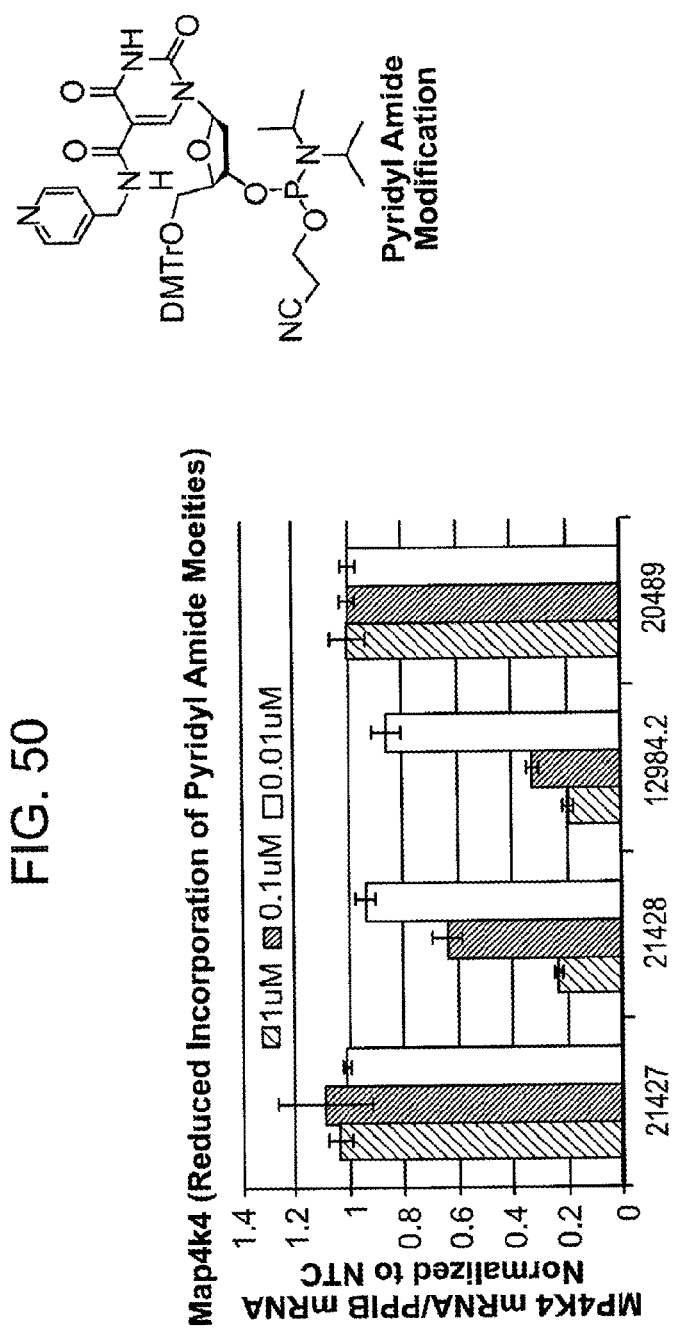
FIG. 50 demonstrates the effects of pyridyl amide modification of sd-rxRNA® targeting MAP4K4. PS Duplex IDs from top to bottom are SEQ ID NOs:526, 527, and 477 respectively. GS Duplex IDs from top to bottom are SEQ ID NO:478.

FIG. 49 reveals that for Map4k4, incorporation of pyridyl amide modifications was not tolerated in either the passenger or guide strand. FIG. 50 reveals that reducing the number of pyridyl incorporations in the sense strand resulted in an active compound (21428). Incorporating (2) pyridyl amides at the 3' end of the sense strand did not reduce activity, however, introduction of (2) pyridyl amides on the 5' end of the sense strand, in some instances, resulted in complete loss of activity (21427).

Figure 51:
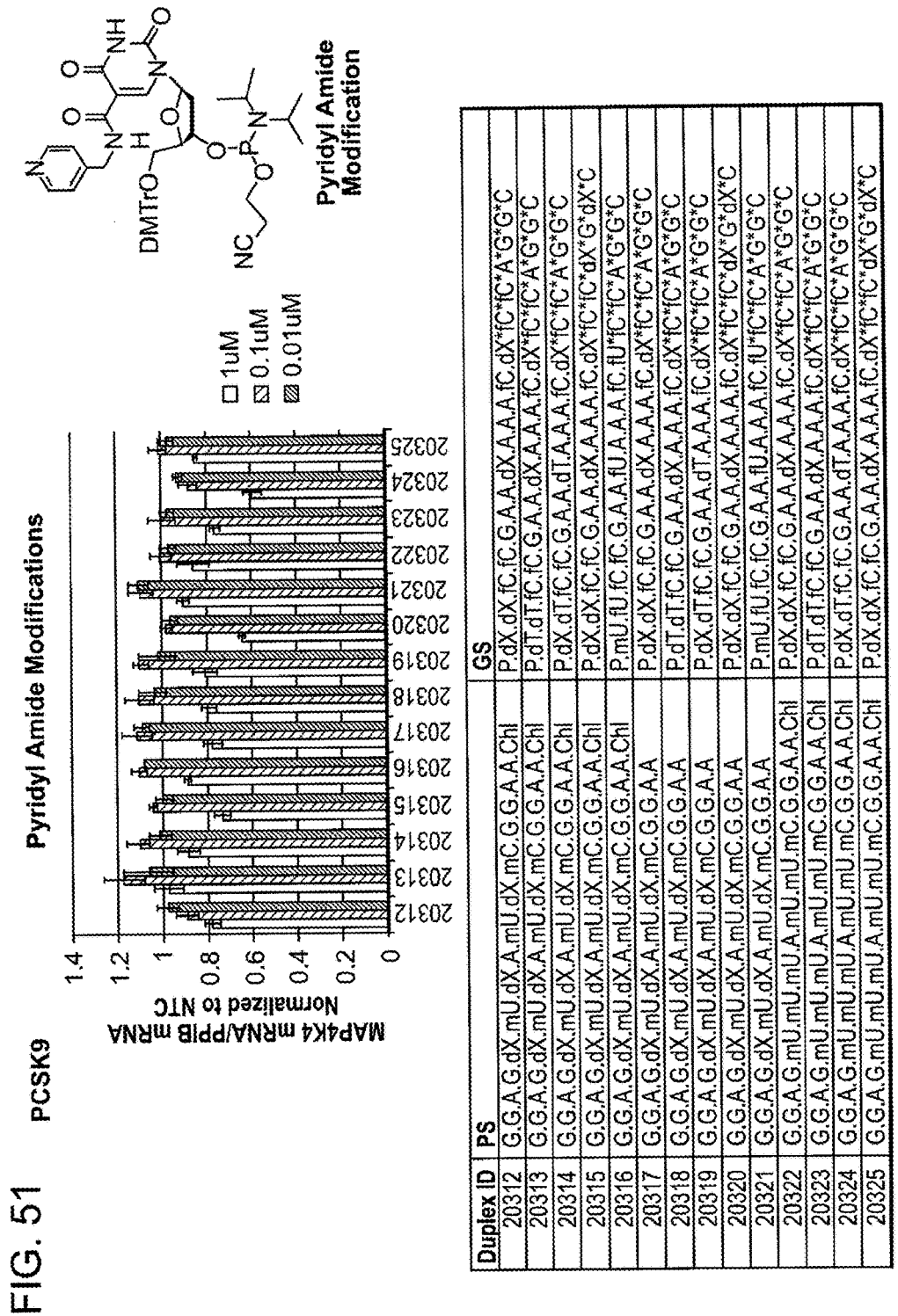
FIG. 51 demonstrates the effects of pyridyl amide modification of sd-rxRNA® targeting PCSK9. PS Duplex IDs 20312-21 are SEQ ID NO:500. PS Duplex IDs 20322-25 are SEQ ID NO:363. GS Duplex IDs from top to bottom are SEQ ID NOs:501-504, 328, 501-504, 328, 501, 502, 503, and 504 respectively.
Figure 52:
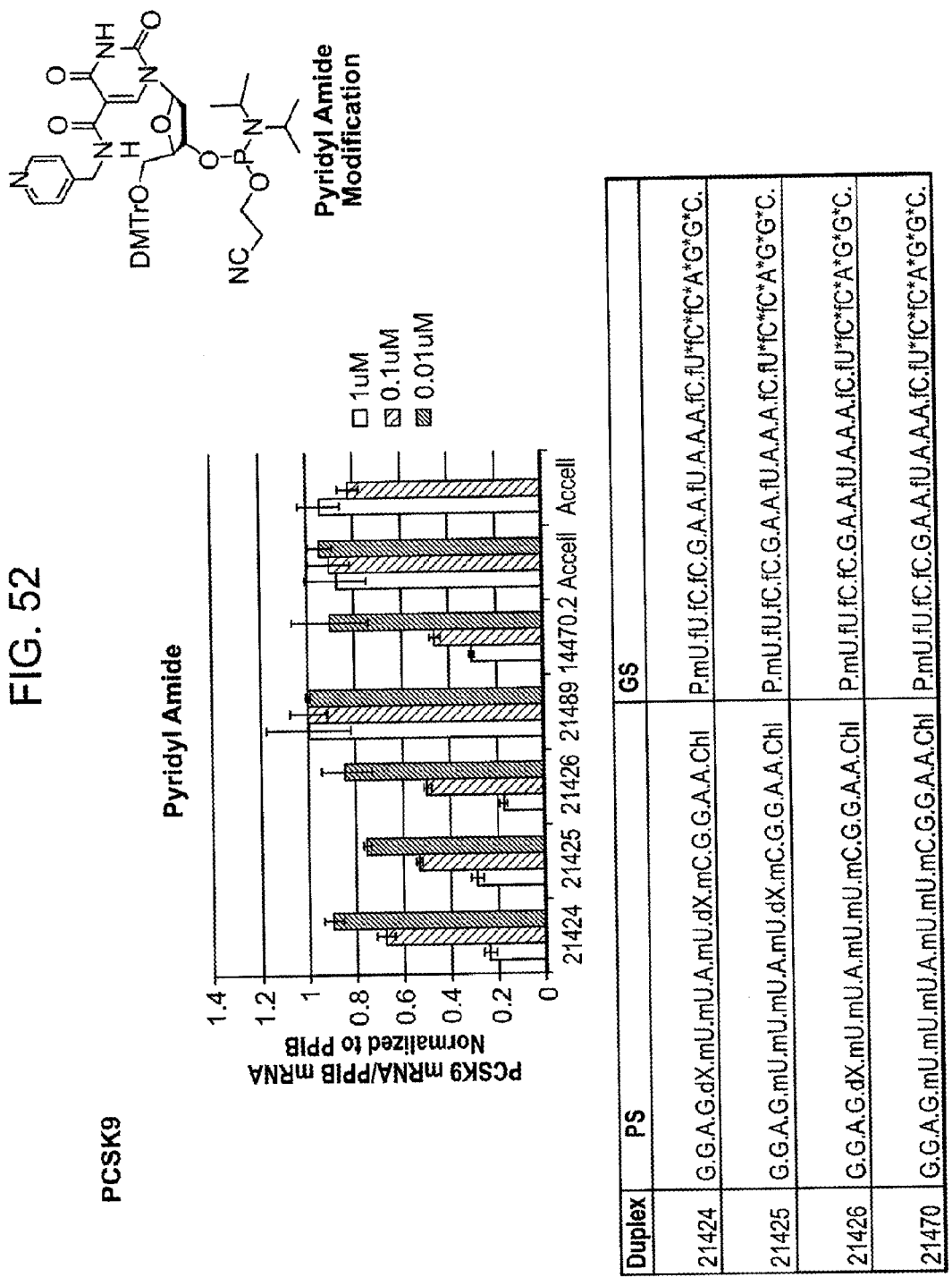
FIG. 52 demonstrates the effects of pyridyl amide modification of sd-rxRNA® targeting PCSK9. PS Duplex IDs from top to bottom are SEQ ID NOs:528, 529, 530 and 363 respectively. GS Duplex IDs from top to bottom are SEQ ID NO:328.

FIG. 51 reveals that for PCSK9, incorporation of pyridyl amide modifications was not well tolerated in either the passenger or guide strand. Reducing the number of pyridyl incorporations in the sense strand resulted in an active compounds (21424-21426).

Figure 53:
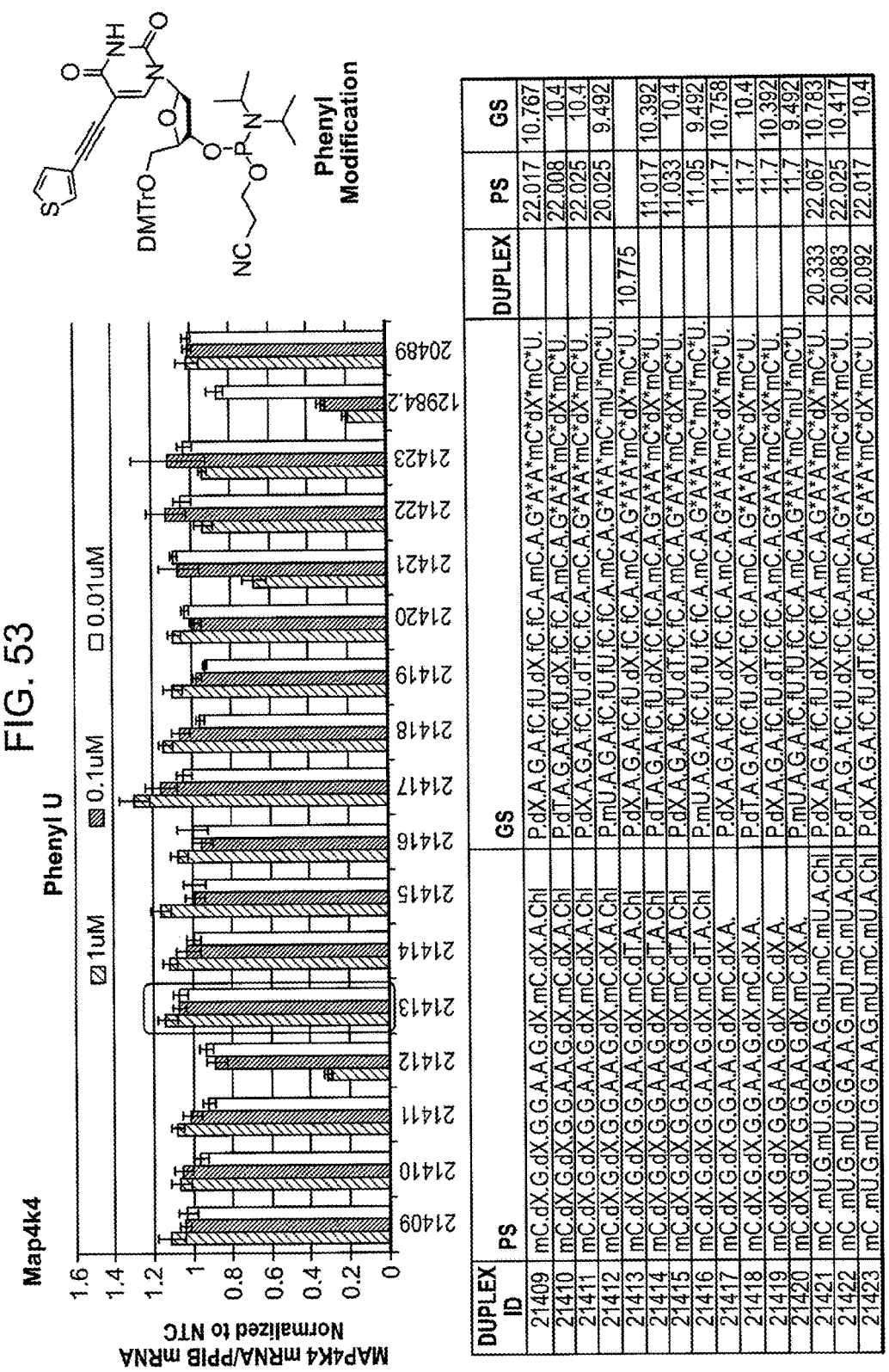
FIG. 53 demonstrates the effects of phenyl modification of sd-rxRNA® targeting MAP4K4. PS Duplex IDs 20409-12 and 20417-20 are SEQ ID NO:614. PS Duplex IDs 20413-16 are SEQ ID NO:509. PS Duplex IDs 20421-23 are SEQ ID NO:477. GS Duplex IDs from top to bottom are SEQ ID NOs:510-524 respectively.
Figure 54:
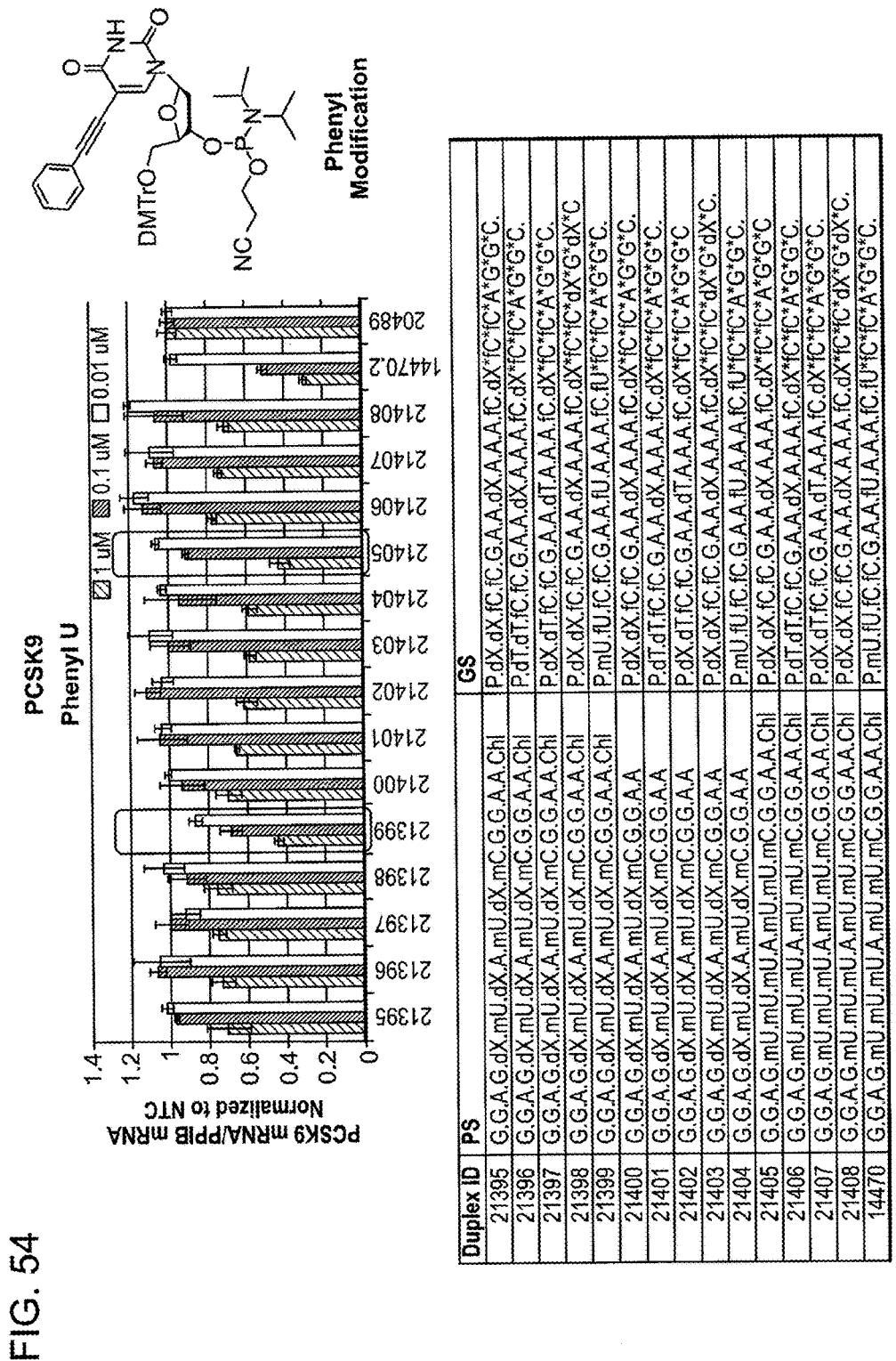
FIG. 54 demonstrates the effects of phenyl modification of sd-rxRNA® targeting PCSK9. PS Duplex IDs 20395-404 are SEQ ID NO:500. PS Duplex IDs 20405-08 and 14470 are SEQ ID NO:363. GS Duplex IDs from top to bottom are SEQ ID NOs:501-504, 328, 501-504, 328, 501-504 and 328 respectively.

FIG. 53 reveals that for Map4k4, phenyl modifications were tolerated in the passenger strand (21412) when duplexed with a non-phenyl-modified guide strand. Phenyl modifications to the guide strand were not tolerated. FIG. 54 reveals that phenyl modifications were tolerated in the passenger strand (21399) when duplexed with a non-phenyl-modified guide strand. Phenyl modifications to the guide strand were not well tolerated. Only one Phenyl modified guide strand demonstrated activity (21405).

FIG. 55 provides a summary of the 5-uridyl modification data. It was found that toleration of 5-uridyl modifications was sequence specific. For example, Map4k4 was more amenable to 5-uridyl modifications than was PCSK9. For Map4k4, 5-uridyl modifications were better tolerated in the sense strand than in the antisense strand. In general, incorporation of 5-uridyl modifications in the guide strand results in compounds with increased hydrophobicity as seen by a shift in retention times on HPLC.

Methods for GIII Screening 48 hrs after addition of sd-rxRNA® molecules, HeLa cells were lysed and mRNA levels were quantitated by a branched DNA (bDNA) assay (Affymetrix). To determine the relative hydrophobicity of GIII compounds, reverse phase HPLC was employed. Column: Hamilton PRP-1, 150×4.6 mm, 10 um). Mobile Phase A—5 mM potassium phosphate, 2% Acetonitrile (pH 7.4). Mobile phase B—85% Acetonitrile in H2O. The following table provides representative results of such analysis:

| Time | % A | % B | Flowrate | Curve |
| --- | --- | --- | --- | --- |
| 0.0 | 100 | 0 | 0.1 | * |
| 0.1 | 100 | 0 | 1.0 | 6 |
| 5.0 | 100 | 0 | 1.0 | 6 |
| 35 | 0 | 100 | 1.0 | 6 |
| 35.1 | 0 | 100 | 1.0 | 6 |
| 38.0 | 0 | 100 | 1.0 | 6 |
| 38.1 | 100 | 0 | 1.0 | 6 |
| 41.0 | 100 | 0 | 1.0 | 6 |

FIG. 56 reveals that modulation of chemistry at position 5 of uridine results in an altered tissue distribution profile in the liver. BALB/c male mice (n=2/group) received a single 50 mg/kg tail vein injection of sd-rxRNA®. Uptake was analyzed by a hybridization assay. The conclusions from this analysis were that incorporation of uridyl modifications increased the levels of the compound in the liver 24 hrs post dose; incorporation of thiophene modifications increased sd-rxRNA® levels in liver more than 10-fold; and octyl modifications on both the passenger strand and guide strand (without cholesterol) resulted in distribution of sd-rxRNA® to the liver.

Similarly, FIG. 57 shows that modulation of chemistry at position 5 of uridine results in an altered tissue distribution profile in heart and fat. BALB/c male mice (n=2/group) received a single 50 mg/kg tail vein injection of sd-rxRNA®. Uptake was analyzed by a hybridization assay. The conclusions from this analysis were that incorporation of octyl uridyl modifications increased levels of sd-rxRNA® in heart and fat 24 hrs post-dose; and octyl modifications on both the passenger strand and guide strand (without cholesterol) resulted in sd-rxRNA® distribution to both heart and fat 24 hrs post dose.

Figure 59:
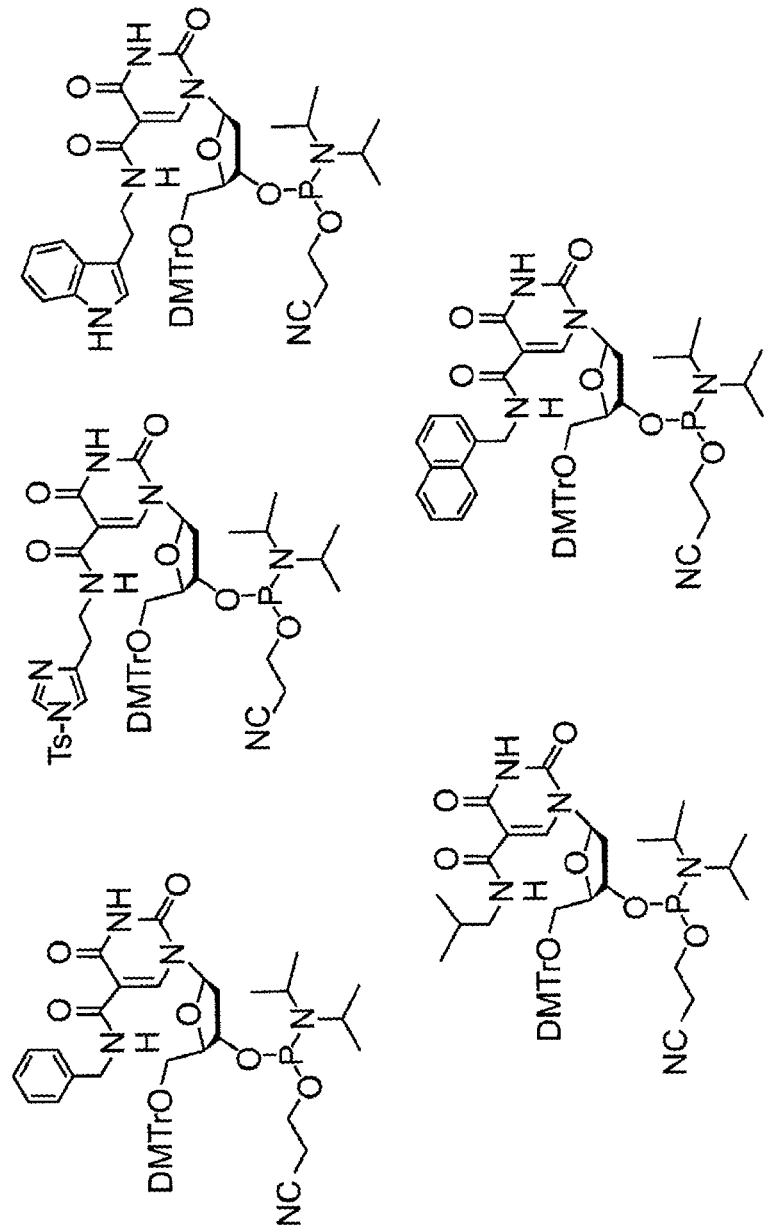
FIG. 59 provides non-limiting examples of synthons.
Figure 60:
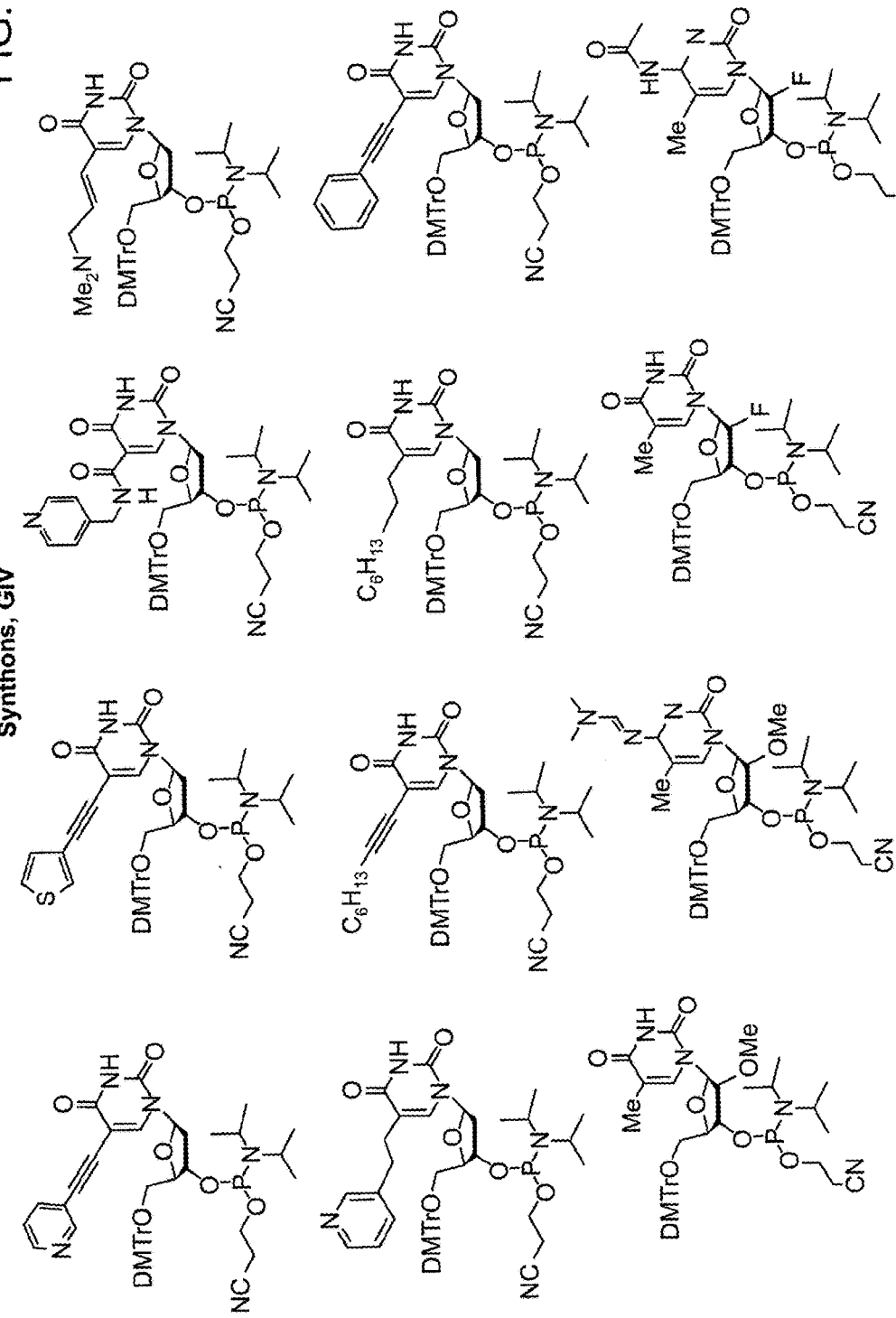
FIG. 60 provides further non-limiting examples of synthons.

Synthons were developed based on O-methyl and 2'F. GIII chemistries that showed promise were selected and the 2'-deoxy chemistry was replaced with 2'-O methyl and 2'-fluoro. Several non-limiting examples of synthons are shown in FIGS. 58-60.

Endosomal Release

Figure 61:
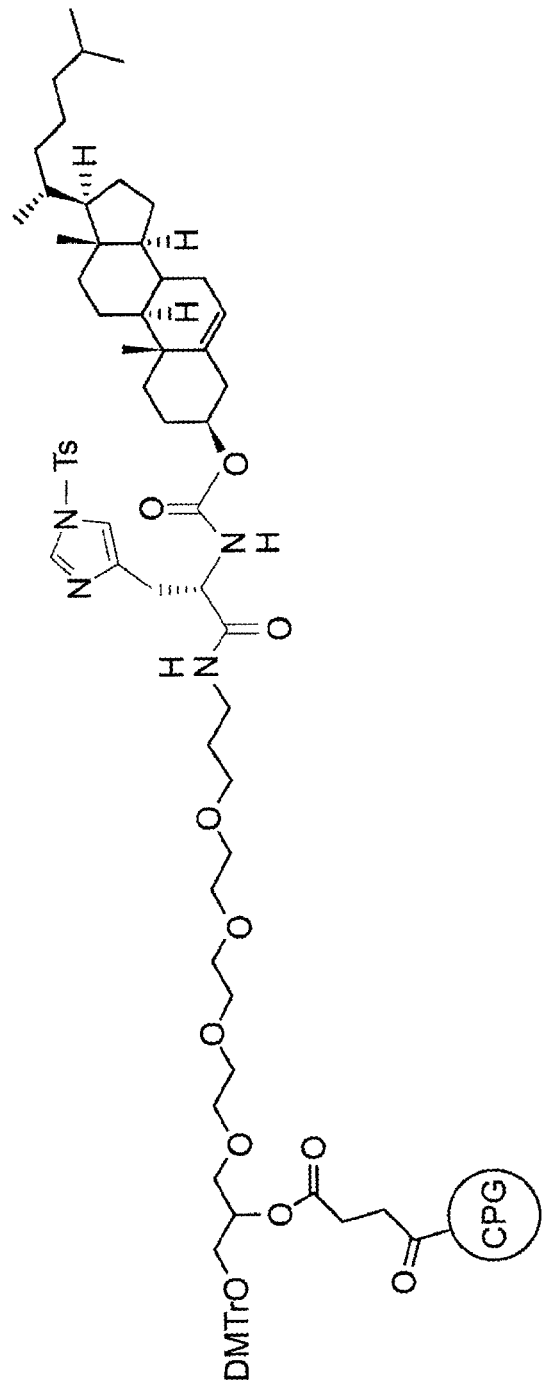
FIG. 61 provides a schematic of a linker containing protonatable amines which promotes endosomal release of sd-rxRNA® molecules.
Figure 62:
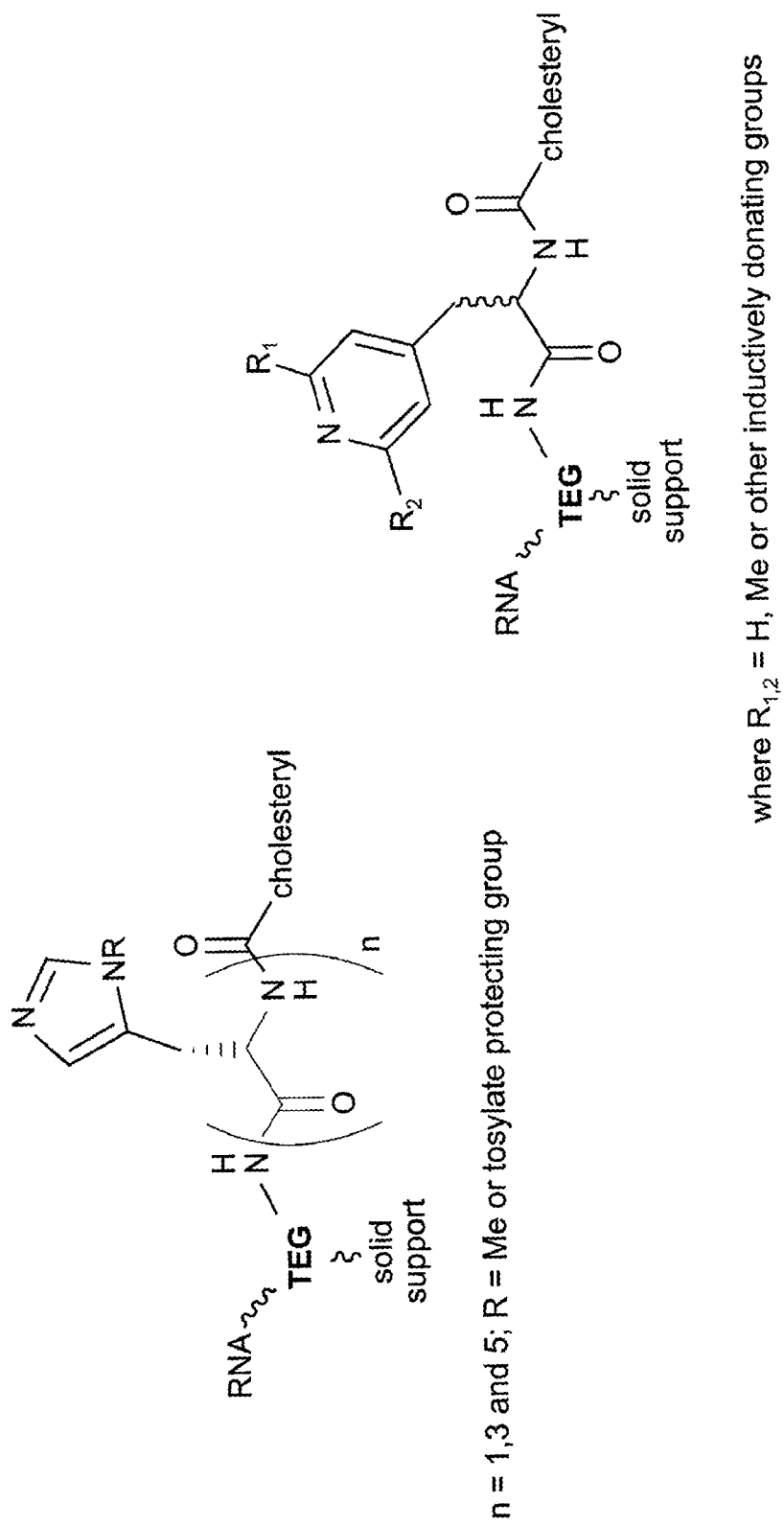
FIG. 62 provides a schematic demonstration of incorporation of protonatable functionalities for promoting endosomal release.
Figure 63:
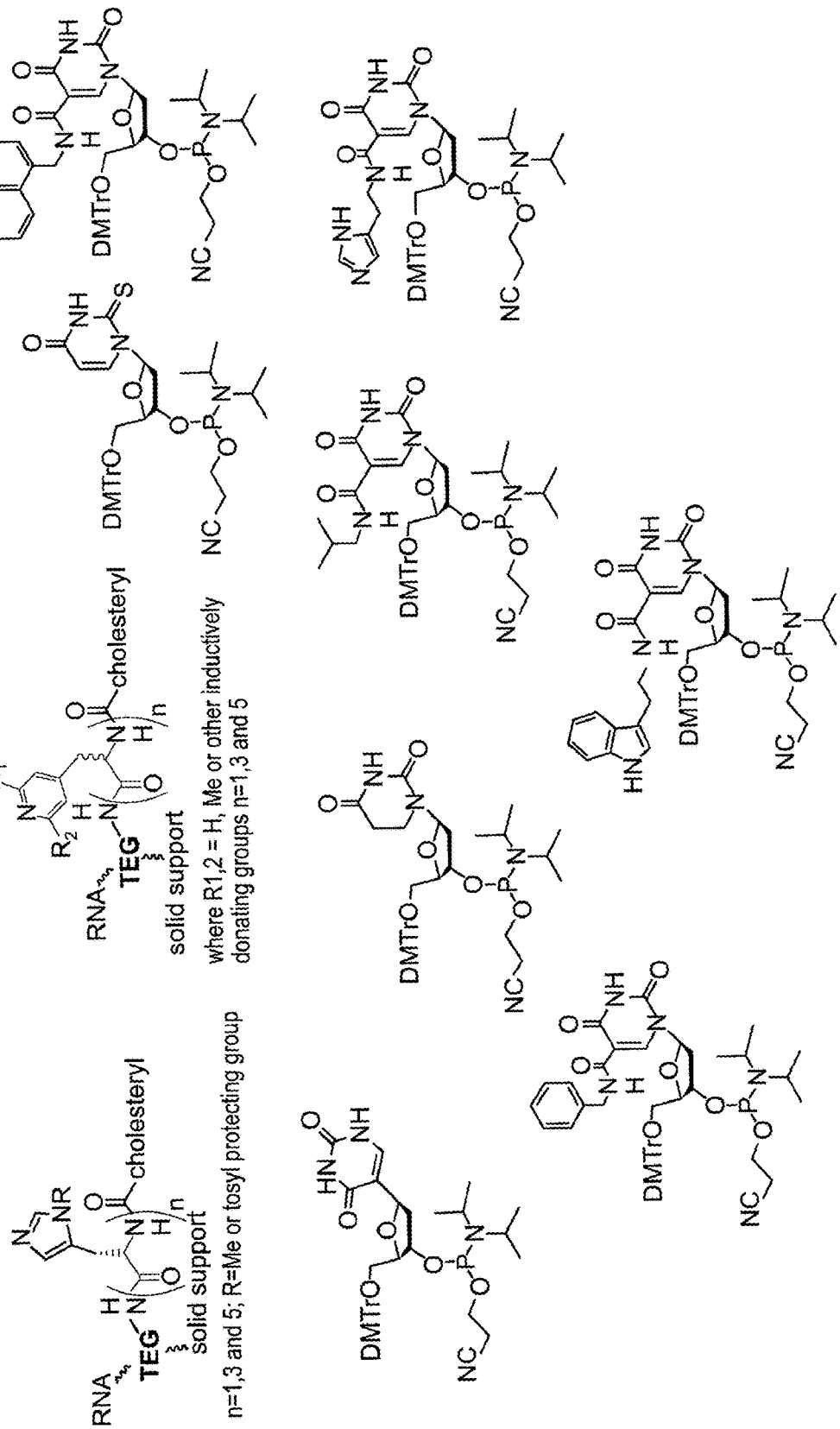
FIG. 63 provides further non-limiting examples of synthons.
Figure 64:
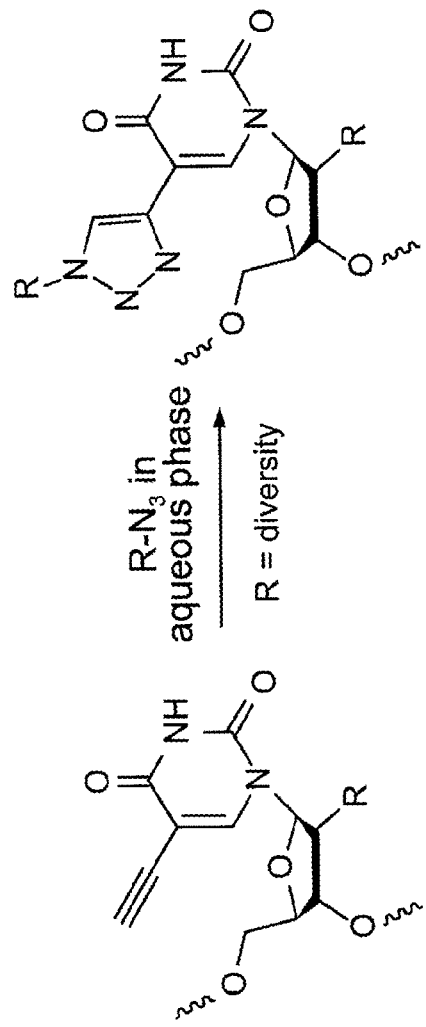
FIG. 64 provides a schematic of GIV "click" chemistry, whereby an oligonucleotide can be diversified rapidly.

Modifications to sd-rxRNA® were also developed to promote endosomal release. For example, as shown in FIG. 61, an sd-rxRNA® can be attached to a linker, such as a protonatable linker. In one example, histidine can be spliced into an existing TEG linker. In some instances, between 2-5 protonatable amine containing chemistries such as histidine may be efficient for promoting endosomal escape. FIGS. 62 and 63 provide several non-limiting examples of improving siRNA endosomal release by incorporating protonatable functionalities. FIG. 64 provides an example of GIV, "click" chemistry for accessing diversity rapidly. By this approach, one oligonucleotide can be diversified rapidly rather than having to manufacture different oligonucleotides from scratch.

Phosphorothioate Modifications

Figure 65:
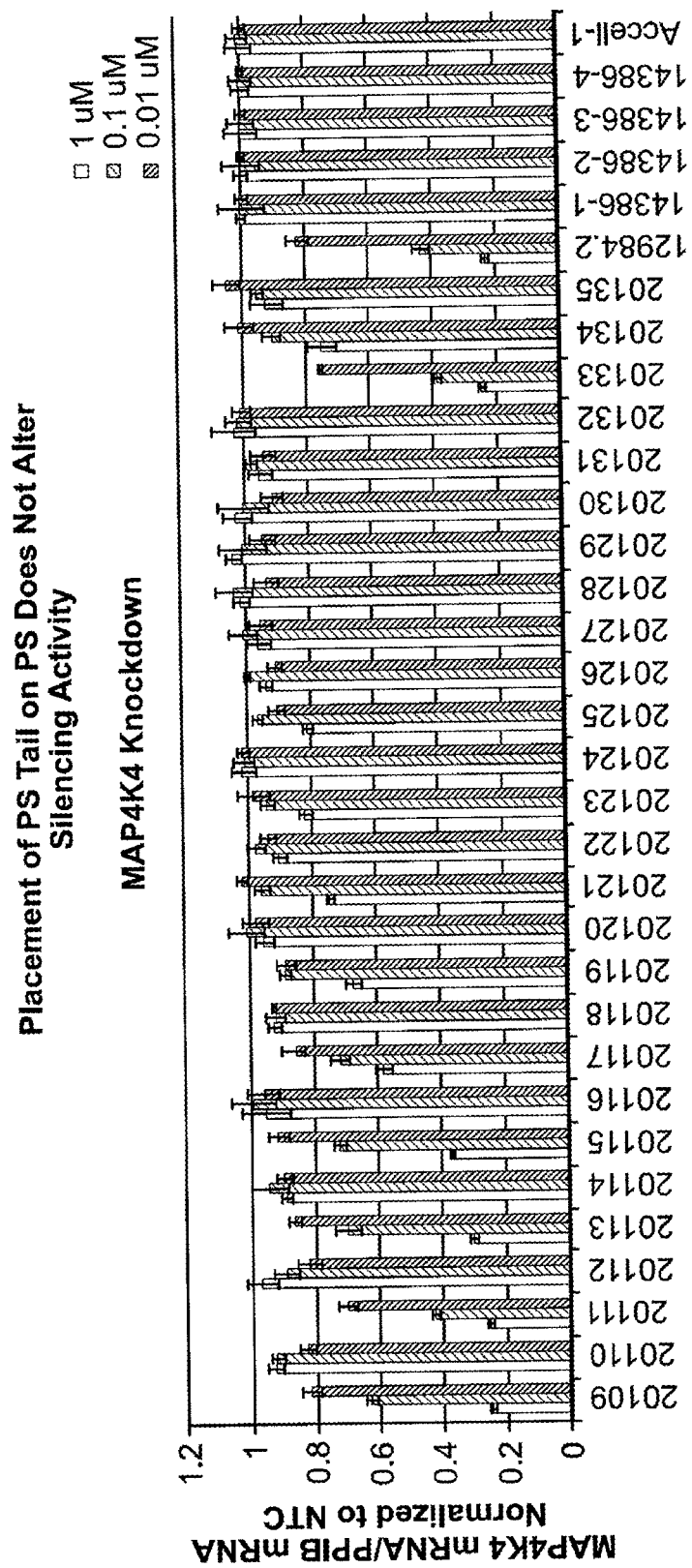
FIG. 65 demonstrates that the placement of the phosphorothioate tail does not alter silencing activity.
Figure 66:
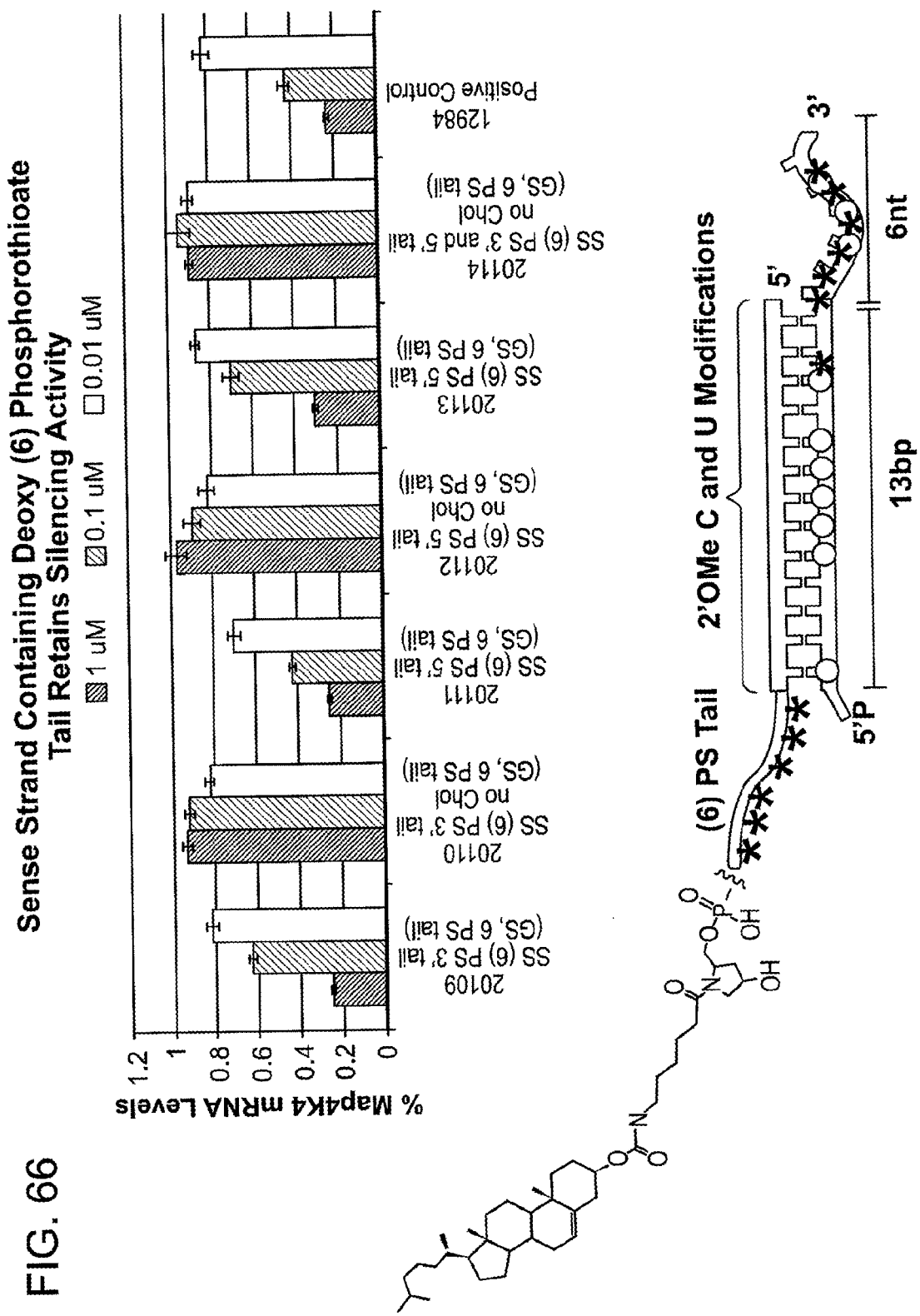
FIG. 66 shows that a sense strand containing a deoxy (6) phosphorothioate tail retains silencing activity.
Figure 67:
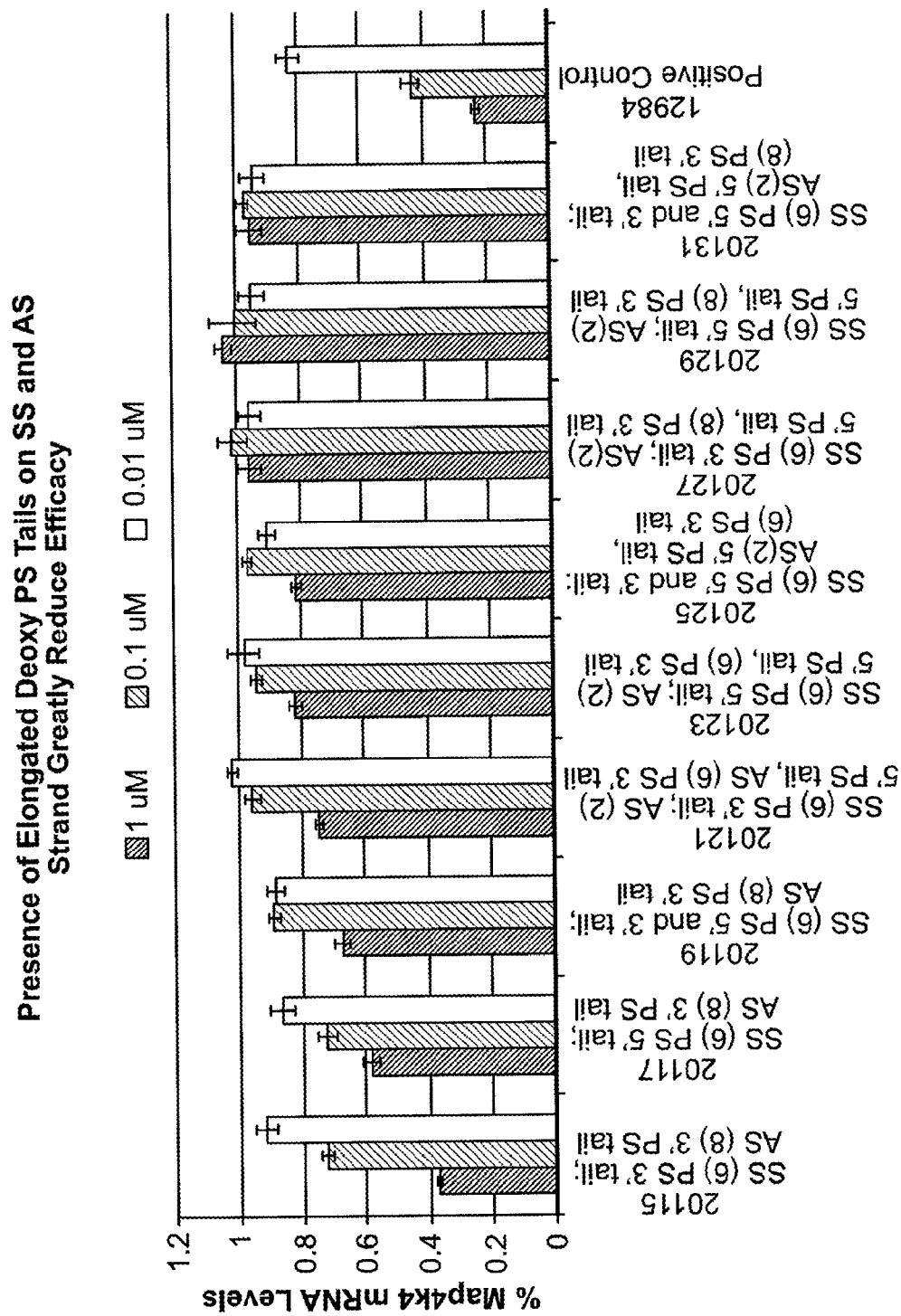
FIG. 67 shows that the presence of elongated deoxy phosphorothioate tails on the sense strand or antisense strand can reduce efficacy.
Figure 68:
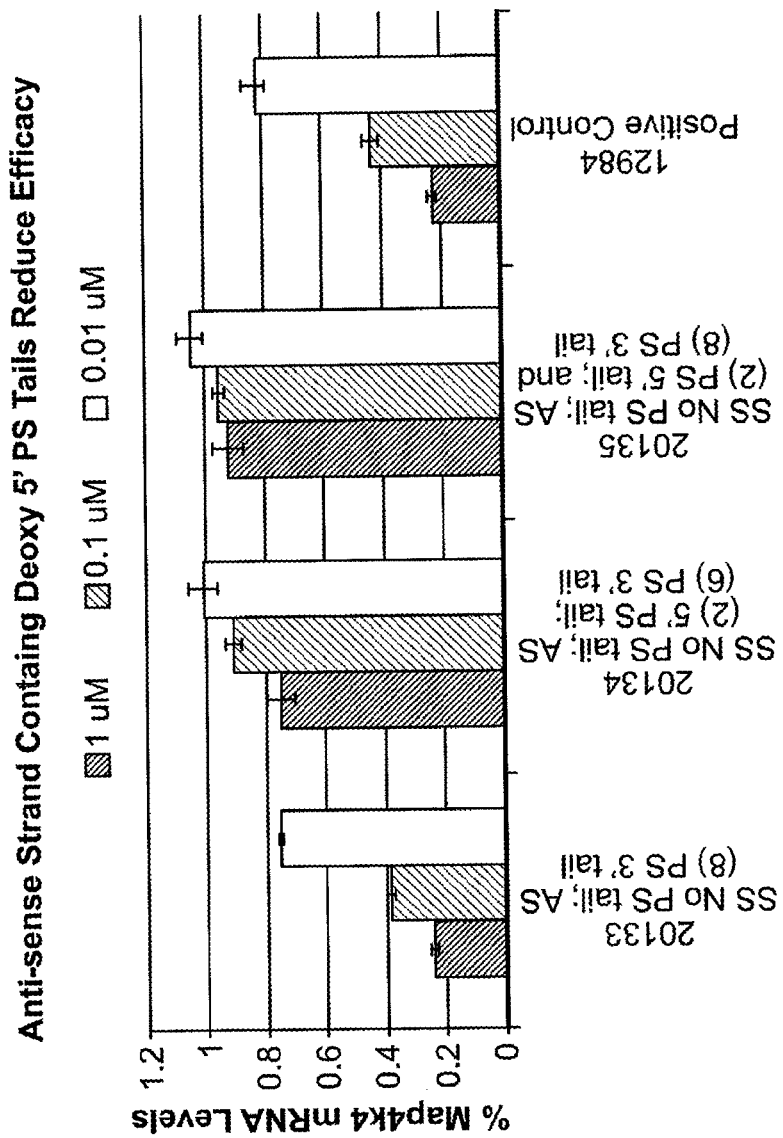
FIG. 68 shows that an antisense strand containing a 5' deoxy phosphorothioate tail can have reduced efficacy.

The effect of placement of a phosphorothioate tail on an sd-rxRNA® on its silencing activity was investigated (FIGS. 65-71). In FIG. 65, a series of sd-rxRNA® molecules with differentially placed phosphorothioate tails was investigated. Placement of a phosphorothioate tail on the sense strand of sd-rxRNA® was found to have minimal effect on activity. sd-rxRNA® compounds containing 6 non basepairing nucleotides on either the 5', 3' or both the 5' and 3' end of the sense strand retained potent activity (20109, 20111 and 20113, respectively) (FIG. 66). Guide strands contained (6) phosphorothioates on the 3' end. Addition of two deoxy nucleotides containing phosphorothioates on the 3' end of the guide strand in addition to a phosphorothioate tail in the sense strands resulted in reduced activity (20115, 20117 and 20119, respectively) (FIG. 67) compared to an sd-rxRNA® containing 8 phosphorothioates on the guide strand alone (20133). In some instances, addition of two deoxy nucleotides containing phosphorothioates on the 5' end of the guide strand resulted in complete loss of activity (20121 through 20132). Without wishing to be bound by any theory, this may be because the seed region of the sd-rxRNA® is shifted by 2 bases.

Figure 69:
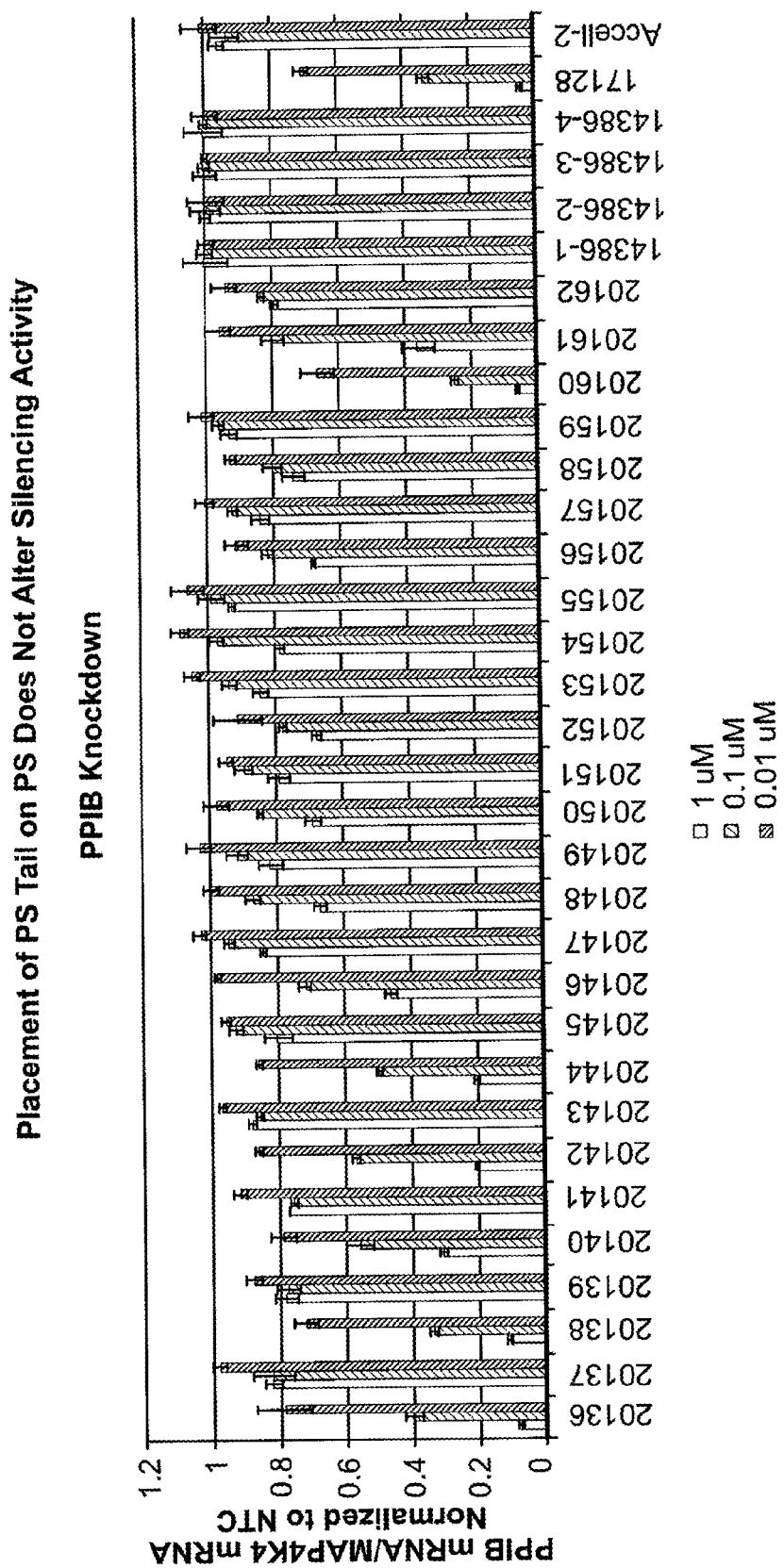
FIG. 69 reveals that placement of the phosphorothioate tail does not alter silencing activity.
Figure 70:
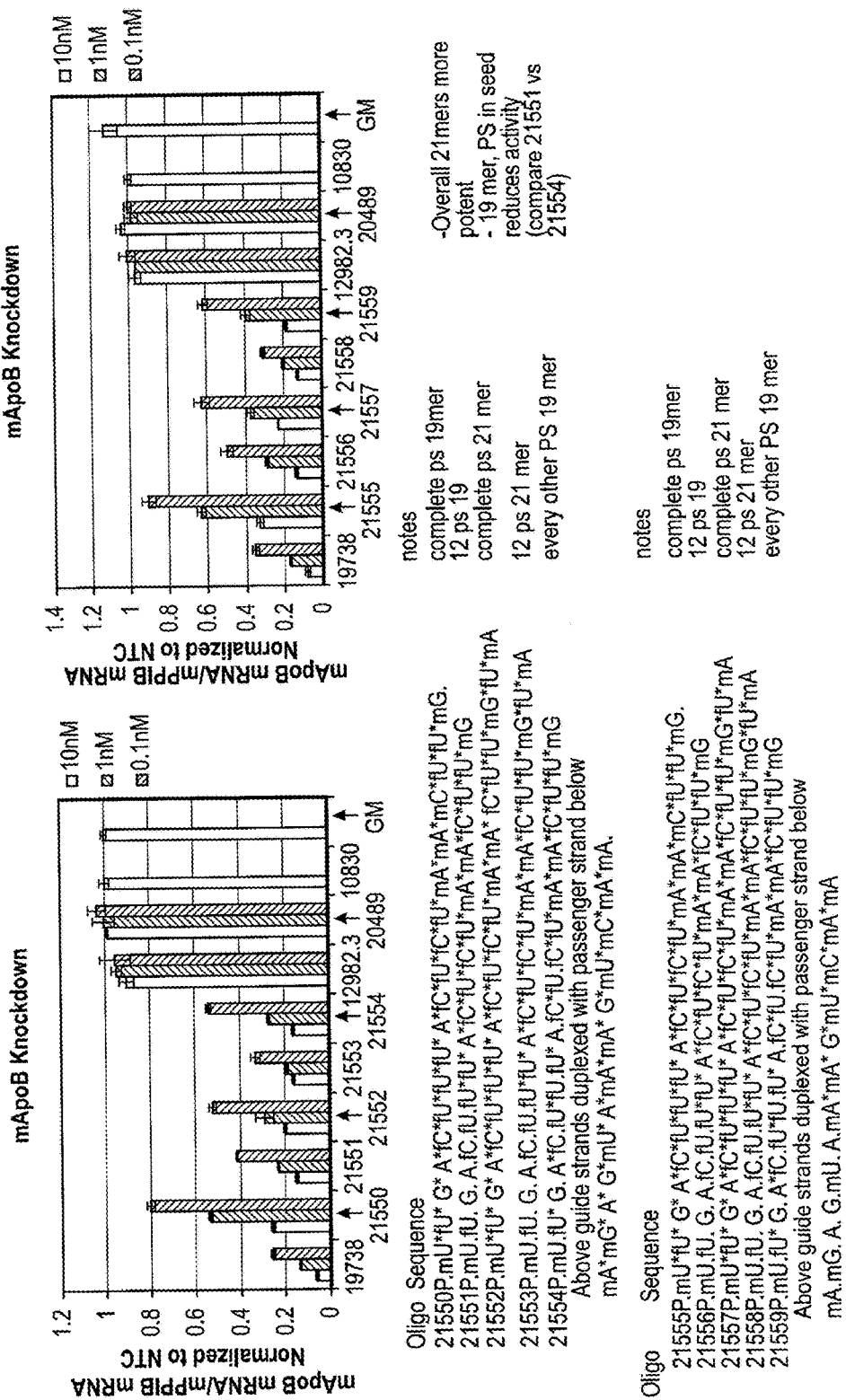
FIG. 70 reveals that an sd-rxRNA® with a 21-mer guide strand that is completely phosphorothioate modified is active. Oligo sequences are SEQ ID NOs:536-547 from top to bottom respectively.

FIG. 69 reveals that for PPIB also, placement of a phosphorothioate tail on the sense strand of sd-rxRNA® has minimal effect on activity. sd-rxRNA® compounds containing 6 non base-pairing nucleotides on either the 5', 3' or both the 5' and 3' end of the sense demonstrate reduced activity with increasing PS content (20136, 20138 and 20140, respectively). Guide strands contain (6) phosphorothioates on the 3' end. Addition of two deoxy nucleotides containing phosphorothioates on the 3' end of the guide strand in addition to a phosphorothioate tail in the sense strands resulted in reduced activity (20142, 20144 and 20146, respectively) compared to an sd-rxRNA® containing 8 phosphorothioates on the guide strand alone (20160). In some instances, addition of two deoxy nucleotides containing phosphorothioates on the 5' end of the guide strand resulted in complete loss of activity (20148 through 20159).

The effect of varying phosphorothioate content on both the guide and passenger strands of RNAi compounds was next investigated. Completely phosphorothioated compounds (21552) that are highly active were identified. Interestingly, compounds that contained a 21 mer guide strand that was completely phosphorothioate modified was active, however, reducing the guide strand length by two nucleotides, e.g., 19 mer guide strand (21550), resulted in reduced activity. Without wishing to be bound by any theory, increasing the guide strand from 19 to 21 nucleotides (fully phosphorothioated guide strands) may increase the melting temperature between the guide strand and mRNA, resulting in enhanced silencing activity. Varying phosphorothioate content on the 13 mer passenger strand such that it was either completely phosphorothioate modified or contained 6 phosphorothioate modifications did not result in altered activity (21551 vs 21556).

Several past groups have tried to develop completely phosphorothioated RNAi compounds. Completely phosphorothioated duplexes, lacking single stranded regions, have been designed and tested before, however, these compounds did not demonstrate the correct pharmacokinetic profile. Completely phosphorothioated single stranded RNAi compounds have also been designed previously, however, these compounds did not efficiently enter RISC. Significantly, herein hybrid RNAi compounds have been developed that efficiently enter RISC and contain complete phosphorothioate backbones.

Figure 71:
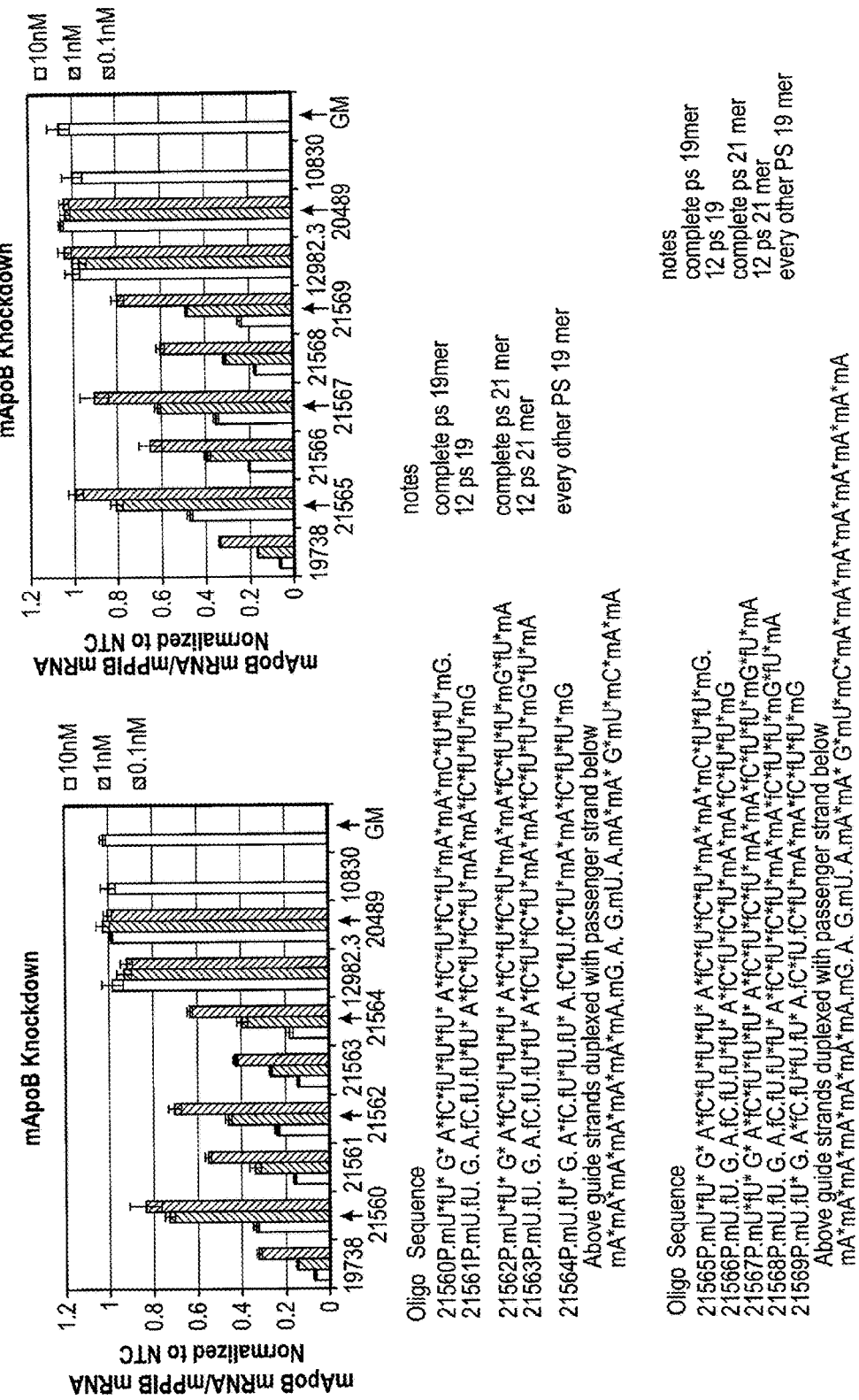
FIG. 71 shows that incorporation of a phosphorothioate tail on the sense strand can lead to reduced silencing activity. Oligo sequences are SEQ ID NOs:548-559 from top to bottom respectively.

FIG. 71 reveals that increasing phosphorothioate content on the passenger strand by incorporating non-basepairing nucleotides on the 5' and 3'end of the strand resulted in slightly reduced activity. AML12 cell lines were transfected with varying concentrations of rxRNAs (with varying phosphorothioate content) using Lipofectamine RNAiMAX (Invitrogen). 48 hrs post transfection, cells were lysed and target gene levels were quantified using branched DNA assay (Affymetrix) according to manufacturer's recommendations.

Figure 72:
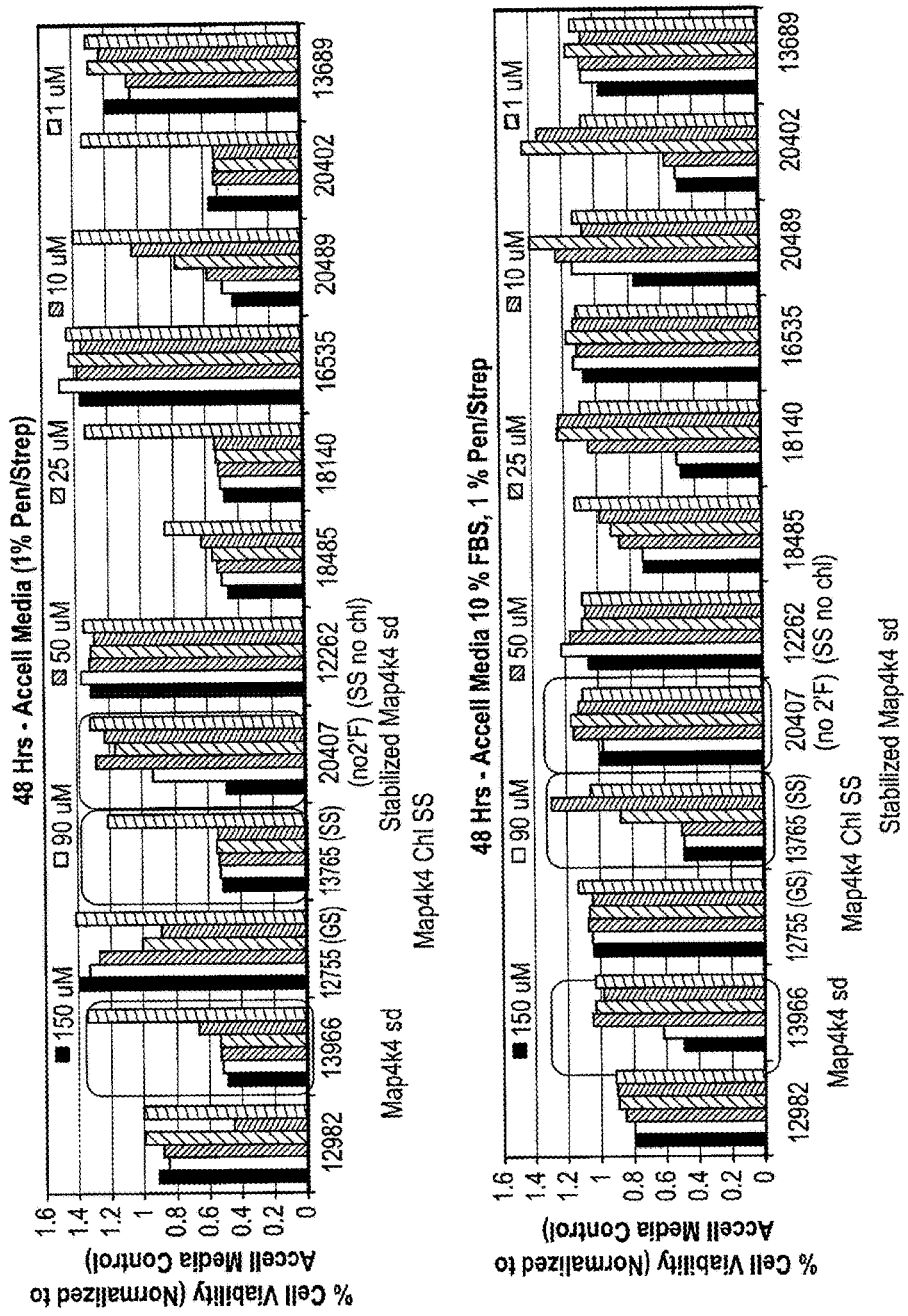
FIG. 72 reveals that stabilization of sd-rxRNA® results in increased cell viability.
Figure 73:
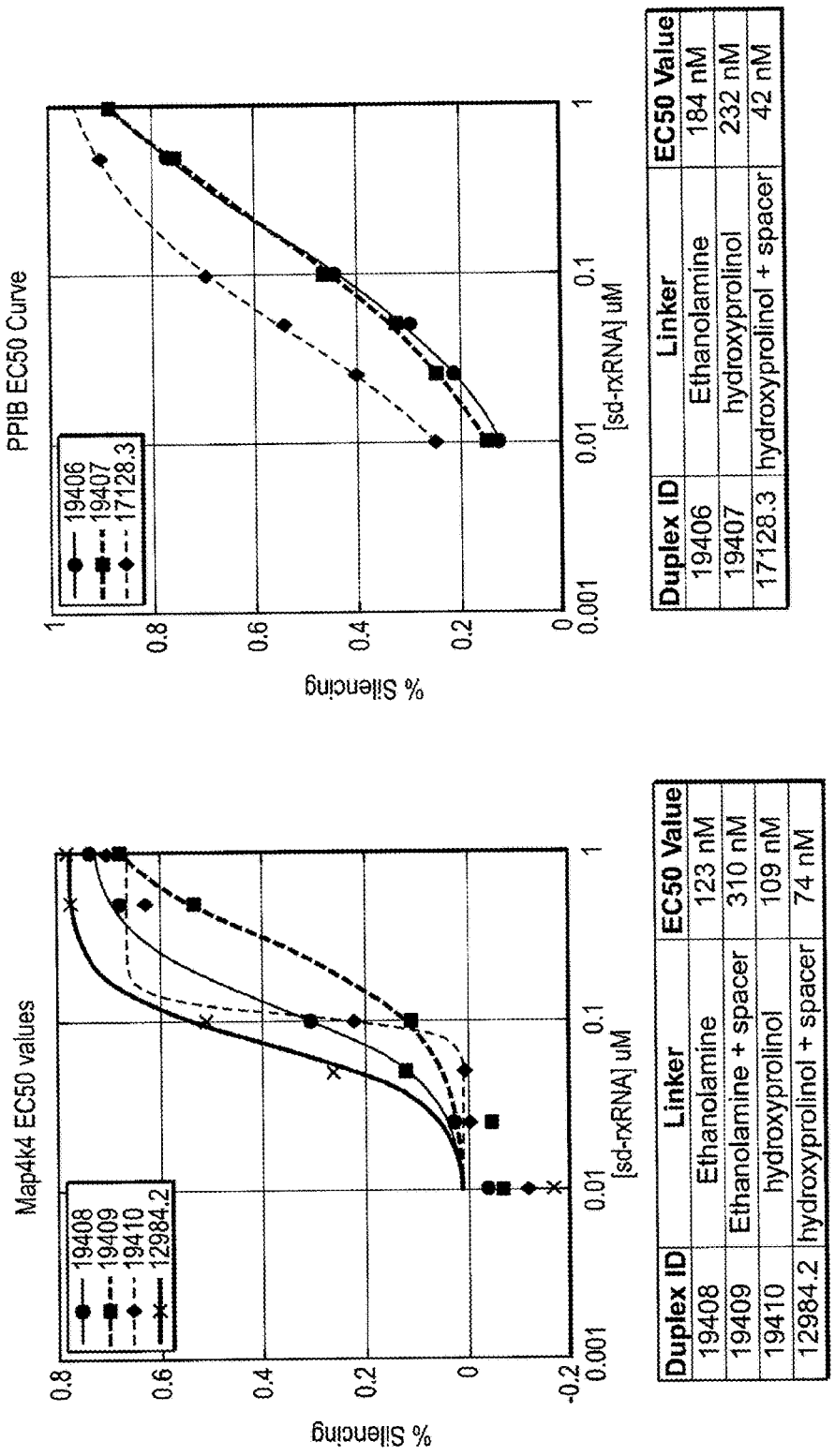
FIG. 73 reveals that sd-rxRNA® molecules can tolerate changes in linker chemistry.
Figure 74:
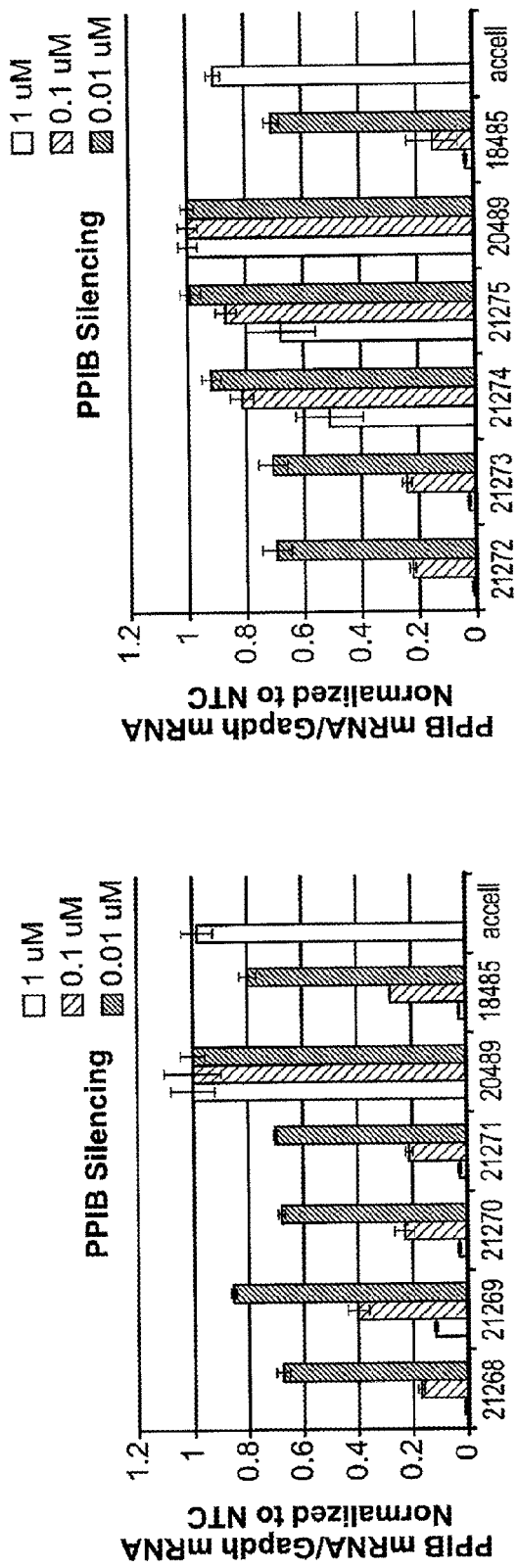
FIG. 74 presents a summary of chemical optimization of sd-rxRNA® targeting PPIB. Duplex IDs 21268-21275 are SEQ ID NOs:560-567 respectively.
Figure 75:
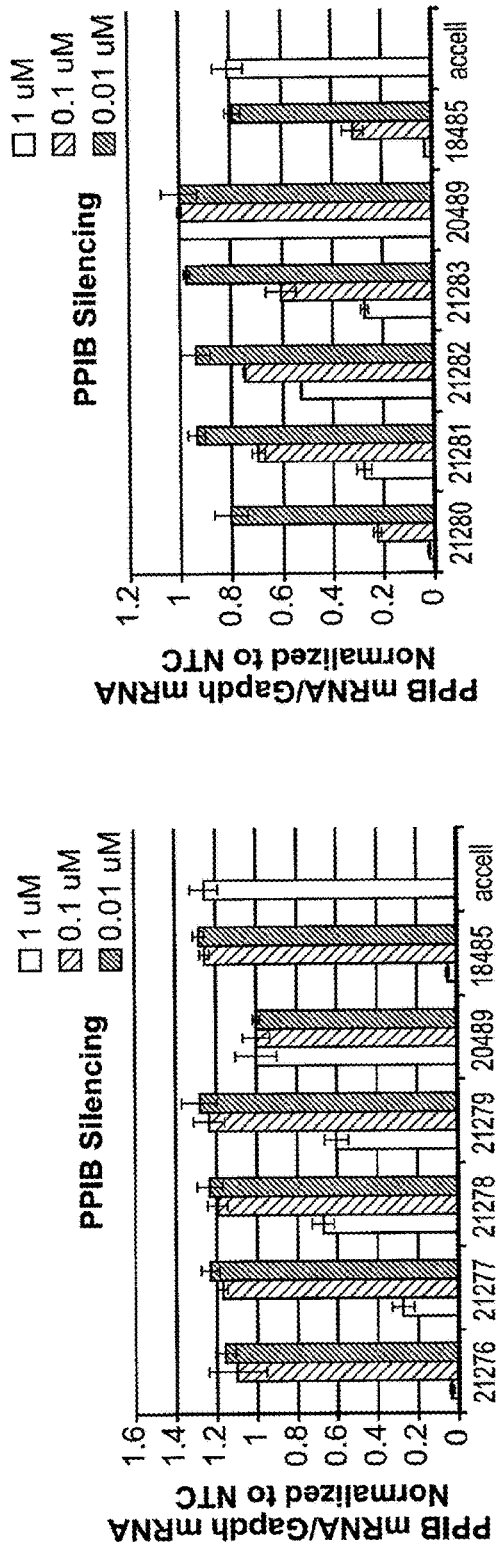
FIG. 75 presents further non-limiting examples of chemical optimization of sd-rxRNA® targeting PPIB. Duplex IDs 21276-21283 are SEQ ID NOs:568-575 respectively.
Figure 76:
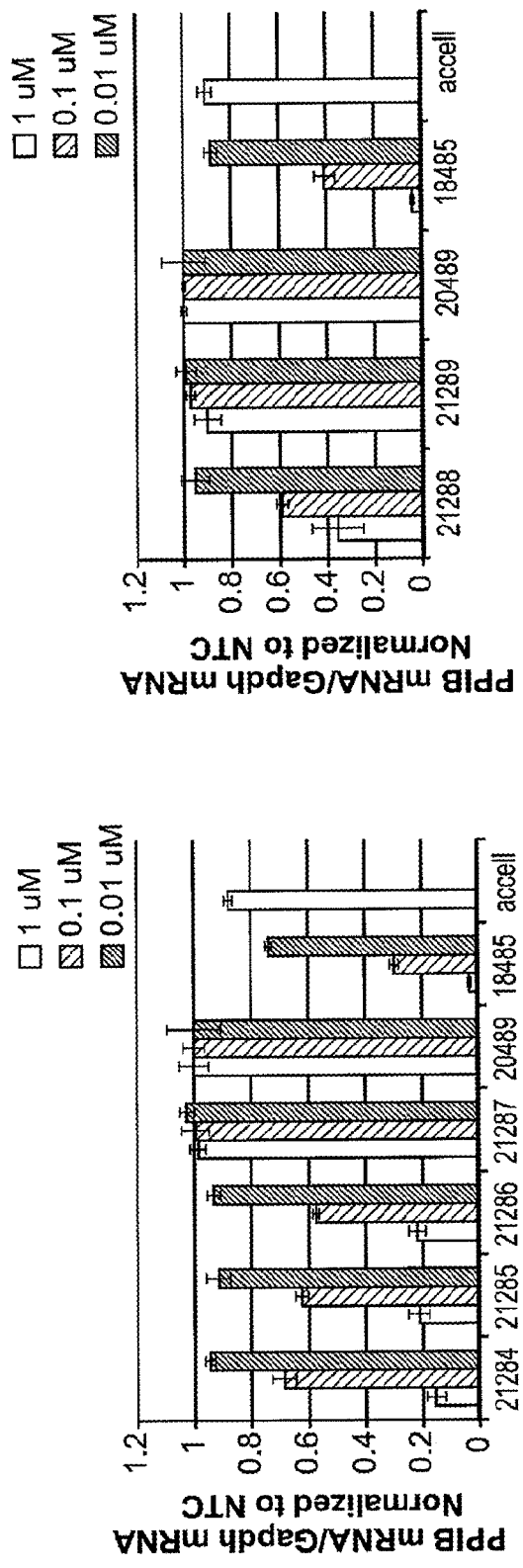
FIG. 76 shows the effects of incorporation of 5-methyl Cs and Us on the activity of sd-rxRNA® targeting PPIB. Duplex IDs 21284-21289 are SEQ ID NOs:576-581 respectively. SEQ ID NO:582 can be found after SEQ ID NO:581.
Figure 77:
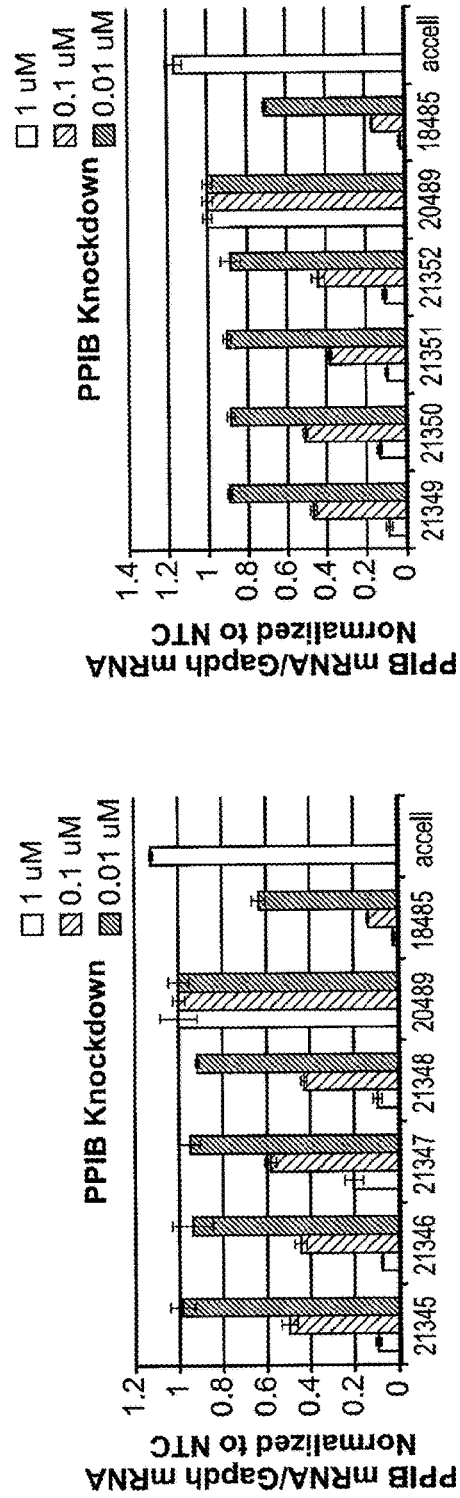
FIG. 77 compares knockdown of PPIB achieved with sd-rxRNA® comprising a 14 mer and 20 mer or comprising a 15 mer and 19 mer. SEQ ID NOs:583-590 can be found on the left from top to bottom respectively. SEQ ID NOs:591-598 can be found on the right from top to bottom respectively.
Figure 78:
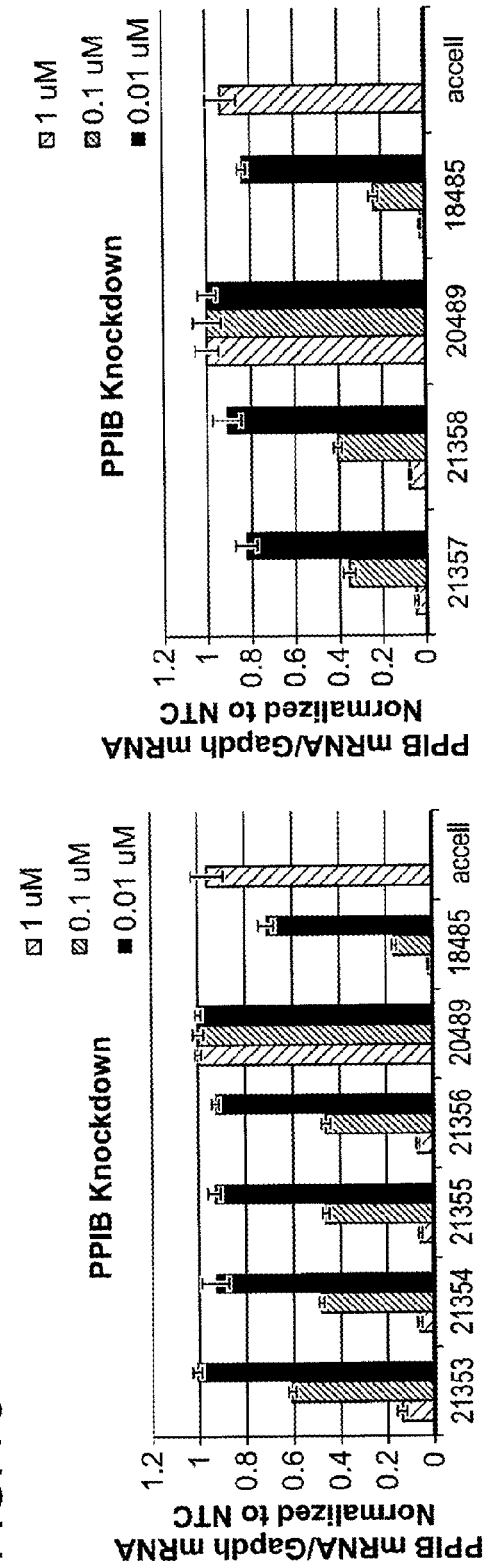
FIG. 78 summarizes the effects of chemical optimization of sd-rxRNA® targeting PPIB. SEQ ID NOs:599-606 can be found on the left from top to bottom respectively. SEQ ID NOs:607-610 can be found on the right from top to bottom respectively.

As shown in FIG. 72, in vitro dose escalation studies were performed to determine the levels of sd-rxRNA® cytotoxicity. Incorporation of stabilizing modifications (ie. complete 2'Ome on the guide strand, duplex 20407) results in reduced cytotoxicity as compared to 13966 (2'F C and Us on guide strand). HeLa cells were treated with varying concentrations of sd-rxRNA® for 48 hrs. Cell viability was assessed using the Alamar Blue assay. FIG. 73 shows that the activity of sd-rxRNA® molecules is retained when linker chemistries are varied.

Figure 79:
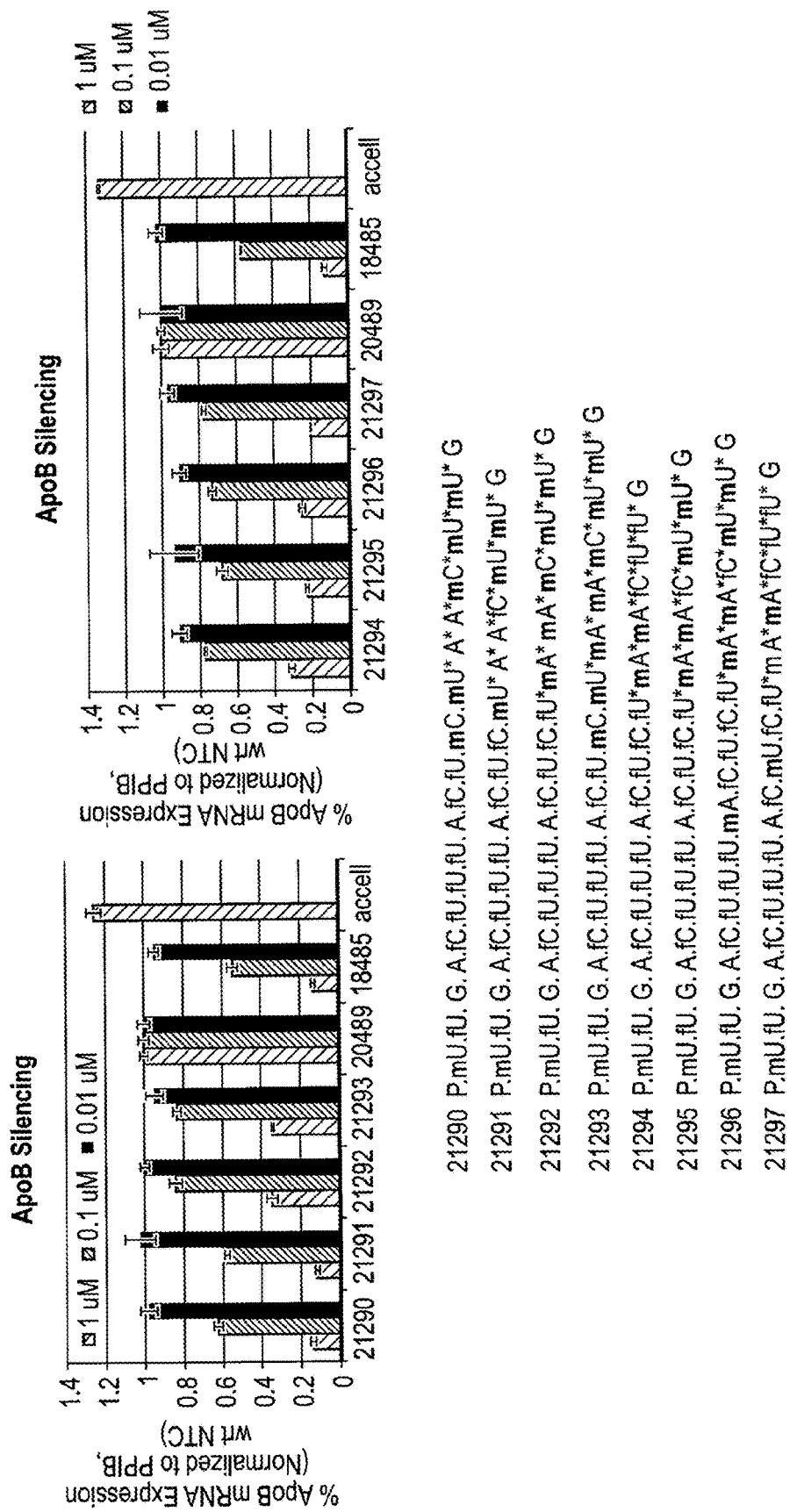
FIG. 79 shows the activity of optimized sd-rxRNA® targeting ApoB. Duplex IDs 21290-21297 are SEQ ID NO:611.
Figure 80:
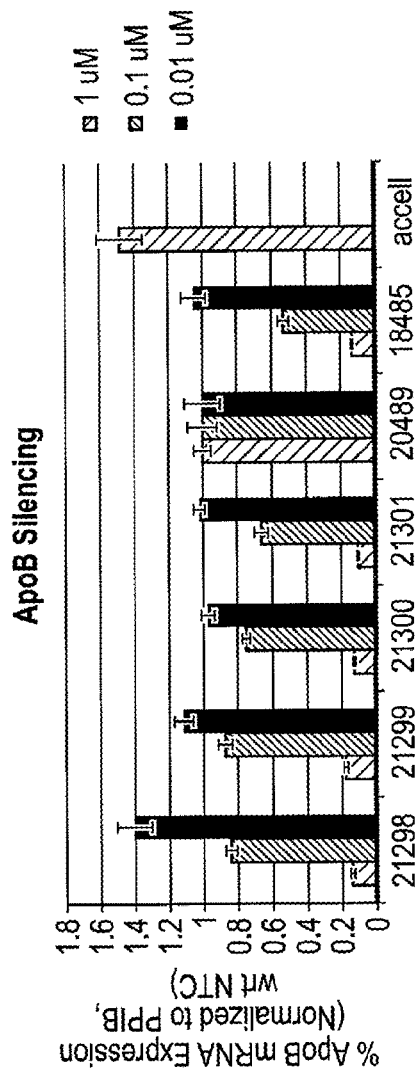
FIG. 80 shows further examples of active chemically optimized sd-rxRNA® targeting ApoB. Duplex IDs 21298-21301 are SEQ ID NO:612.
Figure 81:
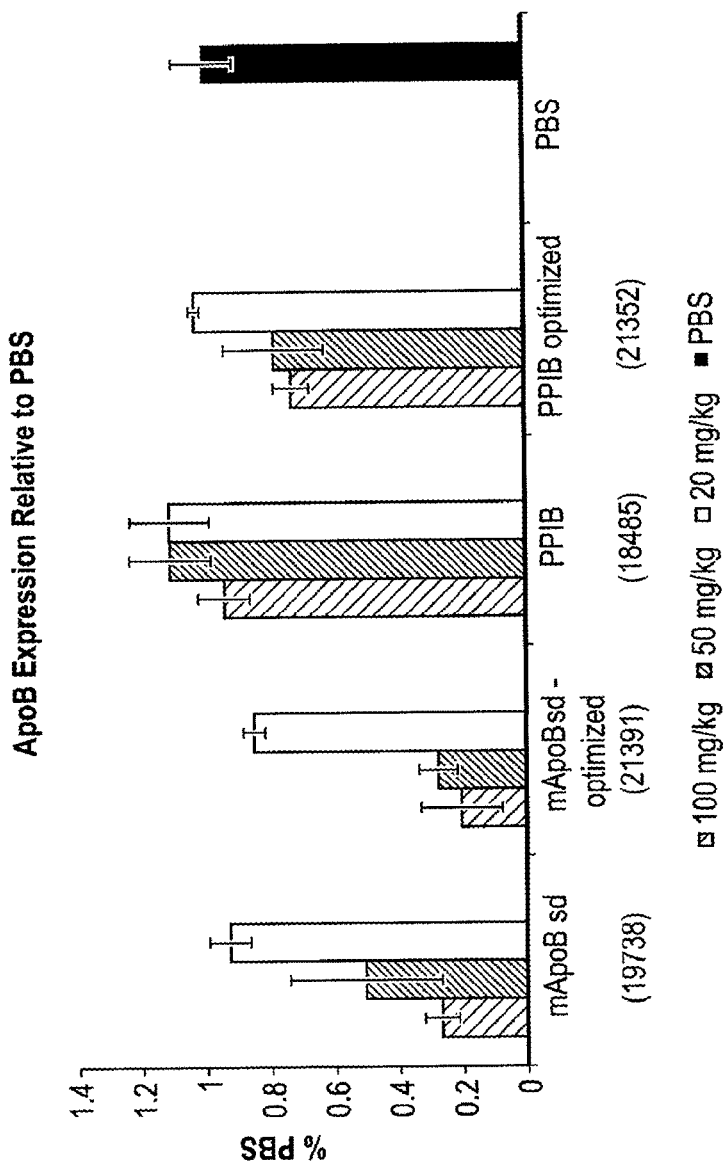
FIG. 81 reveals that a chemically optimized sd-rxRNA® targeting ApoB is more potent in inducing gene silencing in liver than more conventional compounds.

FIGS. 74-78 present non-limiting examples of chemical optimization of sd-rxRNA® targeting PPIB. FIGS. 79 and 80 shows that optimized sd-rxRNA® molecules targeting ApoB are active. FIG. 81 shows that chemically optimized sd-rxRNA® against Apob was more potent in inducing gene silencing in liver than a more conventional compound. With extremely stabilized ApoB compounds, even 50 mg/kg injection resulted in more than 70% silencing in liver. This data confirms that stabilization in critically important for in vivo functionality.

Figure 82:
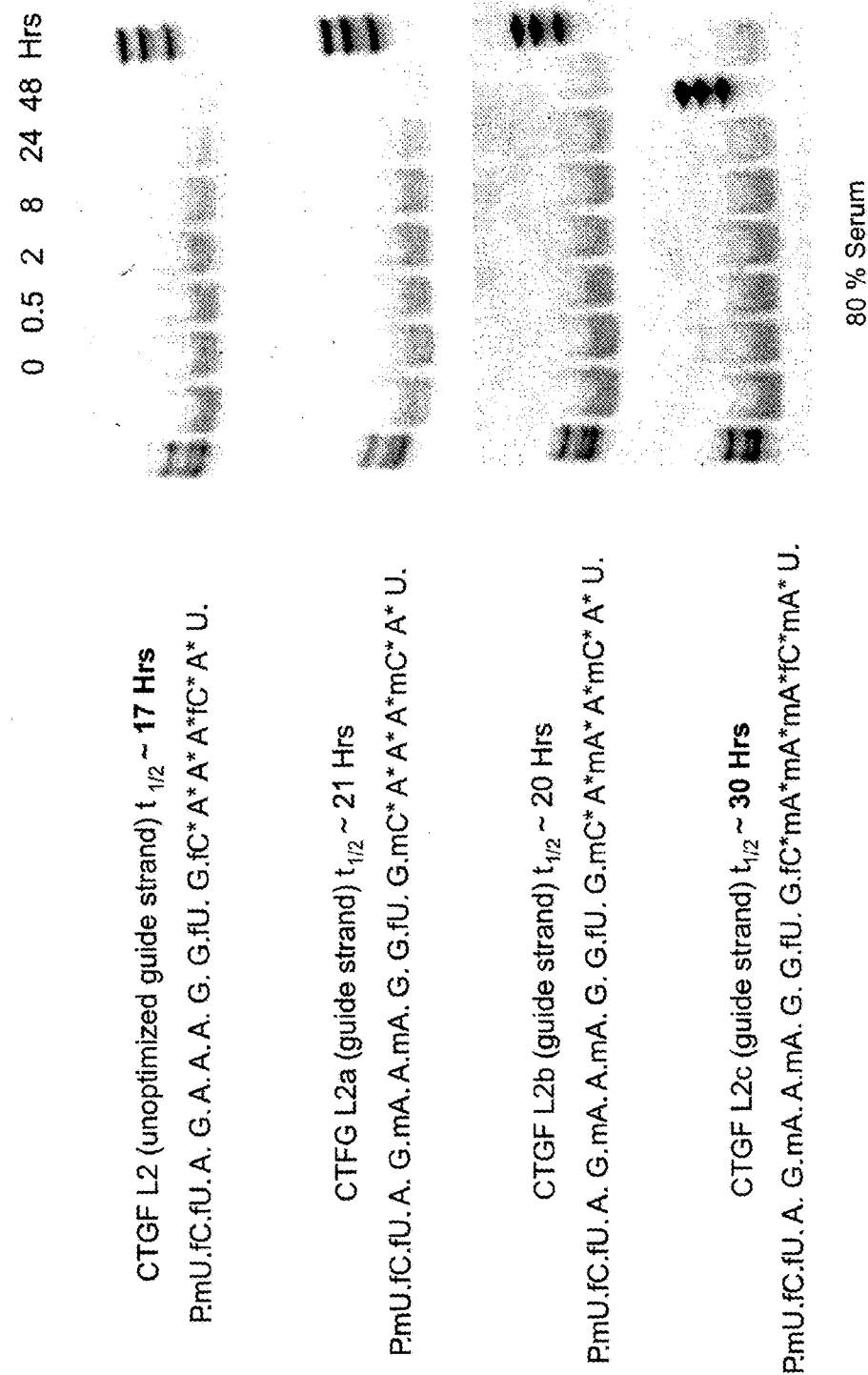
FIG. 82 reveals the stability of sd-rxRNA® in serum. Sequences in FIG. 82 are SEQ ID NO:613.

FIG. 82 reveals stability of sd-rxRNA®. In the presence of 80% serum, RNA was still detectable after 48 hrs.

Figure 83:
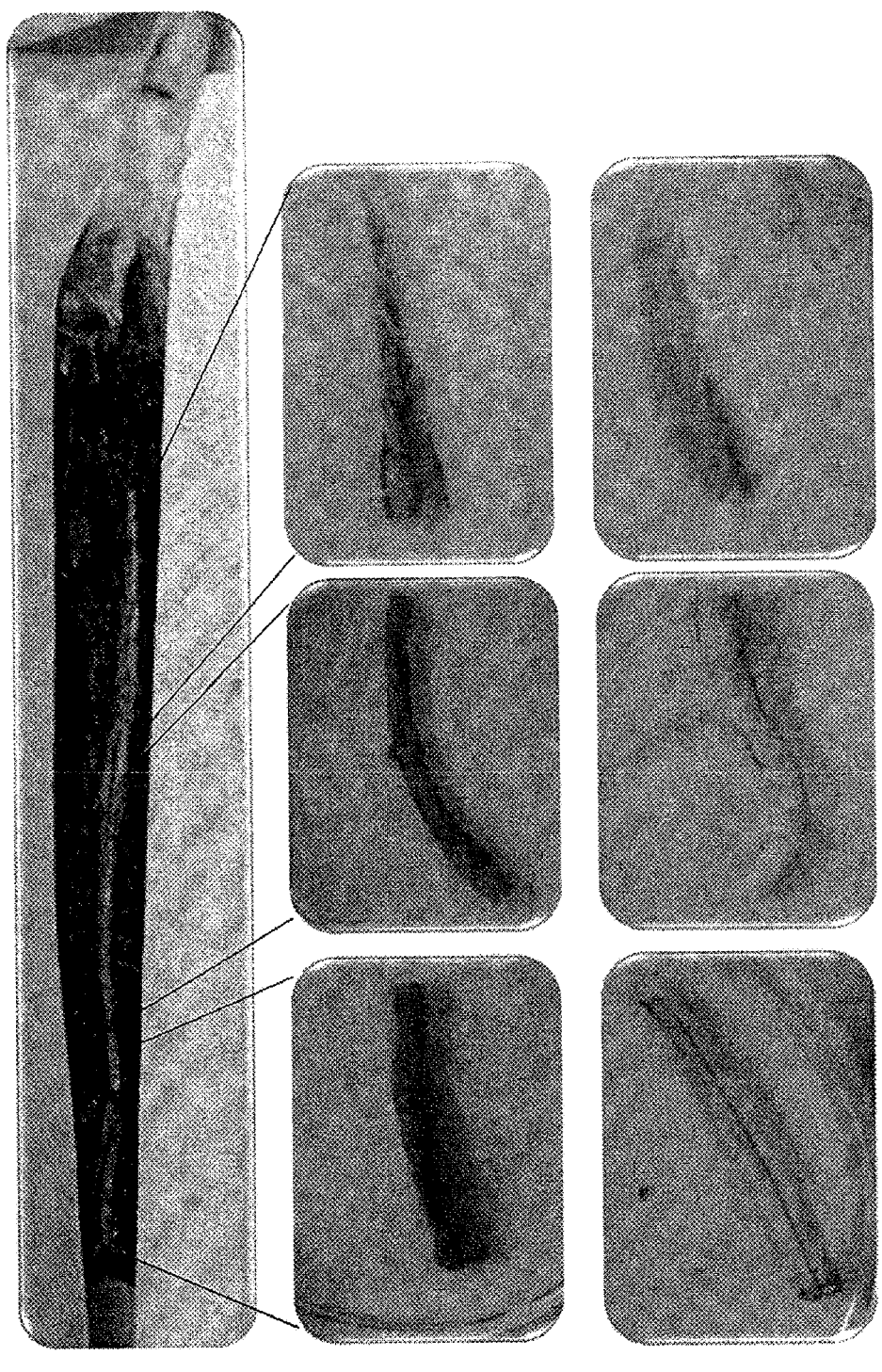
FIG. 83 shows delivery of sd-rxRNA® to the spinal cord following central nervous system injection.
Figure 84:
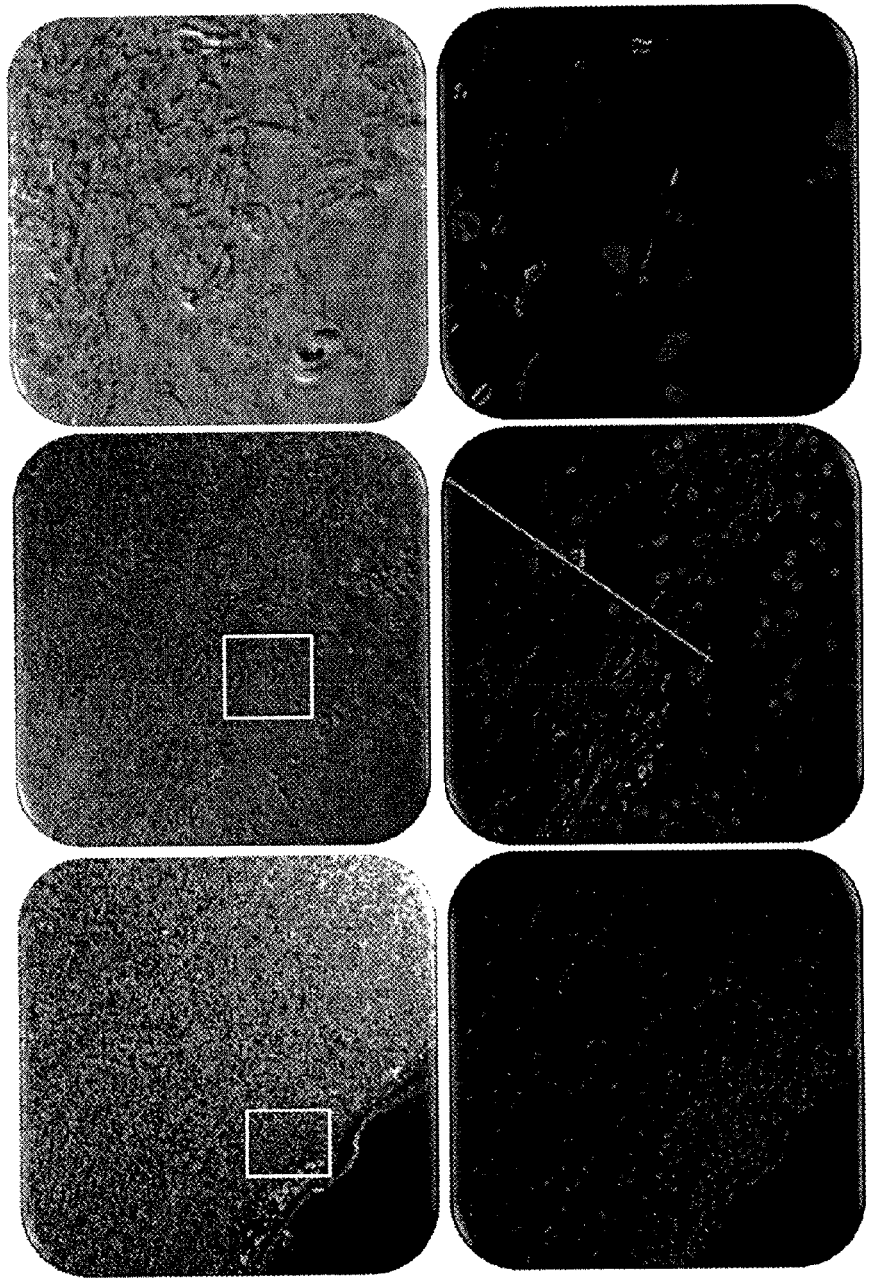
FIG. 84 reveals penetration into the spinal cord after delivery of sd-rxRNA® to the central nervous system.
Figure 85:
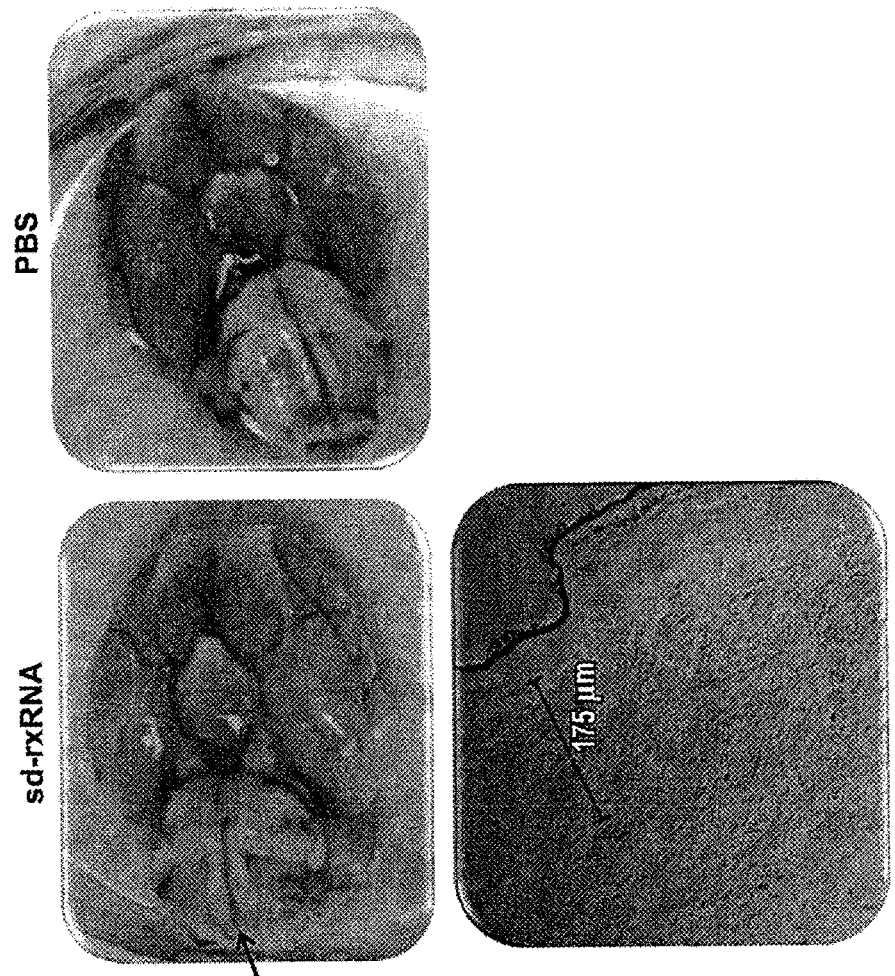
FIG. 85 reveals indication of sd-rxRNA® delivery to the brain stem

FIG. 83 shows delivery of sd-rxRNA® to the spinal cord after injection into the central nervous system. FIG. 84 shows penetration into spinal cord after delivery of sd-rxRNA® to the central nervous system. Uptake of sd-rxRNA® appears to be both in tissue and in cells. FIG. 85 reveals results of a pilot study indicating sd-rxRNA® delivery to the brain stem. While animal to animal variability was observed, these data suggest that CNS diseases of the brain stem (such as Huntington's Disease) could be pursued with direct delivery of sd-rxRNA®.

Example 7: Novel Phosphoramidite Synthesis

Introduction of novel chemistries into oligonucleotides requires synthesis of precursors-phosphoramidites. Synthesis of each novel modified phosphoramidite can be complex. To simplify the process, the initial chemistry screen was limited to a context of 5-dU.

This is an optimal starting point because: (1) dU provides opportunities for most simple chemistry synthesis schemes and does not require additional groups protection; (2) position 5 of the uridine is not on a Watson-Crick surface and modification of this position has been shown to be readily tolerated by the majority of oligonucleotide interacting proteins; and (3) we have identified that deoxy U is tolerated well in multiple positions of the sd-rxRNA® molecule, which enables incorporation in multiple positions of both guide and passenger strand of the sd-rxRNA® leads. The 10 chemistries shown below are being synthesized. Choices were based on both: (1) ease of synthesis and commercial availability of precursors and (2) diversity of extent and structure of hydrophobic modifications.

Structures of Lipophilic 2'-Deoxy Uridine Modification:
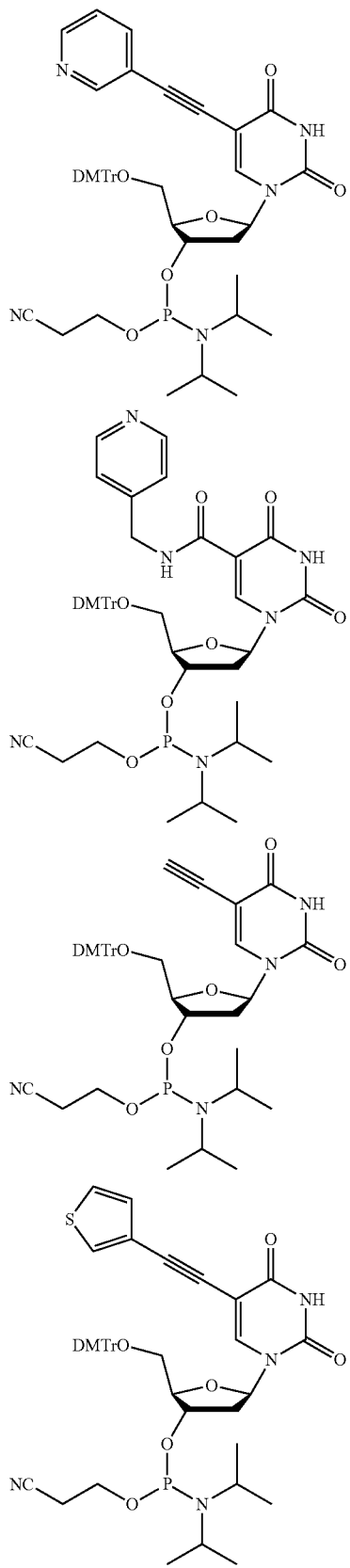
-continued
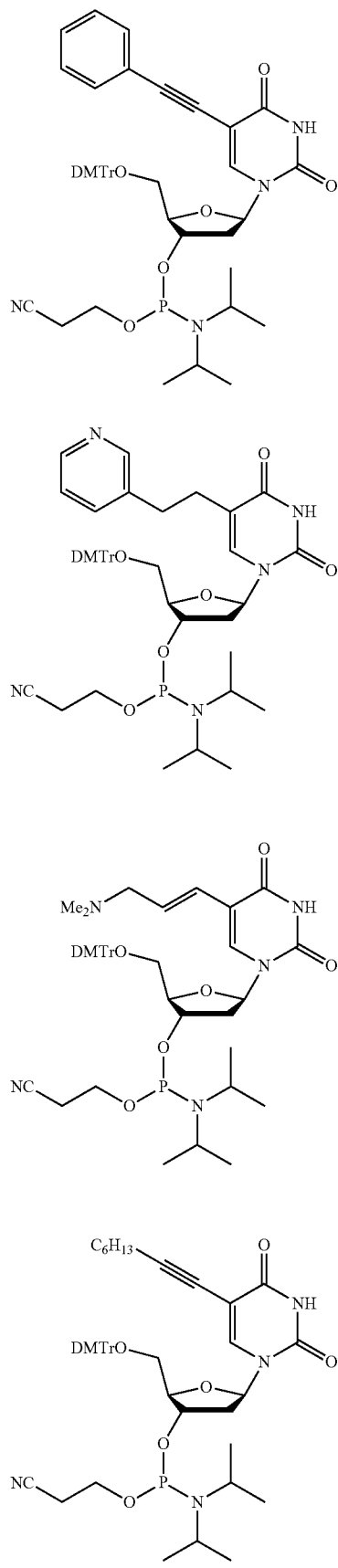

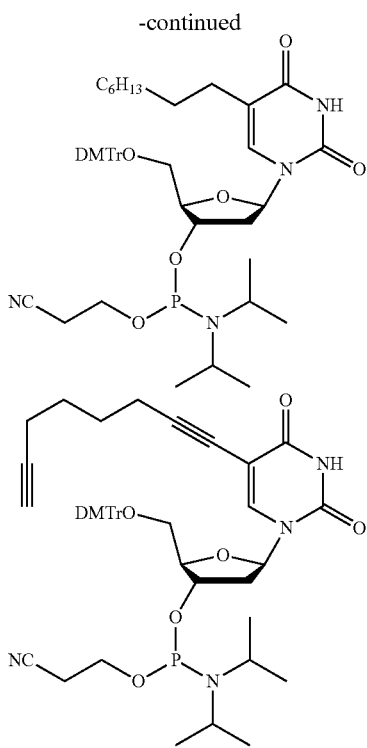

Primarily Sonogashira coupling reactions are used to assemble the main chemical motif though some targets will use Suzuki or Palladium cross coupling. Other chemical reactions used are well elaborated in the literature and are robust and high-yielding.

Compound Design and Synthesis

As discussed above, scaffold sequences targeting MAP4K4 and PCSK9 have shown the efficacy of two different sd-rxRNA® compounds with and without deoxy U modification at several places.

Variants of both passenger and guide strand are being synthesized with and without hydrophobic termini modifications. This enables the evaluation of the impact of hydrophobic modification on uptake properties by itself and in combination with hydrophobic termini modifications currently used.

An array of 108 oligo variants targeting MAP4K4 and PCSK9 with different degrees of lipophilicity, giving rise to more than 288 different compound are being synthesized (12 oligos per chemistry). The panel incorporate from 3 to 7 different lipophilic monomers, in 12 different modification patterns. Use of different configurations will allow "titration" of the amount of lipophilicity and assessment of the effect of positioning within the RNAi. Compounds found to be active in cell culture are made with a fluorescent tag to assess cellular uptake.

The single stranded oligoribonucleotides are synthesized using a MerMade 12 oligonucleotide synthesizer and deprotected using industry standard methodologies. Potentially, as the chemistries involved are not standard with regard to the methodology, some changes may have to be made. The oligoribonucleotides are purified using standard C18 methodology (>70% purity) and assayed using analytical Reverse-Phase Ion Pairing chromatography and a subset by MALDI-TOF. Single stranded Passenger and Guide strands are then duplexed. The impact of additional chemistries on oligonucleotide duplex hydrophobicity is evaluated chromatographically using the methodology of Dagle et al. after establishing a correlation against the octanol-water partition co-efficient. The goal is to increase the log P of the duplexes by an order of magnitude versus current version of sd-rxRNA® chemistry. The best compounds are radioactively labeled and a patrician co-efficient is estimated by conventional octanol-water patrician protocol.

The efficacy of the synthesized compounds is then evaluated in tissue culture assays for cellular uptake, toxicity and efficacy. The following standard assays are used for compound evaluation:

Uptake Assessment

Fluorescently labeled sd-rxRNA® (DY547) variants are evaluated for uptake. Original sd-rxRNA® compound uptake happens within minutes of exposure, so both efficiency and kinetics are evaluated. Cells are incubated in culture media in the presence of varying concentration of sd-rxRNA® variants and fixed at appropriate time points. A Leica SP5 confocal microscope is employed, equipped with a 405 blue diode laser, 458, 476, and 514 argon lasers, a 561 yellow diode laser and a 633 HeNe laser. The 405 laser is used to collect a DAPI or Hoechst image. The confocal also has the ability to capture multiple images from the scanning of multiple lasers at the same time allowing for generation of merged images. Optimal compounds are further evaluated for visualization of kinetics and mechanism of uptake using TIRF microscopy.

In Vitro Toxicity Assessment

An Alamar Blue assay is used according to manufacturer's protocols to evaluate general compound toxicity. Some of chemistries are expected to be toxic and will still be included in tissue culture efficacy evaluation but excluded from any in vivo analysis. In order to determine the potential of compounds for IFN induction, compounds are added to HelaS3 and primary macrophages and the level of mRNA expression for IFIT1, IL6, CD45 and other inflammatory markers is evaluated using Q-PCR and B-DNA. These two cell types were previously identified to be sensitive to compounds toxicity. Poly IC, 45 mer duplex and other positive controls are used. Compounds showing no cellular toxicity and no IFN induction in tissue culture assays are further evaluated for inflammatory response activation using whole blood cytokine release assay.

Gene Silencing Assays

Hela cells and/or primary hepatocytes (and other cell lines if needed) are used to evaluate compound efficacy. To address compatibility with the RNAi cellular machinery (RISC loading and cleavage) sd-rxRNA® constructs are transfected into cells using Lipofectamine RNAiMAX (Invitrogen, Carlsbad, Calif.) according to the manufacturer's instructions. In addition, efficacy in passive uptake enables evaluation of both uptake and RISC entry. Running both assays enables differentiation between impact of chemistry on RISC loading and cellular uptake. After 24 to 48 hours of incubation, cells are lysed and gene silencing activity is measured by qPCR or branched DNA assays (Affymetrix). Target gene expression levels are normalized to housekeeping gene expression. For self-delivery assays (without transfection reagent) the sd-rxRNA® is simply added to the culture media and incubated for 24 to 48 hours before cell lysis for RNA preparation. This analysis allows for identification of compounds which are non toxic and have at least 3-10 fold better EC50 values as compared to original sd-rxRNA® in passive uptake (EC50<10 nM in vitro).

In Vivo Testing

Not toxic and efficacious compounds are further evaluated in vivo in BALB/C male mice. Briefly, animals are IV injected at target dose levels and blood samples are taken at appropriate points to estimate blood retention and clearance rate. Typical endpoints include compound blood and tissue quantification, blood chemistries, liver enzymes, histological examination of all major organs and DY547 labeled sd-rxRNA® uptake (Confocal microscopy). A previously validated hybridization based assay is used for blood and tissue quantitative analysis. For the most promising compounds, studies evaluate the level of targeted mRNA knockdown as compared to a mismatch control and PBS treated groups. N-5 with 3 biopsies per tissue are collected and stored using RNAlater® (Qiagen). All assays are well established. In addition to systemic evaluation, a panel of best non-toxic compounds are tested at different concentrations locally (intra-dermal injections) and compared to original sd-rxRNA®.

Endosomal Escape

While the current version of sd-rxRNA® chemistry gives multiple orders of magnitude enhancement in cellular uptake compared to conventional siRNAs, in some instances, relatively high concentrations of compounds is required to achieve efficacy (5-50 nM EC50 values). When the same sd-rxRNA® are introduced via lipid mediated delivery, the EC50 value goes down by at least 10-50 fold, indicating that a quantity of passively internalized oligonucleotides is not reaching the RISC complex. Visualization and co-staining indicate that uptake is occurring through the endocytosis mechanism. The majority of sd-rxRNA® goes through the multi-vesicular body (MVB) and becomes trapped in lysosomes at 24 hours, while only a small fraction escapes the endosomes and lysosomes and is available for RISC loading.

Without wishing to be bound by any theory, endosomal entrapment may be a potency limiting factor. Additional protonatable amine containing modifications may improve sd-rxRNA® endosomal and lysosomal escape. Encapsulation of oligonucleotides in protonatable amines containing lipids is a major way oligos are currently delivered to cells (most commercially available transfection reagents utilize this approach). Incorporation of protonatable amines in a context of dynamic polyconjugates has been tried before (Rozema, Lewis et al. 2007) and good liver efficacy was demonstrated. Unfortunately accumulation of non-degradable polymer used as a backbone and other properties resulted in a limited toxicity profile. Upon change of pH in the maturation of endosome, the amine is protonated, causing endosome rupture and oligo release.

Herein, a variety of protonatable amines are incorporated in the context of an sd-rxRNA® directly. By addition of a different number and type of amine chemistries in different locations of the sd-rxRNA®, a substantial increase in oligo endosomal escape and thus potency can be achieved. This will provide more potent self-delivering rxRNA designs with improved pharmacology which can be used to develop RNAi drug candidates in multiple therapeutic areas, both for local and systemic applications. These novel designs also provide self-delivering rxRNA for in vivo functional genomics studies. This approach is highly novel. The starting point is compounds which demonstrated unprecedented levels of cellular uptake, where efficacy is limited by intracellular compartmentalization (endosomal entrapment). Incorporation of protonatable amines in the sense strand (part of the molecule which is discarded after RISC loading) is used to significantly increase potency. Furthermore, these studies provide data on the structure/function of protonatable amines containing duplex RNAs that will aid in designing RNAi compounds and microRNA mimics.

Synthesis of Protonatable Amines Containing Precursors to Promote Endosomal Escape Currently, in some embodiments, the sd-rxRNA® sense strand utilizes a TEG linker for attachment of hydrophobic moieties. This is trifunctional, allowing attachment to the solid support upon which oligonucleotide synthesis is performed, to the chemically modified RNA (which forms one half of the siRNA duplex) and to one of hydrophobic functionalities (generically cholesterol). Incorporation of several protonatable amine containing chemistries in the context of a linker is first explored. While the presence of a positively charged linker might flip back, the presence of a hydrophobic core may prevent this from happening.

A carbonyl to nitrogen bond of a carbamate functionality can be elaborated to include amino acids such as histidine. Histidine has a $pK_{BH+}$ of the imidazole side chain of ~6 meaning that it is predominantly neutral at physiological pH but predominantly protonated in the endosomal compartment. A tosylate protecting group is proposed for the imidazole functionality to liberate histidine or a methyl group can be used. Additionally, the imidazole ring can be substituted with electron withdrawing groups to optimize the $pK_{BH+}$ if necessary.

The imidazolyl functionality in its native or a synthetically modified form can also be incorporated into the uridine nucleobase using published methods (Vaught, Bock et al.; Holmes S C 2005).

Other chemical functionalities can be synthesized in subsequent efforts to protonate in the range of pH 5-7, including electron rich pyridines. Pyridyl variants with various degrees of methyl substitution can be synthesized from the commercially available chloromethyl precursors.

A panel of compounds are generated which will incorporate 2 types of protonatable amines in different numbers in a context of a hydprobobic linker and internally within the compound. This material enables synthesis of a panel of sd-rxRNA® variants with variable levels of incorporation of protonatable amines.

A panel of oligos containing 1-5 protonatable amines in a context of a hydrophobic linker attached to the 3'end of the sense strand as well as distributed throughout the sense strand are generated. To minimize the impact of sequence bias, two scaffold sequence (one targeting MAP4K4 and one targeting PCSK9) are used. Both sequences enable incorporation of 3-4 protonatable amines in the context of the sense strand. Initially internal incorporation is limited to the sense strand as the presence of these types of chemistries in the guide strand can in some instances interfere with the RISC function.

An array of 50-70 oligo variants targeting MAP4K4 and PCSK9 with different degrees, types and position of protonatable amines chemistries are synthesized. The panel incorporates from 1 to 5 different monomers, in several modification patterns. Use of these different configurations will allow "titration" of the number and position (terminal or internal) of protonatable amines and assessment of the effect on RISC assembly and cellular uptake. Compounds found to be active in cell culture are made with a fluorescent tag to assess cellular uptake.

The single-stranded oligoribonucleotides are synthesized using a MerMade 12 oligonucleotide synthesizer (BioAutomation, Plano, Tex.) and deprotected using industry standard methodologies. As the chemistries involved are not standard, some changes in coupling and deprotection conditions may have to be made. The crude oligoribonucleotides are then purified using standard C18 methodology (>70% purity) and assayed using analytical Reverse-Phase Ion Pairing chromatography and a subset by MALDI-TOF. Single-stranded Passenger and Guide strands are then duplexed. The impact of additional chemistries on oligonucleotide duplexing is evaluated by gel electrophoresis. As a result, the maximum number of protonatable amines without interfering with duplex formation and compound integrity are incorporated. The following standard assays will be used for compound evaluation.

Uptake Assessment

Fluorescently labeled sd-rxRNA® (DY547) variants are evaluated for uptake. Original sd-rxRNA® compounds are taken up by cells within minutes of exposure, so both efficiency and kinetics are evaluated. Cells are incubated in culture media in the presence of varying concentrations of sd-rxRNA® variants and fixed at appropriate time points. A Leica SP5 confocal microscope is employed, equipped with a 405 blue diode laser, 458, 476, and 514 argon lasers, a 561 yellow diode laser and a 633 HeNe laser. The 405 laser is used to collect a DAPI or Hoechst image. The confocal also has the ability to capture multiple images from the scanning of multiple lasers at the same time allowing for the generation of merged images. The most active compounds are further evaluated for visualization of kinetics and mechanism of uptake using TIRF microscopy.

In Vitro Toxicity Assessment

Alamar Blue assays are used in according to the manufacturer's protocol to evaluate the general toxicity of the compounds. In the event that some compounds are toxic they are included in tissue culture efficacy evaluation but excluded from any in vivo analysis. Compounds are added to HelaS3 and primary macrophages and the level of mRNA expression for IFN, IFIT1, IL6, CD45 and others inflammatory markers is evaluated using Q-PCR and B-DNA. These two cell types were previously identified to be sensitive to proinflammatory effects of siRNA. Poly IC, 45 mer duplex and other positive controls are used. Compounds showing no cellular toxicity and no IFN induction in tissue culture assays are further evaluated for inflammatory response activation using whole blood cytokine release assay (Lankveld, Van et al. 2010). Toxicity is evaluated because novel chemistries may lead to increased toxicity.

Gene Silencing Assays

Hela cells and/or primary hepatocytes (and other cell lines if needed) are used to evaluate compound efficacy. To address compatibility with the RNAi cellular machinery (RISC loading and cleavage), sd-rxRNA® constructs are transfected into cells using Lipofectamine RNAiMAX (Invitrogen, Carlsbad, Calif.) according to the manufacturer's instructions. In addition, efficacy in passive uptake enables evaluation of both uptake and RISC entry. Running both assays enables us to distinguish between impact of chemistry on RISC loading and cellular uptake. After 24 to 48 hours of incubation, cells are lysed and gene silencing activity is measured by qPCR or branched DNA assays (Affymetrix). Target gene expression levels are normalized to housekeeping gene expression. For self-delivery assays (without transfection reagent) the sd-rxRNA® is simply added to the culture media and incubated for 24 to 48 hours before cell lysis for mRNA preparation. This analysis leads to identification of compounds which are non toxic and have at least 3-10 fold better EC50 values as compare to original sd-rxRNA® in passive uptake (EC50<2 nM in vitro).

In Vivo Testing

Compounds shown to be nontoxic and efficacious in cell culture are further evaluated in vivo in BALB/C male mice. Briefly, animals are IV injected at target dose levels and blood samples are taken at appropriate points to estimate blood retention and clearance rate. Typical endpoints include compound blood and tissue quantification, blood chemistries, liver enzymes, histological examination of all major organs and DY547 labeled sd-rxRNA® uptake (Confocal microscopy). In addition, intradermal and intraocular efficacy and toxicity are evaluated. A previously validated hybridization based assay is used for blood and tissue quantitative analysis. The studies evaluate level of targeted mRNA knockdown as compared to mismatch control and PBS treated groups. N-5 with 3 biopsies per tissue are collected and stored RNAlater® (Qiagen). In addition to systemic evaluation, a panel of the most active compounds are tested at different concentrations locally (intra-dermal injections) as compared to the original sd-rxRNA®.

TABLE 1 hApoB sequences

| Target Gene Duplex ID | ApoB Sense Sequence | NM_000384.2% Expression (0.1 nM) | SEQ ID No. |
|---|---|---|---|
| 16567 | CCCAGCUCUGCAGCUUCAUCCUGAA | 69% | 1 |
| 16568 | ACCCUGAAAGAGGUGUAUGGCUUCA | 87% | 2 |
| 16569 | CAGCCAUGUCCAGGUAUGAGCUCAA | 73% | 3 |
| 16570 | AACCUACUUACAUCCUGAACAUCAA | 65% | 4 |
| 16571 | CCCAGAGACAGAAGAAGCCAAGCAA | 72% | 5 |
| 16572 | UGUGGCAACAGAAAUAUCCACUGAA | 87% | 6 |
| 16573 | GUGGCAACAGAAAUAUCCACUGAAA | 86% | 7 |
| 16574 | CAUCAGCCCACUUGCUCUCAUCAAA | 77% | 8 |
| 16575 | AAGUGACACAGACUUUGAAACUUGA | 67% | 9 |
| 16576 | ACAGACUUUGAAACUUGAAGACACA | 80% | 10 |
| 16577 | ACUUUGAAACUUGAAGACACACCAA | 87% | 11 |
| 16578 | CUUUGAAACUUGAAGACACACCAAA | 81% | 12 |
| 16579 | AACUUGAAGACACACCAAAGAUCAA | 87% | 13 |
| 16580 | AGCUGUUUUGAAGACUCUCCAGGAA | 83% | 14 |
| 16581 | UUUUGAAGACUCUCCAGGAACUGAA | 81% | 15 |
| 16582 | GCAAAAUAUCCAGAGAGCUAAUCUA | 49% | 16 |
| 16583 | CACAGCAGCUGCGAGAGAUCUUCAA | 72% | 17 |
| 16584 | GGAGCUGCUGGACAUUGCUAAUUAA | 60% | 18 |
| 16585 | CACUGGGGAUGAAGAUUACACCUAA | 66% | 19 |
| 16586 | UGGAGCAGUUAACUCCAGAACUCAA | 56% | 20 |
| 16587 | CAGUUAACUCCAGAACUCAAGUCUA | 58% | 21 |
| 16588 | UUAACUCCAGAACUCAAGUCUUCAA | 77% | 22 |
| 16589 | GAAAUGUGUCCAAAGUACAAAGCCA | 69% | 23 |
| 16590 | AGGCUCUGCGGAAAAUGGAGCCUAA | 106% | 24 |
| 16591 | GGCUCUGCGGAAAAUGGAGCCUAAA | 100% | 25 |
| 16592 | UCCUUCACAGGCAGAUAUUAACAAA | 86% | 26 |
| 16593 | CCUUCACAGGCAGAUAUUAACAAAA | 68% | 27 |

TABLE 1-continued hApoB sequences

| Target Gene Duplex ID | ApoB Sense Sequence | NM_000384.2% Expression (0.1 nM) | SEQ ID No. |
|---|---|---|---|
| 16594 | CAUGGGAACAGAAUGAGCAAGUGAA | 71% | 28 |
| 16595 | UGUGGCUUCCCAUAUUGCCAAUAUA | 77% | 29 |
| 16596 | AUCUUGAACUCAGAAGAAUUGGAUA | 71% | 30 |
| 16597 | UGAACUCAGAAGAAUUGGAUAUCCA | 81% | 31 |
| 16598 | GUUAGUGAAAGAAGCUCUGAAAGAA | 68% | 32 |
| 16599 | AGCUCUGAAAGAAUCUCAACUUCCA | 59% | 33 |
| 16600 | UGGACUUCAGAAAAUUCUCUCGGAA | 65% | 34 |
| 16601 | UCCAAAUAACUACCUUCCUAAAGAA | 77% | 35 |
| 16602 | UACCUUCCUAAAGAAAGCAUGCUGA | 67% | 36 |
| 16603 | ACCUUCCUAAAGAAAGCAUGCUGAA | 72% | 37 |
| 16604 | UGACCUCAUCGAGAUUGGCUUGGAA | 102% | 38 |
| 16605 | CUCAUCGAGAUUGGCUUGGAAGGAA | 99% | 39 |
| 16606 | UCAUCGAGAUUGGCUUGGAAGGAAA | 87% | 40 |
| 16607 | UUGGAAGGAAAAGGCUUUGAGCCAA | 85% | 41 |
| 16608 | AUUUUUCCCAGACAGUGUCAACAAA | 73% | 42 |
| 16609 | AUGGUGUCUCUAAGGUCUUAGUGGA | 93% | 43 |
| 16610 | AAAGAUGAUAAACAUGAGCAGGAUA | 86% | 44 |
| 16611 | UGAUAAACAUGAGCAGGAUAUGGUA | 63% | 45 |
| 16612 | ACAUGAGCAGGAUAUGGUAAAUGGA | 69% | 46 |
| 16613 | AUAUGGUAAAUGGAAUAAUGCUCAA | 91% | 47 |
| 16614 | UGCUCAGUGUUGAGAAGCUGAUUAA | 48% | 48 |
| 16615 | GCUCAGUGUUGAGAAGCUGAUUAAA | 61% | 49 |
| 16616 | CAUCUUCAUGGAGAAUGCCUUUGAA | 71% | 50 |
| 16617 | GGAGCUGGAUUACAGUUGCAAAUAA | 72% | 51 |
| 16618 | UCCCGGAGCCAAGGCUGGAGUAAAA | 79% | 52 |
| 16619 | GAGCCAAGGCUGGAGUAAAACUGGA | 77% | 53 |
| 16620 | CCGUGUCUGUGGAGUUUGUGACAAA | 66% | 54 |
| 16621 | GGCAACACAUUACAUUUGGUCUCUA | 76% | 55 |
| 16622 | AUUACAUUUGGUCUCUACCACCAAA | 85% | 56 |
| 16623 | CAGUCCUGGUCAGUUUGCAAGCAAA | 70% | 57 |
| 16624 | UGAGGCCACAGGAGAGAUUGAGCA | 84% | 58 |
| 16625 | GCCUACAGGAGAGAUUGAGCAGUAA | 77% | 59 |
| 16626 | UGGAUACCCUGAAGUUUGUAACUCA | 57% | 60 |
| 16627 | CCUGAAGUUUGUAACUCAAGCAGAA | 85% | 61 |
| 16628 | GCAGAGUAUGACCUUGUCAGUGAA | 95% | 62 |
| 16629 | ACCUCGGAACAAUCCUCAGAGUUAA | 65% | 63 |
| 16630 | CGGAACAAUCCUCAGAGUUAAUGAA | 76% | 64 |
| 16631 | GAACAAUCCUCAGAGUUAAUGAUGA | 66% | 65 |
| 16632 | AACAAUCCUCAGAGUUAAUGAUGAA | 79% | 66 |
| 16633 | AGACUCACCCUGGACAUUCAGAACA | 102% | 67 |
| 16634 | ACCCUGGACAUUCAGAACAAGAAAA | 65% | 68 |
| 16635 | CUUCUCCAAAUGGACUCAUCUGCUA | 87% | 69 |
| 16636 | GAGGGUGGCAUGGCAUUAUGAUGAA | 97% | 70 |
| 16637 | AAGAUUGAAUUUGAAUGGAACACAA | 75% | 71 |
| 16638 | AUUUGAAUGGAACACAGGCACCAAA | 86% | 72 |
| 16639 | ACACAGGCACCAAUGUAGAUACCAA | 67% | 73 |
| 16640 | CACAGGCACCAAUGUAGAUACCAAA | 73% | 74 |
| 16641 | GAGCUUGCAUAUGUAUGCUAAUAGA | 70% | 75 |
| 16642 | UGUAUGCUAAUAGACUCCUGGAUCA | 65% | 76 |
| 16643 | CACAUCCCAGAAAACCUCUUCUUAA | 59% | 77 |
| 16644 | GAUUCCUUUGCCUUUUGGUGGCAAA | 96% | 78 |
| 16645 | AAAGAUGUUAGAGACUGUUAGGACA | 69% | 79 |
| 16646 | ACCUCUCCACGAAUGUCUACAGCAA | 77% | 80 |
| 16647 | CUGGAGAAACAACAUAUGACCACAA | 91% | 81 |
| 16648 | GAAACAACAUAUGACCACAAGAAUA | 57% | 82 |
| 16649 | GAAUAUCAAAUUCAGUCAUGUAGAA | 58% | 83 |
| 16650 | AACCCAGUCUCAAAAGGUUUACUAA | 46% | 84 |
| 16651 | CUGGGGACCACAGAUGUCUGCUUCA | 77% | 85 |
| 16652 | AAAAGAAACAGCAUUUGUUUGUCAA | 74% | 86 |
| 16653 | GAAACAGCAUUUGUUUGUCAAAGAA | 51% | 87 |
| 16654 | AGCAUUUGUUUGUCAAAGAAGUCAA | 75% | 88 |
| 16655 | UGUUUGUCAAAGAAGUCAAGAUUGA | 59% | 89 |
| 16656 | AUGGAGAGUCCAACCUGAGGUUUAA | 78% | 90 |
| 16657 | AUAACAGGAAGAUAUGAAGAUGGAA | 86% | 91 |
| 16658 | AUGAGAACUACGAGCUGACUUUAAA | 80% | 92 |
| 16659 | GAAGUAUAAGAACUUUGCCACUUCA | 95% | 93 |
| 16660 | AUGGAUAUGACCUUCUCUAAGCAAA | 47% | 94 |
| 16661 | UCAGCCUGCUUUCUGGAUCACUAAA | 80% | 95 |
| 16662 | UCUUGAGUUAAAUGCUGACAUCUUA | 79% | 96 |
| 16663 | ACAUCUUAGGCACUGACAAAAUUAA | 60% | 97 |
| 16664 | UGACAAAAUUAAUAGUGGUGCUCAA | 101% | 98 |
| 16665 | ACAAAAUUAAUAGUGGUGCUCACAA | 98% | 99 |
| 16666 | AGGAUUGGCCAAGAUGGAAUAUCUA | 80% | 100 |

TABLE 1-continued hApoB sequences

| Target Gene Duplex ID | ApoB Sense Sequence | NM_000384.2% Expression (0.1 nM) | SEQ ID No. |
|---|---|---|---|
| 16667 | AGUGCAACGACCAACUUGAAGUGUA | 68% | 101 |
| 16668 | AAAUUAACAACAAAUGGCCGCUUCA | 95% | 102 |
| 16669 | AAAAACAUUUUCAACUUCAAGGUCA | 85% | 103 |
| 16670 | AGUCAAGAAGGACUUAAGCUCUCAA | 99% | 104 |
| 16671 | GAUGGGCUCAUAUGCUGAAAUGAAA | 67% | 105 |
| 16672 | UAUGCUGAAAUGAAAUUUGACCACA | 78% | 106 |
| 16673 | AAACAGUCUGAACAUUGCAGGCUUA | 100% | 107 |
| 16674 | GGCUUAUCACUGGACUUCUCUUCAA | 64% | 108 |
| 16675 | AGCAAACUGUUAAUUUACAGCUACA | 71% | 109 |
| 16676 | AACUACUUAAACAGUGACCUGAAA | 88% | 110 |
| 16677 | ACUUUAAACAGUGACCUGAAAUACA | 71% | 111 |
| 16678 | CUUUAAACAGUGACCUGAAAUACAA | 67% | 112 |
| 16679 | GGUAACCUAAAAGGAGCCUACCAAA | 76% | 113 |
| 16680 | AACCUAAAAGGAGCCUACCAAAAUA | 57% | 114 |
| 16681 | AAAAGGAGCCUACCAAAAUAAUGAA | 97% | 115 |
| 16682 | AAUGAAAUAAAACACAUCUAUGCCA | 101% | 116 |
| 16683 | CAAACUAUAAUUCAGACUACUGCA | 70% | 117 |
| 16684 | CUCUCAUGAUUACAAAGGCUCCACA | 65% | 118 |
| 16685 | GCAUCAGUGCAGCUCUUGAACACAA | 60% | 119 |
| 16686 | AGCUCUUGAACACAAAGUCAGUGCA | 91% | 120 |
| 16687 | AACAACAAUGAAUACAGCCAGGACA | 98% | 121 |
| 16688 | CAUUUUUUGAGACCUUGCAAGAAUA | 88% | 122 |
| 16689 | ACCUUGCAAGAUAUUUUGAGAGGA | 92% | 123 |
| 16690 | CUGGAAAACGUACAGAGAAACCUGA | 61% | 124 |
| 16691 | CCUGAAGCACAUCAAUAUUGAUCAA | 53% | 125 |
| 16692 | UGGGAAAACUCCCACAGCAAGCUAA | 88% | 126 |
| 16693 | ACUCCCACAGCAAGCUAAUGAUUAA | 59% | 127 |
| 16694 | UGGGAGAGACAAGUUUCACAUGCCA | 85% | 128 |
| 16695 | AUUGCAUUAGAUGAUGCCAAAAUCA | 56% | 129 |
| 16696 | CUCAACUGCAGACAUAUAUGAUACA | 87% | 130 |
| 16697 | CUGGAUUCAAAAUGUGGGAUACUAAA | 92% | 131 |
| 16698 | AGUACCAAAUCAGAAUCCAGAUACA | 64% | 132 |
| 16699 | AAAUCAGAAUCCAGAUACAAGAAAA | 88% | 133 |
| 16700 | CAGCUUAAGAGACACAUACAGAAUA | 94% | 134 |
| 16701 | UUAAGAGACACAUACAGAAUAUAGA | 63% | 135 |
| 16702 | GACACAUACAGAAUAUAGACAUCCA | 101% | 136 |
| 16703 | AUCCAGCACCUAGCUGGAAAGUUAA | 62% | 137 |
| 16704 | AGCACCUAGCUGGAAAGUUAAAACA | 86% | 138 |
| 16705 | AAGUUAAAACAACACAUUGAGGCUA | 93% | 139 |
| 16706 | CUAUUGAUGUUAGAGUGCUUUUAGA | 63% | 140 |
| 16707 | UUGAUGUUAGAGUGCUUUUAGAUCA | 56% | 141 |
| 16708 | UGAUGUUAGAGUGCUUUUAGAUCAA | 56% | 142 |
| 16709 | UGGGGAUUUUGAAGUAGCUGAGAAA | 54% | 143 |
| 16710 | AUUUUGAAGUAGCUGAGAAAAUCAA | 58% | 144 |
| 16711 | UUCAGAGCCAAAGUCCAUGAGUUAA | 62% | 145 |
| 16712 | AAUCGAGAGGUAUGAAGUAGACCAA | 89% | 146 |
| 16713 | CGAGAGGUAUGAAGUAGACCAACAA | 80% | 147 |
| 16714 | GAGAGGUAUGAAGUAGACCAACAAA | 76% | 148 |
| 16715 | CCAACAAAUCCAGGUUUUAAUGGAA | 77% | 149 |
| 16716 | AGGAGACUAUUCAGAAGCUAAGCAA | 53% | 150 |
| 16717 | GGAGACUAUUCAGAAGCUAAGCAAA | 48% | 151 |
| 16718 | AGAAGCUAAGCAAUGUCCUACAACA | 57% | 152 |
| 16719 | UGAUGCUGUCAAGAAGCUUAAUGAA | 51% | 153 |
| 16720 | GUUUGUAGAUGAAACCAAUGACAAA | 48% | 154 |
| 16721 | AGGUGACUCAGAGACUCAAUGGUGA | 63% | 155 |
| 16722 | CUCAGAGACUCAAUGGUGAAAUUCA | 65% | 156 |
| 16723 | GCCACAGUUGCAGUGUAUCUGGAAA | 77% | 157 |
| 16724 | AGUUGCAGUGUAUCUGGAAAGCCUA | 86% | 158 |
| 16725 | GAAAGCCUACAGGACACCAAAAUAA | 81% | 159 |
| 16726 | CCGAAUGUAUCAAAUGGACAUUCAA | 97% | 160 |
| 16727 | ACAUUCAGCAGGAACUUCAACGAUA | 58% | 161 |
| 16728 | UCUGGUAGGCCAGGUUUAUAGCACA | 71% | 162 |
| 16729 | AGGUUUAUAGCACACUUGUCACCUA | 64% | 163 |
| 16730 | GAACCUUACUGACUUUGCAGAGCAA | 75% | 164 |
| 16731 | ACUGACUUUGCAGAGCAAUAUUCUA | 40% | 165 |
| 16732 | CUAAACGUAUGAAAGCAUUGGUAGA | 68% | 166 |
| 16733 | AACGUAUGAAAGCAUUGGUAGAGCA | 51% | 167 |
| 16734 | AAGGGUUCACUGUUCCUGAAAUCAA | 54% | 168 |
| 16735 | UUCACUGUUCCUGAAAUCAAGACCA | 74% | 169 |
| 16736 | CAGAUUUGAGGAUUCCAUCAGUUCA | 51% | 170 |
| 16737 | UGAGGAUUCCAUCAGUUCAGAUAAA | 48% | 171 |
| 16738 | AUUCCAUCAGUUCAGAUAAACUUCA | 40% | 172 |
| 16739 | CCGUUUACCAGAAAUCGCAAUUCCA | 61% | 173 |

TABLE 1-continued hApoB sequences

| Target Gene Duplex ID | ApoB Sense Sequence | NM_000384.2% Expression (0.1 nM) | SEQ ID No. |
|---|---|---|---|
| 16740 | UCAUAAUCCCAACUCUCAACCUUAA | 71% | 174 |
| 16741 | CUGACCUUCACAUACCAGAAUUCCA | 64% | 175 |
| 16742 | CUUCACAUACCAGAAUUCCAGCUUA | 46% | 176 |
| 16743 | UUCCCCACAUCUCACACACAAUUGA | 55% | 177 |
| 16744 | UGGCAAGCUAUACAGUAUUCUGAAA | 51% | 178 |
| 16745 | CACAUUAGAUGCAAAUGCUGACAUA | 67% | 179 |
| 16746 | CGCAGCUUCCAUCACUGCCAAAGGA | 99% | 180 |
| 16747 | CUAAGAUUAAUCCGCUGGCUCUGAA | 104% | 181 |
| 16748 | AGGAGUCAGUGAAGUUCUCCAGCAA | 81% | 182 |
| 16749 | GAGGGAAAAUCAAACACAGUGGCAA | 69% | 183 |
| 16750 | GAAAAUCAAACACAGUGGCAAGUUA | 55% | 184 |
| 16751 | AAAAUCAAACACAGUGGCAAGUUUA | 63% | 185 |
| 16752 | CAGUGGCAAGUUUACACACAGAAAA | 49% | 186 |
| 16753 | AGCUUAGUAAUGGAGUGAUUGUCAA | 48% | 187 |
| 16754 | AGUAAUGGAGUGAUUGUCAAGAUAA | 54% | 188 |
| 16755 | GUAAUGGAGUGAUUGUCAAGAUAAA | 49% | 189 |
| 16756 | AGUGAUUGUCAAGAUAAACAAUCAA | 98% | 190 |
| 16757 | AUAGCAACACUAAAUACUUCCACAA | 74% | 191 |
| 16758 | UCACUCCUUUGGACUGUCCAAUAA | 71% | 192 |
| 16759 | GACUGUCCAAUAAGAUCAAUAGCAA | 49% | 193 |
| 16760 | AGGCAUGAUGCUCAUUUAAAUGGAA | 49% | 194 |
| 16761 | UCAUUUAAAUGGAAAGGUUAUUGGA | 93% | 195 |
| 16762 | GAUCACGGCAUCCACAAACAAUGAA | 88% | 196 |
| 16763 | AAAGUUCGUUUUCCAUUAAGGUUAA | 44% | 197 |
| 16764 | UAACAGGGAAGAUAGACUUCCUGAA | 72% | 198 |
| 16765 | ACAGGGAAGAUAGACUUCCUGAAUA | 55% | 199 |
| 16766 | GAUAGACUUCCUGAAUAACUAUGCA | 75% | 200 |
| 16767 | GCCCAGCAAGCAAGUUGGCAAGUAA | 40% | 201 |
| 16768 | CCCAGCAAGCAAGUUGGCAAGUAAA | 52% | 202 |
| 16769 | AGUUGGCAAGUAAGUGCUAGGUUCA | 42% | 203 |
| 16770 | GUUCAAUCAGUAUAAGUACAACCAA | 84% | 204 |
| 16771 | CAUGUAGGAAUAAAUGGAGAAGCAA | 66% | 205 |
| 16772 | AUGUAGGAAUAAAUGGAGAAGCAAA | 52% | 206 |
| 16773 | CAAUAAUCACAACUCCUCCACUGAA | 94% | 207 |
| 16774 | UGGGAAAAACAGGCUUGAAGGAAA | 56% | 208 |
| 16775 | AGGAAUUCUUGAAAACGACAAAGCA | 55% | 209 |
| 16776 | GGAAUUCUUGAAAACGACAAAGCAA | 61% | 210 |
| 16777 | GAUUUAAGUGUAAAAGCUCAGUAUA | 64% | 211 |
| 16778 | CCUUUGGCUGUGCUUUGUGAGUUUA | 78% | 212 |
| 16779 | GUCAAUGUUGAAGUGUCUCCAUUCA | 66% | 213 |
| 16780 | CUUUCUCUUCCAGAUUUCAAGGAAA | 61% | 214 |
| 16781 | AAUAUUACCUAUGAUUUCUCCUUUA | 44% | 215 |
| 16782 | CUCCUUUAAAUCAAGUGUCAUCACA | 61% | 216 |
| 16783 | UUAAAUCAAGUGUCAUCACACUGAA | 74% | 217 |
| 16784 | CAAGUGUCAUCACACUGAAUACCAA | 56% | 218 |
| 16785 | UGUCAUCACACUGAAUACCAAUGCA | 64% | 219 |
| 16786 | CAUCACACUGAAUACCAAUGCUGAA | 76% | 220 |
| 16787 | UAACCAGUCAGAUAUUGUUGCUCAA | 53% | 221 |
| 16788 | CUUCAUCUGUCAUUGAUGCACUGCA | 59% | 222 |
| 16789 | CUGUCAUUGAUGCACUGCAGUACAA | 43% | 223 |
| 16790 | AUUGAUGCACUGCAGUACAAAUUAA | 49% | 224 |
| 16791 | AAUUUUGAGAAUGAAUUUCAAGCAA | 71% | 225 |
| 16792 | AAUUUCAAGCAAGAACUUAAUGGAA | 79% | 226 |
| 16793 | AGAACUUAAUGGAAAAUACCAAGUCA | 51% | 227 |
| 16794 | GAACUUAAUGGAAAUACCAAGUCAA | 43% | 228 |
| 16795 | CUGUCUCUUCCUCCAUGGAAUUUAA | 59% | 229 |
| 16796 | AGUUGACCACAAGCUUAGCUUGGAA | 57% | 230 |
| 16797 | CUUUUCCAUUGAGUCAUCUACCAAA | 49% | 231 |
| 16798 | CAGGAACUAUUGCUAGUGAGGCCAA | 71% | 232 |
| 16799 | AACACUUACUUGAAUUCCAAGAGCA | 64% | 233 |
| 16800 | AUGAUAUCUGGAACCUUGAAGUAAA | 39% | 234 |
| 16801 | UAUCUGGAACCUUGAAGUAAAAGAA | 44% | 235 |
| 16802 | UGAAUGCUAACACUAAGAACCAGAA | 68% | 236 |
| 16803 | CUAAGAACCAGAAGAUCAGAUGGAA | 71% | 237 |
| 16804 | GCUUUCCAAUGACCAAGAAAAGGCA | 71% | 238 |
| 16805 | CACCAAAAACCCCAAUGGCUAUUCA | 53% | 239 |
| 16806 | CCAUCCCUGUAAAAGUUUUGGCUGA | 46% | 240 |
| 16807 | CAAACUUGACUUCAGAGAAAUACAA | 48% | 241 |
| 16808 | AAUCUAUAAGAAGCUGAGAACUUCA | 44% | 242 |
| 16809 | UAUUCUCAACCAGAAGACUCCUUGA | 46% | 243 |
| 16810 | AUAACCGUGCCUGAAUCUCAGUUAA | 40% | 244 |
| 16811 | CAUUGCUGCUUUGGAUCUAAAUGCA | 83% | 245 |
| 16812 | AAACAAAGCAGAUUAUGUUGAAACA | 50% | 246 |

TABLE 1-continued hApoB sequences

| Target Gene Duplex ID | ApoB Sense Sequence | NM_000384.2% Expression (0.1 nM) | SEQ ID No. |
|---|---|---|---|
| 16813 | GAUGGUACGUUAGCCUCUAAGACUA | 38% | 247 |
| 16814 | GUUAGCCUCUAAGACUAAAGGAACA | 36% | 248 |
| 16815 | CAGCCCUCAGUCCUCUCCAGAUAAA | 56% | 249 |
| 16816 | AAAAACUCACCAUAUUCAAAACUGA | 64% | 250 |
| 16817 | CUCACCCUGAGAGAAGUGUCUUCAA | 52% | 251 |
| 16818 | AAGUGUCUUCAAAGCUGAGAAGAAA | 65% | 252 |
| 16819 | CUUCAAAGCUGAGAAGAAAUCUGCA | 52% | 253 |
| 16820 | CAAAGCUGAGAAGAAAUCUGCAGAA | 71% | 254 |
| 16821 | AUCUGUACCAGGAACUGUUGACUCA | 52% | 255 |
| 16822 | UUGACUCACUCAUUGAUUUUCUGAA | 33% | 256 |
| 16823 | UUCGAAAGUCCAUAAUGGUUCAGAA | 31% | 257 |
| 16824 | UCGAAAGUCCAUAAUGGUUCAGAAA | 34% | 258 |
| 16825 | AUGGUUCAGAAAUACUGUUUUCCUA | 48% | 259 |
| 16826 | GUAUAGGGAACUGUUGAAAGAUUUA | 37% | 260 |
| 16827 | CAUUAAACAGCUGAAAGAGAUGAAA | 46% | 261 |
| 16828 | UUAUAUCCAAGAUGAGAUCAACACA | 69% | 262 |
| 16829 | AUGAGAUCAACACAAUCUUCAGUGA | 73% | 263 |
| 16830 | CUUCUCAAGAGUUACAGCAGAUCCA | 58% | 264 |
| 16831 | UCAAGAGUUACAGCAGAUCCAUCAA | 60% | 265 |
| 16832 | CAAGUAUAGUUGGCUGGACAGUGAA | 58% | 266 |
| 16833 | UAGUUGGCUGGACAGUGAAAUAUUA | 33% | 267 |
| 16834 | ACUUGAAGAAAAGAUAGUCAGUCUA | 31% | 268 |
| 16835 | CCAUUCUGAAUAUAUUGUCAGUGCA | 46% | 269 |
| 16836 | CUUUACUUCCCAACUCUCAAGUCAA | 30% | 270 |
| 16837 | UUUCUGCACAGAAAUAUUCAGGAAA | 60% | 271 |
| 16838 | AGGGAAAGAGAAGAUUGCAGAGCUA | 73% | 272 |
| 16839 | AGGCCAUUGCGACGAAGAAAAUAAA | 54% | 273 |
| 16840 | GACCAACUCUCUGAUUACUAUGAAA | 35% | 274 |
| 16841 | CUGAAUCCAAAAGAUUGAUUGACCA | 51% | 275 |
| 16842 | AAGAUUGAUUGACCUGUCCAUUCAA | 56% | 276 |
| 16843 | AAAACUACCACACAUUUCUGAUAUA | 53% | 277 |
| 16844 | GAACCCCUACAUGAAGCUUGCUCCA | 53% | 278 |
| 16845 | UCUCUGAACUCAGAAGGAUGGCAUA | 30% | 279 |
| 16846 | UAAAGAAAAUCAGGAUCUGAGUUAA | 25% | 280 |

TABLE 2 hApoB sd-rxRNA® sequences

| Duplex ID | Single Strand ID | Sequence | SEQ ID NO |
|---|---|---|---|
| 18727 | 18489 | G.G.A.mU.mC.mU.G.A.G.mU.mA.A.A-chol | 281 |
|  | 18490 | P.mU.fU.A.A.fC.fU.fC.A.G.A.fC.fC*fU*G*A*fU*fU*U | 282 |
| 18728 | 18491 | G.A.A.G.G.A.mU.G.G.mC.A.U.A-chol | 283 |
|  | 18492 | P.mU.A.fU.G.fC.fC.A.fU.fC.fC.fU.fU.fC*fU*G*A*G*fU*U | 284 |
| 18729 | 18493 | A.mC.mU.mC.mU.mC.A.A.G.mU.mC.A.A-chol | 285 |
|  | 18494 | P.mU.fU.G.A.fC.fU.fU.G.A.G.A.G.fU*fU*G*G*G*A*A | 286 |
| 18730 | 18495 | mU.A.A.mU.G.G.mU.mU.mC.A.G.A.A-chol | 287 |
|  | 18496 | P.mU.fU.fC.fU.G.A.A.fC.fC.A.fU.fU.A*fU*G*G*A*fC*U | 288 |
| 18731 | 18497 | G.A.mU.A.G.mU.mC.A.G.mU.mC.mU.A-chol | 289 |
|  | 18498 | P.mU.A.G.A.fC.fU.G.A.fC.fU.A.fU.fC*fU*fU*fU*fU*fC*U | 290 |
| 18732 | 18499 | mC.A.G.mU.G.A.A.A.mU.A.mU.mU.A-chol | 291 |
|  | 18500 | P.mU.A.A.fU.A.fU.fU.fU.fC.A.fC.fU.G*fU*fC*fC*A*G*C | 292 |
| 18733 | 18501 | mU.mU.G.A.mU.mU.mU.mU.mC.mU.G.A.A-chol | 293 |
|  | 18502 | P.mU.fU.fC.A.G.A.A.A.A.fU.fC.A.A*fU*G*A*G*fU*G | 294 |
| 18734 | 18503 | A.A.mU.G.G.mU.mU.mC.A.G.A.A.A-chol | 295 |
|  | 18504 | P.mU.fU.fU.fC.fU.G.A.A.fC.fC.A.fU.fU*A*fU*G*G*A*C | 296 |
| 18735 | 18505 | G.A.mU.mU.A.mC.A.mU.G.A.A.A.A-chol | 297 |
|  | 18506 | P.mU.fU.fU.fC.A.fU.G.fU.A.A.fU.fC*A*G*A*G*A*G | 298 |
| 18736 | 18507 | G.A.mC.mU.A.A.A.G.G.A.A.mC.A-chol | 299 |
|  | 18508 | P.mU.G.fU.fU.fC.fC.fU.fU.fU.A.G.fU.fC*fU*fU*A*G*A*G | 300 |

TABLE 2-continued hApoB sd-rxRNA® sequences

| Duplex ID | Single Strand ID | Sequence | SEQ ID NO |
|---|---|---|---|
| 18737 | 18509 | G.mU.mU.G.A.A.A.G.A.mU.mU.A-chol | 301 |
| | 18510 | P.mU.A.A.A.fU.fC.fU.fU.fU.fC.A.A.fC*A*G*fU*fU*fC*C | 302 |
| 18738 | 18511 | G.mC.mC.mU.mU.A.A.G.A.mC.mU.A-chol | 303 |
| | 18512 | P.mU.A.G.fU.fC.fU.fU.A.G.A.G.G.fC*fU*A*A*fC*G*U | 304 |
| 18739 | 18513 | A.mC.mC.mU.mU.G.A.A.G.mU.A.A-chol | 305 |
| | 18514 | P.mU.fU.fU.A.fC.fU.fU.fC.A.A.G.G.fU*fU*fC*fC*A*G*A | 306 |
| 18740 | 18515 | A.G.mU.mU.G.G.mC.A.A.G.mU.A-chol | 307 |
| | 18516 | P.mU.fU.A.fC.fU.fU.G.fC.fC.A.A.fC.fU*fU*G*fC*fU*U*G | 308 |
| 18741 | 18517 | G.A.G.mC.A.A.mU.A.mU.mU.mC.mU.A-chol | 309 |
| | 18518 | P.mU.A.G.A.A.fU.A.fU.fU.G.fC.fU.fC*fU*G*fC*A*A*A | 310 |
| 18742 | 18519 | A.G.A.mU.A.A.A.mC.mU.mU.mC.A.-chol | 311 |
| | 18520 | P.mU.G.A.A.G.fU.fU.fU.A.fU.fC.fU.G*A*A*fC*fU*G*A | 312 |
| 18743 | 18521 | G.A.A.mU.mC.mU.mC.A.G.mU.mU.A.A-chol | 313 |
| | 18522 | P.mU.fU.A.A.fC.fU.G.A.G.A.fU.fU.fC*A*G*fC*A*C | 314 |
| 18744 | 18523 | A.A.mU.A.mC.mC.A.A.G.mU.mC.A.A-chol | 315 |
| | 18524 | P.mU.fU.G.A.fC.fU.fU.G.G.fU.A.fU.fU*fU*fC*fC*A*fU*U | 316 |
| 18745 | 18525 | G.A.A.mU.mU.mC.mC.A.A.G.mC.mU.mU.A-chol | 317 |
| | 18526 | P.mU.A.A.G.fC.fU.fU.G.G.A.A.fU.fU.fC*fU*G*G*fU*A*U | 318 |
| 18746 | 18527 | A.A.A.G.G.mU.mU.A.mC.mU.A.A-chol | 319 |
| | 18528 | P.mU.fU.A.G.fU.A.A.A.fC.fC.fU.fU.fU*fU*G*A*G*A*C | 320 |
| 18747 | 18529 | mU.A.mC.A.mC.A.mC.A.G.A.A.A.A-chol | 321 |
| | 18530 | P.mU.fU.fU.fU.fC.fU.G.fU.G.fU.G.fU.A*A*A*fC*fU*fU*G | 322 |
| 18748 | 18531 | mC.A.G.mU.A.mC.A.A.A.mU.mU.A.A-chol | 323 |
| | 18532 | P.mU.fU.A.A.fU.fU.fU.G.fU.A.fC.fU.G*fC*A*G*fU*G*C | 324 |
| 18749 | 18533 | mU.mU.A.mU.G.mU.mU.G.A.A.A.mC.A-chol | 325 |
| | 18534 | P.mU.G.fU.fU.fU.fC.A.A.fC.A.fU.A.A*fU*fC*fU*G*fC*U | 326 |

TABLE 3

PCSK9 sd-rxRNA® sequences

| Duplex ID | Single Strand ID | Sequence | SEQ ID NO |
|---|---|---|---|
| 14440 | 13711 | AGmUmUAmUmUmCGGAA-chol | 327 |
| | 13712 | 5'-P-mU(2'-F-U)(2'-F-U)(2'-F-C)GAA(2'-F-U)AAAmCmU*mC*mC*A*G*G*C | 328 |
| 14441 | 13713 | GmUmUAmUmUmCGGAAA-chol | 329 |
| | 13714 | 5'-P-mU(2'-F-U)(2'-F-U)(2'-F-C)GAA(2'-F-U)AAAmC*mU*mC*mC*A*G*G | 330 |
| 14442 | 13715 | GAGmUmUAmUmUmCGGA-chol | 331 |
| | 13716 | 5'-P-mU(2'-F-C)(2'-F-C)GAA(2'-F-U)AAAmCmUmC*mC*A*G*G*mC*C | 332 |
| 14443 | 13717 | AGmUGmUGAmCAGmUmCA-chol | 333 |
| | 13718 | 5'-P-mUGA(2'-F-C)(2'-F-U)G(2'-F-U)(2'-F-C)A(2'-F-C)AmCmU*mU*G*mC*mU*G*G | 334 |
| 14444 | 13719 | mUGmUGGAmCmCmUmCmUmUmU-chol | 335 |
| | 13720 | 5'-P-mAAAGAGG(2'-F-U)(2'-F-C)(2'-F-C)AmCmA*mC*A*G*mC*G*G | 336 |
| 14445 | 13721 | mCAAGmUGmUGAmCAGmU-chol | 337 |
| | 13722 | 5'-P-mA(2'-F-C)(2'-F-U)G(2'-F-U)(2'-F-C)A(2'-F-C)A(2'-F-C)mUmUmUG*mC*mU*G*G*mC*C | 338 |

TABLE 3-continued

PCSK9 sd-rxRNA® sequences

| Duplex ID | Single Strand ID | Sequence | SEQ ID NO |
|---|---|---|---|
| 14446 | 13723 | GmUGGAmCmCmUmCmUmUmUG-chol | 339 |
|  | 13724 | 5'-P-mCAAAGAGG(2'-F-U)(2'-F-C)mCAmC*A*mC*A*G*mC*G | 340 |
| 14447 | 13725 | GmCAAGmUGmUGAmCAG-chol | 341 |
|  | 13726 | 5'-P-mC(2'-F-U)G(2'-F-U)(2'-F-C)A(2'-F-C)A(2'-F-C)(2'-F-U)mUGmC*mU*G*G*mC*U | 342 |
| 14448 | 13727 | GmCGmUGmCmUmCAAmCmUG-chol | 343 |
|  | 13728 | 5'-P-mCAG(2'-F-U)(2'-F-U)GAG(2'-F-C)AmCGmC*G*mC*A*G*C | 344 |
| 14449 | 13729 | AmCmUGmCmCAAGGGAA-chol | 345 |
|  | 13730 | 5'-P-mU(2'-F-U)(2'-F-C)(2'-F-C)(2'-F-C)(2'-F-U)(2'-F-U)GG(2'-F-C)AGmU*mU*G*A*G*mC*A | 346 |
| 14451 | 13733 | GmUmUAmUmUmCGGAAA-chol | 347 |
|  | 13734 | 5'-P-mU(2'-F-U)(2'-F-U)(2'-F-C)(2'-F-C)GAA(2'-F-U)AAAfC*fU*fC*fC*A*G*G | 348 |
| 14452 | 13735 | GAGmUmUAmUmUmCGGA-chol | 349 |
|  | 13736 | 5'-P-mU(2'-F-C)(2'-F-C)GAA(2'-F-U)AAAfCfU*fC*fC*A*G*G*mC*C | 350 |
| 14453 | 13737 | AGmUGmUGAmCAGmUmCA-chol | 351 |
|  | 13738 | 5'-P-mUGA(2'-F-C)(2'-F-U)G(2'-F-U)(2'-F-C)A(2'-F-C)AfCfU*fU*G*fC*fU*G*G | 352 |
| 14454 | 13739 | mUGmUGGAmCmCmUmCmUmUmU-chol | 353 |
|  | 13740 | 5'-P-mAAAGAGG(2'-F-U)(2'-F-C)(2'-F-C)AfCA*fC*A*G*fC*G*G | 354 |
| 14456 | 13743 | GmUGGAmCmCmUmCmUmUmUG-chol | 355 |
|  | 13744 | 5'-P-mCAAAGAGG(2'-F-U)(2'-F-C)fCAfC*A*fC*A*G*fC*G | 356 |
| 14457 | 13745 | GmCAAGmUGmUGAmCAG-chol | 357 |
|  | 13746 | 5'-P-mC(2'-F-U)G(2'-F-U)(2'-F-C)A(2'-F-C)A(2'-F-C)(2'-F-U)fUGfC*fU*G*G*fC*fC*U | 358 |
| 14458 | 13747 | GmCGmUGmCmUmCAAmCmUG-chol | 359 |
|  | 13748 | 5'-P-mCAG(2'-F-U)(2'-F-U)GAG(2'-F-C)AfCGfC*G*fC*A*G*G*C | 360 |
| 14459 | 13749 | AmCmUGmCmCAAGGGAA-chol | 361 |
|  | 13750 | 5'-P-mU(2'-F-U)(2'-F-C)(2'-F-C)(2'-F-C)(2'-F-U)(2'-F-U)GG(2'-F-C)AGfU*fU*G*A*G*fC*A | 362 |
| 14460 | 13751 | GGAGmUmUAmUmUmCGGAA-chol | 363 |
|  | 13752 | 5'-P-mU(2'-F-U)(2'-F-C)(2'-F-C)GAA(2'-F-U)AAAmU*mC*mC*A*G*G*C | 364 |
| 14461 | 13753 | GAGmUmUAmUmUmCGGAAA-chol | 365 |
|  | 13754 | 5'-P-mU(2'-F-U)(2'-F-U)(2'-F-C)(2'-F-C)GAA(2'-F-U)AAAmC*mU*mC*mC*A*G*G | 366 |
| 14462 | 13755 | mUGGAGmUmUAmUmUmCGGA-chol | 367 |
|  | 13756 | 5'-P-mU(2'-F-C)(2'-F-C)GAA(2'-F-U)AAAmCmUmC*mC*A*G*G*mC*C | 368 |
| 14463 | 13757 | mCAAGmUGmUGAmCAGmUmCA-chol | 369 |
|  | 13758 | 5'-P-mUGA(2'-F-C)(2'-F-U)G(2'-F-U)(2'-F-C)A(2'-F-C)AmCmU*mU*G*mC*mU*G*G | 370 |
| 14464 | 13759 | mUGmUGmUGGAmCmCmUmCmUmUmU-chol | 371 |
|  | 13760 | 5'-P-mAAAGAGG(2'-F-U)(2'-F-C)(2'-F-C)AmCA*mC*A*G*mC*G*G | 372 |
| 14465 | 13761 | AGmCAAGmUGmUGAmCAGmU-chol | 373 |
|  | 13762 | 5'-P-mA(2'-F-C)(2'-F-U)G(2'-F-U)(2'-F-C)A(2'-F-C)A(2'-F-C)mUmUG*mC*mU*G*G*mC*C | 374 |
| 14466 | 13763 | GmUGmUGGAmCmCmUmCmUmUmUG-chol | 375 |
|  | 13764 | 5'-P-mCAAAGAGG(2'-F-U)(2'-F-C)mCAmC*A*mC*A*G*mC*G | 376 |
| 14467 | 13765 | mCAGmCAAGmUGmUGAmCAG-chol | 377 |
|  | 13766 | 5'-P-mC(2'-F-U)G(2'-F-U)(2'-F-C)A(2'-F-C)A(2'-F-C)(2'-F-U)mUGmC*mU*G*G*mC*mC*U | 378 |

TABLE 3-continued

PCSK9 sd-rxRNA® sequences

| Duplex ID | Single Strand ID | Sequence | SEQ ID NO |
|---|---|---|---|
| 14468 | 13767 | GmCGmCGmUGmCmUmCAAmCmUG-chol | 379 |
| | 13768 | 5'-P-mCAG(2'-F-U)(2'-F-U)GAG(2'-F-C)AmCGmC*G*mC*A*G*G*C | 380 |
| 14469 | 13769 | mCAAmCmUGmCmCAAGGGAA-chol | 381 |
| | 13770 | 5'-P-mU(2'-F-U)(2'-F-C)(2'-F-C)(2'-F-C)(2'-F-U)(2'-F-U)GG(2'-F-C)AGmU*mU*G*A*G*mC*A | 382 |
| 14471 | 13773 | GAGmUmUAmUmUmCGGAAA-chol | 383 |
| | 13774 | 5'-P-mU(2'-F-U)(2'-F-U)(2'-F-C)(2'-F-C)GAA(2'-F-U)AAAfC*fU*fC*fC*A*G*G | 384 |
| 14472 | 13775 | mUGGAGmUmUAmUmUmCGGA-chol | 385 |
| | 13776 | 5'-P-mU(2'-F-C)(2'-F-C)GAA(2'-F-U)AAAfCfUfC*fC*A*G*G*mC*C | 386 |
| 14474 | 13779 | mUGmUGmUGGAmCmCmUmCmUmUmU-chol | 387 |
| | 13780 | 5'-P-mAAAGAGG(2'-F-U)(2'-F-C)(2'-F-C)AfCA*fC*A*G*fC*G*G | 388 |
| 14475 | 13781 | AGmCAAGmUGmUGAmCAGmU-chol | 389 |
| | 13782 | 5'-P-mA(2'-F-C)(2'-F-U)G(2'-F-U)(2'-F-C)A(2'-F-C)A(2'-F-C)fUfUG*fC*fU*G*G*fC*C | 390 |
| 14476 | 13783 | GmUGmUGGAmCmCmUmCmUmUmUG-chol | 391 |
| | 13784 | 5'-P-mCAAAGAGG(2'-F-U)(2'-F-C)fCAfC*A*fC*A*G*fC*G | 392 |
| 14477 | 13785 | mCAGmCAAGmUGmUGAmCAG-chol | 393 |
| | 13786 | 5'-P-mC(2'-F-U)G(2'-F-U)(2'-F-C)A(2'-F-C)A(2'-F-C)(2'-F-U)fUGfC*fU*G*G*fC*fC*U | 394 |
| 14478 | 13787 | GmCGmCGmUGmCmUmCAAmCmUG-chol | 395 |
| | 13788 | 5'-P-mCAG(2'-F-U)(2'-F-U)GAG(2'-F-C)AfCGfC*G*fC*A*G*G*C | 396 |
| 14479 | 13789 | mCAAmCmUGmCmCAAGGGAA-chol | 397 |
| | 13790 | 5'-P-mU(2'-F-U)(2'-F-C)(2'-F-C)(2'-F-C)(2'-F-U)(2'-F-U)GG(2'-F-C)AGfU*fU*G*A*G*fC*A | 398 |

TABLE 4

PPIB sd-rxRNA® sequences

| Target Gene Duplex ID | PPIB Single Strand ID | NM_000942 Sequence | SEQ ID NO |
|---|---|---|---|
| 17123 | 16523 | G.G.A.mU.mU.mU.G.G.mC.mU.A.mC.A.A.A-chl | 399 |
| | 16524 | P.mU.fU.fU.G.fU.A.G.fC.fC.A.A.A.fU*fC*fC*fU*fU*fU*C | 400 |
| 17124 | 16525 | A.A.A.G.A.mC.mU.G.mU.mU.mC.A.A.A-chl | 401 |
| | 16526 | P.mU.fU.fU.G.A.A.fC.A.G.fU.fC.fU*fU*fU*fC*fC*G*A | 402 |
| 17125 | 16527 | G.A.A.mC.mU.mU.mC.A.A.A.mC.G.A.A-chl | 403 |
| | 16528 | P.mU.fU.fC.A.G.fU.fU.fU.G.A.A.G.fU*fU*fC*fU*fC*A*U | 404 |
| 17126 | 16529 | G.G.A.mC.mU.mU.mC.A.mU.G.A.mU.mC.mC.A-chl | 405 |
| | 16530 | P.mU.G.G.A.fU.C.A.fU.G.A.A.G.fU*fC*fC*fU*fU*G*A | 406 |
| 17127 | 16531 | mC.mU.A.G.A.mU.G.G.mC.A.A.G.mC.A.mU-chl | 407 |
| | 16532 | P.mA.fU.G.fC.fU.fU.G.fC.fC.A.fU.fC*U*A*G*fC*A*G | 408 |
| 17128 | 16533 | mC.A.A.A.mU.mU.mC.mC.A.mU.mC.G.mU.G.mU-chl | 409 |
| | 16535 | P.mA.fC.A.fC.G.A.fU.G.G.A.A.fU.fU*fU*G*fC*fU*G*U | 410 |
| 17129 | 16534 | A.A.mU.mU.mC.mC.A.mU.mC.G.mU.G.mU-chl | 411 |
| | 16535 | P.mA.fC.A.fC.G.A.fU.G.G.A.A.fU.fU*fU*G*fC*fU*G*U | 412 |
| 17130 | 16536 | mU.A.G.mC.mU.A.mC.A.G.G.A.G.A.G.A-chl | 413 |
| | 16537 | P.mU.fC.fU.fC.fU.fC.fC.fU.G.fU.A.G.fC*fU*A*A*G*G*C | 414 |
| 13132 | 13019 | A.A.G.G.A.mU.mU.mU.G.G.mC.mU.A.Chl | 415 |
| | 13020 | P.mU.A.G.fC.fC.A.A.A.fU.C.mC.mU.mU*mU*mC*mU*mC*mU*C | 416 |

TABLE 4-continued

PPIB sd-rxRNA® sequences

| Target Gene Duplex ID | PPIB Single Strand ID | NM_000942 Sequence | SEQ ID NO |
|---|---|---|---|
| 13133 | 13021 | A.mU.mU.mU.G.G.mC.mU.A.mC.A.A.A.Chl | 417 |
|  | 13022 | P.mU.fU.fU.G.fU.A.G.fC.fC.A.A.A.mU*mC*mC*mU*mU*mU*C | 418 |
| 13134 | 13021 | A.mU.mU.mU.G.G.mC.mU.A.mC.A.A.A.Chl | 419 |
|  | 13023 | P.mU.fU.fU.G.fU.A.G.fC.fC.A.A.A.mU*mC*mC*U*mU*mU*C | 420 |
| 13135 | 13021 | A.mU.mU.mU.G.G.mC.mU.A.mC.A.A.A.Chl | 421 |
|  | 13024 | P.mU.U.fU.G.U.A.G.fC.C.A.A.A.mU*mC*mC*mU*mU*mU*C | 422 |
| 13136 | 13025 | G.G.mC.mU.A.mC.A.A.A.A.mC.A.Chl | 423 |
|  | 13026 | P.mU.G.fU.fU.fU.fU.G.fU.A.G.mC.mC*A*A*A*mU*mC*C | 424 |
| 13137 | 13025 | G.G.mC.mU.A.mC.A.A.A.A.mC.A.Chl | 425 |
|  | 13027 | P.mU.G.fU.U.fU.U.fU.G.U.A.G.mC.mC*A*A*A*mU*mC*C | 426 |
| 13138 | 13028 | A.A.mU.mU.mC.mC.A.mU.mC.G.mU.G.mU.Chl | 427 |
|  | 13029 | P.mA.fC.A.fC.G.A.fU.G.G.A.A.mU.mU*mU*G*mC*mU*G*mU | 428 |
| 13139 | 13030 | mU.A.A.mU.mC.A.A.G.G.A.mC.mU.mU.Chl | 429 |
|  | 13031 | P.mA.A.G.fU.fC.fC.fU.fU.G.A.mU.mU.A*mC*A*mC*G*A*mU | 430 |
| 13140 | 13032 | A.A.mC.mU.mU.mC.A.A.A.mC.mU.G.A.Chl | 431 |
|  | 13033 | P.mU.fC.A.G.fU.fU.fU.G.A.A.G.mU.mU*mC*mU*mC*A*mU*C | 432 |
| 13141 | 13032 | A.A.mC.mU.mU.mC.A.A.A.mC.mU.G.A.Chl | 433 |
|  | 13034 | P.mU.fC.A.G.fU.fU.fU.G.A.A.G.mU.mU*C*mU*mC*A*mU*C | 434 |
| 13142 | 13035 | A.A.mC.A.G.mU.G.G.A.mU.A.Chl | 435 |
|  | 13036 | P.mU.A.fU.fC.fC.A.fC.fU.G.U.mU.mU*mU*G*G*A*A*mC | 436 |
| 14426 | 13690 | AGGAAAGAGmCAmUmC-chol | 437 |
|  | 13691 | 5'-P-mGA(2'-F-U)G(2'-F-C)(2'-F-U)(2'-F-C)(2'-F-U)(2'-F-U)(2'-F-U)mCmCmU*mC*mC*mU*G*mU*G | 438 |
| 14427 | 13692 | GmCAmCCAAGAmCAGA-chol | 439 |
|  | 13693 | 5'-P-mU(2'-F-C)(2'-F-U)G(2'-F-U)(2'-F-C)(2'-F-U)(2'-F-U)(2'-F-U)GGmUGmC*mU*mC*mU*mC*A | 440 |
| 14428 | 13694 | GAAmCmUmUmCAAAmCmUG-chol | 441 |
|  | 13695 | 5'-P-mCAG(2'-F-U)(2'-F-U)(2'-F-U)GAAGmUmC*mU*mC*A*mU*mC*G | 442 |
| 14429 | 13696 | AmUmUmCmCAmUmCGmUGmUA-chol | 443 |
|  | 13697 | 5'-P-mUA(2'-F-C)A(2'-F-C)GA(2'-F-U)GGAAmU*mU*mU*G*mC*mU*G | 444 |
| 14430 | 13698 | AAmCmUmUmCAAAmCmUGA-chol | 445 |
|  | 13699 | 5'-P-mU(2'-F-C)AG(2'-F-U)(2'-F-U)(2'-F-U)GAAGmUmU*mC*mU*mC*A*mU*C | 446 |
| 14431 | 13700 | GAmUGGmCAAGmCAmUG-chol | 447 |
|  | 13701 | 5'-P-mCA(2'-F-U)G(2'-F-U)(2'-F-U)G(2'-F-C)(2'-F-C)AmUmC*mU*A*G*mC*mC*A | 448 |
| 14432 | 13702 | GmCAmUmCmUAmCGGmUGA-chol | 449 |
|  | 13703 | 5'-P-mU(2'-F-U)A(2'-F-C)(2'-F-C)G(2'-F-U)AGAmUGmC*mU*mC*mU*mU*C | 450 |
| 14433 | 13690 | AGGAAAGAGmCAmUmC-chol | 451 |
|  | 13704 | 5'-P-mGA(2'-F-U)G(2'-F-C)(2'-F-U)(2'-F-C)(2'-F-U)(2'-F-U)(2'-F-U)fCfCfU*fC*fC*fU*G*fU*G | 452 |
| 14434 | 13692 | GmCAmCCAAGAmCAGA-chol | 453 |
|  | 13705 | 5'-P-mU(2'-F-C)(2'-F-U)G(2'-F-U)(2'-F-C)(2'-F-U)(2'-F-U)(2'-F-U)GGfUGfC*fU*fC*fU*fC*A | 454 |
| 14435 | 13694 | GAAmCmUmUmCAAAmCmUG-chol | 455 |
|  | 13706 | 5'-P-mCAG(2'-F-U)(2'-F-U)(2'-F-U)GAAGfUfUfC*fU*fC*A*fU*fC*G | 456 |

TABLE 4-continued

PPIB sd-rxRNA® sequences

| Target Gene Duplex ID | PPIB Single Strand ID | NM_000942 Sequence | SEQ ID NO |
|---|---|---|---|
| 14436 | 13696 | AmUmUmCmCAmUmCGmUGmUA-chol | 457 |
|  | 13707 | 5'-P-mUA(2'-F-C)A(2'-F-C)GA(2'-F-U)GGAAfU*fU*fU*G*fC*fU*G | 458 |
| 14437 | 13698 | AAmCmUmUmCAAAmCmUGA-chol | 459 |
|  | 13708 | 5'-P-mU(2'-F-C)AG(2'-F-U)(2'-F-U)(2'-F-U)GAAGfUfU*fC*fU*fC*A*fU*C | 460 |
| 14438 | 13700 | GAmUGGmCAAGmCAmUG-chol | 461 |
|  | 13709 | 5'-P-mCA(2'-F-U)G(2'-F-U)(2'-F-U)G(2'-F-C)(2'-F-C)AfUfC*fU*A*G*fC*fC*A | 462 |
| 14439 | 13702 | GmCAmUCmUAmCGGmUGA-chol | 463 |
|  | 13710 | 5'-P-mU(2'-F-U)A(2'-F-C)(2'-F-C)G(2'-F-U)AGAfUGfC*fU*fC*fU*fU*fU*C | 464 |

| Key: | | |
|---|---|---|
| PS | * | = Phosphothioate Backbone Linkage |
| RNA | G | = Guanine |
| RNA | U | = Uracil |
| RNA | C | = Cytosine |

-continued

| Key: | | |
|---|---|---|
| RNA | A | = Adenine |
|  | m | 2' Omethyl |
|  | f | 2'-Fluoro |
| Phosphate | P | 5' Phosphate |

TABLE 5

2'F and 5 methyl C and U modified ApoB, CTGF, MAP4K4 and PPIB sequences

| Gene ID | Accession Number | Oligo ID | Ref Site | Sequence | SEQ ID NO |
|---|---|---|---|---|---|
| mApob | NM_012881.2 | 21779 | 13811 | fA.fG.fA.fG.fU.fA.fA.fG.fU.fC*fA.fA.TEG-Chl | 465 |
| mApob | NM_012881.2 | 21780 | 13811 | P.fU.fU.fG.fA.fC.fU.fU.fA.fC.fU.fC*fA*fA*fC*fU*fG | 466 |
| mApob | NM_012881.2 | 21781 | 13811 | P.fU.fU.fG.fA.fC.fU.fU.fA.fC.fU.mC.mU*fA*fA*mC*mU*mU*G | 467 |
| mApob | NM_012881.2 | 21782 | 13811 | mA.mG.mA.mG.mY.mA.mA.mA.mG.mY.mX*mA*mA.TEG-Chl | 468 |
| mApob | NM_012881.2 | 21783 | 13811 | P.mY.fY.G.A.fX.fY.fY.fY.A.fX.fY.mX.mY*A*A*mX*mY*mY*G | 469 |
| mApob | NM_012881.2 | 21784 | 13811 | P.mY.fY.fG.fA.fX.fY.fY.fA.fX.fY.mX.mY*fA*fA*mX*mY*mY*G | 470 |
| CTGF | NM_001901.2 | 21785 | 2296 | fG.fC.fA.fC.fC.fU.fU.fU.fC.fU.fA*fG*fA.TEG-Chl | 471 |
| CTGF | NM_001901.2 | 21786 | 2296 | P.fU.fC.fU.fA.fG.fA.fA.fA.fG.fG.fU.fG.fC*fA*fA*fA*fC*fA*U | 472 |
| CTGF | NM_001901.2 | 21787 | 2296 | P.fU.fC.fU.fA.fG.mA.fA.mA.fG.fG.fU.fG.mC*fA*mA*fA*mC*fA*U | 473 |
| CTGF | NM_001901.2 | 21788 | 2296 | G.mX.A.mX.mX.mY.mY.mY.mX.mY.A*mG*mA.TEG-Chl | 474 |
| CTGF | NM_001901.2 | 21789 | 2296 | P.fY.fX.fY.A.G.mA.A.mA.G.G.fY.G.mX*A*mA*A*mX*A*U | 475 |
| CTGF | NM_001901.2 | 21790 | 2296 | P.fY.fX.fY.fA.fG.mA.fA.mA.fG.fG.fY.fG.mX*fA*mA*fA*mX*fA*U | 476 |

TABLE 5-continued

2'F and 5 methyl C and U modified ApoB, CTGF, MAP4K4 and PPIB sequences

| Gene ID | Accession Number | Oligo ID | Ref Site | Sequence | SEQ ID NO |
|---|---|---|---|---|---|
| Map4k4 | NM_004834 | 21791 | 2931 | fC.fU.fG.fU.fG.fG.fA.fA.fG.fU.fC*fU*fA.TEG-Chl | 477 |
| Map4k4 | NM_004834 | 21792 | 2931 | P.fU.fA.fG.fA.fC.fU.fU.fC.fC.fA.fC*fA*fG*fA*fA*fC*fU*fC*U | 478 |
| Map4k4 | NM_004834 | 21793 | 2931 | P.fU.fA.fG.fA.fC.fU.fU.fC.fC.fA.mC*fA*mG*fA*mA*mC*mU*mC*U | 479 |
| Map4k4 | NM_004834 | 21794 | 2931 | mX.mY.G.mY.G.G.A.A.G.mY.mX*mY*A.TEG-Chl | 480 |
| Map4k4 | NM_004834 | 21795 | 2931 | P.fY.A.G.A.fX.fY.fY.fX.fC.A.mX*A*mG*A*mA*mX*mY*mX*U | 481 |
| Map4k4 | NM_004834 | 21796 | 2931 | P.fY.fA.fG.fA.fX.fY.fY.fX.fX.fA.mX*fA*mG*fA*mA*mX*mY*mX*U | 482 |
| PPIB | NM_000942 | 21797 | 438 | fA.fA.fA.fU.fU.fC.fC.fA.fU.fC.fG.fU*fG*fU.TEG-Chl | 483 |
| PPIB | NM_000942 | 21798 | 438 | P.fA.fC.fA.fC.fG.fA.fU.fG.fG.fA.fA.fU.fU.fU*fG*fC*fU*fG*fU*U | 484 |
| PPIB | NM_000942 | 21799 | 438 | P.fA.fC.fA.fC.fG.fA.fU.fG.fG.mA.fA.fU.fU.fU*mG*fC*fU*mG*mU*U | 485 |
| PPIB | NM_000942 | 21800 | 438 | mA.mA.mA.mY.mY.mX.mX.mA.mY.mX.mG.mY*mG*mY.TEG-Chl | 486 |
| PPIB | NM_000942 | 21801 | 438 | P.fA.fX.A.fX.G.A.fY.G.G.mA.A.fY.fY.fY*mG*fX*fY*mG*mY*U | 487 |
| PPIB | NM_000942 | 21802 | 438 | P.fA.fX.fA.fX.fG.fA.fY.fG.fG. mA.fA.fY.fY.fY*mG*fX*fY*mG*mY*U | 488 |

Key:
X = 5 methyl C
Y = 5 methyl U
F = 2'fluoro
M = 2'Ome
TEG-Chl = Cholesterol with TEG linker
P = 5'phosphate
* = phosphorothioate linkage
. = phosphodiester linkage

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Publication No. WO2010/033247 (Application No. PCT/US2009/005247), filed on Sep. 22, 2009, and entitled "REDUCED SIZE SELF-DELIVERING RNAI COMPOUNDS" and PCT Publication No. WO2009/102427 (Application No. PCT/US2009/000852), filed on Feb. 11, 2009, and entitled, "MODIFIED RNAI POLYNUCLEOTIDES AND USES THEREOF."

The invention claimed is:

1. A method for delivering a nucleic acid to a remote target tissue in a subject in need thereof, comprising systemically administering to the subject an sd-rxRNA® in an effective amount to promote RNA interference by the sd-rxRNA® in the remote target tissue, wherein the sd-rxRNA® comprises a guide strand and a passenger strand, wherein the sd-rxRNA® includes a double-stranded region and a single stranded region wherein the double stranded region is from 8-15 nucleotides long, wherein the single stranded region is at the 3' end of the guide strand and is 4-12 nucleotides long, wherein the single stranded region contains 3, 4, 5, 6, 7, 8, 9, 10, 11, or 12 phosphorothioate modifications, wherein at least 40% of the nucleotides of the sd-rxRNA® are modified, and wherein at least two Us and/or Cs include a hydrophobic modification selected from the group consisting of a thiophene, octyn-1-yl, and ethynyl modification, located on position 5 of the Us and/or Cs.

2. The method of claim 1, wherein at least 60% of the nucleotides on the guide strand of the sd-rxRNA® are modified.

3. The method of claim 1, wherein the modifications include at least one 2'F or 2'O methyl modification.

4. The method of claim 1, wherein a plurality of Us and/or Cs include a hydrophobic modification, and wherein each of the hydrophobic modifications is selected from the group consisting of a thiophene, octyn-1-yl, and ethynyl modification.

5. The method of claim 1, wherein the sd-rxRNA® is attached to a linker.

6. The method of claim 1, wherein the sd-rxRNA® is linked at the 3' end to cholesterol, and/or wherein the guide strand contains at least 5 phosphorothioate modifications.

7. The method of claim 1, wherein the guide strand of the sd-rxRNA® contains at least two single stranded regions.

8. The method of claim 1, wherein the sd-rxRNA® is delivered to the liver, heart, brain, lung or fat.

9. A method comprising:
administering to a subject having a tumor an sd-rxRNA® in an effective amount to promote RNA interference by the sd-rxRNA® in the tumor, wherein the sd-rxRNA® comprises a guide strand and a passenger strand, wherein the sd-rxRNA® includes a double-stranded region and a single stranded region wherein the double stranded region is from 8-15 nucleotides long, wherein the single stranded region is at the 3' end of the guide strand and is 4-12 nucleotides long, wherein the single stranded region contains 3, 4, 5, 6, 7, 8, 9, 10, 11, or 12 phosphorothioate modifications, and wherein at least 40% of the nucleotides of the sd-rxRNA® are modified, and wherein at least two Us and/or Cs include a hydrophobic modification selected from the group consisting of a thiophene, octyn-1-yl, and ethynyl modification, located on position 5 of the Us and/or Cs.

10. The method of claim 9, wherein the sd-rxRNA® is administered to the tumor through intravenous administration.

11. The method of claim 9, wherein the sd-rxRNA® is administered to the tumor through direct injection into the tumor.

12. The method of claim 9, wherein the sd-rxRNA® is directed against a gene encoding for a protein selected from the group consisting of: VEGF/VEGFR, HER2, PDGF/PDGFR, HDAC, MET, c-kit, CDK, FLT-1, IGF/IGFR, FGF/FGFR, Ras/Raf, Abl, Bcl-2, Src, mTOR, PKC, MAPK, BIRC5, FAS, HIF1A, CDH16, MYC, HRAS and CTNNB1, or a combination thereof.

13. A method comprising:
administering an sd-rxRNA® to the central nervous system of a subject in need thereof, wherein the sd-rxRNA® comprises a guide strand and a passenger strand, wherein the sd-rxRNA® includes a double-stranded region and a single stranded region wherein the double stranded region is from 8-15 nucleotides long, wherein the single stranded region is at the 3' end of the guide strand and is 4-12 nucleotides long, wherein the single stranded region contains 3, 4, 5, 6, 7, 8, 9, 10, 11, or 12 phosphorothioate modifications, and wherein at least 40% of the nucleotides of the sd-rxRNA® are modified, and wherein at least two Us and/or Cs include a hydrophobic modification selected from the group consisting of a thiophene, octyn-1-yl, and ethynyl modification, located on position 5 of the Us and/or Cs.

14. The method of claim 13, wherein the sd-rxRNA® is administered by intrathecal delivery.

15. The method of claim 9, wherein the modifications include at least one 2'F or 2'O methyl modification.

16. The method of claim 9, wherein a plurality of Us and/or Cs include a hydrophobic modification, wherein each of the hydrophobic modifications is selected from the group consisting of a thiophene, octyn-1-yl, and ethynyl modification.

17. The method of claim 9, wherein the sd-rxRNA® is linked at the 3' end to cholesterol, and/or wherein the guide strand contains at least 5 phosphorothioate modifications.

18. The method of claim 13, wherein the modifications include at least one 2'F or 2'O methyl modification.

19. The method of claim 13, wherein a plurality of Us and/or Cs include a hydrophobic modification, wherein each of the hydrophobic modifications is selected from the group consisting of a thiophene, octyn-1-yl, and ethynyl modification.

20. The method of claim 13, wherein the sd-rxRNA® is linked at the 3' end to cholesterol, and/or wherein the guide strand contains at least 5 phosphorothioate modifications.

21. A method for delivering a nucleic acid to a remote target tissue in a subject in need thereof, comprising
systemically administering to the subject an sd-rxRNA® in an effective amount to promote RNA interference by the sd-rxRNA® in the remote target tissue, wherein the sd-rxRNA® comprises a guide strand and a passenger strand, wherein the sd-rxRNA® includes a double-stranded region and a single stranded region wherein the double stranded region is from 8-15 nucleotides long, wherein the single stranded region is at the 3' end of the guide strand and is 4-12 nucleotides long, wherein the single stranded region contains 3, 4, 5, 6, 7, 8, 9, 10, 11, or 12 phosphorothioate modifications, wherein at least 40% of the nucleotides of the sd-rxRNA® are modified, wherein at least two Us include an imidazole modification, and wherein the imidazole modifications are located on position 5 of the Us.

* * * * *